United States Patent
Chandler

(10) Patent No.: US 11,643,473 B2
(45) Date of Patent: May 9, 2023

(54) ANTIBODY IMMUNE CELL INHIBITOR FUSION PROTEINS

(71) Applicant: ALEXION PHARMACEUTICALS, INC., New Haven, CT (US)

(72) Inventor: Julian Chandler, Guilford, CT (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 121 days.

(21) Appl. No.: 16/607,183

(22) PCT Filed: Apr. 23, 2018

(86) PCT No.: PCT/US2018/028963
§ 371 (c)(1),
(2) Date: Oct. 22, 2019

(87) PCT Pub. No.: WO2018/200422
PCT Pub. Date: Nov. 1, 2018

(65) Prior Publication Data
US 2021/0261684 A1    Aug. 26, 2021

Related U.S. Application Data

(60) Provisional application No. 62/489,027, filed on Apr. 24, 2017.

(51) Int. Cl.
*C07K 16/40* (2006.01)
*C07K 14/705* (2006.01)

(52) U.S. Cl.
CPC ........ *C07K 16/40* (2013.01); *C07K 14/70532* (2013.01); *C07K 2317/52* (2013.01); *C07K 2317/71* (2013.01); *C07K 2319/33* (2013.01)

(58) Field of Classification Search
None
See application file for complete search history.

(56) References Cited

U.S. PATENT DOCUMENTS

| 4,931,385 | A * | 6/1990 | Block | G01N 33/535 |
| | | | | 435/188 |
| 6,277,375 | B1 | 8/2001 | Ward | |
| 8,993,524 | B2 * | 3/2015 | Bedi | C07K 16/2827 |
| | | | | 514/19.2 |
| 2004/0221327 | A1 * | 11/2004 | Gershwin | C07K 16/40 |
| | | | | 800/6 |

FOREIGN PATENT DOCUMENTS

| WO | 1997/34631 | 9/1997 |
| WO | 1998/23289 | 5/1998 |
| WO | 2011/109789 | 9/2011 |
| WO | 2016/075278 | 5/2016 |

OTHER PUBLICATIONS

Lloyd et al. Protein Engineering, Design & Selection 2009, 22:159-168.*
Schroeder et al. J Allergy Clin Immunol 2010, 125:S41-S52.*
International Search Report for PCT/US2018/028963, dated Jun. 28, 2018.
Borroto, et al., "First-in-class inhibitor of the T cell receptor got the treatment of autoimmune diseases," Science Translational Medicine, 370-370ra184, Dec. 2016.
Thomson, et al., "Immunogenetic analysis of a panel of monoclonal IgG and IgM anti-PDC-E2/X antibodies derived from patients with primary biliary cirrhosis," Journal of Hepatology, 28(4):582-594, Apr. 1998.
Zamani, et al., "PD-1/PD-L and autoimmunity: A growing relationship," Cellular Immunology, 310:27-41, Dec. 2016.
Zhang, et al., "Co-stimulatory and co-inhibitory pathways in autoimmunity," Immunity, 44(5): 1034-1051, May 2016.
Chen, et al., "Natural and Disease Associated Autoantibodies to the Autoantigen, Dihydrolipoamide Acetyltransferase, Recognise Different Epitopes", J. Autoimmun. 11(2): 151-61, 1998.
Dall'Acqua et al., "Properties of Human IgG1s Engineered for Enhanced Binding to the Neonatal Fc Receptor (FcRN)", J. Biol. Chem. 281(33): 23514-24, 2006.
Datta-Mannan et al., "Humanized IgG Variants with Differential Binding Properties to the Neonatal Fc Receptor Relationship to Pharmacokinetics in Mice and Primates", Drug Metab. Dispos. 35(1): 86-94, 2007.
Datta-Mannan, et al., "Monoclonal Antibody Clearance—Impact of Modulating the Interaction of IgG with the neonatal Fc Receptor", J. Biol. Chem. 282(3): 1709-17, 2007.
Hinton, et al., "Engineered Human IgG Antibodies with Longer Serum Half-lives in Primates", J. Biol. Chem. 279(8): 6213-16, 2004.
Hinton, et al., "An Engineered Human IgG1 Antibdy with Longer Serum Half-Life", J. Immunol. 176(1): 346-56, 2006.
Pascual, et al., "Nucleotide sequence analysis of natural and combinatorial anti-PDC-E2 antibodies in patients with primary bilary cirrohosis. Recapitulating immune selection with molecular biology", J. Immunol. 152(5): 2577-85, 1994.
Petkova, et al., "Enhanced half-life of genetically engineered human igG1 antibodies in a humanized FcRn mouse model: potential application in humorally mediated autoimmune disease", Int. Immunol. 18(12): 1759-69, 2006.

(Continued)

*Primary Examiner* — Sharon X Wen
(74) *Attorney, Agent, or Firm* — McDonnell Boehnen Hulbert & Berghoff, LLP

(57) ABSTRACT

The disclosure provides antibody immune cell inhibitor fusion proteins comprising four polypeptide chains that form two antigen binding sites and at least two immune cell receptor binding sites that inhibit or diminish activation of an immune effector cell when bound to a target antigen. The disclosure also provides antibody immune cell inhibitor fusion proteins comprising two polypeptide chains that form one antigen binding site and at least one immune cell receptor binding site that inhibit or diminish activation of an immune effector cell when bound to a target antigen. The disclosure further provides pharmaceutical compositions and kits that comprise such antibody immune cell inhibitor fusion proteins, and methods of treatment using such proteins.

10 Claims, 69 Drawing Sheets
Specification includes a Sequence Listing.

(56) References Cited

OTHER PUBLICATIONS

Riella, et al., "Role of the PD-1 Pathway in the Immune Response", Am. J. Transplant. 12(10): 2575-87, 2012.
Zak, et al., Structure of the Complex of Human Programmed Death 1, PD-1, and Its Ligand PD-L1:, Structure 23(12): 2341-48, 2015.
Smilek, et al: "Restoring the balance: immunotherapeutic combinations for autoimmune disease", Disease Models & Mechanisms, 7(5): 503-513, May 2014.
Kontermann, "Antibody-cytokine fusion proteins", Archives of Biochemistry and Biophysics, 526(2): 194-205, Oct. 2012.

\* cited by examiner

FIG. 4A
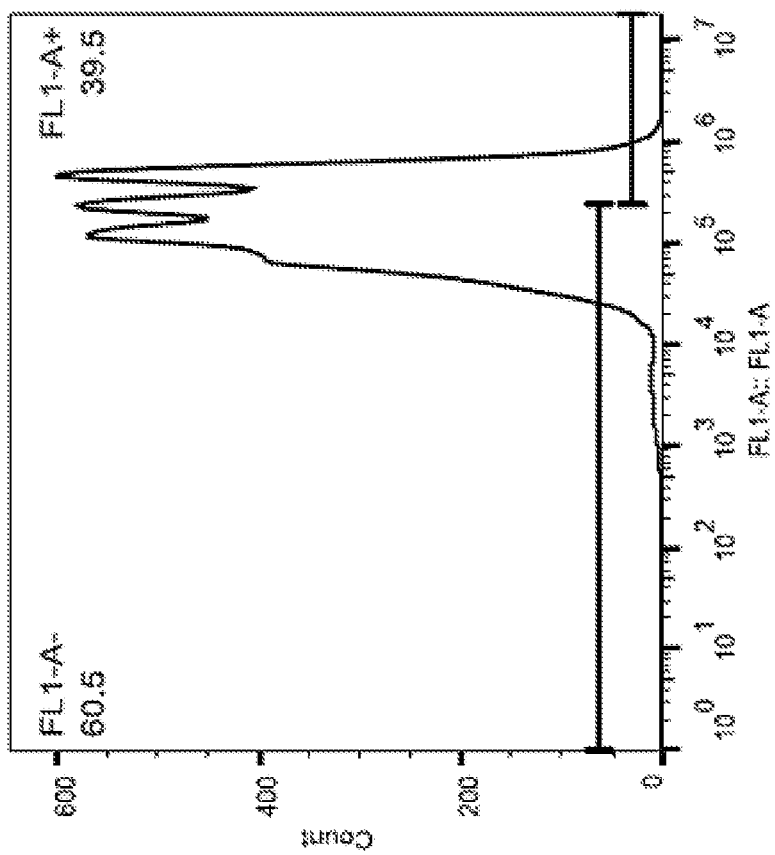
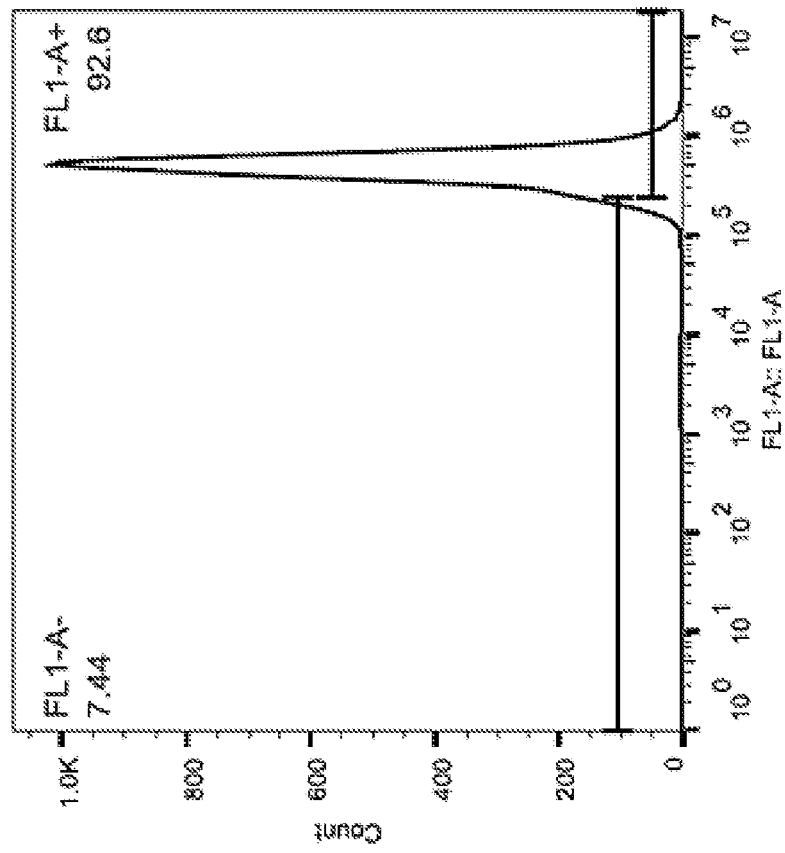

FIG. 4B
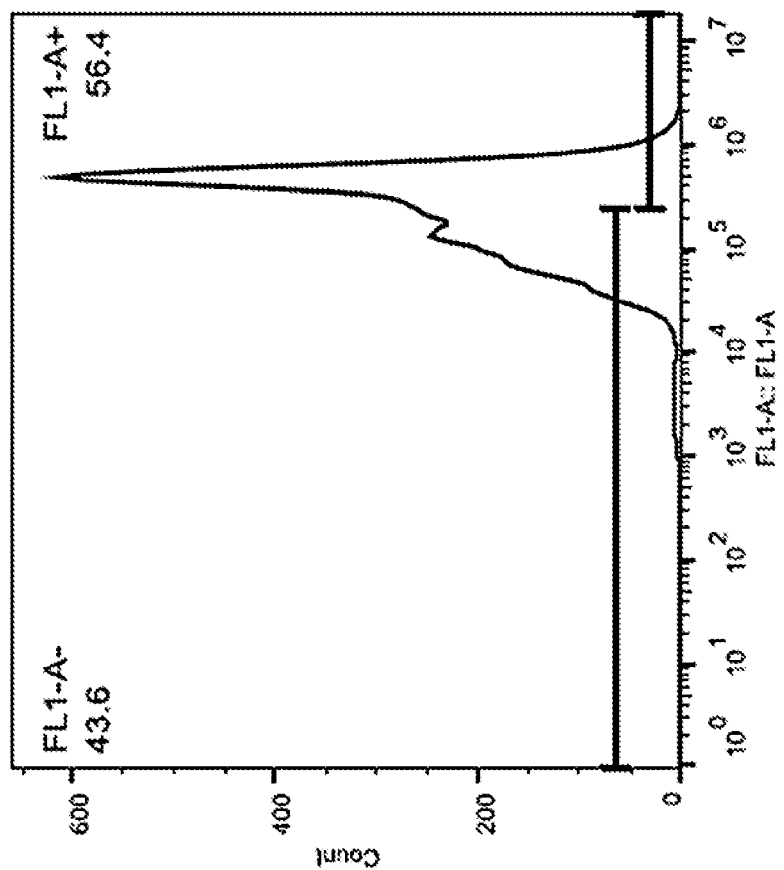
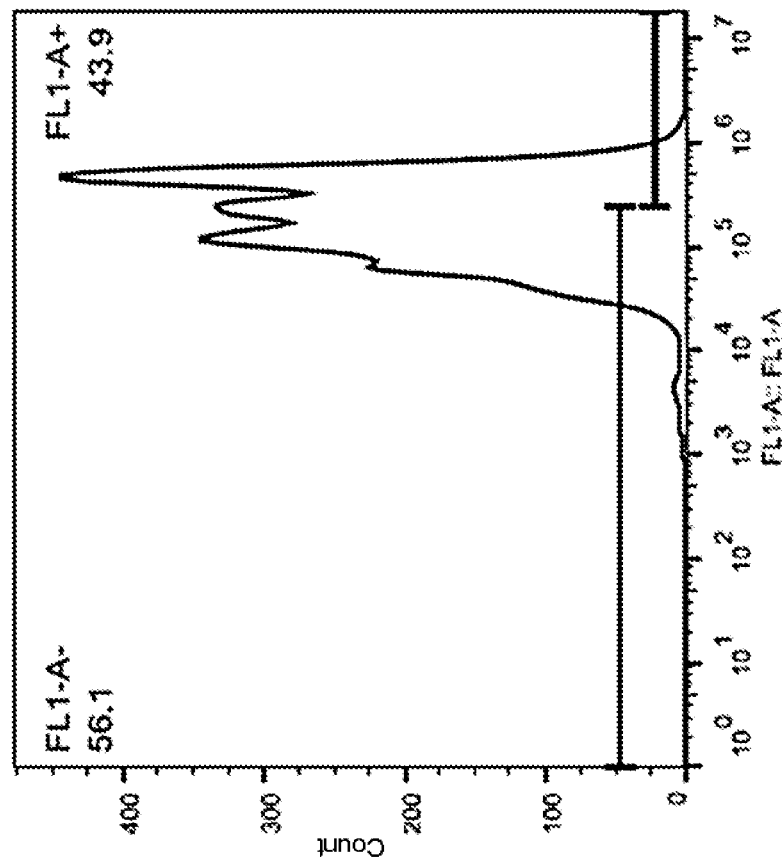

FIG. 4C
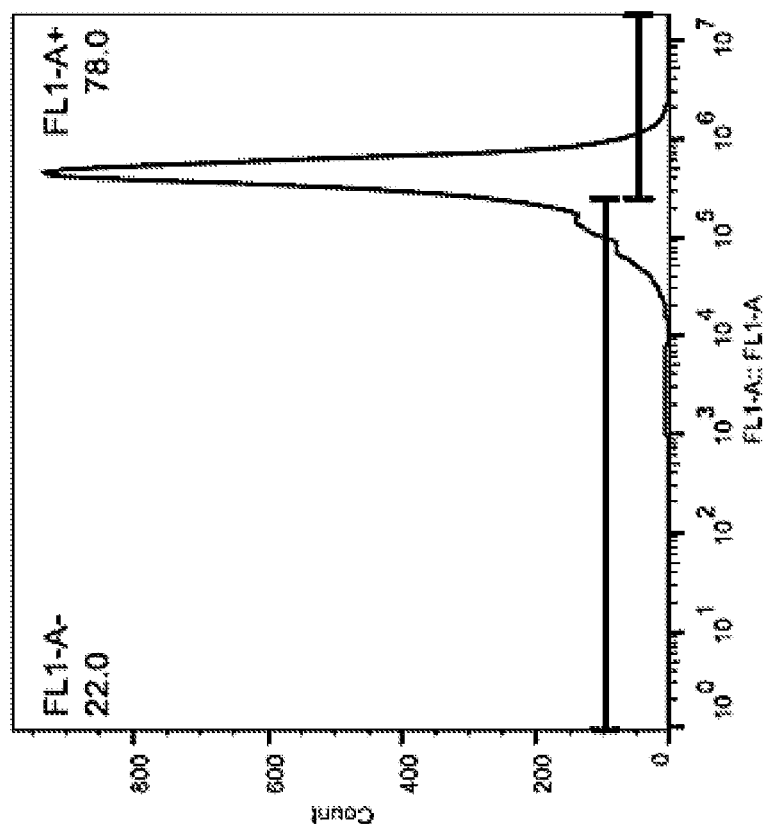
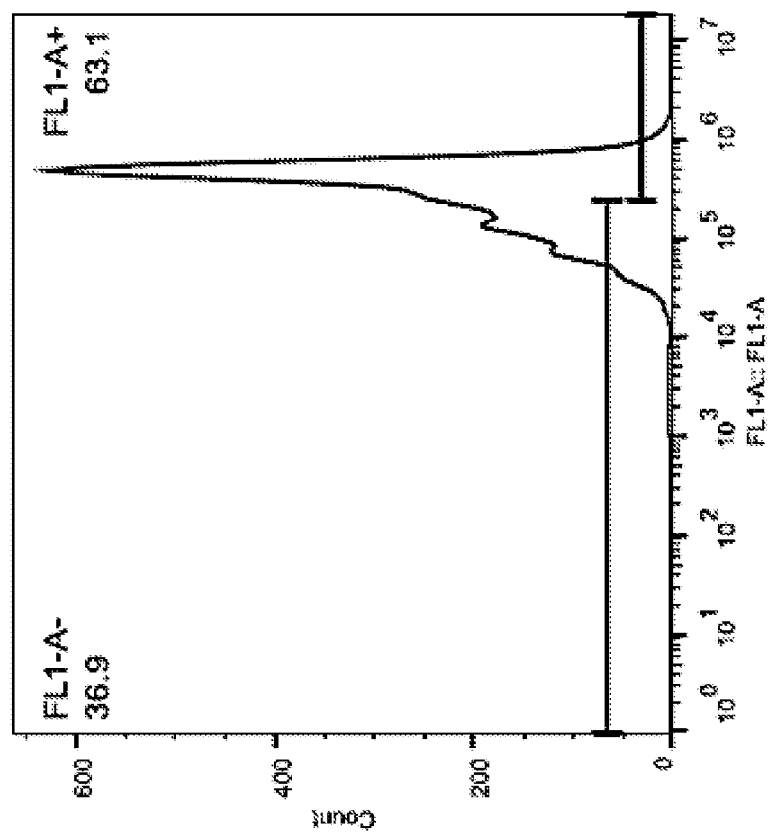

| Tukey's multiple comparisons test | Significant? | P Value |
|---|---|---|
| TA2 Beads vs. TA2 + 985 | No | 0.6874 |
| TA2 Beads vs. TA2 + 986 | No | 0.9967 |
| TA2 Beads vs. TA2 + 992 | No | 0.6602 |
| TA2 + 985 vs. TA2 + 986 | No | 0.846 |
| TA2 + 985 vs. TA2 + 992 | No | 0.2361 |
| TA2 + 986 vs. TA2 + 992 | No | 0.6249 |

FIG. 6B

| Tukey's multiple comparisons test | Summary | P Value |
|---|---|---|
| TPP-985 vs. TPP-986 | **** | <0.0001 |
| TPP-985 vs. TPP-992 | **** | <0.0001 |
| TPP-985 vs. PDL1 Fc | ns | 0.5356 |
| TPP-985 vs. DLAT Beads | ns | 0.1382 |
| TPP-985 vs. NC Beads | **** | <0.0001 |
| TPP-986 vs. TPP-992 | *** | 0.0007 |
| TPP-986 vs. PDL1 Fc | **** | <0.0001 |
| TPP-986 vs. DLAT Beads | **** | <0.0001 |
| TPP-986 vs. NC Beads | **** | <0.0001 |
| TPP-992 vs. PDL1 Fc | **** | <0.0001 |
| TPP-992 vs. DLAT Beads | **** | <0.0001 |
| TPP-992 vs. NC Beads | ns | 0.4644 |
| PDL1 Fc vs. DLAT Beads | ns | 0.9813 |
| PDL1 Fc vs. NC Beads | **** | <0.0001 |
| DLAT Beads vs. NC Beads | **** | <0.0001 |

FIG. 6D

| Tukey's multiple comparisons test | Summary | P Value |
|---|---|---|
| TPP-985 vs. TPP-986 | *** | 0.0009 |
| TPP-985 vs. TPP-992 | **** | <0.0001 |
| TPP-985 vs. PDL1 Fc | ns | 0.2756 |
| TPP-985 vs. DLAT Beads | ns | >0.9999 |
| TPP-985 vs. NC Beads | **** | <0.0001 |
| TPP-986 vs. TPP-992 | * | 0.0132 |
| TPP-986 vs. PDL1 Fc | ns | 0.0597 |
| TPP-986 vs. DLAT Beads | *** | 0.0003 |
| TPP-986 vs. NC Beads | **** | <0.0001 |
| TPP-992 vs. PDL1 Fc | **** | <0.0001 |
| TPP-992 vs. DLAT Beads | **** | <0.0001 |
| TPP-992 vs. NC Beads | ** | 0.0016 |
| PDL1 Fc vs. DLAT Beads | ns | 0.2051 |
| PDL1 Fc vs. NC Beads | **** | <0.0001 |
| DLAT Beads vs. NC Beads | **** | <0.0001 |

FIG. 7A

| Sample | Description | Purpose |
|---|---|---|
| DLAT 2.5uL beads | Beads only | T-Cell Activation |
| DLAT 2.5uL + PDL1 Fc | Beads with PDL1 Fc chimera (R&D Systems) | Non-targeted PD-L1 control |
| DLAT 2.5uL + TPP-985 (PD5 Hu IgG2/4) | PD5 naked antibody | No PD-L1 targeting control |
| DLAT 2.5uL + TPP-986 (PD5 PDL1_HC_IgG2/4) | PD5 with N-terminus PDL1 V-domain fusion to Heavy chain | Targeted T-cell Activation inhibition |
| DLAT 2.5uL + TPP-992 (PD5 PDL1_LC_IgG2/4) | PD5 with N-terminus PDL1 V-domain fusion to Light chain | Targeted T-cell Activation inhibition |

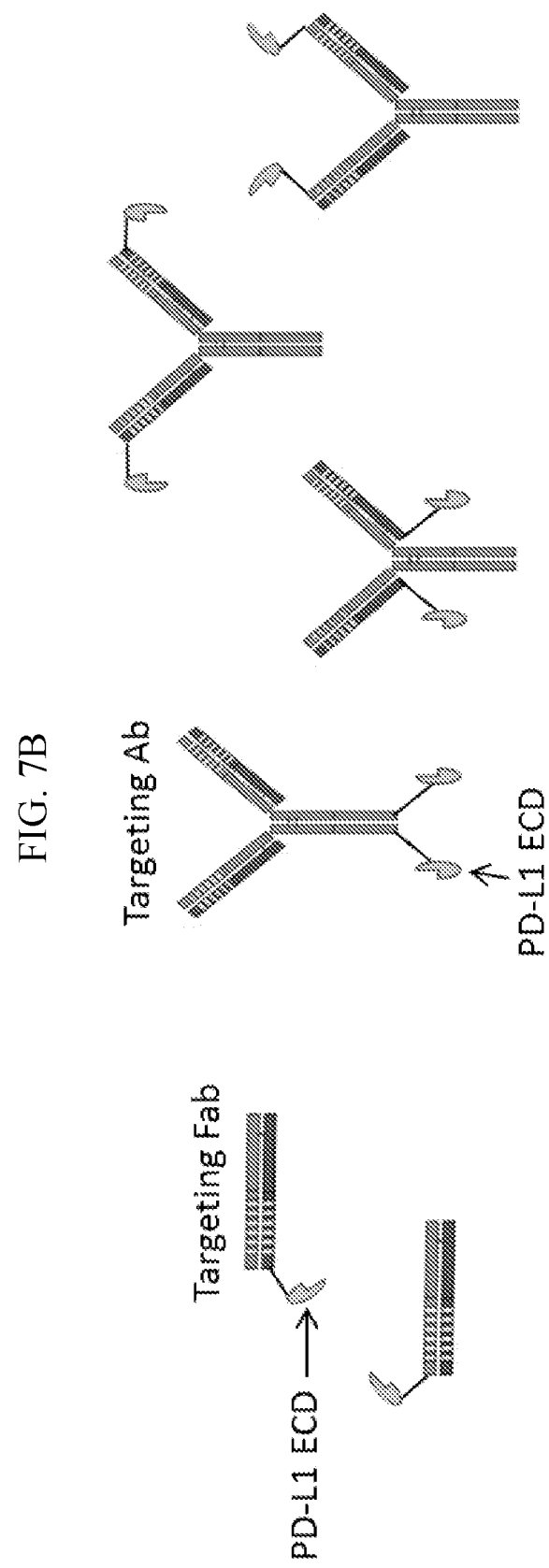

FIG. 11A

| Sample | $k_a$ (1/Ms) | $k_d$ (1/s) | $K_D$ (M) | $Chi^2$ |
|---|---|---|---|---|
| TPP1003 | 1.93e5 | 4.68e-5 | 2.42e-10 | 0.07 |
| TPP1004 | 3.69e4 | 1.94e-5 | 5.26e-10 | 0.02 |
| TPP1005 | 8.63e4 | 1.49e-4 | 1.72e-9 | 0.28 |

FIG. 12A
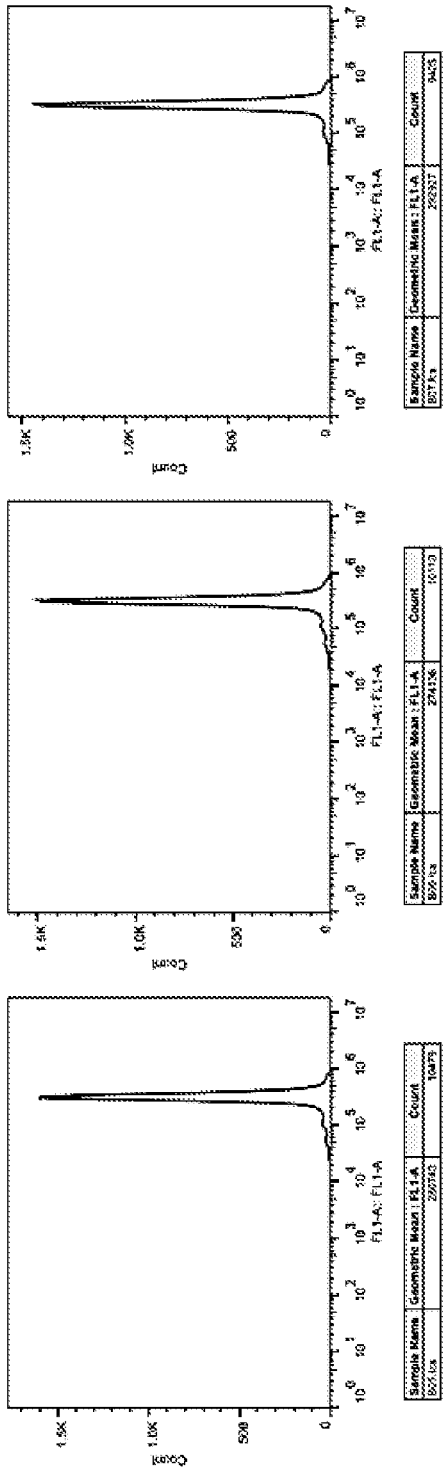
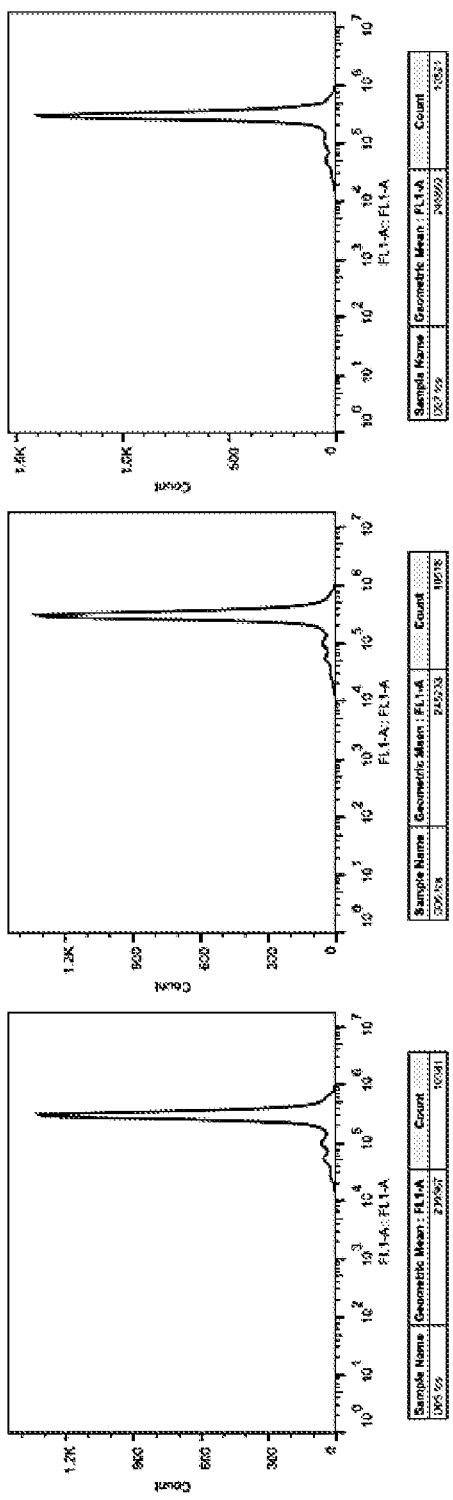

FIG. 12B
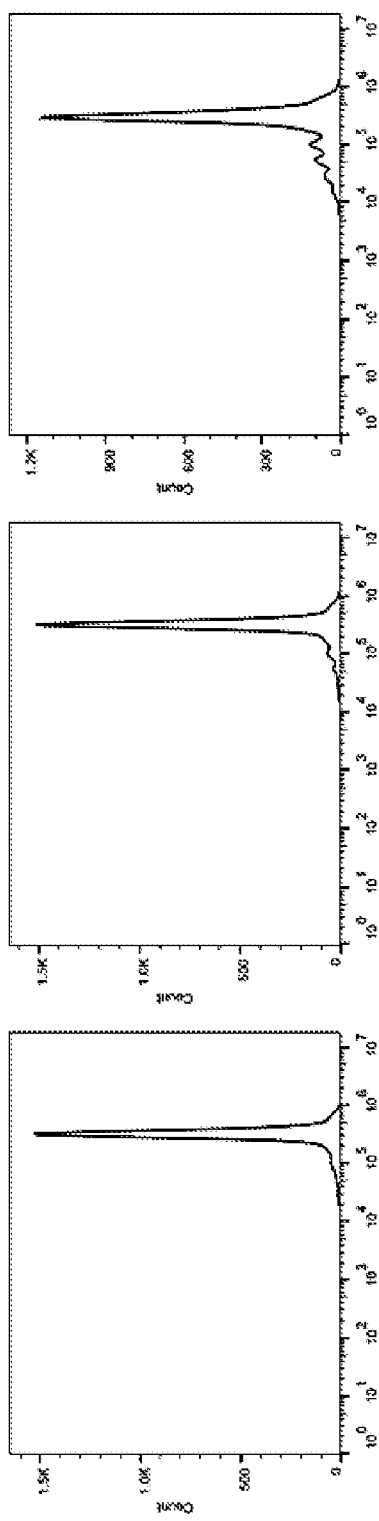
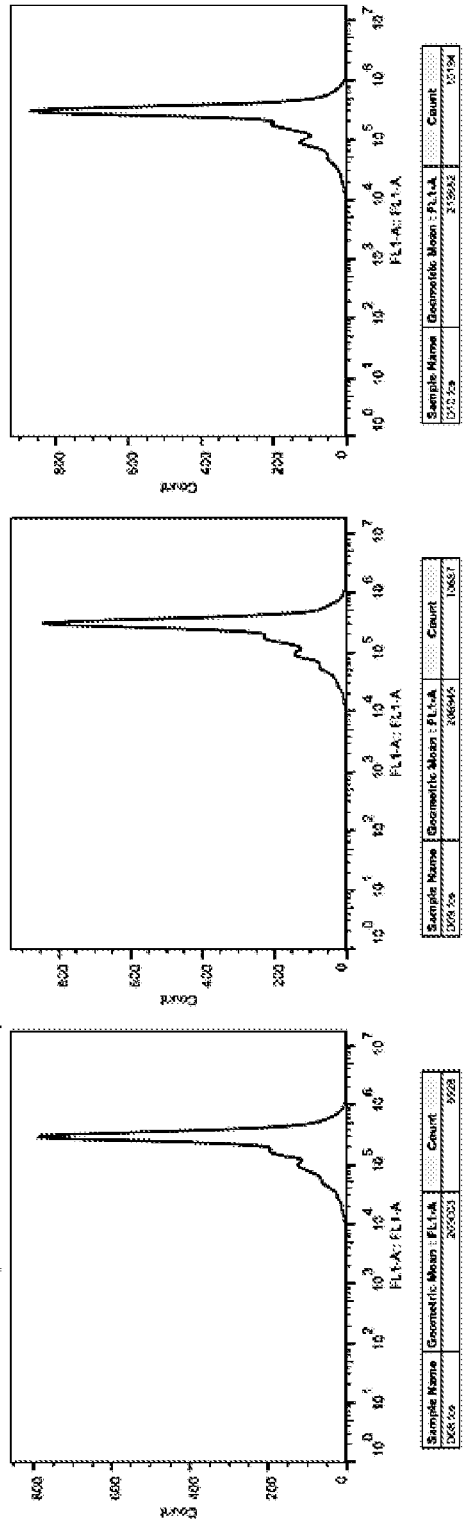

FIG. 12C
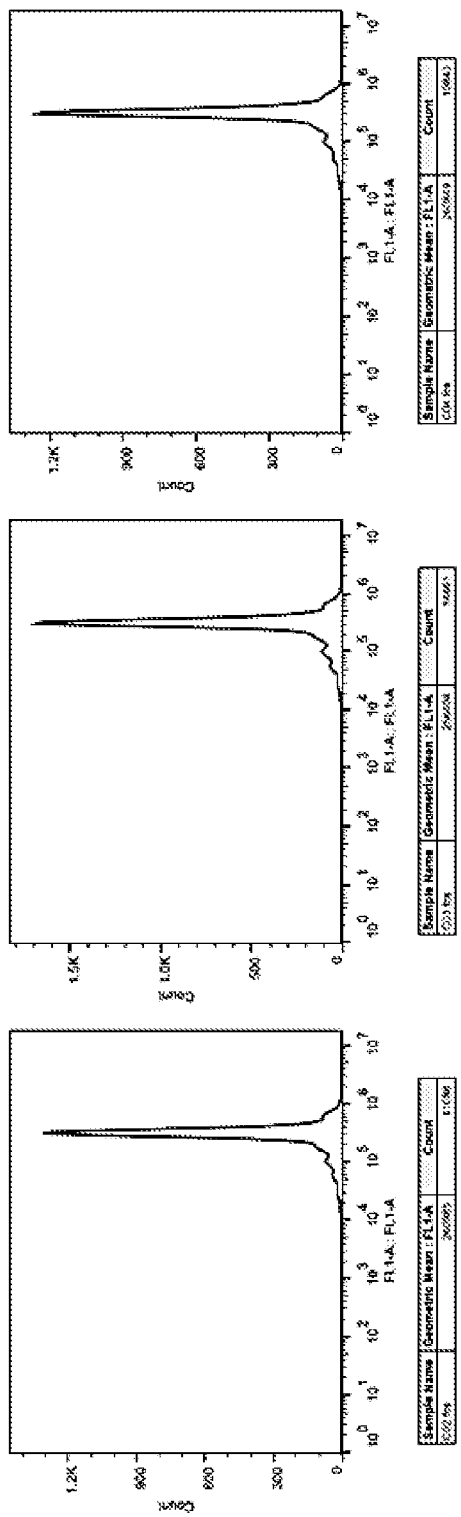
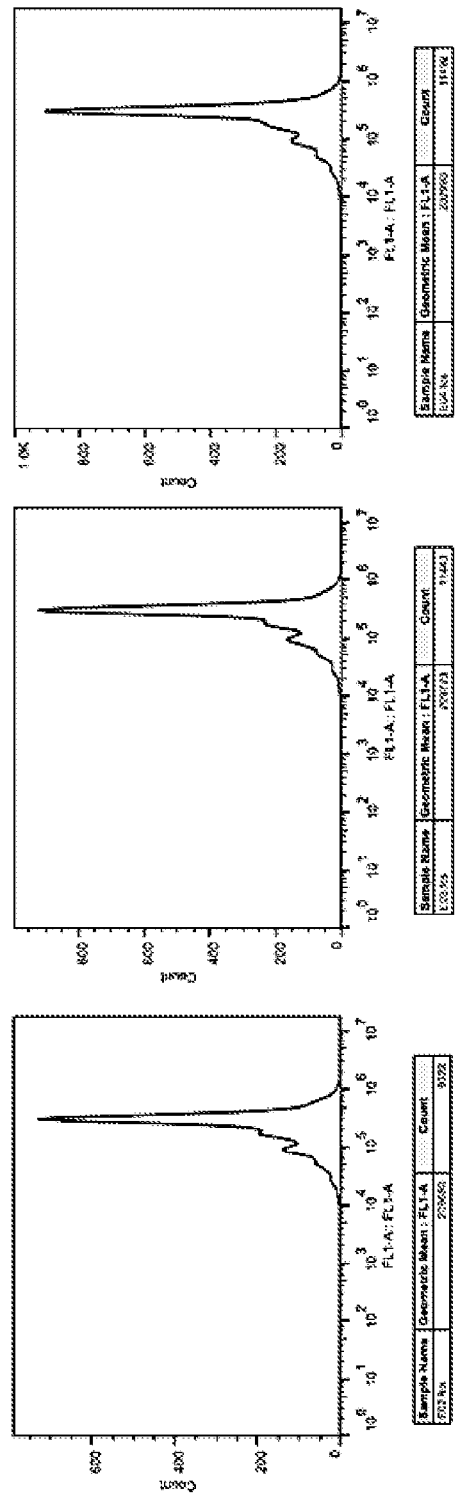

FIG. 12D
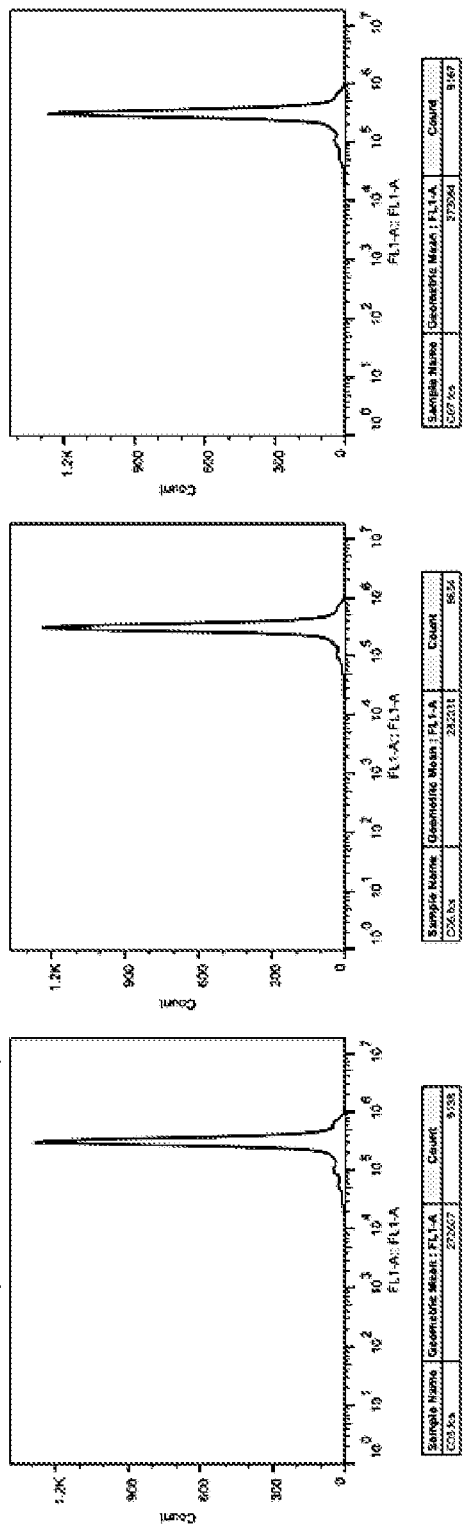
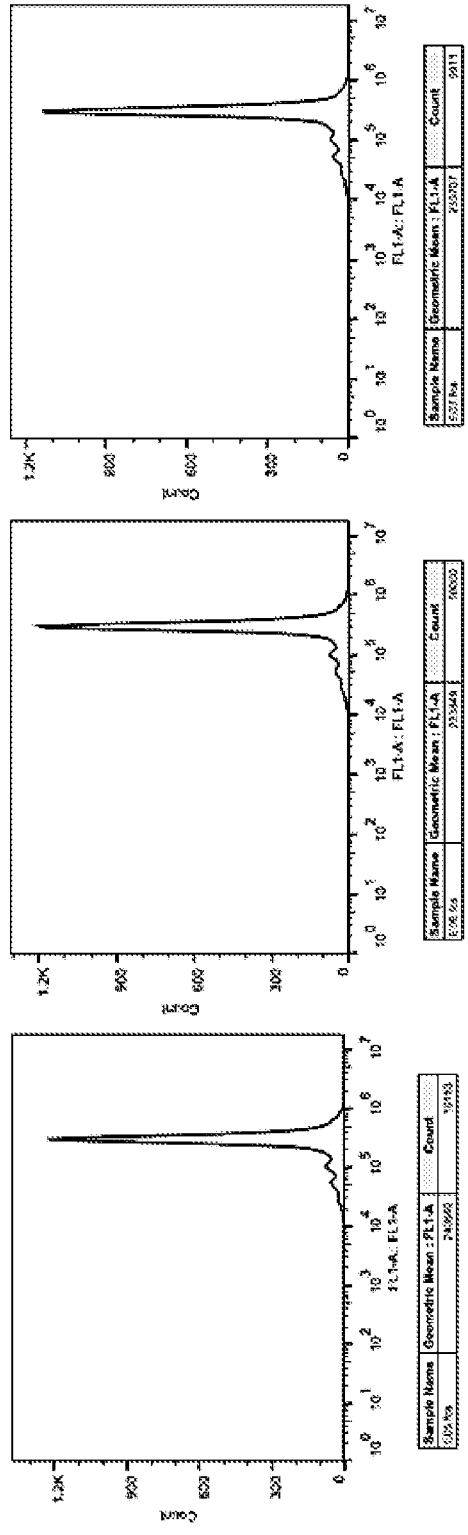

FIG. 12E
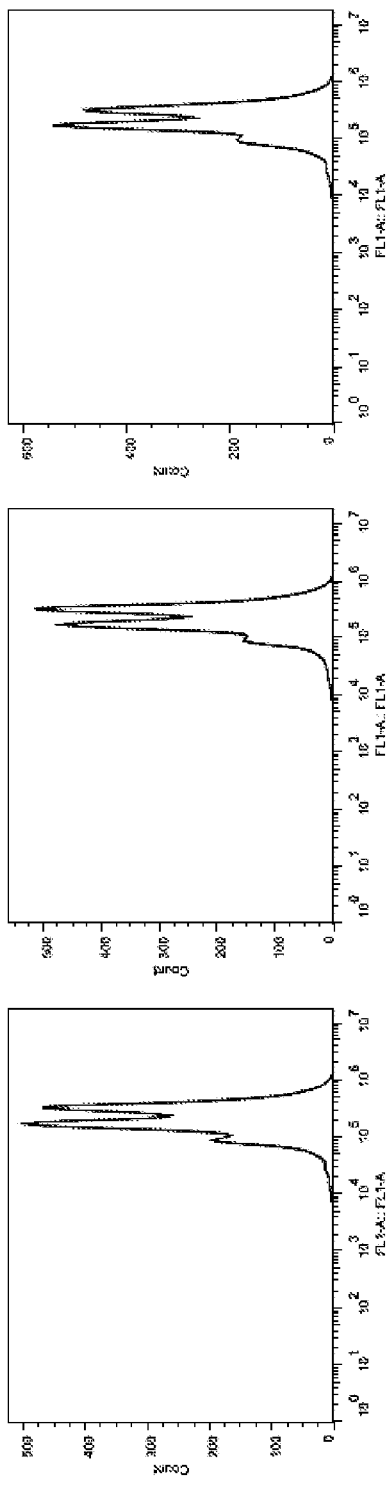
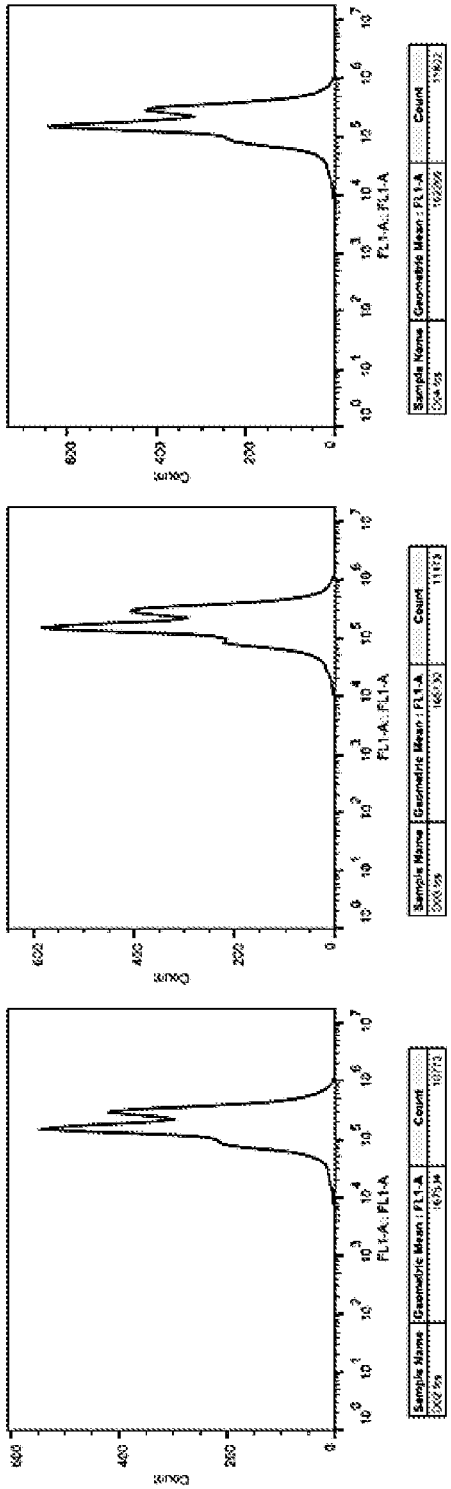

FIG. 12F
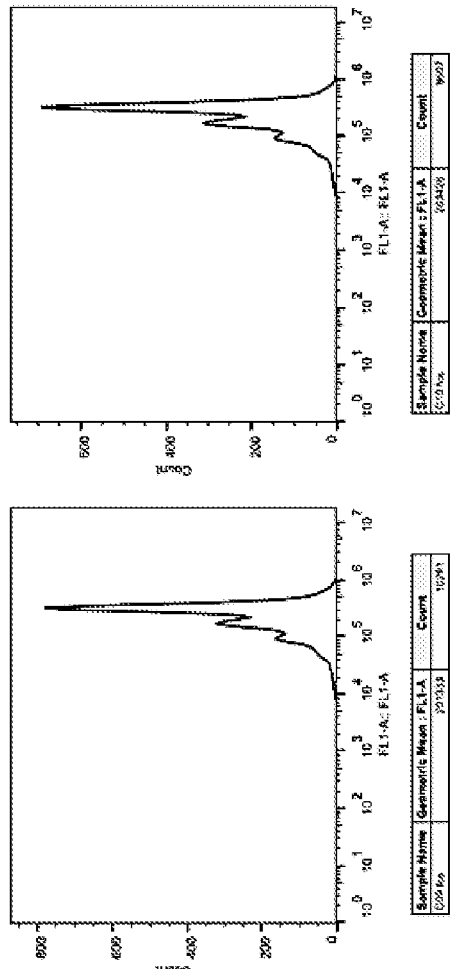
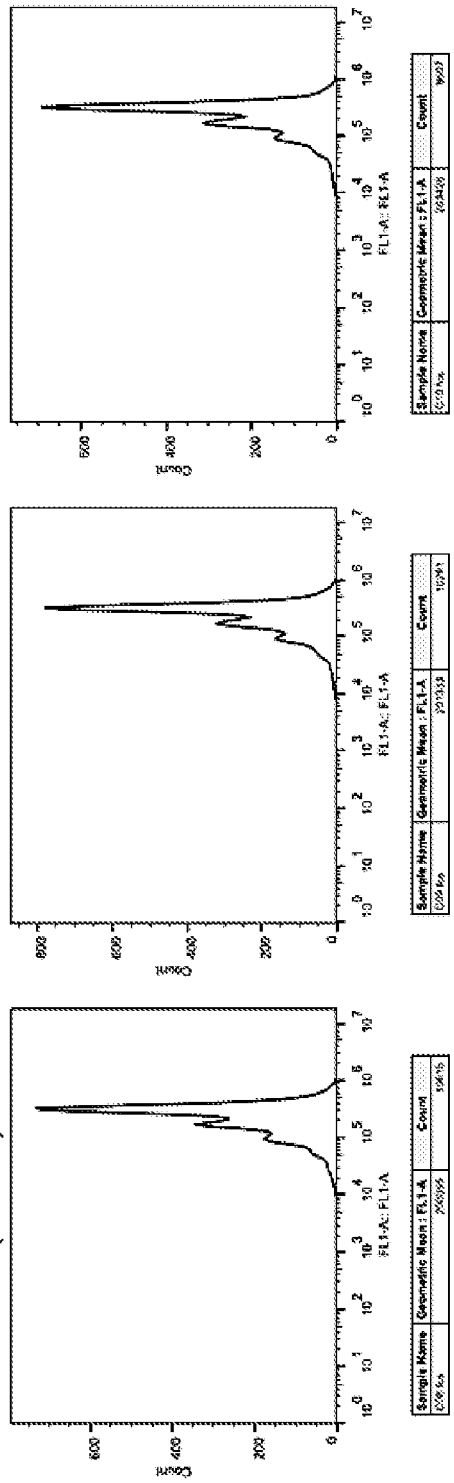
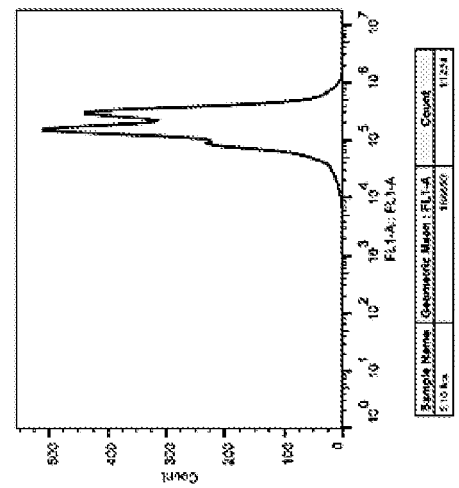
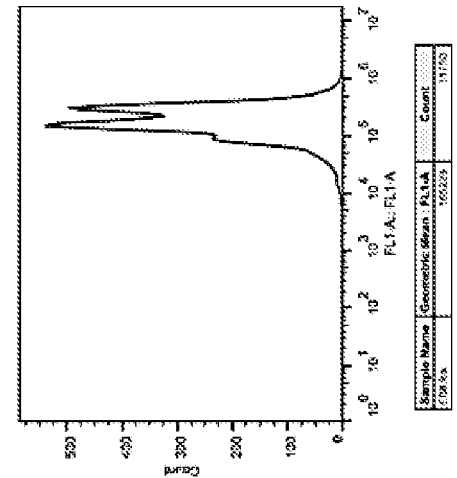

FIG. 13B

| Tukey's multiple comparisons test | Summary | P Value |
|---|---|---|
| 1X beads vs. TPP-1697 (12B4 mPDL1) | ns | 0.0565 |
| TPP-1697 (12B4 mPDL1) vs. TPP-1004 (mPD5) | ns | 0.569 |
| TPP-1697 (12B4 mPDL1) vs. TPP-1986 (mPD5 hPDL1) | **** | <0.0001 |
| TPP-1697 (12B4 mPDL1) vs. TPP-1694 (mPD5 mPDL1) | **** | <0.0001 |
| TPP-1697 (12B4 mPDL1) vs. TPP-1695 (mDWZ mPDL1) | **** | <0.0001 |
| TPP-1697 (12B4 mPDL1) vs. TPP-992 (hPD5 hPDL1) | **** | <0.0001 |
| TPP-1697 (12B4 mPDL1) vs. NC beads | **** | <0.0001 |
| TPP-1004 (mPD5) vs. TPP-1986 (mPD5 hPDL1) | **** | <0.0001 |
| TPP-1004 (mPD5) vs. TPP-1694 (mPD5 mPDL1) | **** | <0.0001 |
| TPP-1004 (mPD5) vs. TPP-1695 (mDWZ mPDL1) | **** | <0.0001 |
| TPP-1004 (mPD5) vs. TPP-992 (hPD5 hPDL1) | **** | <0.0001 |
| TPP-1004 (mPD5) vs. NC beads | **** | <0.0001 |
| TPP-1986 (mPD5 hPDL1) vs. TPP-1694 (mPD5 mPDL1) | ns | 0.3613 |
| TPP-1986 (mPD5 hPDL1) vs. TPP-1695 (mDWZ mPDL1) | ** | 0.0011 |
| TPP-1986 (mPD5 hPDL1) vs. TPP-992 (hPD5 hPDL1) | ns | 0.7567 |
| TPP-1986 (mPD5 hPDL1) vs. NC beads | ns | 0.4275 |
| TPP-1694 (mPD5 mPDL1) vs. TPP-1695 (mDWZ mPDL1) | ns | 0.0832 |
| TPP-1694 (mPD5 mPDL1) vs. TPP-992 (hPD5 hPDL1) | ns | 0.9958 |
| TPP-1694 (mPD5 mPDL1) vs. NC beads | ** | 0.0078 |
| TPP-1695 (mDWZ mPDL1) vs. TPP-992 (hPD5 hPDL1) | * | 0.0223 |
| TPP-1695 (mDWZ mPDL1) vs. NC beads | **** | <0.0001 |
| TPP-992 (hPD5 hPDL1) vs. NC beads | * | 0.0304 |

FIG. 14B

| Tukey's multiple comparisons test | Summary | P Value |
|---|---|---|
| 1X beads vs. TPP-1697 (12B4 mPDL1) | ns | 0.4932 |
| 1X beads vs. TPP-1986 (mPD5 hPDL1) | **** | <0.0001 |
| 1X beads vs. TPP-1504 (hPD5 hB7-H4) | **** | <0.0001 |
| 1X beads vs. TPP-1505 (hPD5 hB7-H5) | ns | 0.769 |
| 1X beads vs. TPP-992 (hPD5 hPDL1) | **** | <0.0001 |
| 1X beads vs. NC beads | **** | <0.0001 |
| TPP-1697 (12B4 mPDL1) vs. TPP-1986 (mPD5 hPDL1) | **** | <0.0001 |
| TPP-1697 (12B4 mPDL1) vs. TPP-1504 (hPD5 hB7-H4) | **** | <0.0001 |
| TPP-1697 (12B4 mPDL1) vs. TPP-1505 (hPD5 hB7-H5) | ns | 0.9987 |
| TPP-1697 (12B4 mPDL1) vs. TPP-992 (hPD5 hPDL1) | **** | <0.0001 |
| TPP-1697 (12B4 mPDL1) vs. NC beads | **** | <0.0001 |
| TPP-1986 (mPD5 hPDL1) vs. TPP-1504 (hPD5 hB7-H4) | ns | 0.1189 |
| TPP-1986 (mPD5 hPDL1) vs. TPP-1505 (hPD5 hB7-H5) | **** | <0.0001 |
| TPP-1986 (mPD5 hPDL1) vs. TPP-992 (hPD5 hPDL1) | ns | 0.9672 |
| TPP-1986 (mPD5 hPDL1) vs. NC beads | ns | 0.8745 |
| TPP-1504 (hPD5 hB7-H4) vs. TPP-1505 (hPD5 hB7-H5) | **** | <0.0001 |
| TPP-1504 (hPD5 hB7-H4) vs. TPP-992 (hPD5 hPDL1) | ns | 0.4455 |
| TPP-1504 (hPD5 hB7-H4) vs. NC beads | * | 0.0135 |
| TPP-1505 (hPD5 hB7-H5) vs. TPP-992 (hPD5 hPDL1) | **** | <0.0001 |
| TPP-1505 (hPD5 hB7-H5) vs. NC beads | **** | <0.0001 |
| TPP-992 (hPD5 hPDL1) vs. NC beads | ns | 0.3934 |

FIG. 15B

| Tukey's multiple comparisons test | Summary | P Value |
|---|---|---|
| 1X beads vs. TPP-1697 (12B4 mPDL1) | ns | 0.9679 |
| 1X beads vs. TPP-1004 (mPD5) | ns | 0.7914 |
| TPP-1697 (12B4 mPDL1) vs. TPP-1004 (mPD5) | ns | 0.9994 |
| TPP-1697 (12B4 mPDL1) vs. TPP-1986 (mPD5 hPDL1) | **** | <0.0001 |
| TPP-1697 (12B4 mPDL1) vs. TPP-1694 (mPD5 mPDL1) | **** | <0.0001 |
| TPP-1697 (12B4 mPDL1) vs. TPP-1695 (mDWZ mPDL1) | **** | <0.0001 |
| TPP-1697 (12B4 mPDL1) vs. TPP-992 (hPD5 hPDL1) | **** | <0.0001 |
| TPP-1697 (12B4 mPDL1) vs. NC beads | **** | <0.0001 |
| TPP-1004 (mPD5) vs. TPP-1986 (mPD5 hPDL1) | **** | <0.0001 |
| TPP-1004 (mPD5) vs. TPP-1694 (mPD5 mPDL1) | **** | <0.0001 |
| TPP-1004 (mPD5) vs. TPP-1695 (mDWZ mPDL1) | **** | <0.0001 |
| TPP-1004 (mPD5) vs. TPP-992 (hPD5 hPDL1) | **** | <0.0001 |
| TPP-1004 (mPD5) vs. NC beads | **** | <0.0001 |
| TPP-1986 (mPD5 hPDL1) vs. TPP-1694 (mPD5 mPDL1) | **** | <0.0001 |
| TPP-1986 (mPD5 hPDL1) vs. TPP-1695 (mDWZ mPDL1) | **** | <0.0001 |
| TPP-1986 (mPD5 hPDL1) vs. TPP-992 (hPD5 hPDL1) | ns | 0.1524 |
| TPP-1986 (mPD5 hPDL1) vs. NC beads | **** | <0.0001 |

FIG. 16B

| Tukey's multiple comparisons test | Summary | P Value |
|---|---|---|
| 1X beads vs. TPP-1697 (12B4 mPDL1) | ns | 0.9996 |
| 1X beads vs. TPP-1986 (mPD5 hPDL1) | **** | <0.0001 |
| 1X beads vs. TPP-1504 (hPD5 hB7-H4) | **** | <0.0001 |
| 1X beads vs. TPP-1505 (hPD5 hB7-H5) | ns | 0.9797 |
| 1X beads vs. TPP-992 (hPD5 hPDL1) | **** | <0.0001 |
| 1X beads vs. NC beads | **** | <0.0001 |
| TPP-1697 (12B4 mPDL1) vs. TPP-1986 (mPD5 hPDL1) | **** | <0.0001 |
| TPP-1697 (12B4 mPDL1) vs. TPP-1504 (hPD5 hB7-H4) | **** | <0.0001 |
| TPP-1697 (12B4 mPDL1) vs. TPP-1505 (hPD5 hB7-H5) | ns | 0.9994 |
| TPP-1697 (12B4 mPDL1) vs. TPP-992 (hPD5 hPDL1) | **** | <0.0001 |
| TPP-1697 (12B4 mPDL1) vs. NC beads | **** | <0.0001 |
| TPP-1986 (mPD5 hPDL1) vs. TPP-1504 (hPD5 hB7-H4) | * | 0.0387 |
| TPP-1986 (mPD5 hPDL1) vs. TPP-1505 (hPD5 hB7-H5) | **** | <0.0001 |
| TPP-1986 (mPD5 hPDL1) vs. TPP-992 (hPD5 hPDL1) | ns | 0.9192 |
| TPP-1986 (mPD5 hPDL1) vs. NC beads | *** | 0.0002 |
| TPP-1504 (hPD5 hB7-H4) vs. TPP-1505 (hPD5 hB7-H5) | **** | <0.0001 |
| TPP-1504 (hPD5 hB7-H4) vs. TPP-992 (hPD5 hPDL1) | ns | 0.2439 |
| TPP-1504 (hPD5 hB7-H4) vs. NC beads | **** | <0.0001 |
| TPP-1505 (hPD5 hB7-H5) vs. TPP-992 (hPD5 hPDL1) | **** | <0.0001 |
| TPP-1505 (hPD5 hB7-H5) vs. NC beads | **** | <0.0001 |
| TPP-992 (hPD5 hPDL1) vs. NC beads | **** | <0.0001 |

TPP-1964 (msPDL1)          TPP-1986 (huPDL1)

FIG. 18B

| Tukey's multiple comparisons test | Summary | Adjusted P Value |
|---|---|---|
| TPP-1986 (HuPDL1_HuPD5) vs. TPP-1694 (mPDL1_mPD5) | * | 0.0142 |
| TPP-1986 (HuPDL1_HuPD5) ) vs. TPP-1504 (B7H4_PD5) | ns | 0.3212 |
| TPP-1986 (HuPDL1_HuPD5) ) vs. TPP-1505 (B7H5_PD5) | * | 0.0133 |
| TPP-1986 (HuPDL1_HuPD5) vs. TPP-1506 (HVEM_PD5) | ns | >0.9999 |
| TPP-1986 (HuPDL1_HuPD5) vs. TPP-1894 (B7H6_PD5) | ns | 0.4935 |
| TPP-1986 (HuPDL1_HuPD5) vs. TPP-1898 (CTLA4_PD5) | ** | 0.0040 |
| TPP-1986 (HuPDL1_HuPD5) vs. DLAT Beads | ** | 0.0092 |
| TPP-1986 (HuPDL1_HuPD5) vs. TPP-1697 (PDL1_12B4) | * | 0.0108 |
| TPP-1986 (HuPDL1_HuPD5) vs. NC Beads | ns | 0.9995 |

FIG. 18D

| Tukey's multiple comparisons test | Summary | Adjusted P Value |
|---|---|---|
| DLAT Beads vs. TPP-1697 (PDL1_12B4) | ns | 0.5874 |
| DLAT Beads vs. TPP-2215 (PDL2_PD5) | **** | <0.0001 |
| DLAT Beads vs. PDL2_Fc | *** | 0.0001 |
| DLAT Beads vs. TPP-2216 (CD200_PD5) | * | 0.0338 |
| DLAT Beads vs. CD200_Fc | ** | 0.0026 |
| DLAT Beads vs. TPP-2218 (B7H3_PD5) | ns | 0.9990 |
| DLAT Beads vs. TPP-2220 (TIM-3_PD5) | **** | <0.0001 |
| DLAT Beads vs. TPP-992 (hPD5 hPDL1) | **** | <0.0001 |
| DLAT Beads vs. NC Beads | **** | <0.0001 |
| TPP-1697 (PDL1_12B4) vs. TPP-2215 (PDL2_PD5) | **** | <0.0001 |
| TPP-1697 (PDL1_12B4) vs. PDL2_Fc | ns | 0.0920 |
| TPP-1697 (PDL1_12B4) vs. TPP-2216 (CD200_PD5) | ns | 0.9412 |
| TPP-1697 (PDL1_12B4) vs. CD200_Fc | ns | 0.4831 |
| TPP-1697 (PDL1_12B4) vs. TPP-2218 (B7H3_PD5) | ns | 0.9842 |
| TPP-1697 (PDL1_12B4) vs. TPP-2220 (TIM-3_PD5) | **** | <0.0001 |
| TPP-1697 (PDL1_12B4) vs. TPP-992 (hPD5 hPDL1) | **** | <0.0001 |
| TPP-1697 (PDL1_12B4) vs. NC Beads | **** | <0.0001 |

FIG. 19B

| Tukey's multiple comparisons test | Summary | Adjusted P Value |
|---|---|---|
| DLAT Beads vs. V-HC-Fab | **** | <0.0001 |
| DLAT Beads vs. V-C-HC-Fab | ns | >0.9999 |
| DLAT Beads vs. V-LC-Fab | **** | <0.0001 |
| DLAT Beads vs. V-C-LC-Fab | ns | >0.9999 |
| DLAT Beads vs. TPP-992 (hPD5 hPDL1) | **** | <0.0001 |
| DLAT Beads vs. NC Beads | **** | <0.0001 |
| V-HC-Fab vs. V-C-HC-Fab | *** | 0.0003 |
| V-HC-Fab vs. V-LC-Fab | ns | 0.9973 |
| V-HC-Fab vs. V-C-LC-Fab | *** | 0.0004 |
| V-HC-Fab vs. TPP-992 (hPD5 hPDL1) | **** | <0.0001 |
| V-HC-Fab vs. NC Beads | **** | <0.0001 |
| V-C-HC-Fab vs. V-LC-Fab | **** | <0.0001 |
| V-C-HC-Fab vs. V-C-LC-Fab | ns | >0.9999 |
| V-C-HC-Fab vs. TPP-992 (hPD5 hPDL1) | **** | <0.0001 |
| V-C-HC-Fab vs. NC Beads | **** | <0.0001 |
| V-LC-Fab vs. V-C-LC-Fab | *** | 0.0001 |
| V-LC-Fab vs. TPP-992 (hPD5 hPDL1) | **** | <0.0001 |
| V-LC-Fab vs. NC Beads | **** | <0.0001 |
| V-C-LC-Fab vs. TPP-992 (hPD5 hPDL1) | **** | <0.0001 |
| V-C-LC-Fab vs. NC Beads | **** | <0.0001 |
| TPP-992 (hPD5 hPDL1) vs. NC Beads | ns | 0.9376 |

FIG. 20D

| CD4+ Mouse T-cell Activation Geometric Mean of CFSE | 500nM | | 125nM | | 32nM | |
|---|---|---|---|---|---|---|
| Tukey's multiple comparisons test (N = 3) | Summary | P Value | Summary | P Value | Summary | P Value |
| TPP-1985 (msPDL1_ms12b4) vs. TPP-1984 (msPDL1_msPD5) | **** | <0.0001 | * | 0.0262 | * | 0.0326 |
| TPP-1985 (msPDL1_ms12b4) vs. TPP-1694 (msPDL1_msPD5) | **** | <0.0001 | ns | 0.9001 | Ns | 0.0748 |
| TPP-1985 (msPDL1_ms12b4) vs. TPP-2246 (msPD5) | Ns | 0.3653 | ns | >0.9999 | Ns | 0.9978 |
| TPP-1985 (msPDL1_ms12b4) vs. Abatacept | Ns | 0.1348 | ns | >0.9999 | Ns | 0.4718 |
| TPP-1985 (msPDL1_ms12b4) vs. TPP-1898 (CTLA4_PD5) | **** | <0.0001 | **** | <0.0001 | **** | <0.0001 |
| TPP-1984 (msPDL1_msPD5) vs. TPP-1694 (msPDL1_msPD5) | Ns | 0.0538 | ns | 0.1424 | Ns | 0.9954 |
| TPP-1984 (msPDL1_msPD5) vs. TPP-2246 (msPD5) | **** | <0.0001 | * | 0.0204 | Ns | 0.066 |
| TPP-1984 (msPDL1_msPD5) vs. Abatacept | **** | <0.0001 | * | 0.0195 | Ns | 0.5214 |
| TPP-1984 (msPDL1_msPD5) vs. TPP-1898 (CTLA4_PD5) | Ns | >0.9999 | *** | 0.0005 | **** | <0.0001 |
| TPP-1984 (msPDL1_msPD5) vs. NC beads | Ns | 0.7524 | ** | 0.0029 | **** | <0.0001 |
| TPP-2246 (msPD5) vs. Abatacept | Ns | 0.9798 | ns | >0.9999 | Ns | 0.7099 |
| TPP-2246 (msPD5) vs. TPP-1898 (CTLA4_PD5) | **** | <0.0001 | **** | <0.0001 | **** | <0.0001 |
| Abatacept vs. TPP-1898 (CTLA4_PD5) | **** | <0.0001 | **** | <0.0001 | **** | <0.0001 |
| Abatacept vs. NC beads | **** | <0.0001 | **** | <0.0001 | **** | <0.0001 |
| TPP-1898 (CTLA4_PD5) vs. NC beads | Ns | 0.8548 | ns | 0.5594 | Ns | 0.1607 |

| Dunnett's multiple comparisons test (N = 3) | Summary | P Value |
|---|---|---|
| CD80 Beads vs. anti-CD80 500nM | *** | 0.0003 |
| CD80 Beads vs. anti-CD80 250nM | *** | 0.0002 |
| CD80 Beads vs. anti-CD80 100nM | * | 0.0241 |
| CD80 Beads vs. anti-CD80 50nM | ns | 0.9939 |
| CD80 Beads vs. No Beads | *** | 0.0004 |

| Dunnett's multiple comparisons test (N = 3) | Summary | P Value |
|---|---|---|
| CD20 Beads vs. anti-CD20 500nM | **** | 0.0001 |
| CD20 Beads vs. anti-CD20 250nM | **** | 0.0001 |
| CD20 Beads vs. anti-CD20 100nM | **** | 0.0001 |
| CD20 Beads vs. anti-CD20 50nM | *** | 0.0007 |
| CD20 Beads vs. No Beads | **** | 0.0001 |

SEQUENCE LISTING

<160> NUMBER OF SEQ ID NOS: 48

<210> SEQ ID NO 1
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 1

```
Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Arg Asn
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Ser Thr Tyr His Gln Pro Ser
    50                  55                  60

Leu Lys Ser Arg Val Thr Ile Phe Leu Asp Thr Ser Lys Asn Gln Phe
65                  70                  75                  80

Phe Leu Lys Leu Thr Ser Val Thr Ala Ala Asp Thr Ala Val Tyr Tyr
```

```
            85                  90                  95
Cys Ala Arg Gly Thr Arg Ala Thr Thr Trp Pro Pro Ile Gly Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys
225

<210> SEQ ID NO 2
<211> LENGTH: 358
<212> TYPE: PRT
<213> ORGANISM: Artificial Sequence
<220> FEATURE:
<223> OTHER INFORMATION: Synthetic polypeptide

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Arg Asn
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Ser Thr Tyr His Gln Pro Ser
    50                  55                  60

Leu Lys Ser Arg Val Thr Ile Phe Leu Asp Thr Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Gly Thr Arg Ala Thr Thr Trp Pro Pro Ile Gly Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
```

```
                    210                 215                 220
Ser Cys Gly Gly Ser Ser Arg Ser Ser Ser Gly Gly Gly Ser
225                 230                 235                 240

Gly Gly Gly Gly Phe Thr Val Thr Val Pro Lys Asp Leu Tyr Val Val
                245                 250                 255

Glu Tyr Gly Ser Asn Met Thr Ile Glu Cys Lys Phe Pro Val Glu Lys
            260                 265                 270

Gln Leu Asp Leu Ala Ala Leu Ile Val Tyr Trp Glu Met Glu Asp Lys
        275                 280                 285

Asn Ile Ile Gln Phe Val His Gly Glu Glu Asp Leu Lys Val Gln His
    290                 295                 300

Ser Ser Tyr Arg Gln Arg Ala Arg Leu Leu Lys Asp Gln Leu Ser Leu
305                 310                 315                 320

Gly Asn Ala Ala Leu Gln Ile Thr Asp Val Lys Leu Gln Asp Ala Gly
                325                 330                 335

Val Tyr Arg Cys Met Ile Ser Tyr Gly Gly Ala Asp Tyr Lys Arg Ile
            340                 345                 350

Thr Val Lys Val Asn Ala
        355
```

<210> SEQ ID NO 3
<211> LENGTH: 358
<212> TYPE: PRT
<213> ORGANISM: Artificial Sequence
<220> FEATURE:
<223> OTHER INFORMATION: Synthetic polypeptide

<400> SEQUENCE: 3

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Ser
    115                 120                 125

Gly Gly Gly Gly Gln Leu Gln Leu Gln Glu Ser Gly Pro Gly Leu Val
130                 135                 140

Lys Pro Ser Glu Thr Leu Ser Leu Thr Cys Ile Val Ser Gly Gly Ser
145                 150                 155                 160

Ile Ser Arg Asn Ser Tyr Tyr Trp Gly Trp Ile Arg Gln Pro Pro Gly
                165                 170                 175

Lys Gly Leu Glu Trp Ile Gly Ser Ile Val Tyr Ser Gly Ser Thr Tyr
            180                 185                 190

His Gln Pro Ser Leu Lys Ser Arg Val Thr Ile Phe Leu Asp Thr Ser
    195                 200                 205

Lys Asn Gln Phe Phe Leu Lys Leu Thr Ser Val Thr Ala Ala Asp Thr
```

```
              210                 215                 220
Ala Val Tyr Tyr Cys Ala Arg Gly Thr Arg Ala Thr Thr Trp Pro Pro
225                 230                 235                 240

Pro Ile Gly Tyr Trp Gly Gln Gly Thr Leu Val Thr Val Ser Ser Ala
                245                 250                 255

Ser Thr Lys Gly Pro Ser Val Phe Pro Leu Ala Pro Ser Ser Lys Ser
            260                 265                 270

Thr Ser Gly Gly Thr Ala Ala Leu Gly Cys Leu Val Lys Asp Tyr Phe
                275                 280                 285

Pro Glu Pro Val Thr Val Ser Trp Asn Ser Gly Ala Leu Thr Ser Gly
            290                 295                 300

Val His Thr Phe Pro Ala Val Leu Gln Ser Ser Gly Leu Tyr Ser Leu
305                 310                 315                 320

Ser Ser Val Val Thr Val Pro Ser Ser Ser Leu Gly Thr Gln Thr Tyr
                325                 330                 335

Ile Cys Asn Val Asn His Lys Pro Ser Asn Thr Lys Val Asp Lys Arg
                340                 345                 350

Val Glu Pro Lys Ser Cys
            355

<210> SEQ ID NO 4
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 4

Gln Ser Val Leu Thr Gln Pro Pro Ser Val Ser Ala Ala Pro Gly Gln
1               5                   10                  15

Lys Val Thr Val Ser Cys Phe Gly Ser Ser Ser Asn Ile Gly Asn Tyr
                20                  25                  30

Phe Ala Ser Trp Tyr Gln Gln Leu Pro Gly Ala Ala Pro Arg Leu Leu
            35                  40                  45

Ile Tyr Gly Asn Asn Glu Arg Pro Ser Gly Ile Pro Asp Arg Phe Ser
50                  55                  60

Gly Ser Lys Ser Gly Thr Ser Ala Thr Leu Val Ile Thr Gly Leu Gln
65                  70                  75                  80

Thr Gly Asp Glu Ala Ala Tyr Tyr Cys Ala Thr Trp Asp Ser Ser Leu
                85                  90                  95

Ser Ala Val Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
```

<210> SEQ ID NO 5
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 5

```
Gln Ser Val Leu Thr Gln Pro Pro Ser Val Ser Ala Ala Pro Gly Gln
1               5                   10                  15

Lys Val Thr Val Ser Cys Phe Gly Ser Ser Asn Ile Gly Asn Tyr
            20                  25                  30

Phe Ala Ser Trp Tyr Gln Gln Leu Pro Gly Ala Ala Pro Arg Leu Leu
        35                  40                  45

Ile Tyr Gly Asn Asn Glu Arg Pro Ser Gly Ile Pro Asp Arg Phe Ser
    50                  55                  60

Gly Ser Lys Ser Gly Thr Ser Ala Thr Leu Val Ile Thr Gly Leu Gln
65                  70                  75                  80

Thr Gly Asp Glu Ala Ala Tyr Tyr Cys Ala Thr Trp Asp Ser Ser Leu
                85                  90                  95

Ser Ala Val Val Phe Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Gly Gly Ser Ser Arg Ser Ser Ser
    210                 215                 220

Ser Gly Gly Gly Gly Ser Gly Gly Gly Phe Thr Val Thr Val Pro
225                 230                 235                 240

Lys Asp Leu Tyr Val Val Glu Tyr Gly Ser Asn Met Thr Ile Glu Cys
                245                 250                 255

Lys Phe Pro Val Glu Lys Gln Leu Asp Leu Ala Ala Leu Ile Val Tyr
            260                 265                 270

Trp Glu Met Glu Asp Lys Asn Ile Ile Gln Phe Val His Gly Glu Glu
        275                 280                 285

Asp Leu Lys Val Gln His Ser Ser Tyr Arg Gln Arg Ala Arg Leu Leu
    290                 295                 300

Lys Asp Gln Leu Ser Leu Gly Asn Ala Ala Leu Gln Ile Thr Asp Val
305                 310                 315                 320

Lys Leu Gln Asp Ala Gly Val Tyr Arg Cys Met Ile Ser Tyr Gly Gly
                325                 330                 335

Ala Asp Tyr Lys Arg Ile Thr Val Lys Val Asn Ala
            340                 345
```

<210> SEQ ID NO 6
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 6

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Gly Ser
        115                 120                 125

Gly Gly Gly Gly Gln Ser Val Leu Thr Gln Pro Pro Ser Val Ser Ala
    130                 135                 140

Ala Pro Gly Gln Lys Val Thr Val Ser Cys Phe Gly Ser Ser Ser Asn
145                 150                 155                 160

Ile Gly Asn Tyr Phe Ala Ser Trp Tyr Gln Gln Leu Pro Gly Ala Ala
                165                 170                 175

Pro Arg Leu Leu Ile Tyr Gly Asn Asn Glu Arg Pro Ser Gly Ile Pro
            180                 185                 190

Asp Arg Phe Ser Gly Ser Lys Ser Gly Thr Ser Ala Thr Leu Val Ile
        195                 200                 205

Thr Gly Leu Gln Thr Gly Asp Glu Ala Ala Tyr Tyr Cys Ala Thr Trp
    210                 215                 220

Asp Ser Ser Leu Ser Ala Val Val Phe Gly Gly Thr Lys Leu Thr
225                 230                 235                 240

Val Leu Gly Gln Pro Lys Ala Asn Pro Thr Val Thr Leu Phe Pro Pro
                245                 250                 255

Ser Ser Glu Glu Leu Gln Ala Asn Lys Ala Thr Leu Val Cys Leu Ile
            260                 265                 270

Ser Asp Phe Tyr Pro Gly Ala Val Thr Val Ala Trp Lys Ala Asp Gly
        275                 280                 285

Ser Pro Val Lys Ala Gly Val Glu Thr Thr Lys Pro Ser Lys Gln Ser
    290                 295                 300

Asn Asn Lys Tyr Ala Ala Ser Ser Tyr Leu Ser Leu Thr Pro Glu Gln
305                 310                 315                 320

Trp Lys Ser His Arg Ser Tyr Ser Cys Gln Val Thr His Glu Gly Ser
                325                 330                 335

Thr Val Glu Lys Thr Val Ala Pro Thr Glu Cys Ser
            340                 345

<210> SEQ ID NO 7
<211> LENGTH: 234
<212> TYPE: PRT

<213> ORGANISM: Artificial Sequence
<220> FEATURE:
<223> OTHER INFORMATION: Synthetic polypeptide

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Ser Tyr
            20                  25                  30

Ser Met Thr Trp Val Arg Gln Ala Pro Gly Lys Gly Leu Glu Trp Val
        35                  40                  45

Ser Phe Ile Ser Thr Val Ser Thr Tyr Ile Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Gly Arg Gly Ser Ala Ala Arg Asp Gly Glu Lys Gly
            100                 105                 110

Thr Tyr Tyr Tyr Tyr Met Asp Val Trp Gly Lys Gly Thr Thr Val Thr
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Arg Val Glu Pro Lys Ser Cys
225                 230

<210> SEQ ID NO 8
<211> LENGTH: 366
<212> TYPE: PRT
<213> ORGANISM: Artificial Sequence
<220> FEATURE:
<223> OTHER INFORMATION: Synthetic polypeptide

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Ser Tyr
            20                  25                  30

Ser Met Thr Trp Val Arg Gln Ala Pro Gly Lys Gly Leu Glu Trp Val
        35                  40                  45

Ser Phe Ile Ser Thr Val Ser Thr Tyr Ile Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

-continued

Ala Arg Val Ser Gly Arg Gly Ser Ala Ala Arg Asp Gly Glu Lys Gly
            100                 105                 110

Thr Tyr Tyr Tyr Tyr Met Asp Val Trp Gly Lys Gly Thr Thr Val Thr
            115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Arg Val Glu Pro Lys Ser Cys Gly Gly Ser Ser Arg Ser
225                 230                 235                 240

Ser Ser Ser Gly Gly Gly Gly Ser Gly Gly Gly Gly Phe Thr Val Thr
                245                 250                 255

Val Pro Lys Asp Leu Tyr Val Val Glu Tyr Gly Ser Asn Met Thr Ile
            260                 265                 270

Glu Cys Lys Phe Pro Val Glu Lys Gln Leu Asp Leu Ala Ala Leu Ile
        275                 280                 285

Val Tyr Trp Glu Met Glu Asp Lys Asn Ile Ile Gln Phe Val His Gly
    290                 295                 300

Glu Glu Asp Leu Lys Val Gln His Ser Ser Tyr Arg Gln Arg Ala Arg
305                 310                 315                 320

Leu Leu Lys Asp Gln Leu Ser Leu Gly Asn Ala Ala Leu Gln Ile Thr
                325                 330                 335

Asp Val Lys Leu Gln Asp Ala Gly Val Tyr Arg Cys Met Ile Ser Tyr
            340                 345                 350

Gly Gly Ala Asp Tyr Lys Arg Ile Thr Val Lys Val Asn Ala
        355                 360                 365

<210> SEQ ID NO 9
<211> LENGTH: 366
<212> TYPE: PRT
<213> ORGANISM: Artificial Sequence
<220> FEATURE:
<223> OTHER INFORMATION: Synthetic polypeptide

<400> SEQUENCE: 9

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Ser
        115                 120                 125

Gly Gly Gly Gly Glu Val Gln Leu Val Glu Ser Gly Gly Gly Leu Val
        130                 135                 140

Lys Pro Gly Gly Ser Leu Arg Leu Ser Cys Ala Ala Ser Gly Phe Thr
145                 150                 155                 160

Phe Gly Ser Tyr Ser Met Thr Trp Val Arg Gln Ala Pro Gly Lys Gly
                165                 170                 175

Leu Glu Trp Val Ser Phe Ile Ser Thr Val Ser Thr Tyr Ile Tyr Tyr
            180                 185                 190

Pro Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Val Ser Gly Arg Gly Ser Ala Ala Arg Asp
225                 230                 235                 240

Gly Glu Lys Gly Thr Tyr Tyr Tyr Met Asp Val Trp Gly Lys Gly
                245                 250                 255

Thr Thr Val Thr Val Ser Ser Ala Ser Thr Lys Gly Pro Ser Val Phe
            260                 265                 270

Pro Leu Ala Pro Ser Ser Lys Ser Thr Ser Gly Gly Thr Ala Ala Leu
        275                 280                 285

Gly Cys Leu Val Lys Asp Tyr Phe Pro Glu Pro Val Thr Val Ser Trp
    290                 295                 300

Asn Ser Gly Ala Leu Thr Ser Gly Val His Thr Phe Pro Ala Val Leu
305                 310                 315                 320

Gln Ser Ser Gly Leu Tyr Ser Leu Ser Ser Val Val Thr Val Pro Ser
                325                 330                 335

Ser Ser Leu Gly Thr Gln Thr Tyr Ile Cys Asn Val Asn His Lys Pro
            340                 345                 350

Ser Asn Thr Lys Val Asp Lys Arg Val Glu Pro Lys Ser Cys
        355                 360                 365

<210> SEQ ID NO 10
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 10

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Phe
        35                  40                  45

Gly Lys Asn Asn Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Phe Cys Asp Ser Arg Asp Ser Ser Ala Asn His
                85                  90                  95

Trp Val Phe Gly Gly Thr Lys Leu Thr Val Leu Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 11
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 11

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Phe
        35                  40                  45

Gly Lys Asn Asn Arg Pro Ser Gly Ile Pro Asp Arg Phe Ser Gly Ser
50                  55                  60

Arg Ser Gly Asn Thr Ala Ser Leu Thr Ile Thr Gly Ala Gln Ala Glu
65                  70                  75                  80

Asp Glu Ala Asp Tyr Phe Cys Asp Ser Arg Asp Ser Ser Ala Asn His
                85                  90                  95

Trp Val Phe Gly Gly Thr Lys Leu Thr Val Leu Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser Gly Gly Ser Ser Arg Ser Ser Ser Ser Gly Gly
    210                 215                 220

Gly Gly Ser Gly Gly Gly Gly Phe Thr Val Thr Val Pro Lys Asp Leu
225                 230                 235                 240

```
Tyr Val Val Glu Tyr Gly Ser Asn Met Thr Ile Glu Cys Lys Phe Pro
            245                 250                 255

Val Glu Lys Gln Leu Asp Leu Ala Ala Leu Ile Val Tyr Trp Glu Met
        260                 265                 270

Glu Asp Lys Asn Ile Ile Gln Phe Val His Gly Glu Asp Leu Lys
        275                 280                 285

Val Gln His Ser Ser Tyr Arg Gln Arg Ala Arg Leu Leu Lys Asp Gln
    290                 295                 300

Leu Ser Leu Gly Asn Ala Ala Leu Gln Ile Thr Asp Val Lys Leu Gln
305                 310                 315                 320

Asp Ala Gly Val Tyr Arg Cys Met Ile Ser Tyr Gly Gly Ala Asp Tyr
                325                 330                 335

Lys Arg Ile Thr Val Lys Val Asn Ala
            340                 345

<210> SEQ ID NO 12
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 12

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Thr Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Phe Gly Lys Asn Asn Arg Pro Ser Gly Ile Pro Asp Arg
            180                 185                 190

Phe Ser Gly Ser Arg Ser Gly Asn Thr Ala Ser Leu Thr Ile Thr Gly
        195                 200                 205

Ala Gln Ala Glu Asp Glu Ala Asp Tyr Phe Cys Asp Ser Arg Asp Ser
    210                 215                 220

Ser Ala Asn His Trp Val Phe Gly Gly Gly Thr Lys Leu Thr Val Leu
225                 230                 235                 240

Gln Pro Lys Ala Ala Pro Ser Val Thr Leu Phe Pro Pro Ser Ser Glu
                245                 250                 255
```

```
Glu Leu Gln Ala Asn Lys Ala Thr Leu Val Cys Leu Ile Ser Asp Phe
                260                 265                 270

Tyr Pro Gly Ala Val Thr Val Ala Trp Lys Ala Asp Ser Ser Pro Val
            275                 280                 285

Lys Ala Gly Val Glu Thr Thr Thr Pro Ser Lys Gln Ser Asn Asn Lys
        290                 295                 300

Tyr Ala Ala Ser Ser Tyr Leu Ser Leu Thr Pro Glu Gln Trp Lys Ser
305                 310                 315                 320

His Lys Ser Tyr Ser Cys Gln Val Thr His Glu Gly Ser Thr Val Glu
                325                 330                 335

Lys Thr Val Ala Pro Thr Glu Cys Ser
                340                 345

<210> SEQ ID NO 13
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Ser Tyr
            20                  25                  30

Ser Met Thr Trp Val Arg Gln Ala Pro Gly Lys Gly Leu Glu Trp Val
        35                  40                  45

Ser Phe Ile Ser Thr Val Ser Thr Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Gly Arg Gly Ser Ala Ala Arg Asp Gly Glu Lys Gly
            100                 105                 110

Thr Tyr Tyr Tyr Tyr Met Asp Val Trp Gly Lys Gly Thr Thr Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly Lys
    450                 455

<210> SEQ ID NO 14
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 14

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Arg Asn
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Ser Thr Tyr His Gln Pro Ser
    50                  55                  60

Leu Lys Ser Arg Val Thr Ile Phe Leu Asp Thr Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Gly Thr Arg Ala Thr Thr Trp Pro Pro Ile Gly Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
                435                 440                 445

Lys

<210> SEQ ID NO 15
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 15

Glu Val Gln Leu Leu Glu Ser Gly Gly Asp Val Val Gln Pro Gly Gly
1               5                   10                  15

Ser Leu Arg Leu Ser Cys Val Ala Ser Gly Phe Thr Leu Thr Asn Tyr
                20                  25                  30

Val Thr Ala Trp Val Arg Arg Pro Gly Lys Gly Leu Glu Trp Ile
            35                  40                  45

Ser Gly Met Thr His Gly Ala Val Ala Thr Tyr Tyr Ser Asp Ser Val
        50                  55                  60

Arg Gly Arg Phe Ser Ser Arg Asp Thr Ser Arg Ser Thr Leu Tyr
65                  70                  75                  80

Leu Gln Met Asn Asp Leu Thr Val Glu Asp Thr Ala Ile Tyr Tyr Cys
```

```
                85                  90                  95
Ala Lys Ser Leu His Arg Ser Gly Thr Ser Leu Ser Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 16
<211> LENGTH: 589
<212> TYPE: PRT
<213> ORGANISM: Artificial Sequence
<220> FEATURE:
<223> OTHER INFORMATION: Synthetic polypeptide

<400> SEQUENCE: 16

Phe Thr Val Thr Val Pro Lys Asp Leu Tyr Val Val Glu Tyr Gly Ser
```

-continued

```
1               5                   10                  15
Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
                35                  40                  45

Phe Val His Gly Glu Glu Asp Leu Lys Val Gln His Ser Ser Tyr Arg
                50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Gly Gly Ser Ser Arg Ser Ser Ser Gly Gly Gly Ser
                115                 120                 125

Gly Gly Gly Gly Glu Val Gln Leu Val Glu Ser Gly Gly Gly Leu Val
130                 135                 140

Lys Pro Gly Gly Ser Leu Arg Leu Ser Cys Ala Ala Ser Gly Phe Thr
145                 150                 155                 160

Phe Gly Ser Tyr Ser Met Thr Trp Val Arg Gln Ala Pro Gly Lys Gly
                165                 170                 175

Leu Glu Trp Val Ser Phe Ile Ser Thr Val Ser Thr Tyr Ile Tyr Tyr
                180                 185                 190

Pro Asp Ser Val Lys Gly Arg Phe Thr Ile Ser Arg Asp Asn Ala Lys
                195                 200                 205

Asn Ser Leu Tyr Leu Gln Met Asn Ser Leu Arg Ala Glu Asp Thr Ala
                210                 215                 220

Val Tyr Tyr Cys Ala Arg Val Ser Gly Arg Gly Ser Ala Ala Arg Asp
225                 230                 235                 240

Gly Glu Lys Gly Thr Tyr Tyr Tyr Met Asp Val Trp Gly Lys Gly
                245                 250                 255

Thr Thr Val Thr Val Ser Ser Ala Ser Thr Lys Gly Pro Ser Val Phe
                260                 265                 270

Pro Leu Ala Pro Cys Ser Arg Ser Thr Ser Glu Ser Thr Ala Ala Leu
                275                 280                 285

Gly Cys Leu Val Lys Asp Tyr Phe Pro Glu Pro Val Thr Val Ser Trp
                290                 295                 300

Asn Ser Gly Ala Leu Thr Ser Gly Val His Thr Phe Pro Ala Val Leu
305                 310                 315                 320

Gln Ser Ser Gly Leu Tyr Ser Leu Ser Ser Val Val Thr Val Pro Ser
                325                 330                 335

Ser Asn Phe Gly Thr Gln Thr Tyr Thr Cys Asn Val Asp His Lys Pro
                340                 345                 350

Ser Asn Thr Lys Val Asp Lys Thr Val Glu Arg Lys Cys Cys Val Glu
                355                 360                 365

Cys Pro Pro Cys Pro Ala Pro Pro Val Ala Gly Pro Ser Val Phe Leu
                370                 375                 380

Phe Pro Pro Lys Pro Lys Asp Thr Leu Met Ile Ser Arg Thr Pro Glu
385                 390                 395                 400

Val Thr Cys Val Val Val Asp Val Ser Gln Glu Asp Pro Glu Val Gln
                405                 410                 415

Phe Asn Trp Tyr Val Asp Gly Val Glu Val His Asn Ala Lys Thr Lys
                420                 425                 430
```

```
Pro Arg Glu Glu Gln Phe Asn Ser Thr Tyr Arg Val Ser Val Leu
        435                 440                 445

Thr Val Leu His Gln Asp Trp Leu Asn Gly Lys Glu Tyr Lys Cys Lys
450                 455                 460

Val Ser Asn Lys Gly Leu Pro Ser Ser Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Gln Glu Glu Met Thr Lys Asn Gln Val Ser Leu Thr Cys Leu Val Lys
                500                 505                 510

Gly Phe Tyr Pro Ser Asp Ile Ala Val Glu Trp Glu Ser Asn Gly Gln
                515                 520                 525

Pro Glu Asn Asn Tyr Lys Thr Thr Pro Pro Val Leu Asp Ser Asp Gly
                530                 535                 540

Ser Phe Phe Leu Tyr Ser Arg Leu Thr Val Asp Lys Ser Arg Trp Gln
545                 550                 555                 560

Glu Gly Asn Val Phe Ser Cys Ser Val Met His Glu Ala Leu His Asn
                565                 570                 575

His Tyr Thr Gln Lys Ser Leu Ser Leu Gly Lys
                580                 585

<210> SEQ ID NO 17
<211> LENGTH: 581
<212> TYPE: PRT
<213> ORGANISM: Artificial Sequence
<220> FEATURE:
<223> OTHER INFORMATION: Synthetic polypeptide

<400> SEQUENCE: 17

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Gly Gly Ser Ser Arg Ser Ser Ser Gly Gly Gly Gly Ser
            115                 120                 125

Gly Gly Gly Gly Gln Leu Gln Leu Gln Glu Ser Gly Pro Gly Leu Val
            130                 135                 140

Lys Pro Ser Glu Thr Leu Ser Leu Thr Cys Ile Val Ser Gly Gly Ser
145                 150                 155                 160

Ile Ser Arg Asn Ser Tyr Tyr Trp Gly Trp Ile Arg Gln Pro Pro Gly
                165                 170                 175

Lys Gly Leu Glu Trp Ile Gly Ser Ile Val Tyr Ser Gly Ser Thr Tyr
                180                 185                 190

His Gln Pro Ser Leu Lys Ser Arg Val Thr Ile Phe Leu Asp Thr Ser
            195                 200                 205
```

```
Lys Asn Gln Phe Phe Leu Lys Leu Thr Ser Val Thr Ala Ala Asp Thr
    210                 215                 220

Ala Val Tyr Tyr Cys Ala Arg Gly Thr Arg Ala Thr Thr Trp Pro Pro
225                 230                 235                 240

Pro Ile Gly Tyr Trp Gly Gln Gly Thr Leu Val Thr Val Ser Ser Ala
                245                 250                 255

Ser Thr Lys Gly Pro Ser Val Phe Pro Leu Ala Pro Cys Ser Arg Ser
            260                 265                 270

Thr Ser Glu Ser Thr Ala Ala Leu Gly Cys Leu Val Lys Asp Tyr Phe
        275                 280                 285

Pro Glu Pro Val Thr Val Ser Trp Asn Ser Gly Ala Leu Thr Ser Gly
    290                 295                 300

Val His Thr Phe Pro Ala Val Leu Gln Ser Ser Gly Leu Tyr Ser Leu
305                 310                 315                 320

Ser Ser Val Val Thr Val Pro Ser Ser Asn Phe Gly Thr Gln Thr Tyr
                325                 330                 335

Thr Cys Asn Val Asp His Lys Pro Ser Asn Thr Lys Val Asp Lys Thr
            340                 345                 350

Val Glu Arg Lys Cys Cys Val Glu Cys Pro Pro Cys Pro Ala Pro Pro
        355                 360                 365

Val Ala Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
                405                 410                 415

Glu Val His Asn Ala Lys Thr Lys Pro Arg Glu Glu Gln Phe Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Gly Leu Pro Ser
    450                 455                 460

Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Arg Leu
    530                 535                 540

Thr Val Asp Lys Ser Arg Trp Gln Glu Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Leu Gly Lys
            580

<210> SEQ ID NO 18
<211> LENGTH: 217
<212> TYPE: PRT
<213> ORGANISM: Artificial Sequence
<220> FEATURE:
```

<223> OTHER INFORMATION: Synthetic polypeptide

<400> SEQUENCE: 18

```
Gln Ser Val Leu Thr Gln Pro Pro Ser Ala Ser Gly Thr Pro Gly Gln
1               5                   10                  15

Asn Ile Asn Ile Ser Cys Ser Gly Thr Thr Ser Asn Ile Gly Gly Ser
            20                  25                  30

Asn Val Asp Trp Tyr Gln His Val Pro Gly Thr Ala Pro Lys Leu Phe
        35                  40                  45

Ile His Ser Asn Asn Gln Arg Pro Ser Gly Val Pro Ala Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Val Arg Leu
                85                  90                  95

Leu Ala Tyr Val Phe Gly Ser Ala Thr Glu Val Thr Val Leu Arg His
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 19
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 19

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Ser Tyr
            20                  25                  30

Ser Met Thr Trp Val Arg Gln Ala Pro Gly Lys Gly Leu Glu Trp Val
        35                  40                  45

Ser Phe Ile Ser Thr Val Ser Thr Tyr Ile Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Gly Arg Gly Ser Ala Ala Arg Asp Gly Glu Lys Gly
            100                 105                 110

Thr Tyr Tyr Tyr Tyr Met Asp Val Trp Gly Lys Gly Thr Thr Val Thr
        115                 120                 125
```

Val Ser Ser Ala Lys Thr Thr Pro Pro Ser Val Tyr Pro Leu Ala Pro
    130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Gln Thr Val Thr Cys Asn Val Ala His Pro Ala Ser Ser Thr Lys Val
    210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Lys Pro Arg Glu Glu Gln Ile
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asn Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455

<210> SEQ ID NO 20
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 20

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Arg Ser Tyr Tyr Ala
            20                  25                  30

```
Ser Trp Tyr Gln Gln Lys Pro Gly Gln Ala Pro Val Leu Val Ile Phe
         35                  40                  45

Gly Lys Asn Asn Arg Pro Ser Gly Ile Pro Asp Arg Phe Ser Gly Ser
 50                  55                  60

Arg Ser Gly Asn Thr Ala Ser Leu Thr Ile Thr Gly Ala Gln Ala Glu
 65                  70                  75                  80

Asp Glu Ala Asp Tyr Phe Cys Asp Ser Arg Asp Ser Ser Ala Asn His
                 85                  90                  95

Trp Val Phe Gly Gly Gly Thr Lys Leu Thr Val Leu Gln Pro Lys Arg
                100                 105                 110

Ala Asp Ala Ala Pro Thr Val Ser Ile Phe Pro Pro Ser Ser Glu Gln
             115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
210                 215

<210> SEQ ID NO 21
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Arg Asn
             20                  25                  30

Ser Tyr Tyr Trp Gly Trp Ile Arg Gln Pro Pro Gly Lys Gly Leu Glu
         35                  40                  45

Trp Ile Gly Ser Ile Val Tyr Ser Gly Ser Thr Tyr His Gln Pro Ser
 50                  55                  60

Leu Lys Ser Arg Val Thr Ile Phe Leu Asp Thr Ser Lys Asn Gln Phe
 65                  70                  75                  80

Phe Leu Lys Leu Thr Ser Val Thr Ala Ala Asp Thr Ala Val Tyr Tyr
                 85                  90                  95

Cys Ala Arg Gly Thr Arg Ala Thr Thr Trp Pro Pro Ile Gly Tyr
                100                 105                 110

Trp Gly Gln Gly Thr Leu Val Thr Val Ser Ser Ala Lys Thr Thr Pro
            115                 120                 125

Pro Ser Val Tyr Pro Leu Ala Pro Gly Ser Ala Ala Gln Thr Asn Ser
130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175
```

-continued

Pro Ala Val Leu Gln Ser Asp Leu Tyr Thr Leu Ser Ser Val Thr
            180                 185                 190

Val Pro Ser Ser Thr Trp Pro Ser Gln Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Asp Ile Ser Lys Asp Asp Pro Glu
            260                 265                 270

Val Gln Phe Ser Trp Phe Val Asp Asp Val Glu Val His Thr Ala Gln
                275                 280                 285

Thr Lys Pro Arg Glu Glu Gln Ile Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asn Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 22
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 22

Gln Ser Val Leu Thr Gln Pro Pro Ser Val Ser Ala Ala Pro Gly Gln
1               5                   10                  15

Lys Val Thr Val Ser Cys Phe Gly Ser Ser Ser Asn Ile Gly Asn Tyr
            20                  25                  30

Phe Ala Ser Trp Tyr Gln Gln Leu Pro Gly Ala Ala Pro Arg Leu Leu
        35                  40                  45

Ile Tyr Gly Asn Asn Glu Arg Pro Ser Gly Ile Pro Asp Arg Phe Ser
    50                  55                  60

Gly Ser Lys Ser Gly Thr Ser Ala Thr Leu Val Ile Thr Gly Leu Gln
65                  70                  75                  80

Thr Gly Asp Glu Ala Ala Tyr Tyr Cys Ala Thr Trp Asp Ser Ser Leu
                85                  90                  95

```
Ser Ala Val Val Phe Gly Gly Thr Lys Leu Thr Val Leu Gly Gln
            100                 105                 110

Pro Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
        130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
            195                 200                 205

Ser Pro Ile Val Lys Ser Phe Asn Arg Asn Glu Cys
            210                 215                 220

<210> SEQ ID NO 23
<211> LENGTH: 444
<212> TYPE: PRT
<213> ORGANISM: Artificial Sequence
<220> FEATURE:
<223> OTHER INFORMATION: Synthetic polypeptide

<400> SEQUENCE: 23

Glu Val Gln Leu Leu Glu Ser Gly Gly Asp Val Val Gln Pro Gly Gly
1               5                   10                  15

Ser Leu Arg Leu Ser Cys Val Ala Ser Gly Phe Thr Leu Thr Asn Tyr
            20                  25                  30

Val Thr Ala Trp Val Arg Arg Pro Gly Lys Gly Leu Glu Trp Ile
        35                  40                  45

Ser Gly Met Thr His Gly Ala Val Ala Thr Tyr Tyr Ser Asp Ser Val
    50                  55                  60

Arg Gly Arg Phe Ser Ser Ser Arg Asp Thr Ser Arg Ser Thr Leu Tyr
65                  70                  75                  80

Leu Gln Met Asn Asp Leu Thr Val Glu Asp Thr Ala Ile Tyr Tyr Cys
                85                  90                  95

Ala Lys Ser Leu His Arg Ser Gly Thr Ser Leu Ser Tyr Trp Gly Gln
            100                 105                 110

Gly Thr Leu Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240
```

```
Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
                260                 265                 270

Ser Trp Phe Val Asp Val Glu Val His Thr Ala Gln Thr Lys Pro
                275                 280                 285

Arg Glu Glu Gln Ile Asn Ser Thr Phe Arg Ser Val Ser Glu Leu Pro
                290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
                340                 345                 350

Glu Gln Met Ala Lys Asp Lys Val Ser Leu Thr Cys Met Ile Thr Asn
                355                 360                 365

Phe Phe Pro Glu Asp Ile Thr Val Glu Trp Gln Trp Asn Gly Gln Pro
                370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440

<210> SEQ ID NO 24
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 24

Gln Ser Val Leu Thr Gln Pro Pro Ser Ala Ser Gly Thr Pro Gly Gln
1               5                   10                  15

Asn Ile Asn Ile Ser Cys Ser Gly Thr Thr Ser Asn Ile Gly Gly Ser
                20                  25                  30

Asn Val Asp Trp Tyr Gln His Val Pro Gly Thr Ala Pro Lys Leu Phe
                35                  40                  45

Ile His Ser Asn Asn Gln Arg Pro Ser Gly Val Pro Ala Arg Phe Ser
        50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Val Arg Leu
                85                  90                  95

Leu Ala Tyr Val Phe Gly Ser Ala Thr Glu Val Thr Val Leu Arg His
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
            130                 135                 140

Tyr Pro Lys Asp Ile Asn Val Lys Trp Lys Ile Asp Gly Ser Glu Arg
145                 150                 155                 160
```

Gln Asn Gly Val Leu Asn Ser Trp Thr Asp Gln Asp Ser Lys Asp Ser
             165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 25
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 25

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Gly Ser
            115                 120                 125

Gly Gly Gly Gly Gln Ser Val Leu Thr Gln Pro Pro Ser Val Ser Ala
        130                 135                 140

Ala Pro Gly Gln Lys Val Thr Val Ser Cys Phe Gly Ser Ser Ser Asn
145                 150                 155                 160

Ile Gly Asn Tyr Phe Ala Ser Trp Tyr Gln Gln Leu Pro Gly Ala Ala
                165                 170                 175

Pro Arg Leu Leu Ile Tyr Gly Asn Asn Glu Arg Pro Ser Gly Ile Pro
            180                 185                 190

Asp Arg Phe Ser Gly Ser Lys Ser Gly Thr Ser Ala Thr Leu Val Ile
            195                 200                 205

Thr Gly Leu Gln Thr Gly Asp Glu Ala Ala Tyr Tyr Cys Ala Thr Trp
        210                 215                 220

Asp Ser Ser Leu Ser Ala Val Val Phe Gly Gly Gly Thr Lys Leu Thr
225                 230                 235                 240

Val Leu Gly Gln Pro Lys Ser Pro Ser Val Thr Leu Phe Pro Pro
                245                 250                 255

Ser Ser Glu Glu Leu Glu Thr Asn Lys Ala Thr Leu Val Cys Thr Ile
            260                 265                 270

Thr Asp Phe Tyr Pro Gly Val Val Thr Val Asp Trp Lys Val Asp Gly
        275                 280                 285

Thr Pro Val Thr Gln Gly Met Glu Thr Thr Gln Pro Ser Lys Gln Ser
    290                 295                 300

```
Asn Asn Lys Tyr Met Ala Ser Ser Tyr Leu Thr Leu Thr Ala Arg Ala
305                 310                 315                 320

Trp Glu Arg His Ser Ser Tyr Ser Cys Gln Val Thr His Glu Gly His
                325                 330                 335

Thr Val Glu Lys Ser Leu Ser Arg Ala Asp Cys Ser
            340                 345

<210> SEQ ID NO 26
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Arg Asn
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Ser Thr Tyr His Gln Pro Ser
    50                  55                  60

Leu Lys Ser Arg Val Thr Ile Phe Leu Asp Thr Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Gly Thr Arg Ala Thr Thr Trp Pro Pro Ile Gly Tyr
            100                 105                 110

Trp Gly Gln Gly Thr Leu Val Thr Val Ser Ser Ala Lys Thr Thr Pro
            115                 120                 125

Pro Ser Val Tyr Pro Leu Ala Pro Gly Ser Ala Ala Gln Thr Asn Ser
        130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Gln Thr Val Thr Cys Asn Val Ala
        195                 200                 205

His Pro Ala Ser Ser Thr Lys Val Asp Lys Ile Val Pro Arg Asp
    210                 215                 220

Cys Gly Cys Lys Pro Cys Ile Cys Thr Val Pro Glu Gln Ser Ser Val
225                 230                 235                 240

Phe Ile Phe Pro Pro Lys Pro Lys Asp Val Leu Met Ile Ser Leu Thr
                245                 250                 255

Pro Lys Val Thr Cys Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Lys Pro Arg Glu Glu Gln Ile Asn Ser Thr Phe Arg Ser Val Ser
    290                 295                 300

Glu Leu Pro Ile Leu His Gln Asp Trp Leu Asn Gly Lys Glu Phe Lys
305                 310                 315                 320
```

Cys Arg Val Asn Ser Ala Ala Phe Pro Ala Pro Ile Glu Lys Thr Ile
            325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
            355                 360                 365

Ile Thr Asn Phe Phe Pro Glu Asp Ile Thr Val Glu Trp Gln Trp Asn
        370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly Lys
            435                 440                 445

<210> SEQ ID NO 27
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 27

Leu Glu Val Gln Leu Gln Gln Ser Gly Ala Glu Leu Val Arg Pro Gly
1               5                   10                  15

Ser Ser Val Lys Ile Ser Cys Lys Ala Ser Gly Tyr Val Phe Ser Asn
            20                  25                  30

Tyr Trp Met Asn Trp Val Lys Gln Arg Pro Gly Gln Gly Leu Glu Trp
        35                  40                  45

Ile Gly Gln Ile Tyr Pro Gly Asp Gly Asp Thr Asn Tyr Asn Gly Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Arg Glu Ile Tyr Phe Asp Tyr Trp Gly Gln Gly Thr Thr
            100                 105                 110

Val Thr Val Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

```
Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
        435                 440

<210> SEQ ID NO 28
<211> LENGTH: 346
<212> TYPE: PRT
<213> ORGANISM: Artificial Sequence
<220> FEATURE:
<223> OTHER INFORMATION: Synthetic polypeptide

<400> SEQUENCE: 28

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Gly Gly Ser Ser Arg Ser Ser Ser Gly Gly Gly Ser
        115                 120                 125

Gly Gly Gly Gly Asp Ile Leu Leu Thr Gln Ser Pro Ala Ile Leu Ser
    130                 135                 140

Val Ser Pro Gly Glu Arg Val Ser Phe Ser Cys Arg Ala Ser Gln Ser
145                 150                 155                 160
```

Ile Gly Thr Ser Ile His Trp Tyr Gln Gln Arg Thr Asn Gly Ser Pro
                165                 170                 175

Arg Leu Leu Ile Glu Tyr Ala Ser Glu Ser Ile Ser Gly Ile Pro Ser
            180                 185                 190

Arg Phe Ser Gly Ser Gly Ser Gly Thr Asp Phe Thr Leu Ser Ile Asn
        195                 200                 205

Ser Val Glu Ser Glu Asp Phe Ala Tyr Tyr Cys Gln Gln Ser Asn
    210                 215                 220

Gly Trp Pro Ile Thr Phe Gly Gly Gly Thr Lys Leu Glu Ile Lys Arg
225                 230                 235                 240

Thr Val Ala Ala Pro Ser Val Phe Ile Phe Pro Pro Ser Asp Glu Gln
                245                 250                 255

Leu Lys Ser Gly Thr Ala Ser Val Val Cys Leu Leu Asn Asn Phe Tyr
            260                 265                 270

Pro Arg Glu Ala Lys Val Gln Trp Lys Val Asp Asn Ala Leu Gln Ser
        275                 280                 285

Gly Asn Ser Gln Glu Ser Val Thr Glu Gln Asp Ser Lys Asp Ser Thr
    290                 295                 300

Tyr Ser Leu Ser Ser Thr Leu Thr Leu Ser Lys Ala Asp Tyr Glu Lys
305                 310                 315                 320

His Lys Val Tyr Ala Cys Glu Val Thr His Gln Gly Leu Ser Ser Pro
                325                 330                 335

Val Thr Lys Ser Phe Asn Arg Gly Glu Cys
            340                 345

<210> SEQ ID NO 29
<211> LENGTH: 132
<212> TYPE: PRT
<213> ORGANISM: Artificial Sequence
<220> FEATURE:
<223> OTHER INFORMATION: Synthetic polypeptide

<400> SEQUENCE: 29

Gly Gly Ser Ser Arg Ser Ser Ser Gly Gly Gly Ser Gly Gly
1               5                   10                  15

Gly Gly Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala
    130

<210> SEQ ID NO 30
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 30

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 31
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 31

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 32
<211> LENGTH: 458
<212> TYPE: PRT
<213> ORGANISM: Artificial Sequence
<220> FEATURE:
<223> OTHER INFORMATION: Synthetic polypeptide

<400> SEQUENCE: 32

```
Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
                20                  25                  30
Ala Ala Leu Ile Val Tyr Trp Glu Met Glu Asp Lys Asn Ile Ile Gln
            35                  40                  45
Phe Val His Gly Glu Glu Asp Leu Lys Val Gln His Ser Ser Tyr Arg
        50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Gly Gly Ser Ser Arg Ser Ser Ser Gly Gly Gly Gly Ser
        115                 120                 125
Gly Gly Gly Gly Ala Ser Thr Lys Gly Pro Ser Val Phe Pro Leu Ala
130                 135                 140
Pro Cys Ser Arg Ser Thr Ser Glu Ser Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Asn Phe
        195                 200                 205
Gly Thr Gln Thr Tyr Thr Cys Asn Val Asp His Lys Pro Ser Asn Thr
    210                 215                 220
Lys Val Asp Lys Thr Val Glu Arg Lys Cys Cys Val Glu Cys Pro Pro
225                 230                 235                 240
Cys Pro Ala Pro Pro Val Ala Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser Gln Glu Asp Pro Glu Val Gln Phe Asn Trp
        275                 280                 285
Tyr Val Asp Gly Val Glu Val His Asn Ala Lys Thr Lys Pro Arg Glu
    290                 295                 300
Glu Gln Phe Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Gly Leu Pro Ser Ser Ile Glu Lys Thr Ile Ser Lys Ala Lys Gly
            340                 345                 350
Gln Pro Arg Glu Pro Gln Val Tyr Thr Leu Pro Pro Ser Gln Glu Glu
        355                 360                 365
```

```
Met Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Arg Leu Thr Val Asp Lys Ser Arg Trp Gln Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Leu Gly Lys
    450                 455

<210> SEQ ID NO 33
<211> LENGTH: 352
<212> TYPE: PRT
<213> ORGANISM: Artificial Sequence
<220> FEATURE:
<223> OTHER INFORMATION: Synthetic polypeptide

<400> SEQUENCE: 33

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Gly Gly Ser Ser Arg Ser Ser Ser Gly Gly Gly Gly Ser
        115                 120                 125

Gly Gly Gly Gly Gln Ser Val Leu Thr Gln Pro Pro Ser Val Ser Ala
    130                 135                 140

Ala Pro Gly Gln Lys Val Thr Val Ser Cys Phe Gly Ser Ser Ser Asn
145                 150                 155                 160

Ile Gly Asn Tyr Phe Ala Ser Trp Tyr Gln Gln Leu Pro Gly Ala Ala
                165                 170                 175

Pro Arg Leu Leu Ile Tyr Gly Asn Asn Glu Arg Pro Ser Gly Ile Pro
            180                 185                 190

Asp Arg Phe Ser Gly Ser Lys Ser Gly Thr Ser Ala Thr Leu Val Ile
        195                 200                 205

Thr Gly Leu Gln Thr Gly Asp Glu Ala Ala Tyr Tyr Cys Ala Thr Trp
    210                 215                 220

Asp Ser Ser Leu Ser Ala Val Val Phe Gly Gly Gly Thr Lys Leu Thr
225                 230                 235                 240

Val Leu Gly Gln Pro Arg Ala Asp Ala Ala Pro Thr Val Ser Ile Phe
                245                 250                 255

Pro Pro Ser Ser Glu Gln Leu Thr Ser Gly Gly Ala Ser Val Val Cys
            260                 265                 270
```

```
Phe Leu Asn Asn Phe Tyr Pro Lys Asp Ile Asn Val Lys Trp Lys Ile
            275                 280                 285

Asp Gly Ser Glu Arg Gln Asn Gly Val Leu Asn Ser Trp Thr Asp Gln
290                 295                 300

Asp Ser Lys Asp Ser Thr Tyr Ser Met Ser Thr Leu Thr Leu Thr
305                 310                 315                 320

Lys Asp Glu Tyr Glu Arg His Asn Ser Tyr Thr Cys Glu Ala Thr His
                325                 330                 335

Lys Thr Ser Thr Ser Pro Ile Val Lys Ser Phe Asn Arg Asn Glu Cys
            340                 345                 350

<210> SEQ ID NO 34
<211> LENGTH: 351
<212> TYPE: PRT
<213> ORGANISM: Artificial Sequence
<220> FEATURE:
<223> OTHER INFORMATION: Synthetic polypeptide

<400> SEQUENCE: 34

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Gly Gly Ser Ser Arg Ser Ser Ser Gly Gly Gly Gly Ser
        115                 120                 125

Gly Gly Gly Gly Gln Ser Val Leu Thr Gln Pro Ser Ala Ser Gly
    130                 135                 140

Thr Pro Gly Gln Asn Ile Asn Ile Ser Cys Ser Gly Thr Thr Ser Asn
145                 150                 155                 160

Ile Gly Gly Ser Asn Val Asp Trp Tyr Gln His Val Pro Gly Thr Ala
                165                 170                 175

Pro Lys Leu Phe Ile His Ser Asn Asn Gln Arg Pro Ser Gly Val Pro
            180                 185                 190

Ala Arg Phe Ser Ala Ser Lys Ser Gly Thr Ser Ala Ser Leu Ala Ile
        195                 200                 205

Ser Gly Leu Gln Ser Glu Asp Glu Ala Asp Tyr Tyr Cys Ala Thr Trp
    210                 215                 220

Asp Val Arg Leu Leu Ala Tyr Val Phe Gly Ser Ala Thr Glu Val Thr
225                 230                 235                 240

Val Leu Arg His Arg Ala Asp Ala Ala Pro Thr Val Ser Ile Phe Pro
                245                 250                 255

Pro Ser Ser Glu Gln Leu Thr Ser Gly Gly Ala Ser Val Val Cys Phe
            260                 265                 270

Leu Asn Asn Phe Tyr Pro Lys Asp Ile Asn Val Lys Trp Lys Ile Asp
        275                 280                 285
```

Gly Ser Glu Arg Gln Asn Gly Val Leu Asn Ser Trp Thr Asp Gln Asp
            290                 295                 300

Ser Lys Asp Ser Thr Tyr Ser Met Ser Ser Thr Leu Thr Leu Thr Lys
305                 310                 315                 320

Asp Glu Tyr Glu Arg His Asn Ser Tyr Thr Cys Glu Ala Thr His Lys
                    325                 330                 335

Thr Ser Thr Ser Pro Ile Val Lys Ser Phe Asn Arg Asn Glu Cys
                340                 345                 350

<210> SEQ ID NO 35
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 36
<211> LENGTH: 339
<212> TYPE: PRT
<213> ORGANISM: Artificial Sequence
<220> FEATURE:
<223> OTHER INFORMATION: Synthetic polypeptide

<400> SEQUENCE: 36

Phe Thr Val Thr Val Pro Lys Glu Leu Tyr Ile Ile Glu His Gly Ser
1               5                   10                  15

Asn Val Thr Leu Glu Cys Asn Phe Asp Thr Gly Ser His Val Asn Leu
            20                  25                  30

Gly Ala Ile Thr Ala Ser Leu Gln Lys Val Glu Asn Asp Thr Ser Pro
        35                  40                  45

His Arg Glu Arg Ala Thr Leu Leu Glu Glu Gln Leu Pro Leu Gly Lys
    50                  55                  60

Ala Ser Phe His Ile Pro Gln Val Gln Val Arg Asp Glu Gly Gln Tyr
65                  70                  75                  80

Gln Cys Ile Ile Ile Tyr Gly Val Ala Trp Asp Tyr Lys Tyr Leu Thr
                85                  90                  95

Leu Lys Val Lys Ala Gly Gly Ser Ser Arg Ser Ser Ser Gly Gly Gly
            100                 105                 110

Gly Gly Ser Gly Gly Gly Gln Ser Val Leu Thr Gln Pro Pro Ser
        115                 120                 125

Val Ser Ala Ala Pro Gly Gln Lys Val Thr Val Ser Cys Phe Gly Ser
    130                 135                 140

Ser Ser Asn Ile Gly Asn Tyr Phe Ala Ser Trp Tyr Gln Gln Leu Pro
145                 150                 155                 160

Gly Ala Ala Pro Arg Leu Leu Ile Tyr Gly Asn Asn Glu Arg Pro Ser
                165                 170                 175

Gly Ile Pro Asp Arg Phe Ser Gly Ser Lys Ser Gly Thr Ser Ala Thr
            180                 185                 190

Leu Val Ile Thr Gly Leu Gln Thr Gly Asp Glu Ala Ala Tyr Tyr Cys
        195                 200                 205

Ala Thr Trp Asp Ser Ser Leu Ser Ala Val Phe Gly Gly Gly Thr
    210                 215                 220

Lys Leu Thr Val Leu Gly Gln Pro Arg Thr Val Ala Ala Pro Ser Val
225                 230                 235                 240

Phe Ile Phe Pro Pro Ser Asp Glu Gln Leu Lys Ser Gly Thr Ala Ser
                245                 250                 255

Val Val Cys Leu Leu Asn Asn Phe Tyr Pro Arg Glu Ala Lys Val Gln
            260                 265                 270

Trp Lys Val Asp Asn Ala Leu Gln Ser Gly Asn Ser Gln Glu Ser Val
        275                 280                 285

Thr Glu Gln Asp Ser Lys Asp Ser Thr Tyr Ser Leu Ser Ser Thr Leu
    290                 295                 300

Thr Leu Ser Lys Ala Asp Tyr Glu Lys His Lys Val Tyr Ala Cys Glu
305                 310                 315                 320

Val Thr His Gln Gly Leu Ser Ser Pro Val Thr Lys Ser Phe Asn Arg
                325                 330                 335

Gly Glu Cys

<210> SEQ ID NO 37
<211> LENGTH: 438
<212> TYPE: PRT
<213> ORGANISM: Artificial Sequence
<220> FEATURE:
<223> OTHER INFORMATION: Synthetic polypeptide

<400> SEQUENCE: 37

Phe Thr Val Thr Val Pro Lys Glu Leu Tyr Ile Ile Glu His Gly Ser
1               5                   10                  15

Asn Val Thr Leu Glu Cys Asn Phe Asp Thr Gly Ser His Val Asn Leu
            20                  25                  30

Gly Ala Ile Thr Ala Ser Leu Gln Lys Val Glu Asn Asp Thr Ser Pro
        35                  40                  45

His Arg Glu Arg Ala Thr Leu Leu Glu Glu Gln Leu Pro Leu Gly Lys
    50                  55                  60

Ala Ser Phe His Ile Pro Gln Val Gln Val Arg Asp Glu Gly Gln Tyr
65                  70                  75                  80

Gln Cys Ile Ile Ile Tyr Gly Val Ala Trp Asp Tyr Lys Tyr Leu Thr
                85                  90                  95

Leu Lys Val Lys Ala Ser Tyr Arg Lys Ile Asn Thr His Ile Leu Lys
            100                 105                 110

Val Pro Glu Thr Asp Glu Val Glu Leu Thr Cys Gln Ala Thr Gly Tyr
        115                 120                 125

Pro Leu Ala Glu Val Ser Trp Pro Asn Val Ser Val Pro Ala Asn Thr
    130                 135                 140

Ser His Ser Arg Thr Pro Glu Gly Leu Tyr Gln Val Thr Ser Val Leu
145                 150                 155                 160

Arg Leu Lys Pro Pro Pro Gly Arg Asn Phe Ser Cys Val Phe Trp Asn
                165                 170                 175

Thr His Val Arg Glu Leu Thr Leu Ala Ser Ile Asp Leu Gln Ser Gln
            180                 185                 190

Met Glu Pro Arg Thr His Pro Thr Gly Gly Ser Arg Ser Ser Ser
        195                 200                 205

Ser Gly Gly Gly Gly Ser Gly Gly Gly Gln Ser Val Leu Thr Gln
    210                 215                 220

Pro Pro Ser Val Ser Ala Ala Pro Gly Gln Lys Val Thr Val Ser Cys
225                 230                 235                 240

Phe Gly Ser Ser Ser Asn Ile Gly Asn Tyr Phe Ala Ser Trp Tyr Gln
                245                 250                 255

Gln Leu Pro Gly Ala Ala Pro Arg Leu Leu Ile Tyr Gly Asn Asn Glu
            260                 265                 270

Arg Pro Ser Gly Ile Pro Asp Arg Phe Ser Gly Ser Lys Ser Gly Thr
        275                 280                 285

Ser Ala Thr Leu Val Ile Thr Gly Leu Gln Thr Gly Asp Glu Ala Ala
    290                 295                 300

Tyr Tyr Cys Ala Thr Trp Asp Ser Ser Leu Ser Ala Val Val Phe Gly
305                 310                 315                 320

Gly Gly Thr Lys Leu Thr Val Leu Gly Gln Pro Arg Thr Val Ala Ala
                325                 330                 335

Pro Ser Val Phe Ile Phe Pro Ser Asp Glu Gln Leu Lys Ser Gly
            340                 345                 350

```
Thr Ala Ser Val Val Cys Leu Leu Asn Asn Phe Tyr Pro Arg Glu Ala
            355                 360                 365

Lys Val Gln Trp Lys Val Asp Asn Ala Leu Gln Ser Gly Asn Ser Gln
    370                 375                 380

Glu Ser Val Thr Glu Gln Asp Ser Lys Asp Ser Thr Tyr Ser Leu Ser
385                 390                 395                 400

Ser Thr Leu Thr Leu Ser Lys Ala Asp Tyr Glu Lys His Lys Val Tyr
                405                 410                 415

Ala Cys Glu Val Thr His Gln Gly Leu Ser Ser Pro Val Thr Lys Ser
            420                 425                 430

Phe Asn Arg Gly Glu Cys
            435

<210> SEQ ID NO 38
<211> LENGTH: 440
<212> TYPE: PRT
<213> ORGANISM: Artificial Sequence
<220> FEATURE:
<223> OTHER INFORMATION: Synthetic polypeptide

<400> SEQUENCE: 38

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly Gly Ser Ser Arg Ser
        195                 200                 205

Ser Ser Ser Gly Gly Gly Ser Gly Gly Gly Gln Ser Val Leu
210                 215                 220

Thr Gln Pro Pro Ser Val Ser Ala Ala Pro Gly Gln Lys Val Thr Val
225                 230                 235                 240

Ser Cys Phe Gly Ser Ser Ser Asn Ile Gly Asn Tyr Phe Ala Ser Trp
                245                 250                 255

Tyr Gln Gln Leu Pro Gly Ala Ala Pro Arg Leu Leu Ile Tyr Gly Asn
            260                 265                 270
```

Asn Glu Arg Pro Ser Gly Ile Pro Asp Arg Phe Ser Gly Ser Lys Ser
            275                 280                 285

Gly Thr Ser Ala Thr Leu Val Ile Thr Gly Leu Gln Thr Gly Asp Glu
290                 295                 300

Ala Ala Tyr Tyr Cys Ala Thr Trp Asp Ser Ser Leu Ser Ala Val Val
305                 310                 315                 320

Phe Gly Gly Gly Thr Lys Leu Thr Val Leu Gly Gln Pro Arg Thr Val
                325                 330                 335

Ala Ala Pro Ser Val Phe Ile Phe Pro Ser Asp Glu Gln Leu Lys
            340                 345                 350

Ser Gly Thr Ala Ser Val Val Cys Leu Leu Asn Asn Phe Tyr Pro Arg
            355                 360                 365

Glu Ala Lys Val Gln Trp Lys Val Asp Asn Ala Leu Gln Ser Gly Asn
370                 375                 380

Ser Gln Glu Ser Val Thr Glu Gln Asp Ser Lys Asp Ser Thr Tyr Ser
385                 390                 395                 400

Leu Ser Ser Thr Leu Thr Leu Ser Lys Ala Asp Tyr Glu Lys His Lys
                405                 410                 415

Val Tyr Ala Cys Glu Val Thr His Gln Gly Leu Ser Ser Pro Val Thr
            420                 425                 430

Lys Ser Phe Asn Arg Gly Glu Cys
        435                 440

<210> SEQ ID NO 39
<211> LENGTH: 676
<212> TYPE: PRT
<213> ORGANISM: Artificial Sequence
<220> FEATURE:
<223> OTHER INFORMATION: Synthetic polypeptide

<400> SEQUENCE: 39

Leu Glu Val Gln Val Pro Glu Asp Pro Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
        50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

-continued

Leu Val Arg Asn Pro Val Leu Gln Gln Asp Ala His Ser Val Thr
            195                 200                 205
Ile Thr Pro Gln Arg Ser Pro Thr Gly Ala Val Glu Val Gln Val Pro
210                 215                 220
Glu Asp Pro Val Val Ala Leu Val Gly Thr Asp Ala Thr Leu Arg Cys
225                 230                 235                 240
Ser Phe Ser Pro Glu Pro Gly Phe Ser Leu Ala Gln Leu Asn Leu Ile
            245                 250                 255
Trp Gln Leu Thr Asp Thr Lys Gln Leu Val His Ser Phe Thr Glu Gly
            260                 265                 270
Arg Asp Gln Gly Ser Ala Tyr Ala Asn Arg Thr Ala Leu Phe Pro Asp
            275                 280                 285
Leu Leu Ala Gln Gly Asn Ala Ser Leu Arg Leu Gln Arg Val Arg Val
            290                 295                 300
Ala Asp Glu Gly Ser Phe Thr Cys Phe Val Ser Ile Arg Asp Phe Gly
305                 310                 315                 320
Ser Ala Ala Val Ser Leu Gln Val Ala Ala Pro Tyr Ser Lys Pro Ser
            325                 330                 335
Met Thr Leu Glu Pro Asn Lys Asp Leu Arg Pro Gly Asp Thr Val Thr
            340                 345                 350
Ile Thr Cys Ser Ser Tyr Arg Gly Tyr Pro Glu Ala Glu Val Phe Trp
            355                 360                 365
Gln Asp Gly Gln Gly Val Pro Leu Thr Gly Asn Val Thr Thr Ser Gln
            370                 375                 380
Met Ala Asn Glu Gln Gly Leu Phe Asp Val His Ser Val Leu Arg Val
385                 390                 395                 400
Val Leu Gly Ala Asn Gly Thr Tyr Ser Cys Leu Val Arg Asn Pro Val
            405                 410                 415
Leu Gln Gln Asp Ala His Gly Ser Val Thr Ile Thr Gly Gln Pro Met
            420                 425                 430
Thr Phe Pro Pro Glu Ala Gly Gly Ser Ser Arg Ser Ser Ser Ser Gly
            435                 440                 445
Gly Gly Gly Ser Gly Gly Gly Gly Gln Ser Val Leu Thr Gln Pro Pro
450                 455                 460
Ser Val Ser Ala Ala Pro Gly Gln Lys Val Thr Val Ser Cys Phe Gly
465                 470                 475                 480
Ser Ser Ser Asn Ile Gly Asn Tyr Phe Ala Ser Trp Tyr Gln Gln Leu
            485                 490                 495
Pro Gly Ala Ala Pro Arg Leu Leu Ile Tyr Gly Asn Asn Glu Arg Pro
            500                 505                 510
Ser Gly Ile Pro Asp Arg Phe Ser Gly Ser Lys Ser Gly Thr Ser Ala
            515                 520                 525
Thr Leu Val Ile Thr Gly Leu Gln Thr Gly Asp Glu Ala Ala Tyr Tyr
            530                 535                 540
Cys Ala Thr Trp Asp Ser Ser Leu Ser Ala Val Val Phe Gly Gly Gly
545                 550                 555                 560
Thr Lys Leu Thr Val Leu Gly Gln Pro Arg Thr Val Ala Ala Pro Ser
            565                 570                 575
Val Phe Ile Phe Pro Pro Ser Asp Glu Gln Leu Lys Ser Gly Thr Ala
            580                 585                 590
Ser Val Val Cys Leu Leu Asn Asn Phe Tyr Pro Arg Glu Ala Lys Val
            595                 600                 605
Gln Trp Lys Val Asp Asn Ala Leu Gln Ser Gly Asn Ser Gln Glu Ser

```
                    610                 615                 620
Val Thr Glu Gln Asp Ser Lys Asp Ser Thr Tyr Ser Leu Ser Ser Thr
625                 630                 635                 640

Leu Thr Leu Ser Lys Ala Asp Tyr Glu Lys His Lys Val Tyr Ala Cys
                    645                 650                 655

Glu Val Thr His Gln Gly Leu Ser Ser Pro Val Thr Lys Ser Phe Asn
                660                 665                 670

Arg Gly Glu Cys
            675

<210> SEQ ID NO 40
<211> LENGTH: 419
<212> TYPE: PRT
<213> ORGANISM: Artificial Sequence
<220> FEATURE:
<223> OTHER INFORMATION: Synthetic polypeptide

<400> SEQUENCE: 40

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
        130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Gly Gly Ser Ser Arg Ser Ser Ser Gly Gly
            180                 185                 190

Gly Gly Ser Gly Gly Gly Gln Ser Val Leu Thr Gln Pro Pro Ser
        195                 200                 205

Val Ser Ala Ala Pro Gly Gln Lys Val Thr Val Ser Cys Phe Gly Ser
210                 215                 220

Ser Ser Asn Ile Gly Asn Tyr Phe Ala Ser Trp Tyr Gln Gln Leu Pro
225                 230                 235                 240

Gly Ala Ala Pro Arg Leu Leu Ile Tyr Gly Asn Asn Glu Arg Pro Ser
                245                 250                 255

Gly Ile Pro Asp Arg Phe Ser Gly Ser Lys Ser Gly Thr Ser Ala Thr
            260                 265                 270

Leu Val Ile Thr Gly Leu Gln Thr Gly Asp Glu Ala Ala Tyr Tyr Cys
        275                 280                 285

Ala Thr Trp Asp Ser Ser Leu Ser Ala Val Val Phe Gly Gly Gly Thr
```

```
        290                 295                 300
Lys Leu Thr Val Leu Gly Gln Pro Arg Thr Val Ala Ala Pro Ser Val
305                 310                 315                 320

Phe Ile Phe Pro Pro Ser Asp Glu Gln Leu Lys Ser Gly Thr Ala Ser
                325                 330                 335

Val Val Cys Leu Leu Asn Asn Phe Tyr Pro Arg Glu Ala Lys Val Gln
            340                 345                 350

Trp Lys Val Asp Asn Ala Leu Gln Ser Gly Asn Ser Gln Glu Ser Val
        355                 360                 365

Thr Glu Gln Asp Ser Lys Asp Ser Thr Tyr Ser Leu Ser Ser Thr Leu
    370                 375                 380

Thr Leu Ser Lys Ala Asp Tyr Glu Lys His Lys Val Tyr Ala Cys Glu
385                 390                 395                 400

Val Thr His Gln Gly Leu Ser Ser Pro Val Thr Lys Ser Phe Asn Arg
                405                 410                 415

Gly Glu Cys

<210> SEQ ID NO 41
<211> LENGTH: 476
<212> TYPE: PRT
<213> ORGANISM: Artificial Sequence
<220> FEATURE:
<223> OTHER INFORMATION: Synthetic polypeptide

<400> SEQUENCE: 41

Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
                20                  25                  30

Asn Ile Thr Ser Met Gly Ile Thr Trp Phe Trp Lys Ser Leu Thr Phe
            35                  40                  45

Asp Lys Glu Val Lys Val Phe Glu Phe Phe Gly Asp His Gln Glu Ala
        50                  55                  60

Phe Arg Pro Gly Ala Ile Val Ser Pro Trp Arg Leu Lys Ser Gly Asp
65                  70                  75                  80

Ala Ser Leu Arg Leu Pro Gly Ile Gln Leu Glu Glu Ala Gly Glu Tyr
                85                  90                  95

Arg Cys Glu Val Val Val Thr Pro Leu Lys Ala Gln Gly Thr Val Gln
                100                 105                 110

Leu Glu Val Val Ala Ser Pro Ala Ser Arg Leu Leu Leu Asp Gln Val
            115                 120                 125

Gly Met Lys Glu Asn Glu Asp Lys Tyr Met Cys Glu Ser Ser Gly Phe
        130                 135                 140

Tyr Pro Glu Ala Ile Asn Ile Thr Trp Glu Lys Gln Thr Gln Lys Phe
145                 150                 155                 160

Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
            180                 185                 190

Ser Ser Gln Glu Asp Pro Gly Thr Val Tyr Gln Cys Val Val Arg His
        195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser Gly Gly
225                 230                 235                 240
```

```
Ser Ser Arg Ser Ser Ser Gly Gly Gly Ser Gly Gly Gly
            245                 250                 255

Gln Ser Val Leu Thr Gln Pro Pro Ser Val Ala Ala Pro Gly Gln
            260                 265                 270

Lys Val Thr Val Ser Cys Phe Gly Ser Ser Asn Ile Gly Asn Tyr
            275                 280                 285

Phe Ala Ser Trp Tyr Gln Gln Leu Pro Gly Ala Ala Pro Arg Leu Leu
            290                 295                 300

Ile Tyr Gly Asn Asn Glu Arg Pro Ser Gly Ile Pro Asp Arg Phe Ser
305                 310                 315                 320

Gly Ser Lys Ser Gly Thr Ser Ala Thr Leu Val Ile Thr Gly Leu Gln
                325                 330                 335

Thr Gly Asp Glu Ala Ala Tyr Tyr Cys Ala Thr Trp Asp Ser Ser Leu
            340                 345                 350

Ser Ala Val Val Phe Gly Gly Gly Thr Lys Leu Thr Val Leu Gly Gln
            355                 360                 365

Pro Arg Thr Val Ala Ala Pro Ser Val Phe Ile Phe Pro Pro Ser Asp
            370                 375                 380

Glu Gln Leu Lys Ser Gly Thr Ala Ser Val Val Cys Leu Leu Asn Asn
385                 390                 395                 400

Phe Tyr Pro Arg Glu Ala Lys Val Gln Trp Lys Val Asp Asn Ala Leu
                405                 410                 415

Gln Ser Gly Asn Ser Gln Glu Ser Val Thr Glu Gln Asp Ser Lys Asp
            420                 425                 430

Ser Thr Tyr Ser Leu Ser Ser Thr Leu Thr Leu Ser Lys Ala Asp Tyr
            435                 440                 445

Glu Lys His Lys Val Tyr Ala Cys Glu Val Thr His Gln Gly Leu Ser
            450                 455                 460

Ser Pro Val Thr Lys Ser Phe Asn Arg Gly Glu Cys
465                 470                 475

<210> SEQ ID NO 42
<211> LENGTH: 473
<212> TYPE: PRT
<213> ORGANISM: Artificial Sequence
<220> FEATURE:
<223> OTHER INFORMATION: Synthetic polypeptide

<400> SEQUENCE: 42

Leu Ile Ile Gly Phe Gly Ile Ser Gly Arg His Ser Ile Thr Val Thr
1               5                   10                  15

Thr Val Ala Ser Ala Gly Asn Ile Gly Glu Asp Gly Ile Leu Ser Cys
            20                  25                  30

Thr Phe Glu Pro Asp Ile Lys Leu Ser Asp Ile Val Ile Gln Trp Leu
            35                  40                  45

Lys Glu Gly Val Leu Gly Leu Val His Glu Phe Lys Glu Gly Lys Asp
        50                  55                  60

Glu Leu Ser Glu Gln Asp Glu Met Phe Arg Gly Arg Thr Ala Val Phe
65                  70                  75                  80

Ala Asp Gln Val Ile Val Gly Asn Ala Ser Leu Arg Leu Lys Asn Val
                85                  90                  95

Gln Leu Thr Asp Ala Gly Thr Tyr Lys Cys Tyr Ile Ile Thr Ser Lys
            100                 105                 110

Gly Lys Gly Asn Ala Asn Leu Glu Tyr Lys Thr Gly Ala Phe Ser Met
        115                 120                 125
```

-continued

Pro Glu Val Asn Val Asp Tyr Asn Ala Ser Ser Glu Thr Leu Arg Cys
    130                 135                 140

Glu Ala Pro Arg Trp Phe Pro Gln Pro Thr Val Val Trp Ala Ser Gln
145                 150                 155                 160

Val Asp Gln Gly Ala Asn Phe Ser Glu Val Ser Asn Thr Ser Phe Glu
                165                 170                 175

Leu Asn Ser Glu Asn Val Thr Met Lys Val Ser Val Leu Tyr Asn
                180                 185                 190

Val Thr Ile Asn Asn Thr Tyr Ser Cys Met Ile Glu Asn Asp Ile Ala
            195                 200                 205

Lys Ala Thr Gly Asp Ile Lys Val Thr Glu Ser Glu Ile Lys Arg Arg
    210                 215                 220

Ser His Leu Gln Leu Leu Asn Ser Lys Ala Ser Gly Gly Ser Arg
225                 230                 235                 240

Ser Ser Ser Ser Gly Gly Gly Ser Gly Gly Gly Gln Ser Val
                245                 250                 255

Leu Thr Gln Pro Pro Ser Val Ser Ala Ala Pro Gly Gln Lys Val Thr
                260                 265                 270

Val Ser Cys Phe Gly Ser Ser Asn Ile Gly Asn Tyr Phe Ala Ser
            275                 280                 285

Trp Tyr Gln Gln Leu Pro Gly Ala Ala Pro Arg Leu Leu Ile Tyr Gly
    290                 295                 300

Asn Asn Glu Arg Pro Ser Gly Ile Pro Asp Arg Phe Ser Gly Ser Lys
305                 310                 315                 320

Ser Gly Thr Ser Ala Thr Leu Val Ile Thr Gly Leu Gln Thr Gly Asp
                325                 330                 335

Glu Ala Ala Tyr Tyr Cys Ala Thr Trp Asp Ser Ser Leu Ser Ala Val
                340                 345                 350

Val Phe Gly Gly Gly Thr Lys Leu Thr Val Leu Gly Gln Pro Arg Thr
            355                 360                 365

Val Ala Ala Pro Ser Val Phe Ile Phe Pro Pro Ser Asp Glu Gln Leu
    370                 375                 380

Lys Ser Gly Thr Ala Ser Val Val Cys Leu Leu Asn Asn Phe Tyr Pro
385                 390                 395                 400

Arg Glu Ala Lys Val Gln Trp Lys Val Asp Asn Ala Leu Gln Ser Gly
                405                 410                 415

Asn Ser Gln Glu Ser Val Thr Glu Gln Asp Ser Lys Asp Ser Thr Tyr
                420                 425                 430

Ser Leu Ser Ser Thr Leu Thr Leu Ser Lys Ala Asp Tyr Glu Lys His
            435                 440                 445

Lys Val Tyr Ala Cys Glu Val Thr His Gln Gly Leu Ser Ser Pro Val
    450                 455                 460

Thr Lys Ser Phe Asn Arg Gly Glu Cys
465                 470

<210> SEQ ID NO 43
<211> LENGTH: 400
<212> TYPE: PRT
<213> ORGANISM: Artificial Sequence
<220> FEATURE:
<223> OTHER INFORMATION: Synthetic polypeptide

<400> SEQUENCE: 43

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His
            20                  25                  30

Asp Val Thr Phe Tyr Lys Thr Trp Tyr Arg Ser Ser Arg Gly Glu Val
            35                  40                  45

Gln Thr Cys Ser Glu Arg Arg Pro Ile Arg Asn Leu Thr Phe Gln Asp
50                  55                  60

Leu His Leu His His Gly Gly His Gln Ala Ala Asn Thr Ser His Asp
65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr
            100                 105                 110

Cys Cys Leu Val Val Glu Ile Arg His His Ser Glu His Arg Val
            115                 120                 125

His Gly Ala Met Glu Leu Gln Val Gln Thr Gly Lys Asp Ala Pro Ser
130                 135                 140

Asn Cys Val Val Tyr Pro Ser Ser Gln Asp Ser Glu Asn Ile Thr
145                 150                 155                 160

Ala Ala Gly Gly Ser Ser Arg Ser Ser Ser Gly Gly Gly Ser
                165                 170                 175

Gly Gly Gly Gly Gln Ser Val Leu Thr Gln Pro Pro Ser Val Ser Ala
            180                 185                 190

Ala Pro Gly Gln Lys Val Thr Val Ser Cys Phe Gly Ser Ser Ser Asn
            195                 200                 205

Ile Gly Asn Tyr Phe Ala Ser Trp Tyr Gln Gln Leu Pro Gly Ala Ala
210                 215                 220

Pro Arg Leu Leu Ile Tyr Gly Asn Asn Glu Arg Pro Ser Gly Ile Pro
225                 230                 235                 240

Asp Arg Phe Ser Gly Ser Lys Ser Gly Thr Ser Ala Thr Leu Val Ile
                245                 250                 255

Thr Gly Leu Gln Thr Gly Asp Glu Ala Ala Tyr Tyr Cys Ala Thr Trp
            260                 265                 270

Asp Ser Ser Leu Ser Ala Val Val Phe Gly Gly Thr Lys Leu Thr
            275                 280                 285

Val Leu Gly Gln Pro Arg Thr Val Ala Ala Pro Ser Val Phe Ile Phe
290                 295                 300

Pro Pro Ser Asp Glu Gln Leu Lys Ser Gly Thr Ala Ser Val Val Cys
305                 310                 315                 320

Leu Leu Asn Asn Phe Tyr Pro Arg Glu Ala Lys Val Gln Trp Lys Val
                325                 330                 335

Asp Asn Ala Leu Gln Ser Gly Asn Ser Gln Glu Ser Val Thr Glu Gln
            340                 345                 350

Asp Ser Lys Asp Ser Thr Tyr Ser Leu Ser Ser Thr Leu Thr Leu Ser
            355                 360                 365

Lys Ala Asp Tyr Glu Lys His Lys Val Tyr Ala Cys Glu Val Thr His
370                 375                 380

Gln Gly Leu Ser Ser Pro Val Thr Lys Ser Phe Asn Arg Gly Glu Cys
385                 390                 395                 400

<210> SEQ ID NO 44
<211> LENGTH: 402
<212> TYPE: PRT
<213> ORGANISM: Artificial Sequence
<220> FEATURE:

<223> OTHER INFORMATION: Synthetic polypeptide

<400> SEQUENCE: 44

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Lys Cys Ser Trp Leu Val Thr Lys Ala Gly Ala Gly Thr Ser Ser
145                 150                 155                 160

Ser His Trp Val Gly Gly Ser Arg Ser Ser Ser Gly Gly Gly
                165                 170                 175

Gly Ser Gly Gly Gly Gly Gln Ser Val Leu Thr Gln Pro Pro Ser Val
            180                 185                 190

Ser Ala Ala Pro Gly Gln Lys Val Thr Val Ser Cys Phe Gly Ser Ser
        195                 200                 205

Ser Asn Ile Gly Asn Tyr Phe Ala Ser Trp Tyr Gln Gln Leu Pro Gly
    210                 215                 220

Ala Ala Pro Arg Leu Leu Ile Tyr Gly Asn Asn Glu Arg Pro Ser Gly
225                 230                 235                 240

Ile Pro Asp Arg Phe Ser Gly Ser Lys Ser Gly Thr Ser Ala Thr Leu
                245                 250                 255

Val Ile Thr Gly Leu Gln Thr Gly Asp Glu Ala Ala Tyr Tyr Cys Ala
            260                 265                 270

Thr Trp Asp Ser Ser Leu Ser Ala Val Val Phe Gly Gly Gly Thr Lys
        275                 280                 285

Leu Thr Val Leu Gly Gln Pro Arg Thr Val Ala Ala Pro Ser Val Phe
    290                 295                 300

Ile Phe Pro Pro Ser Asp Glu Gln Leu Lys Ser Gly Thr Ala Ser Val
305                 310                 315                 320

Val Cys Leu Leu Asn Asn Phe Tyr Pro Arg Glu Ala Lys Val Gln Trp
                325                 330                 335

Lys Val Asp Asn Ala Leu Gln Ser Gly Asn Ser Gln Glu Ser Val Thr
            340                 345                 350

Glu Gln Asp Ser Lys Asp Ser Thr Tyr Ser Leu Ser Ser Thr Leu Thr
        355                 360                 365

Leu Ser Lys Ala Asp Tyr Glu Lys His Lys Val Tyr Ala Cys Glu Val
    370                 375                 380

Thr His Gln Gly Leu Ser Ser Pro Val Thr Lys Ser Phe Asn Arg Gly
385                 390                 395                 400

Glu Cys

<210> SEQ ID NO 45
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 45

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Gln Ser Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
```

```
                355                 360                 365
Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 46
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 46

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
            35                  40                  45

Phe Val Ala Gly Glu Glu Asp Leu Lys Pro Gln His Ser Asn Phe Arg
        50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
                100                 105                 110

Asn Ala Gly Gly Ser Ser Arg Ser Ser Ser Gly Gly Gly Gly Ala
            115                 120                 125

Gly Gly Gly Gly Gln Ile Val Leu Ser Gln Ser Pro Ala Ile Leu Ser
        130                 135                 140

Ala Ser Pro Gly Glu Lys Val Thr Met Thr Cys Arg Ala Ser Ser Ser
145                 150                 155                 160

Val Ser Tyr Ile His Trp Phe Gln Gln Lys Pro Gly Ser Ser Pro Lys
                165                 170                 175

Pro Trp Ile Tyr Ala Thr Ser Asn Leu Ala Ser Gly Val Pro Val Arg
            180                 185                 190

Phe Ser Gly Ser Gly Ser Gly Thr Ser Tyr Ser Leu Thr Ile Ser Arg
        195                 200                 205

Val Glu Ala Glu Asp Ala Ala Thr Tyr Tyr Cys Gln Gln Trp Thr Ser
    210                 215                 220

Asn Pro Pro Thr Phe Gly Gly Gly Thr Lys Leu Glu Ile Lys Arg Thr
225                 230                 235                 240

Val Ala Ala Pro Ser Val Phe Ile Phe Pro Pro Ser Asp Glu Gln Leu
                245                 250                 255

Lys Ser Gly Thr Ala Ser Val Val Cys Leu Leu Asn Asn Phe Tyr Pro
```

```
            260                 265                 270
Arg Glu Ala Lys Val Gln Trp Lys Val Asp Asn Ala Leu Gln Ser Gly
            275                 280                 285

Asn Ser Gln Glu Ser Val Thr Glu Gln Asp Ser Lys Asp Ser Thr Tyr
        290                 295                 300

Ser Leu Ser Ser Thr Leu Thr Leu Ser Lys Ala Asp Tyr Glu Lys His
305                 310                 315                 320

Lys Val Tyr Ala Cys Glu Val Thr His Gln Gly Leu Ser Ser Pro Val
                325                 330                 335

Thr Lys Ser Phe Asn Arg Gly Glu Cys
                340                 345

<210> SEQ ID NO 47
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Gly Trp Gly Trp Ile Arg Gln Pro Pro Gly Lys Gly Leu Glu Trp
        35                  40                  45

Ile Gly Ser Phe Tyr Ser Ser Gly Asn Thr Tyr Tyr Asn Pro Ser
50                  55                  60

Leu Lys Ser Gln Val Thr Ile Ser Thr Asp Thr Ser Lys Asn Gln Phe
65                  70                  75                  80

Ser Leu Lys Leu Asn Ser Met Thr Ala Ala Asp Thr Ala Val Tyr Tyr
                85                  90                  95

Cys Val Arg Asp Arg Leu Phe Ser Val Val Gly Met Val Tyr Asn Asn
            100                 105                 110

Trp Phe Asp Val Trp Gly Pro Gly Val Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Gln Ser Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
```

```
              275                 280                 285
Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 48
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 48

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
            35                  40                  45

Phe Val Ala Gly Glu Glu Asp Leu Lys Pro Gln His Ser Asn Phe Arg
        50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
                100                 105                 110

Asn Ala Gly Gly Ser Ser Arg Ser Ser Ser Gly Gly Gly Gly Ser
            115                 120                 125

Gly Gly Gly Gly Glu Ser Val Leu Thr Gln Pro Pro Ser Val Ser Gly
        130                 135                 140

Ala Pro Gly Gln Lys Val Thr Ile Ser Cys Thr Gly Ser Thr Ser Asn
145                 150                 155                 160

Ile Gly Gly Tyr Asp Leu His Trp Tyr Gln Gln Leu Pro Gly Thr Ala
                165                 170                 175

Pro Lys Leu Leu Ile Tyr Asp Ile Asn Lys Arg Pro Ser Gly Ile Ser
```

```
                  180                 185                 190
Asp Arg Phe Ser Gly Ser Lys Ser Gly Thr Ala Ala Ser Leu Ala Ile
            195                 200                 205

Thr Gly Leu Gln Thr Glu Asp Glu Ala Asp Tyr Tyr Cys Gln Ser Tyr
            210                 215                 220

Asp Ser Ser Leu Asn Ala Gln Val Phe Gly Gly Thr Arg Leu Thr
225                 230                 235                 240

Val Leu Gly Gln Pro Lys Ala Ala Pro Ser Val Thr Leu Phe Pro Pro
                245                 250                 255

Ser Ser Glu Glu Leu Gln Ala Asn Lys Ala Thr Leu Val Cys Leu Ile
            260                 265                 270

Ser Asp Phe Tyr Pro Gly Ala Val Thr Val Ala Trp Lys Ala Asp Ser
            275                 280                 285

Ser Pro Val Lys Ala Gly Val Glu Thr Thr Thr Pro Ser Lys Gln Ser
            290                 295                 300

Asn Asn Lys Tyr Ala Ala Ser Ser Tyr Leu Ser Leu Thr Pro Glu Gln
305                 310                 315                 320

Trp Lys Ser His Arg Ser Tyr Ser Cys Gln Val Thr His Glu Gly Ser
                325                 330                 335

Thr Val Glu Lys Thr Val Ala Pro Thr Glu Cys Ser
                340                 345
```

ANTIBODY IMMUNE CELL INHIBITOR FUSION PROTEINS

CROSS REFERENCE

This application is a national stage application under 35 U.S.C. § 371 of International Application No. PCT/US2018/028963, filed Apr. 23, 2018, which claims priority to U.S. Provisional Patent Application Ser. No. 62/489,027, filed Apr. 24, 2017, the disclosures of which are incorporated by referenced herein in is their entirety.

FIELD OF THE INVENTION

The disclosure relates to antibody immune cell inhibitor fusion proteins comprising four polypeptide chains that form two antigen binding sites and at least two immune cell receptor binding sites that inhibit or diminish activation of an immune effector cell when bound to a target antigen. The disclosure also relates to antibody immune cell inhibitor fusion proteins comprising two polypeptide chains that form one antigen binding site and at least one immune cell receptor binding site that inhibit or diminish activation of an immune effector cell when bound to a target antigen. The disclosure further relates to pharmaceutical compositions and kits that comprise such antibody immune cell inhibitor fusion proteins, and methods of treatment using such proteins.

BACKGROUND

Autoimmune disorders are diseases caused by a dysfunction of the immune system, wherein the body produces an inappropriate immune response against its own tissues. As a result, the immune system creates B and T lymphocytes, autoantibodies, monocytes, NK cells, antigen presenting cells, and other immune factors that attack or facilitate immune responses to an individual's own cells, tissues, and/or organs.

Autoimmune diseases are among the most prevalent diseases in the United States. The National Institutes of Health (NIH) estimates that up to 23.5 million Americans suffer from an autoimmune disease, and that the prevalence of such diseases is rising. Some of the current treatments for autoimmune diseases include administration of corticosteroid drugs, non-steroidal anti-inflammatory drugs (NSAIDs), or more powerful immunosuppressant drugs such as cyclophosphamide, methotrexate, and azathioprine that suppress the immune response and stop the progression of the disease. Radiation of the lymph nodes and plasmapheresis (a procedure that removes the diseased cells and harmful molecules from a patient's blood circulation) are other ways of treating an autoimmune disease. However, these treatments often have devastating long-term side effects.

Primary Biliary Cholangitis (PBC) is an autoimmune disease of the liver characterized by T-lymphocyte mediated destruction of the intrahepatic bile ducts. The continuous attack on the bile duct epithelial cells leads to cholestasis, fibrosis, cirrhosis, liver failure, and death. Symptomatic patients generally become very ill in 3 to 5 years, and require a liver transplant soon thereafter. Ursodeoxycholic acid (UDCA) is the only FDA approved treatment for PBC, which ameliorates symptoms of the disease by primarily sequestering bile acid. Once symptoms manifest in an individual, life expectancy is less than 10 years, unless a liver transplant becomes available.

The hallmark diagnosis for PBC is through the detection of serum autoantibodies known as anti-mitochondrial antibodies (AMAs) found in >95% of PBC patients. Most AMAs are reported to react with dihydrolipoamide S-acetyl-transferase (DLAT), the E2 subunit of the mitochondrial pyruvate dehydrogenase complex. Aberrant expression of DLAT or mimic antigens on biliary epithelial cells provide the target for an autoimmune attack in PBC.

SUMMARY

The disclosure provides an antibody immune cell inhibitor fusion protein comprising four polypeptide chains that form two antigen binding sites and at least two immune cell receptor binding sites; wherein two polypeptide chains have a structure represented by the formula $II_1\text{-}V_L\text{-}C_L\text{-}II_2$, and two polypeptide chains have a structure represented by the formula $II_3\text{-}V_H\text{-}C_{H1}\text{-}Fc\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;

Fc is the immunoglobulin hinge region and $C_{H2}$ and $C_{H3}$ immunoglobulin heavy chain constant domains; and $II_1$, $II_2$, $II_3$, and $II_4$ are each independently an immune cell inhibitor domain of an immunoglobulin superfamily member or are absent;

wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

The disclosure also provides an antibody immune cell inhibitor fusion protein comprising four polypeptide chains that form two antigen binding sites and at least two immune cell receptor binding sites; wherein two polypeptide chains have a structure represented by the formula $II_1\text{-}L_1\text{-}V_L\text{-}C_L\text{-}L_2\text{-}II_2$, and two polypeptide chains have a structure represented by the formula $II_3\text{-}L_3\text{-}V_H\text{-}C_{H1}\text{-}Fc\text{-}L_4\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;

Fc is the immunoglobulin hinge region and $C_{H2}$ and $C_{H3}$ immunoglobulin heavy chain constant domains;

$L_1$, $L_2$, $L_3$ and $L_4$ are each independently a linker domain or are absent; and $II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

The disclosure further provides an antibody immune cell inhibitor fusion protein comprising two polypeptide chains that form one antigen binding site and at least one immune cell receptor binding site; wherein one polypeptide chain has a structure represented by the formula $II_1\text{-}V_L\text{-}C_L\text{-}II_2$, and one polypeptide chain has a structure represented by the formula $II_3\text{-}V_H\text{-}C_{H1}\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain; and
$II_1$, $II_2$, $II_3$, and $II_4$ are each independently an immune cell inhibitor domain of an immunoglobulin superfamily member or are absent;

wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

The disclosure further provides an antibody immune cell inhibitor fusion protein comprising two polypeptide chains that form one antigen binding site and at least one immune cell receptor binding site; wherein one polypeptide chain has a structure represented by the formula $II_1$-$L_1$-$V_L$-$C_L$-$L_2$-$II_2$, and one polypeptide chain has a structure represented by the formula $II_3$-$L_3$-$V_H$-$C_{H1}$-$L_4$-$II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
$L_1$, $L_2$, $L_3$ and $L_4$ are each independently a linker domain or are absent; and
$II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

Specific embodiments of the disclosure will become evident from the following more detailed description of certain embodiments and the claims.

BRIEF DESCRIPTION OF THE DRAWINGS

FIG. 1A illustrates that TPP-993 (PD2 Fab having no PD-L1 domain and no linker) did not bind to PD-1 Fc because TPP-993 lacks a PD-L1 domain. FIGS. 1B and 1D illustrate that TPP-994 (PD2 with PD-L1 fused to the C-terminus of the heavy chain) and TPP-999 (PD2 with PD-L1 fused to the C-terminus of the light chain) exhibited very little binding to PD-1 Fc. FIGS. 1C and 1E illustrate that TPP-995 (PD2 with PD-L1 fused to the N-terminus of the heavy chain) and TPP-1001 (PD2 with PD-L1 fused to the N-terminus of the light chain) both exhibited binding to PD-1 Fc. FIG. 1F illustrates that PD-L1 Fc (a dimeric protein having two PD-L1 proteins fused to a human Fc) bound PD-1 very strongly. FIG. 1G illustrates that PD-1 Fc did not bind to itself, demonstrating that the Fc portion of PD-L1 Fc is not interacting with the tips.

FIG. 2A illustrates slow on-rates and fast off-rates for the TPP-1003 PD2 antibody. FIGS. 2B and 2C illustrate slow off-rates for the TPP-1004 and TPP-1005 anti-DLAT antibodies.

FIG. 3A illustrates that TPP-985 (human IgG2/4 PD5 antibody) bound to the DLAT antigen, but did not bind to PD-1 Fc. FIGS. 3B and 3D illustrate that TPP-986 and TPP-992 (fusions of the PD-L1 V-like domain to the N-terminus of anti-DLAT antibodies) both exhibited the ability to simultaneously bind the DLAT antigen and PD-1 Fc. FIG. 3C illustrates that TPP-990 (PD-L1 V-like domain fused to the C-terminus of an anti-DLAT antibody) bound the DLAT antigen, but did not bind PD-1 Fc. FIG. 3E illustrates that the PD-L1 Fc control bound to PD-1 Fc, but did not bind to the DLAT antigen.

FIGS. 4A-4F show human T-cell activation for targeted PD-L1 fusion inhibition. Representative histograms of one of three replicates are shown for each sample at 260 nM and 65 nM concentrations of antibody fusions or non-targeted PD-L1 Fc. FIG. 4A illustrates that NC beads exhibited no activation of T-cells, whereas the DLAT-aCD3 beads demonstrated clear activation of the pan T-cells. FIG. 4B illustrates that TPP-985 (an anti-DLAT IgG2-4 antibody with no PD-L1 variable-like domain) exhibited no significant inhibition of T-cell activation. FIG. 4C illustrates that TPP-986 (an anti-DLAT antibody with PD-L1 fused at the N-terminus of the heavy chain) exhibited significant inhibition of T-cell activation at both the 65 nM and 260 nM concentrations. FIG. 4D ill

FIGS. 11A-11D illustrate the BIAcore kinetics results for TPP-1003, TPP-1004, and TPP-1005. FIG. 11A illustrates that TPP-1003 and TPP-1004 had pico-molar binding to the DLAT antigen and TPP-1005 had a single digit nano-molar affinity to the DLAT antigen. FIGS. 11B, 11C and 11D illustrate the BIAcore kinetics for TPP-1003, TPP-1004, and TPP 1005, respectively.

FIGS. 12A-12F show mouse T-cell activation for targeted PD-L1 fusion inhibition. Samples were gated to exclude the low Forward Scatter (FSC) and the FL-4+(SYTOX™ Red) dead cells. The same gate was utilized to analyze all samples. The histograms shown are gated on the live mouse T-cells. The decrease in signal of the FL-1 mean fluorescence measurement represents the activated T-cells that have expanded new generations of T-cells, with decreasing dye concentration in each respective generation. FIG. 12A illustrates complete inhibition of mouse T-cell activation for TPP-1986 at 500 nM with an incomplete inhibition observed for 100 nM. FIG. 12B illustrates that TPP-1694 had a significant difference compared to the NC beads, but showed no significant difference compared to TPP-1986 at 500 nM. A significant difference was observed at 100 nM for human TPP-1986 and TPP-992 versus mouse PD-L1-TPP-1694. FIG. 12C illustrates that TPP-1695 demonstrated a lower potency compared to the PD5 human PD-L1 fusion variants at 500 nM and 100 nM concentrations with similar results observed for TPP-1694. FIG. 12D illustrates complete inhibition of mouse T-cell activation for TPP-992 at 500 nM with an incomplete inhibition for 100 nM. FIGS. 12E and 12F illustrate that TPP-1697 (non-targeted isotype control with human PD-L1) and TPP-1004 (murine IgG1 PD5 with no PD-L1 variable-like domain present), showed no significant inhibition of mouse T-cell activation.

FIGS. 13A and 13B show the statistical analysis of the mouse T-cell activation results at 500 nM. FIG. 13A illustrates complete inhibition of TPP-1986 and TPP-992 fusions containing human PD-L1 demonstrated by a not significant difference compared to the NC beads. An expected decrease in the geometric mean fluorescence intensity (Geo MFI) of FL-1 representing the CFSE dye diffusion into progeny cells for the 1× beads, TPP-1697, and TPP-1004 was observed, illustrating activation of the murine T-cells with no significant differences between samples. FIG. 13B is a table of statistical analysis between samples at 500 nM concentrations using Tukey's multiple comparisons test.

FIGS. 14A and 14B show the statistical analysis of the mouse T-cell activation results at 500 nM. FIG. 14A illustrates complete inhibition of TPP-1986 and TPP-992 fusions containing human PD-L1 demonstrated by a not significant difference compared to the NC beads and incomplete inhibition of TPP-1504 containing hB7-H4. An expected decrease in the geometric mean fluorescence intensity (Geo MFI) of FL-1 representing the CFSE dye diffusion into progeny cells for the 1× beads, TPP-1697 and TPP-1505 was observed, illustrating activation of the murine T-cells. FIG. 14B is a table of statistical analysis between samples at 500 nM concentrations using Tukey's multiple comparisons test.

FIGS. 15A and 15B show the statistical analysis of the mouse T-cell activation results at 100 nM. FIG. 15A illustrates incomplete inhibition using fusions containing human PD-L1 compared to the NC beads. A significant difference of human versus murine PD-L1 containing fusions was observed, suggesting human PD-L1 results in greater inhibition of mouse T-cells than mouse PD-L1 V-like domain. An expected decrease in the geometric mean fluorescence intensity (Geo MFI) of FL-1 representing the CFSE dye diffusion into progeny cells for the 1× beads, TPP-1697, and TPP-1004 was observed, illustrating activation of the murine T-cells with no significant differences between samples. FIG. 15B is a table of statistical analysis between samples at 100 nM concentrations using Tukey's multiple comparisons test.

FIGS. 16A and 16B show the statistical analysis of the mouse T-cell activation results at 100 nM. FIG. 16A illustrates incomplete inhibition using fusions containing human PD-L1 and hB7-H4 as compared to the NC beads. An expected decrease in the geometric mean fluorescence intensity (Geo MFI) of FL-1 representing the CFSE dye diffusion into progeny cells for the 1× beads, TPP-1697 and TPP 1505 was observed illustrating activation of the murine T-cells. FIG. 16B is a table of statistical analysis between samples at 100 nM concentrations using Tukey's multiple comparisons test.

FIGS. 18A-18D show the statistical analysis of the human T-cell activation results. FIG. 18A illustrates that at the 500 nM concentration of the anti-DLAT PD-L1 (TPP-1986), B7H4 (TPP-1504), HVEM (TPP-1506), B7H6 (TPP-1894) and CTLA4 (TPP-1898) fusions tested at day 7 inhibited T-cell activation. FIG. 18B illustrates the statistical analysis summary of all samples in the T-cell activation assay. FIG. 18C illustrates that at the 500 nM concentration of the anti-DLAT fusions only PDL-2 (TPP-2215), CD200 (TPP-2216), TIM-3 (TPP-2220) and PD-L1 (TTP-992) showed inhibition of T cell activation at day 4. FIG. 18D illustrates the statistical analysis summary of T-cell activation inhibition for anti-DLAT antibody fusion proteins.

FIGS. 19A and 19B illustrates human T-cell activation at 4 days for 500 nM concentration of PD-L1 Fab fusions. FIG. 19B illustrates the statistical analysis summary of T-cell activation inhibition for PD-L1 fab fusions. V=V-like domain of PDL1; V–C=V–+C-like domains of PDL1; HC=PDL1 fused to N-terminus of Heavy Chain and LC=PDL1 fused to N-terminus of Light Chain.

FIGS. 20A-20D show the statistical analysis of the mouse CD4+ T-cell activation results. FIG. 20A illustrates that at 500 nM concentration of the anti-DLAT PD-L1 (TPP-1984), PD-5 (TPP-1694), and CTLA4 (TPP-1898) fusions tested at day 7 inhibited T-cell activation. FIG. 20B illustrates the statistical analysis summary of all samples in the T-cell activation assay. FIG. 20C illustrates that at the 125 nM a lower level of T-cell activation inhibition was observed with TPP-1898 showing the highest level of inhibition. FIG. 20D illustrates the statistical analysis summary of T-cell activation inhibition for anti-DLAT antibody fusion proteins.

FIG. 21A illustrate flow cytometry results demonstrating low levels of CD25 for the no activation control (labeled NO BEADS) with 1.71% in quadrant 2 (Q2) representing the CD4+, CD25+ population. The histogram shown below the dot plot represents the intracellular staining with FoxP3 of the Q2 gated events. The activated T-cells (labeled DLAT) showed a significant increase in effector T-cells (Teff) in Q2, however a small percentage of these CD4+, CD25+ cells were Tregs (FoxP3+). FIG. 21B illustrates inhibition of the Teff population shown as 7% in Q2 with the addition of TPP-992 (labeled DLAT DRUG) to the DLAT activation beads, compared to 32% for DLAT beads only. In addition, from the Q2 population, the FoxP3 positive events went from 7% to 16% with the drug. Anti-VAP-1_PDL1 previously showed weaker inhibition in the T-cell activation assay using proliferation dye compared to the anti-DLAT_PDL1 (data not shown). This intermediate effect of anti-VAP-1 fusion was confirmed by the results of this assay; a higher percentage of Q2 events were observed (18%), with a lower induction of Tregs 12% compared to anti-DLAT_PDL1.

DETAILED DESCRIPTION

Figure 1A:
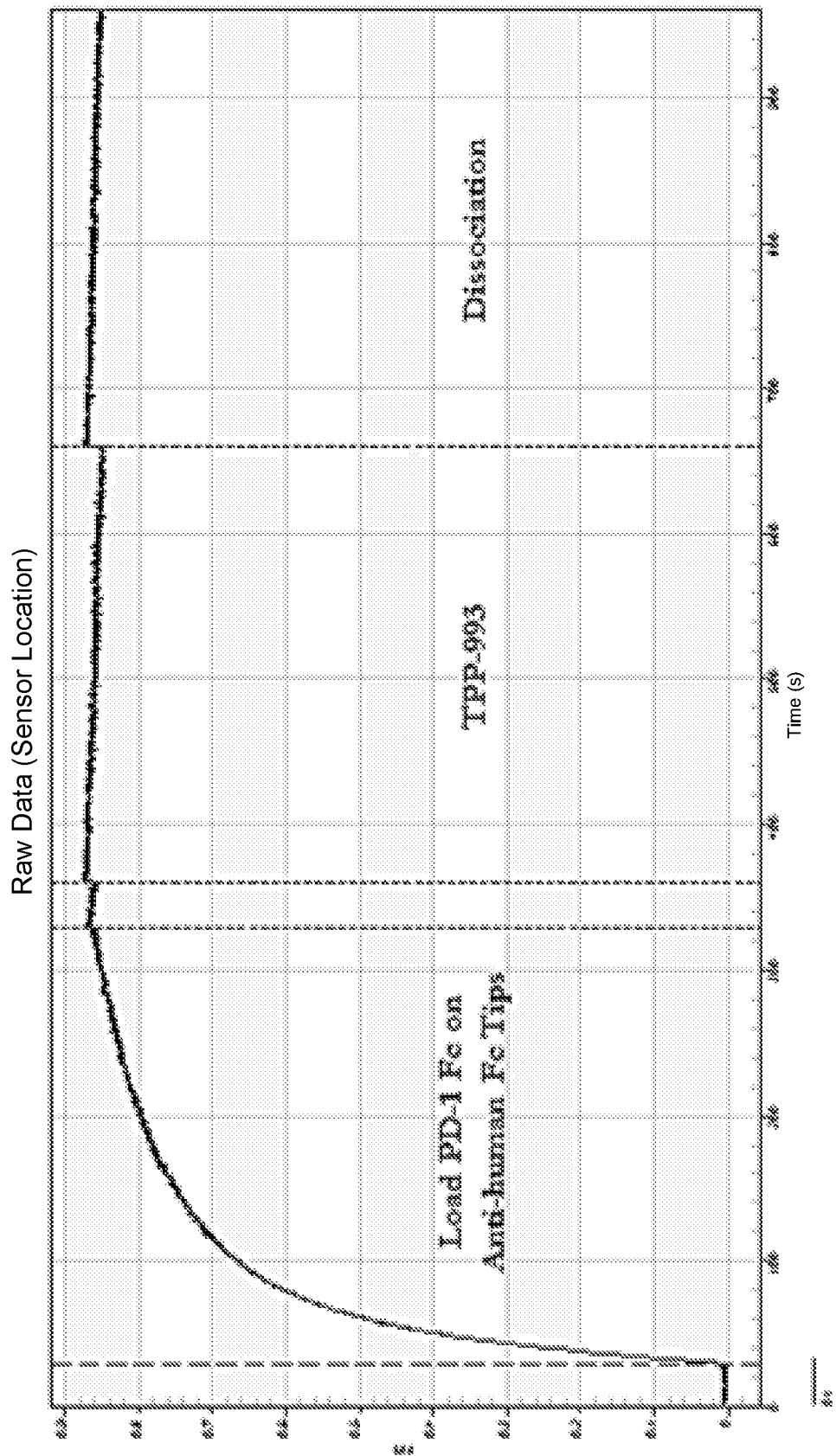
FIGS. 1A-1G show bio-layer interferometry results of PD-1 binding to PD-L1 fusion proteins.

The disclosure provides antibody immune cell inhibitor fusion proteins comprising four polypeptide chains that form two antigen binding sites and at least two immune cell receptor binding sites and that inhibit or diminish activation of an immune effector cell when bound to a target antigen. The disclosure also provides antibody immune cell inhibitor fusion proteins comprising two polypeptide chains that form one antigen binding site and at least one immune cell receptor binding site that inhibit or diminish activation of an immune effector cell when bound to a target antigen. The disclosure further provides pharmaceutical compositions and kits that comprise such antibody immune cell inhibitor fusion proteins, and methods of treatment using such proteins.

Standard recombinant DNA methodologies are used to construct the polynucleotides that encode the polypeptides that form the antibody immune cell inhibitor fusion proteins of the disclosure, incorporate these polynucleotides into recombinant expression vectors, and introduce such vectors into host cells. See e.g., Green and Sambrook, 2012, MOLECULAR CLONING: A LABORATORY MANUAL (Cold Spring Harbor Laboratory Press, 4th ed.). Enzymatic reactions and purification techniques may be performed according to manufacturer's protocols, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

1. General Definitions

As utilized in accordance with the present disclosure, the following terms, unless otherwise indicated, shall be understood to have the following meanings. Unless otherwise required by context, singular terms shall include pluralities and plural terms shall include the singular.

The term "antibody immune cell inhibitor fusion protein" as used herein refers to a non-naturally occurring (or recombinant) molecule which comprises four polypeptide chains that form two antigen binding sites and at least two immune cell receptor binding sites; wherein two polypeptide chains have a structure represented by the formula $II_1\text{-}V_L\text{-}C_L\text{-}II_2$, and two polypeptide chains have a structure represented by the formula $II_3\text{-}V_H\text{-}C_{H1}\text{-}Fc\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$ and $C_{H3}$ immunoglobulin heavy chain constant domains; and
$II_1$, $II_2$, $II_3$, and $II_4$ are each independently an immune cell inhibitor domain of an immunoglobulin superfamily member or are absent;
wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

The term "antibody immune cell inhibitor fusion protein" as used herein also refers to a non-naturally occurring (or recombinant) molecule which comprises four polypeptide chains that form two antigen binding sites and at least two immune cell receptor binding sites; wherein two polypeptide chains have a structure represented by the formula $II_1\text{-}L_1\text{-}$ $V_L$-$C_L$-$L_2$-$II_2$, and two polypeptide chains have a structure represented by the formula $II_3$-$L_3$-$V_H$-$C_{H1}$-Fc-$L_4$-$II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$ and $C_{H3}$ immunoglobulin heavy chain constant domains;

$L_1$, $L_2$, $L_3$ and $L_4$ are each independently a linker domain or are absent; and $II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

The term "antibody immune cell inhibitor fusion protein" as used herein also refers to a non-naturally occurring (or recombinant) molecule which comprises two polypeptide chains that form one antigen binding site and at least one immune cell receptor binding site; wherein one polypeptide chain has a structure represented by the formula $II_1$-$V_L$-$C_L$-$II_2$, and one polypeptide chain has a structure represented by the formula $II_3$-$V_H$-$C_{H1}$-$II_4$, wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain;

$II_1$, $II_2$, $II_3$, and $II_4$ are each independently an immune cell inhibitor domain of an immunoglobulin superfamily member or are absent;

wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

The term "antibody immune cell inhibitor fusion protein" as used herein also refers to a non-naturally occurring (or recombinant) molecule which comprises two polypeptide chains that form one antigen binding site and at least one immune cell receptor binding site, wherein one polypeptide chain has a structure represented by the formula $II_1$-$L_1$-$V_L$-$C_L$-$L_2$-$II_2$, and one polypeptide chain has a structure represented by the formula $II_3$-$L_3$-$V_H$-$C_{H1}$-$L_4$-$II_4$, wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain;

$L_1$, $L_2$, $L_3$ and $L_4$ are each independently a linker domain or are absent; and $II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

The term "antibody" as used herein refers to a protein that is capable of recognizing and specifically binding to an antigen. Ordinary or conventional mammalian antibodies comprise a tetramer, which is typically composed of two identical pairs of polypeptide chains, each pair consisting of one "light" chain (typically having a molecular weight of about 25 kDa) and one "heavy" chain (typically having a molecular weight of about 50-70 kDa). The terms "heavy chain" and "light chain," as used herein, refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The variable domain may be subjected to further protein engineering to humanize the framework regions if the antibody was derived from a non-human source. The carboxyl-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$) and a hinge region between $C_{H1}$ and $C_{H2}$, wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Within full-length light and heavy chains, the variable and constant domains typically are joined by a "J" region of about 12 or more amino acids, with the heavy chain also including a "D" region of about 10 more amino acids. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "IgG2/4" as used herein refers to the non-naturally occurring, protein-engineered, heavy chain developed for use in eculizumab ($C_{H1}$-Hinge-$C_{H2}$-$C_{H3}$) and designed to reduce immune effector function and immune cell activation, minimize immunogenicity, and contribute to a longer half-life. This non-IgG 1, 2, 3 or 4 heavy chain is a chimera containing sequence elements of IgG4 and IgG2 including two disulfide bonds in the hinge and changes in the constant regions $C_{H1}$ and $C_{H2}$.

The term "human antibody" as used herein includes antibodies having variable and constant regions substantially corresponding to circulating human antibodies and human germline immunoglobulin sequences. In some embodiments, human antibodies are produced in non-human transgenic mammals, including, but not limited to, rodents, such as mice and rats, and lagomorphs, such as rabbits. In other embodiments, human antibodies are produced in hybridoma cells. In still other embodiments, human antibodies are produced recombinantly.

The term "antibody fragment" refers to a portion of an intact or full-length chain or an antibody, generally the target binding or variable region. Examples of antibody fragments include, but are not limited to, $F_{ab}$, $F_{ab'}$, $F_{(ab')2}$ and $F_v$ fragments. As used herein, the term "functional fragment" is generally synonymous with "antibody fragment," and with respect to antibodies, can refer to antibody fragments such as $F_v$, $F_{ab}$, $F_{(ab')2}$.

The term "autoantibody" as used herein refers to a naturally obtained antibody produced by an individual, wherein the antibody recognizes and binds to an antigen derived from or which mimics an antigen derived from a human tissue. An autoantibody can facilitate an immune response against a self-tissue or self-antigen (i.e., antigens that are native to the individual, e.g., an antigen on a cell or tissue, or an endogenous peptide or protein). Autoantibodies frequently arise or are triggered by an infection with an infectious agent such as a virus, bacteria or parasite, where the infectious agent carried a structure that induces antibodies to the structure. The induced antibodies can become harmful in the infection aftermath where that inducing biologic structure is also found on naturally occurring human tissues, thus creating an aberrant and continuing autoantibody response in the aftermath of the infection. The autoantibody can be redesigned and repurposed, as described herein, from the natural autoantibody to modify the original structure found in a diseased individual. The autoantibody may be re-humanized and the heavy chain may be modified to alter the isotype or to otherwise modulate harmful secondary immune functions of the autoantibody. The modified autoantibody can be used to produce a therapeutic fusion protein to treat the disorder created by an aberrant autoantibody response. The autoantibody may also be re-engineered and/or re-derived from or into a single chain Camelid VHH antibody format.

The term "antigen" or "target antigen" as used herein refers to a molecule or a portion of a molecule that is capable of being recognized by and bound by an antibody or the antigen binding portion of the antibody immune cell inhibitor fusion proteins of the disclosure. The target antigen is capable of being used in an animal to produce antibodies capable of binding to an epitope of that antigen. A target antigen may have one or more epitopes. With respect to each target antigen recognized by an antibody or the antigen binding portion of the antibody immune cell inhibitor fusion protein, the antibody or the antigen binding portion of the fusion protein is capable of competing with an intact antibody that recognizes the target antigen.

The term "epitope" as used herein refers to a region or structural element of an antigen that is recognized and bound by an antibody or the antigen binding portion of the antibody immune cell inhibitor fusion protein of the disclosure. More precisely, the epitope is the specific structure that is bound by the CDRs of the antibody. Epitopes can comprise protein structural elements, carbohydrates or even portions of lipid structures found in membranes. An antibody or the antigen binding portion of the antibody immune cell inhibitor fusion protein is said to specifically bind an antigen when it preferentially recognizes its antigen target in a complex mixture of proteins and/or macromolecules. The term "specifically binds," as used herein, refers to the ability of an antibody or antigen binding portion of the antibody immune cell inhibitor fusion protein to bind to an antigen containing an epitope with an Kd of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or to bind to an epitope with an affinity that is at least two-fold greater than its affinity for a nonspecific antigen.

The term "antigen binding site" as used herein refers to a site created on the surface of an antibody or the antigen binding portion of the antibody immune cell inhibitor fusion protein of the disclosure where an antigen or an epitope on an antigen is bound. The antigen binding site of an antibody or the antigen binding portion or surface of the antibody immune cell inhibitor fusion protein is typically described by reference to the loop structures created by complementarity determining regions (CDRs) of the antibody or antibody immune cell inhibitor fusion protein.

The term "ligand" as used herein refers to a chemical molecule or biological molecule that can bind readily to a receptor with a specific binding affinity constant. The ligand may be natural or synthetic.

The term "receptor" as used herein refers to a protein capable of interacting (binding) with a ligand. In some embodiments, such a protein is capable of transmitting information resulting from interaction with a ligand, into a cell.

In some circumstances, the terms ligand and receptor may be interchangeable because both the ligand and receptor may be surface bound proteins on different cells that interact with each other. Depending on which cell is the focal point, a receptor on one cell is a ligand of another receptor on a different cell however if the cell which is the focal point is reversed, so is the receptor ligand relationship. In some circumstances both interacting molecules are surface bound and the receptor-ligand relationship is not strict, but merely designates two different molecules interacting with another and causing cell signaling consequences.

The term "native Fc" as used herein refers to a molecule comprising the sequence of a non-antigen binding fragment resulting from digestion of an antibody or produced by other means, whether in monomeric or multimeric form, and can contain the hinge region. The original immunoglobulin source of the native Fc is preferably of human origin and can be any of the immunoglobulins. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed or mutated to produce an Fc variant to alter certain residues that provide structural features or biological activity that are not required for the antibody immune cell inhibitor fusion proteins of the disclosure. Thus, the term "Fc variant" comprises a molecule or sequence that lacks one or more native Fc sites or residues, or in which one or more Fc sites or residues has been modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

Modifications to the Fc Region

An antibody or antibody immune cell inhibitor fusion protein of the disclosure described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody or antibody immune cell inhibitor fusion protein containing the variant Fc constant region to FcRn at pH 6.0, while maintaining the pH dependence of the interaction. See, e.g., Hinton et al., 2004, *J. Biol. Chem.* 279(8): 6213-16; and Datta-Mannan et al., 2007, *Drug Metab. Dispos.* 35(1): 86-94. Methods for testing whether one or more substitutions in the Fc constant region of an antibody increases the affinity of the Fc constant region for FcRn at pH 6.0 (while maintaining pH dependence of the interaction) are known in the art. See, e.g., Datta-Mannan et al., 2007, *J. Biol. Chem.* 282(3): 1709-17; International Publication Nos. WO 98/23289 and WO 97/34631; and U.S. Pat. No. 6,277,375, the disclosures of each of which are incorporated herein by reference in their entirety.

Substitutions that enhance the binding affinity of an antibody Fc constant region for FcRn are known in the art and include, for example: (1) the M252Y/S254T/T256E triple substitution described by Dall'Acqua et al., 2006, *J. Biol. Chem.* 281(33): 23514-24; (2) the M428L or T250Q/ M428L substitutions described in Hinton et al., 2004, *J. Biol. Chem.* 279(8): 6213-16, and Hinton et al., 2006, *J. Immunol.* 176(1): 346-56; and (3) the N434A or T307/ E380A/N434A substitutions described in Petkova et al., 2006, *Int. Immunol.* 18(12): 1759-69, the disclosures of which are incorporated herein by reference in their entirety. The additional substitution pairings P257I/Q311I, P257I/ N434H, and D376V/N434H are described in, for example, Datta-Mannan et al., 2007, *J. Biol. Chem.* 282(3): 1709-17, the disclosure of which is incorporated herein by reference in its entirety.

Many mutations to modify Fc biological properties have been identified and may be useful depending on the biology of the disease being treated. In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386 for leucine.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, 9, 8, 7, 6, 5, 4, 3, or 2) amino acid substitutions, insertions, or deletions relative to the native constant region from which it was derived. In some embodiments, the variant Fc constant region comprises one or more amino acid substitutions selected from the group consisting of M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, for example, U.S. Pat. No. 9,079,949.

In some embodiments, when the eculizumab heavy chain is used as the starting heavy chain, the 428L/434S mutations are shifted to 429L/435S as a result of the IgG2/4 chimerization engineering. Furthermore, the precise mutations in the eculizumab heavy chain are Met-429-Leu and Asn-435-Ser. See U.S. Pat. No. 9,079,949, the disclosure of which is hereby incorporated by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436 (all in EU numbering).

An "immune cell inhibitor domain" as used herein refers to an immunoglobulin domain of an immunoglobulin superfamily member that can cause suppression of immune responses upon binding to the specific receptor on an immune system cell, including inhibition of T-cells, B-cells, monocytes, and antigen presenting cells, inhibition of a particular immune cell function, including cytotoxicity, or any combination of the above responses. The immune cell inhibitor domains of the antibody immune cell inhibitor fusion proteins of the disclosure are referred to herein as follows: $II_1$, which, when present, is fused (with or without an intervening linker) to the N-terminal end of the light chain; $II_2$, which, when present, is fused (with or without an intervening linker) to the C-terminal end of the light chain; $II_3$, which, when present, is fused (with or without an intervening linker) to the N-terminal end of the heavy chain; and $II_4$, which, when present, (with or without an intervening linker) is fused to the C-terminal end of the heavy chain. Linkers may or may not be needed depending on the where the stop and start residues of protein fusions are chosen because often natural linkers are found between immunoglobulin domains.

The term "immunoglobulin superfamily member" as used herein refers to a class of proteins that are associated with the adhesion, binding, and recognition processes of cells. Exemplary members of the immunoglobulin superfamily include, but are not limited to, Programmed Death Ligand 1 (PD-L1), also known as B7 Homolog 1 (B7-H1), or CD274; Programmed Death Ligand 2 (PD-L2), also known as B7-DC; B7 Homolog 3 (B7-H3), as known as CD276; B7 Homolog 4 (B7-H4), also known as V-set Domain Containing T-cell Activation Inhibitor 1 (VTCN1), B7 Superfamily, Member 1 (B7S1), or B7x; Herpesvirus Entry Mediator (HVEM), also known as Herpesvirus Entry Mediator A (HVEA), Tumor Necrosis Factor Receptor Superfamily, Member 14 (TNFRSF14), or CD270; V-type Immunoglobulin Domain-Containing Suppressor of T-cell Activation; Chromosome 10 Open reading Frame 54 (C10orf54), also known as Death Domain 1-Alpha (DD1-Alpha); B7 Homolog 6 (B7-H6), also known as Natural Cytotoxicity Triggering Receptor 3 ligand 1; Human Endogenous Retrovirus-H Long Terminal Repeat-Associating 2 (HHLA2), also known as B7 Homolog 7 (B7-H7), B7 Homolog 5 (B7-H5), or HERV-H LTR-Associating 2; Cytotoxic T Lymphocyte-Associated 4 (CTLA-4), also known as CD152; CD200, also known as Membrane Glycoprotein MRC OX-2 or MOX2; Killer-cell Immunoglobulin-Like Receptor (KIR); T-cell Immunoglobulin and Mucin Domains-Containing Protein 3 (TIM-3), also known as Hepatitis A Virus Cellular Receptor 2 (HAVCR2); and Lymphocyte Activation Gene 3 (LAG3), also known as CD223.

The term "immune effector cell" as used herein refers to the cells of the immune system that mount immune responses to an antigen. Suitable effector cells include but are not limited to populations of antigen presenting cells, cytotoxic T-cells, and T helper cells that mediate cellular immunity. In addition to antigen-specific effector T-cells, the effector cell populations may include, but are not limited to, other cytotoxic immune cells against a selected antigen such as natural killer cells, lymphocytes, monocytes, macrophages, neutrophils, and eosinophils.

The term "linker" as used herein refers to one or more amino acid residues inserted between immunoglobulin domains and/or immune cell inhibitor domains of the antibody immune cell inhibitor fusion proteins of the disclosure. For example, a linker may be inserted between an immunoglobulin domain and an immune cell inhibitor domain, at the sequence level. The precise location of a domain transition can be determined by locating peptide stretches that do not form secondary structural elements such as beta-sheets or alpha-helices as demonstrated by experimental data or as can be assumed by techniques of modeling or secondary structure prediction. Linkers may or may not be needed depending on the where the stop and start residues of protein fusions are chosen because often natural linkers are found between immunoglobulin domains. The linkers of the antibody immune cell inhibitor fusion proteins of the disclosure are referred to herein as follows: $L_1$, which, when present, is located on the light chain between the $II_1$ and $V_L$ domains; $L_2$, which, when present, is located on the light chain between the $C_L$ and $II_2$ domains; $L_3$, which, when present, is located on the heavy chain between the $II_3$ and $L_3$ domains; and $L_4$, which, when present, is located on the heavy chain between the Fc and $II_4$ domains. The linkers $L_1$, $L_2$, $L_3$, and $L_4$ are independent, but in some embodiments of the antibody immune cell inhibitor fusion proteins of the disclosure may have the same sequence and/or length.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally occurring. Similarly, "non-naturally occurring" as used herein refers to a protein molecule that is not found in nature or that has been structurally modified through protein engineering and synthesized, manufactured, or produced by man using recombinant DNA technologies in appropriate cells such as, for example, CHO cells.

A "recombinant" molecule is one that has been prepared, expressed, created, or isolated by recombinant DNA technology means.

The term "fusion protein" as used herein refers to protein constructs comprising an immunoglobulin domain and an immune cell inhibitor protein. The immune cell inhibitor protein in some fusion proteins of the disclosure may not constitute the entire natural protein but may be limited to an active domain of the entire protein responsible for binding to a corresponding receptor on the surface of an immune function cell. In addition, an immunoglobulin domain in some fusion proteins of the disclosure may not constitute the entire natural immunoglobulin domain but may be limited to a portion of the natural immunoglobulin domain responsible for specifically binding a target antigen or epitope or conferring other properties of the natural immunoglobulin domain. Importantly, the fragment of the immune cell inhibitor protein or immunoglobulin domain in some fusion proteins of the disclosure would not be naturally occurring as the fragment, but may retain the same protein sequence for the fragment and incorporated into a therapeutic fusion protein.

The terms "inhibit" or "diminish" as used herein refer to a complete or partial arrest of immune effector cell activation.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The phrases "biological property," "biological characteristic," and the term "activity" in reference to an antibody or an antibody immune cell inhibitor fusion protein of the disclosure are used interchangeably herein and include, but are not limited to, epitope affinity and specificity, ability to antagonize the activity of the antigen target (or targeted polypeptide), the in vivo stability of the antibody or antibody immune cell inhibitor fusion protein, and the immunogenic properties of the antibody or antibody immune cell inhibitor fusion protein. Other identifiable biological properties or characteristics of an antibody or an antibody immune cell inhibitor fusion protein include, for example, cross-reactivity, (i.e., with non-human homologs of the antigen target, or with other antigen targets or tissues, generally), and ability to preserve high expression levels of protein in mammalian cells. The aforementioned properties or characteristics can be observed or measured using art-recognized techniques.

A "neutralizing effect" of an antibody immune cell inhibitor fusion protein as used herein refers to a fusion protein of an antibody and an immune cell inhibitor ligand that is able to first, bind an antigen for which the antigen binding portion of the antibody immune cell inhibitor fusion protein specifically recognizes, then, through simultaneous binding of the fused immune cell inhibitor domain to a specific receptor, to block or substantially reduce an unwanted deleterious or autoimmune effector function carried out by the cell expressing the immune cell inhibitor receptor. As used herein, "substantially reduce" means at least about 60%, preferably at least about 70%, more preferably at least about 75%, even more preferably at least about 80%, still more preferably at least about 85%, most preferably at least about 90% reduction of the unwanted or autoimmune effector function of the cell carrying the ligand's receptor.

The term "neutralizing antibody" refers to an antibody that can neutralize the function of the protein or infectious agent the antibody specifically recognizes and binds. Typically, neutralizing antibodies refer to antibodies specific for viral, bacterial, or other infectious agents. Where therapeutic antibodies are used as drug candidates to treat human disease, neutralizing antibodies can arise as anti-drug antibodies (ADA) but have the undesirable function of neutralizing the therapeutic benefit of the therapeutic antibody. Neutralizing antibodies to the antigen binding portions of the fusion proteins of the present disclosure would represent an undesirable development.

The term "$K_D$," as used herein, refers to the dissociation constant ($K_D$=[A]×[B]/[AB]) of the interaction between an antibody or an antibody immune cell inhibitor fusion protein of the disclosure and an antigen target and has the units of moles/liter. An antibody or antibody immune cell inhibitor fusion protein of the disclosure typically has a dissociation constant ($K_D$) of $10^{-5}$ to $10^{-12}$ moles/liter or less, or $10^{-7}$ to $10^{-12}$ moles/liter or less, or $10^{-3}$ to $10^{-12}$ moles/liter, and/or with a binding affinity of at least $10^7$ $M^{-1}$, or at least $10^8$ $M^{-1}$, or at least $10^9$ $M^{-1}$, or at least $10^{12}$ $M^{-1}$. Any $K_D$ value greater than $10^{-4}$ moles/liter is generally considered to indicate non-specific binding. Therefore, the lower the $K_D$ value, the greater the affinity. In some embodiments, a monovalent antibody or antibody immune cell inhibitor fusion protein of the disclosure will bind to a desired antigen with an affinity less than 500 nM, or less than 200 nM, or less than 10 nM, or less than 500 pM. High affinity or very strong binding is often associated with greater efficacy, but it is not always the case that the greater the affinity the greater the efficacy.

The dissociation constant ($K_D$) can be determined, for example, by surface plasmon resonance (SPR). Generally, surface plasmon resonance analysis measures real-time binding interactions (both on rate and off rate) between a ligand (a target antigen on a biosensor matrix) and an analyte by surface plasmon resonance using, for example, the BIAcore system (Pharmacia Biosensor; Piscataway, N.J.). Surface plasmon analysis can also be performed by immobilizing the analyte and presenting the ligand. Specific binding of an antibody or an antibody immune cell inhibitor fusion protein of the disclosure to an antigen or antigenic determinant can also be determined in any suitable manner known in the art, including, for example, Scatchard analysis and/or competitive binding assays, such as radioimmunoassays (RIA), enzyme linked immunosorbent assays (ELISA), enzyme immunoassays (EIA), and sandwich competition assays.

The term "vector," as used herein, refers to any molecule (e.g., nucleic acid, plasmid, or virus) that is used to transfer coding information to a host cell. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "expression vectors."

The term "operably linked" is used herein to refer to an arrangement of flanking sequences wherein the flanking sequences are configured or assembled so as to perform their usual function. Thus, a flanking sequence operably linked to a coding sequence may be capable of effecting the replication, transcription, and/or translation of the coding sequence. For example, a coding sequence is operably linked to a promoter when the promoter is capable of directing transcription of that coding sequence.

The term "host cell," as used herein, refers to a cell into which an expression vector has been introduced. A host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the antibody immune cell inhibitor fusion proteins of the disclosure, including bacterial, yeast, baculoviral, and mammalian expression systems (as well as phage display expression systems).

Examples of cultured mammalian cell lines include Chinese Hamster ovary (CHO) simian cells such as COS, murine cell lines such as NS0, and human cell lines such as HEK and HeLa, which may be used to produce the antibody immune cell inhibitor fusion proteins of the disclosure. Vectors are transfected into the cells and the DNA may be integrated into the genome by homologous recombination in the case of stable transfection, or the cells may be transiently transfected. Examples of mammalian expression vectors include adenoviral vectors, the pSV and the pCMV series of plasmid vectors, vaccinia and retroviral vectors, as well as baculovirus. The promoters for cytomegalovirus (CMV) and simian virus 40 (SV40) are commonly used in mammalian expression vectors to drive gene expression. Non-viral promoters, such as the elongation factor (EF)-1 promoter, may also be used.

One embodiment of the disclosure provides nucleic acid molecules comprising nucleotide sequences encoding polypeptide chains that form an antibody immune cell inhibitor fusion protein of the disclosure. Another embodiment of the disclosure provides expression vectors comprising nucleic acid molecules comprising nucleotide sequences encoding polypeptide chains that form the antibody immune cell inhibitor fusion proteins of the disclosure. Yet another embodiment of the disclosure provides host cells that express such antibody immune cell inhibitor fusion proteins (i.e., comprising nucleic acid molecules or vectors encoding polypeptide chains that form such antibody immune cell inhibitor fusion proteins).

In some embodiments, the disclosure provides methods for preparing an antibody immune cell inhibitor fusion protein of the disclosure, wherein such methods comprise cultivating or maintaining a host cell under conditions such that the host cell produces or expresses such antibody immune cell inhibitor fusion proteins, and optionally further comprises isolating the antibody immune cell inhibitor fusion protein so produced.

A skilled artisan will be able to determine suitable variants of the polypeptide chains of the antibody immune cell inhibitor fusion proteins of the disclosure using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects.

A "disorder" is any condition that would benefit from treatment using the antibody immune cell inhibitor fusion proteins of the disclosure. "Disorder" and "condition" are used interchangeably herein and include chronic and acute disorders or diseases, including those pathological conditions that predispose a patient to the disorder in question. A "T-cell mediated-condition" is a condition directly or indirectly effected by the T-cells of the immune system.

The terms "treatment" or "treat" as used herein refer to both therapeutic treatment and prophylactic or preventative measures. Those in need of treatment include those having a disorder as well as those prone to have the disorder or those in which the disorder is to be prevented.

The terms "pharmaceutical composition" or "therapeutic composition" as used herein refer to a compound or composition capable of inducing a desired therapeutic effect when properly administered to a patient. One embodiment of the disclosure provides a pharmaceutical composition comprising a pharmaceutically acceptable carrier and a therapeutically effective amount of at least one antibody immune cell inhibitor fusion protein of the disclosure.

The term "pharmaceutically acceptable carrier" or "physiologically acceptable carrier" as used herein refers to one or more formulation materials suitable for accomplishing or enhancing the delivery of one or more antibody immune cell inhibitor fusion proteins of the disclosure.

The terms "effective amount" and "therapeutically effective amount" when used in reference to a pharmaceutical composition comprising one or more antibody immune cell inhibitor fusion proteins of the disclosure refer to an amount or dosage sufficient to produce a desired therapeutic result. More specifically, a therapeutically effective amount is an amount of an antibody immune cell inhibitor fusion protein sufficient to inhibit, for some period of time, one or more of the clinically defined pathological processes associated with the condition being treated. The effective amount may vary depending on the specific antibody immune cell inhibitor fusion protein that is being used, and may also depend on a variety of factors and conditions related to the patient being treated and the severity of the disorder. For example, if the antibody immune cell inhibitor fusion protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is within the ability of those skilled in the art.

2. Antibody Immune Cell Inhibitor Fusion Proteins

In one embodiment of the disclosure, the antibody immune cell inhibitor fusion protein comprises four polypeptide chains that form two antigen binding sites at least two immune cell receptor binding sites, wherein two polypeptide chains have a structure represented by the formula $II_1$-$V_L$-$C_L$-$II_2$, and two polypeptide chains have a structure represented by the formula $II_3$-$V_H$-$C_{H1}$-Fc-$II_4$; wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain;

Fc is the immunoglobulin hinge region and $C_{H2}$ and $C_{H3}$ immunoglobulin heavy chain constant domains; and $II_1$, $II_2$, $II_3$, and $II_4$ are each independently an immune cell inhibitor domain of an immunoglobulin superfamily member or are absent;

wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

In another embodiment of the disclosure, the antibody immune cell inhibitor fusion protein comprises four polypeptide chains that form two antigen binding sites and at least two immune cell receptor binding sites, wherein two polypeptide chains have a structure represented by the formula $II_1$-$L_1$-$V_L$-$C_L$-$L_2$-$II_2$, and two polypeptide chains have a structure represented by the formula $II_3$-$L_3$-$V_H$-$C_{H1}$-Fc-$L_4$-$II_4$; wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain;

Fc is the immunoglobulin hinge region and $C_{H2}$ and $C_{H3}$ immunoglobulin heavy chain constant domains;

$L_1$, $L_2$, $L_3$ and $L_4$ are each independently a linker domain or are absent; and $II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at one or both of the antigen binding sites.

In another embodiment of the disclosure, the antibody immune cell inhibitor fusion protein comprises two polypeptide chains that form one antigen binding site and at least one immune cell receptor binding site; wherein one polypeptide chain has a structure represented by the formula $II_1$-$V_L$-$C_L$-$II_2$, and one polypeptide chain has a structure represented by the formula $II_3$-$V_H$-$C_{H1}$-$II_4$; wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain; and $II_1$, $II_2$, $II_3$, and $II_4$ are each independently an immune cell inhibitor domain of an immunoglobulin superfamily member or are absent;

wherein at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

In another embodiment of the disclosure, the antibody immune cell inhibitor fusion protein comprises two polypeptide chains that form one antigen binding site and at least one immune cell receptor binding site; wherein one polypeptide chain has a structure represented by the formula $II_1$-$L_1$-$V_L$-$C_L$-$L_2$-$II_2$, and one polypeptide chain has a structure represented by the formula $II_3$-$L_3$-$V_H$-$C_{H1}$-$L_4$-$II_4$; wherein:

$V_L$ is an immunoglobulin light chain variable domain;

$V_H$ is an immunoglobulin heavy chain variable domain;

$C_L$ is an immunoglobulin light chain constant domain;

$C_{H1}$ is the immunoglobulin $C_{H1}$ heavy chain constant domain;

$L_1$, $L_2$, $L_3$ and $L_4$ are each independently a linker domain or are absent; and $II_1$, $II_2$, $II_3$, and $II_4$ are each independently an immune cell inhibitor domain of an immunoglobulin superfamily member or are absent;

wherein at least one of $L_1$, $L_2$, $L_3$ and $L_4$ is a linker domain, and at least one of $II_1$, $II_2$, $II_3$, and $II_4$ is an immune cell inhibitor domain of an immunoglobulin superfamily member; and wherein the antibody immune cell inhibitor fusion protein inhibits or diminishes activation of an immune effector cell only when bound to a target antigen at the antigen binding site.

The antibody immune cell inhibitor fusion proteins of the disclosure may be prepared using domains or sequences obtained or derived from any human or non-human antibody, including, for example, human, murine, or humanized antibodies. In some antibody immune cell inhibitor fusion proteins of the disclosure, the $V_L$, $V_H$, $C_L$, $C_{H1}$, and/or Fc domains of the antibody immune cell inhibitor fusion protein may not constitute the entire natural immunoglobulin domain, provided, however, that the portion of the $V_L$, $V_H$, $C_L$, $C_{H1}$, and/or Fc domain used in the antibody immune cell inhibitor fusion protein is capable of functioning in the same manner as the full-length natural immunoglobulin domain. In other embodiments, the antibody immune cell inhibitor fusion proteins of the disclosure may further comprise additional $V_L$, $V_H$, $C_L$, $C_{H1}$, and/or Fc domains.

In some antibody immune cell inhibitor fusion proteins of the disclosure, one or more of $II_1$, $II_2$, $II_3$, and $II_4$ is an immune cell inhibitor domain. In some embodiments, at least one of the immune cell inhibitor domains can inhibit or diminish activation of an immune effector cell involved in the immune response to self-tissue. In other embodiments, at least one of the immune cell inhibitor domains can inhibit or diminish activation of an immune effector cell involved in the immune response to self-tissue when an autoantibody is bound to the antigen at the site of an ongoing disease process. In other embodiments, at least one of $II_1$, $II_2$, $II_3$, and $II_4$ is an immune cell inhibitor domain of an immunoglobulin domain superfamily member. In other embodiments, at least one of $II_1$, $II_2$, $II_3$ and $II_4$ is absent.

In some embodiments, the immune cell inhibitor domain is obtained or derived from a member of the immunoglobulin superfamily. In certain embodiments, the immune cell inhibitor domain comprises a Programmed Death Ligand 1 (PD-L1), B7 Homolog 1 (B7-H1), or CD274 domain; Programmed Death Ligand 2 (PD-L2) or B7-DC domain; B7 Homolog 3 (B7-H3) or CD276 domain; B7 Homolog 4 (B7-H4), V-set Domain-Containing T-cell Activation Inhibitor 1 (VTCN1), B7 Superfamily, Member 1 (B7S1), or B7x domain; Herpesvirus Entry Mediator (HVEM), Herpesvirus Entry Mediator A (HVEA), Tumor Necrosis Factor Receptor Superfamily, Member 14 (TNFRSF14), or CD270 domain (also known as Tumor necrosis factor receptor superfamily member 14); V-type Immunoglobulin Domain-Containing Suppressor of T-cell Activation domain; B7 Homolog 6 (B7-H6) or Natural cytotoxicity triggering receptor 3 ligand 1 domain; Human Endogenous Retrovirus-H Long Terminal Repeat-Associating 2 (HHLA2), B7 Homolog 7 (B7-H7), B7 Homolog 5 (B7-H5), or HERV-H LTR-associating protein 2 domain; Cytotoxic T-Lymphocyte-Associated protein 4 (CTLA-4) or CD152 domain; CD200, Membrane Glycoprotein MRC OX-2, or MOX2 domain; Killer-cell Immunoglobulin-like Receptor (KIR) domain; T-cell Immunoglobulin and Mucin Domains-Containing Protein 3 (TIM-3) or Hepatitis A Virus Cellular Receptor 2 (HAVCR2) domain; or Lymphocyte Activation Gene-3 (LAG3) or CD223 domain.

In some embodiments, the immune cell inhibitor domain comprises a PD-L1 extracellular domain (wherein PD-L1 is also known as CD274, B7-H, B7H1, PDCD1L1, or PDCD1LG1) or a PD-L2 extracellular domain (wherein PD-L2 is also known as CD273). PD-L1 when bound to Programmed Death 1 (PD-1) inhibitory receptor (also known as CD279) acts as an immune checkpoint inhibitor of B-cells, T-cells, monocytes, and antigen presenting cells. For example, an activated T-cell expresses PD-1 on its surface upon antigen recognition and produces interferons, which induce expression of PD-L1 in multiple tissues. Binding of PD-1 to its ligand limits T-cell activity. Under normal conditions, the PD-1/PD-L1 pathway prevents excessive stimulation and maintains the immune tolerance to self-antigens by negatively regulating the immune response (Riella et al., 2012, *Am. J. Transplant.* 12(10): 2575-87).

In one embodiment of the disclosure, the antibody immune cell inhibitor fusion protein comprises four polypeptide chains that form two antigen binding sites and at least two PD-1 binding sites; wherein two polypeptide chains have a structure represented by the formula $II_1\text{-}V_L\text{-}C_L\text{-}II_2$, and two polypeptide chains have a structure represented by the formula $II_3\text{-}V_H\text{-}C_{H1}\text{-}Fc\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$ and $C_{H3}$ immunoglobulin heavy chain constant domains; and
$II_1$, $II_2$, $II_3$, and $II_4$ are each independently an immune cell inhibitor domain of an immunoglobulin superfamily member capable of binding PD-1 or are absent; wherein at least one of $II_1$, $II_2$, $II_3$, and $II_4$ is an immune cell inhibitor domain of an immunoglobulin superfamily member capable of binding PD-1; and wherein the antibody immune cell inhibitor fusion protein inhibits or diminishes activation of an immune effector cell only when bound to a target antigen at one or both of the antigen binding sites.

In another embodiment of the disclosure, the antibody immune cell inhibitor fusion protein comprises four polypeptide chains that form two antigen binding sites and at least two PD-1 binding sites; wherein two polypeptide chains have a structure represented by the formula $II_1\text{-}L_1\text{-}V_L\text{-}C_L\text{-}L_2\text{-}II_2$, and two polypeptide chains have a structure represented by the formula $II_3\text{-}L_3\text{-}V_H\text{-}C_{H1}\text{-}Fc\text{-}L_4\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$ and $C_{H3}$ immunoglobulin heavy chain constant domains;
$L_1$, $L_2$, $L_3$ and $L_4$ are each independently a linker domain or are absent; and
$II_1$, $II_2$, $II_3$, and $II_4$ are each independently an immune cell inhibitor domain of an immunoglobulin superfamily member capable of binding PD-1 or are absent; wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member capable of binding PD-1; and wherein the antibody immune cell inhibitor fusion protein inhibits or diminishes activation of an immune effector cell only when bound to a target antigen at one or both of the antigen binding sites.

In another embodiment of the disclosure, the antibody immune cell inhibitor fusion protein comprises two polypeptide chains that form one antigen binding site and at least one PD-1 binding site; wherein one polypeptide chain has a structure represented by the formula $II_1\text{-}V_L\text{-}C_L\text{-}II_2$, and one polypeptide chain has a structure represented by the formula $II_3\text{-}V_H\text{-}C_{H1}\text{-}II_4$; wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
$II_1$, $II_2$, $II_3$, and $II_4$ are each independently an immune cell inhibitor domain of an immunoglobulin superfamily member capable of binding PD-1 or are absent; wherein at least one of $II_1$, $II_2$, $II_3$, and $II_4$ is an immune cell inhibitor domain of an immunoglobulin superfamily member capable of binding PD-1; and wherein the antibody immune cell inhibitor fusion protein inhibits or diminishes activation of an immune effector cell only when bound to a target antigen at the antigen binding site.

In another embodiment of the disclosure, the antibody immune cell inhibitor fusion protein comprises two polypeptide chains that form one antigen binding site and at least one PD-1 binding site; wherein one polypeptide chain has a structure represented by the formula $II_1\text{-}L_1\text{-}V_L\text{-}C_L\text{-}L_2\text{-}II_2$, and one polypeptide chain has a structure represented by the formula $II_3\text{-}L_3\text{-}V_H\text{-}C_{H1}\text{-}L_4\text{-}II_4$, wherein:

$V_L$ is an immunoglobulin light chain variable domain;
$V_H$ is an immunoglobulin heavy chain variable domain;
$C_L$ is an immunoglobulin light chain constant domain;
$C_{H1}$ is the immunoglobulin $C_{H1}$ heavy chain constant domain;
$L_1$, $L_2$, $L_3$ and $L_4$ are each independently a linker domain or are absent; and
$II_1$, $II_2$, $II_3$, and $II_4$ are each independently an immune cell inhibitor domain of an immunoglobulin superfamily member capable of binding PD-1 or are absent; wherein at least one of $L_1$, $L_2$, $L_3$ and $L_4$ is a linker domain and at least one of $II_1$, $II_2$, $II_3$, and $II_4$ is an immune cell inhibitor domain of an immunoglobulin superfamily member capable of binding PD-1; and wherein the antibody immune cell inhibitor fusion protein inhibits or diminishes activation of an immune effector cell only when bound to a target antigen at the antigen binding site.

In some embodiments, the $V_L$, $V_H$, $C_L$, and $C_{H1}$ domains of the antibody immune cell inhibitor fusion proteins of the disclosure form an autoantibody that recognizes and binds an antigen derived from or mimicking an antigen derived from a human tissue. In some embodiments, the autoantibody facilitates an immune response to a self-tissue.

In some embodiments of the disclosure, the antibody immune cell inhibitor fusion proteins of the disclosure are capable of specifically binding one or more antigen targets. In certain embodiments of the disclosure, the antibody immune cell inhibitor fusion protein is capable of specifically binding at least one antigen target that is Human serum albumin, Bone mineral (hydroxyapatite), Complement component 3d (C3d), Glutamic acid decarboxylase 65 (GAD65), Asialoglycoprotein receptor (ASGPR), Asialoglycoprotein receptor 2 (ASGPR2) Transferrin receptor protein 2 (TFR2), Solute carrier family 2, facilitated glucose (SLC2A2), Solute carrier organic anion transporter family member 1B1 (SLCO1B1), Solute carrier organic anion transporter family member 1B3 (SLCO1B3), Multidrug resistance-associated protein 6 (ABCC6), Major histocompatibility complex I (MHC I), Major histocompatibility complex II (MHC II), T-cell receptor (TCR), B-Cell receptor (BCR), Transforming growth factor beta, Cluster differentiation 4 (CD4), Cluster differentiation 8 (CD8), Cluster differentiation 11c (CD11c), cluster differentiation 14 (CD14), Fas ligand/Tumor necrosis factor super family 6 (Fas Ligand/TNFSF6), Fibrinogen (1F3), collagen type I, collagen type II, collagen type III, collagen type IV, Cystatin C, Cluster differentiation 133 (CD133), Cluster differentiation 10 (CD10), Cluster differentiation 13 (CD13), Cluster differentiation 20 (CD20), Cluster differentiation 80 (CD80), Neural cell adhesion molecule 1 (NCAM1), E-cadherin, Epithelial cell adhesion molecule (EPCAM), Epithelial Membrane Antigen (EMA), Transthyretin, Vascular adhesion protein 1, Lymphocyte function-associated antigen 3, or Dihydrolipoamide acetyltransferase. In some embodiments of the disclosure, the antibody immune cell inhibitor fusion protein is capable of inhibiting the function of one or more of the antigen targets.

In some embodiments, the antibody immune cell inhibitor fusion proteins of the disclosure comprise a linker joining at least one immune cell inhibitor domain to at least one immunoglobulin light chain or heavy chain or domain. In some antibody immune cell inhibitor fusion proteins, $L_1$, when present, may be 5 to 30 amino acid residues in length; $L_2$, when present, may be 5 to 30 amino acid residues in length; $L_3$, when present, may be 5 to 30 amino acid residues in length; and $L_4$, when present, may be 5 to 30 amino acid residues in length.

In some antibody immune cell inhibitor fusion proteins of the disclosure, at least one of $L_1$, $L_2$, $L_3$ and $L_4$ is absent.

The identity and sequence of amino acid residues in the linker may vary depending on the type of secondary structural element necessary to be achieved. For example, glycine, serine, and alanine are best for linkers having maximum flexibility. Some combination of glycine, proline, threonine, and serine are useful if a more rigid and extended linker is necessary. Any amino acid residue may be considered as a linker in combination with one or more other amino acid residues, which may be the same as or different as the first amino acid residue, to construct larger peptide linkers as necessary depending on the desired properties.

3. Antibody Immune Cell Inhibitor Fusion Protein Therapeutic Compositions and Administration Thereof Therapeutic or pharmaceutical compositions comprising one or more antibody immune cell inhibitor fusion proteins of the disclosure are within the scope of the disclosure. Such therapeutic or pharmaceutical compositions can comprise a therapeutically effective amount of an antibody immune cell inhibitor fusion protein, or antibody immune cell inhibitor fusion protein-drug conjugate, in admixture with a pharmaceutically or physiologically acceptable formulation agent selected for suitability with the mode of administration.

Acceptable formulation materials are preferably nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference in their entirety for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the antibody immune cell inhibitor fusion proteins of the disclosure.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, antibody immune cell inhibitor fusion protein compositions can be prepared for storage by mixing the selected composition having the desired degree of purity with optional formulation agents in the form of a lyophilized cake or an aqueous solution. Further, the antibody immune cell inhibitor fusion protein can be formulated as a lyophilizate using appropriate excipients such as sucrose.

The pharmaceutical compositions of the disclosure can be selected for parenteral delivery. Alternatively, the compositions can be selected for inhalation or for delivery through the digestive tract, such as orally. The preparation of such pharmaceutically acceptable compositions is within one of skill in the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this disclosure can be in the form of a pyrogen-free, parenterally acceptable, aqueous solution comprising the desired antibody immune cell inhibitor fusion protein in a pharmaceutically acceptable vehicle. One suitable vehicle for parenteral injection is sterile distilled water in which an antibody immune cell inhibitor fusion protein of the disclosure is formulated as a sterile, isotonic solution, properly preserved. Yet another preparation can involve the formulation of the antibody immune cell inhibitor fusion protein with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the antibody immune cell inhibitor fusion protein include implantable drug delivery devices.

Additional pharmaceutical compositions of the disclosure will be evident to those skilled in the art, including formulations involving antibody immune cell inhibitor fusion proteins in sustained- or controlled-delivery formulations. Techniques for formulating a variety of other sustained- or controlled-delivery means, such as liposome carriers, bioerodible microparticles, or porous beads and depot injections, are also known to those skilled in the art. Additional examples of sustained-release preparations include semipermeable polymer matrices in the form of shaped articles, e.g., films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D (−)-3-hydroxybutyric acid. Sustained-release compositions can also include liposomes, which can be prepared by any of several methods known in the art.

Pharmaceutical compositions of the disclosure to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

Also encompassed by the disclosure are kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of pharmaceutical composition containing an antibody immune cell inhibitor fusion protein to be employed therapeutically will depend, for example, upon the therapeutic context and objectives. One skilled in the art will appreciate that the appropriate dosage levels for treatment will thus vary depending, in part, upon the molecule delivered, the indication for which the antibody immune cell inhibitor fusion protein is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 mg/kg to up to about 100 mg/kg or more, depending on the factors mentioned above. In other embodiments, the dosage can range from 0.1 mg/kg up to about 100 mg/kg; or 1 mg/kg up to about 100 mg/kg; or 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, up to about 100 mg/kg.

Dosing frequency will depend upon the pharmacokinetic parameters of the antibody immune cell inhibitor fusion protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In some embodiments of the disclosure, the antibody immune cell inhibitor fusion proteins of the disclosure are used to treat a patient having Primary Biliary Cholangitis (PBC), Type 1 Diabetes, Goodpasture's syndrome, Amyloidosis, Ankylosing spondylitis, Anti-glomerular basement membrane/anti-tubular basement membrane nephritis, Antiphospholipid syndrome, Autoimmune hepatitis, Autoimmune oophoritis Autoimmune pancreatitis, Autoimmune retinopathy, Behcet's disease, Crohn's disease, Devic's disease, Lupus, Dressler's syndrome, Fibrosing alveolitis, Glomerulonephritis, Graves' disease, Guillain-Barre syndrome, IgA Nephropathy, IgG4-related sclerosing disease, Immune thrombocytopenic purpura (ITP), Microscopic polyangiitis (MPA), Mixed connective tissue disease (MCTD), Multiple sclerosis, Polyneuropathy, Organomegaly, Endocrinopathy, Monoclonal syndrome (POEMS), Polyarteritis nodosa, Rheumatoid arthritis, Schmidt syndrome, Scleritis, Scleroderma, Sjögren's syndrome Sperm & testicular autoimmunity, Stiff person syndrome (SPS), Takayasu's arteritis, Temporal arteritis, Giant cell arteritis, Thrombocytopenic purpura (TTP), Tolosa-Hunt syndrome (THS), Vasculitis or a T-cell mediated condition.

4. EXAMPLES

The Examples that follow are illustrative of specific embodiments of the disclosure, and various uses thereof. They are set forth for explanatory purposes only, and should not be construed as limiting the scope of the disclosure in any way.

Example 1. Construction of Anti-DLAT Fusion Antibody

An antibody immune inhibitor fusion protein was designed comprising a human autoimmune antibody to a self-antigen identified as driving the disease process known as Primary Biliary Cholangitis (PBC), previously considered cirrhosis. The self-antigen recognized by the autoimmune antibody was shown to be Pyruvate Dehydrogenase Complex subunit E2 (PDC-E2, also known as Dihydrolipoamide Acetyltransferase or DLAT). The original fusion protein fused the extracellular domain of Programmed Death Ligand 1 (PD-L1, also known as CD274, or B7 Homolog 1 (B7-H1)), to each of the N- and C-termini of an engineered autoantibody containing the V regions of the autoantibody and an engineered Fc variant known as IgG2/4 to minimize effector function. See Pascual et al., 1994, *J. Immunol.* 152(5): 2577-85; and Chen et al., 1998, *J. Autoimmun.* 11(2): 151-61. The PD-L1 domain was fused to the antibody to interact with Programmed Death 1 (PD-1, CD279) receptor on T-cells believed to be driving the disease process, thereby inhibiting activation of the T-cells and subsequent activation of other immune system actors such as antigen presenting cells, B-cells, and any associated excreted cytokines to thus ameliorate the immune response causing the disease.

Initially, multiple anti-DLAT antibodies were identified in the literature (Thomson et al., 1998, *J. Hepatol.* 28(4): 582-94). Two of them (designated PD2 and PD5) were initially selected for cloning as: (i) human full-length antibodies and were constructed with the autoantibody $V_H$ and $V_L$ regions fused with a non-naturally occurring engineered heavy chain including $C_{H1}$-hinge-$C_{H2}$-$C_{H3}$ (SEQ ID NO: 35)(IgG2/4); and (ii) human CH Fabs. Each of these antibodies or antibody fragments were constructed with or without the variable-like domain of the extracellular domain (ECD) of PD-L1 linked to either the C-terminus or the N-terminus of the heavy and/or light chains. Upon review of the crystal structure of the PD-1/PD-L1 complex, it was determined that the variable-like domain of PD-L1 was the binding portion, and thus the variable-like domain of PD-L1 was fused to each of the N- and C-termini of the anti-DLAT antibody to determine which orientation was most effective for this particular antibody-immune inhibitor pair. See Zak et al., 2015, *Structure* 23(12): 2341-48.

Using Geneious 8.1.5 software, reference sequences (see Table 1) were imported and modified for construct design. Constructs were synthesized and cloned into suitable vectors and were sequence-verified prior to transient transfections. Protein expression was performed by transfection of constructs shown in Table 2 using the Invitrogen EXPI293F system. Protein A columns were used for purification of antibodies and antibody fusions or Nickel NTA was used for purification of the 6× His-tagged Fab proteins using commercial columns.

Sequences for the constructs are shown in Table 3. The sequences are shown as monomeric sequences, but all full-length antibodies expressed and purified were, of course, dimeric. The heavy chain of the antibody is shown in regular text, the light chain of the antibody is shown in underlined text, the linker is shown in italicized text, and the immune cell inhibitor domain of an immunoglobulin superfamily member are shown in bold text.

TABLE 1

| Reference Sequences | | |
|---|---|---|
| Reference Sequences | Accession # | Source |
| Human PD-L1 Reference Protein Sequence | Q9NZQ7 | UniProt |
| Human PD-L1 Reference Protein Sequence | NP_054862.1 | NCBI |
| Murine PD-L1 Reference Protein Sequence | NP_068693.1 | NCBI |
| Murine PD-L1 Reference Protein Sequence | Q9EP73 | UniProt |
| Crystal Structure of human PD-1 and its ligand PD-L1 | 4ZQK | Protein Data Bank |
| PD-1 binding domain from human PD-L1 | 5C3T | Protein Data Bank |
| DWZ Heavy Chain Reference Protein Sequence | AJ001167.1 | GenBank |
| DWZ Light Chain Reference Protein Sequence | AJ001168.1 | GenBank |
| PD2 Heavy Chain Reference Protein Sequence | AJ001171.1 | GenBank |
| PD2 Light Chain Reference Protein Sequence | AJ001172.1 | GenBank |
| Human B7 Dendritic Cell Molecule (B7-DC), Programmed cell death 1 ligand 2 (PD-L2) | Q9BQ51 | UniProt |
| Human B7-Homolog 3 (B7-H3), (CD276) | Q5ZPR3 | UniProt |
| Human B7-H4, V-set domain-containing T-cell activation inhibitor 1 (VTCN1) | Q7Z7D3 | UniProt |
| Human B7-H5, V-type immunoglobulin domain-containing suppressor of T-cell activation (VISTA) | Q9H7M9 | UniProt |
| Human B7-H6 (NCR3LG1), Natural cytotoxicity triggering receptor 3 ligand 1 | Q68D85 | UniProt |
| Human B7-H7, HERV-H LTR-associating protein 2 (HHLA2) | Q9UM44 | UniProt |
| Human Cytotoxic T-lymphocyte protein 4 (CTLA-4) | P16410 | UniProt |
| Human Tumor necrosis factor receptor superfamily member 14 (TNFRSF14), Herpesvirus Entry Mediator (HVEM) | Q92956 | UniProt |
| Human T-Cell Immunoglobulin Mucin Family Member 3 (TIM-3), Hepatitis A virus cellular receptor 2 (HAVCR2) | Q8TDQ0 | UniProt |

TABLE 2

Construct Descriptions

| Protein ID | Isotype | Transfection Constructs | Molecular Weight (kDa) | Description |
|---|---|---|---|---|
| TPP-985 | Human IgG2/4 | pME074 + pME090 | 144 | PD5_IgG2-4 |
| TPP-986 | Human IgG2/4 | pME074 + pME095 | 172.8 | N-Terminus_PDL1_HC_PD5 |
| TPP-992 | Human IgG2/4 | pME076 + pME090 | 172.8 | N-terminus_PDL1_LC_PD5 |
| TPP-990 | Human IgG2/4 | pME075 + pME090 | 172.8 | PD5_LC_C-terminus_PDL1 |
| TPP-996 | Human IgG2/4 | pME080 + pME092 | 174.4 | N-Terminus_PDL1_HC_PD2 |
| TPP-1002 | Human IgG2/4 | pME082 + pME089 | 175 | N-terminus_PDL1_LC_PD2 |
| TPP-1007 | Human IgG2/4 | pME091 + pME102 | 144 | DWZ_IgG2-4 |
| TPP-1006 | Human IgG2/4 | pME089 + pME080 | 145.7 | PD2_IgG2-4 |
| TPP-955 | Human Fab | pME071 + pME074 | 46.7 | PD5_Human_Fab |
| TPP-983 | Human Fab | pME072 + pME074 | 61.1 | PD5_LC_C-terminus linker PDL1 |
| TPP-984 | Human Fab | pME073 + pME074 | 61.1 | N-terminus_PDL1_LC_PD5 |
| TPP-991 | Human Fab | pME076 + pME071 | 61.1 | N-terminus_PDL1_HC_PD5 |
| TPP-989 | Human Fab | pME075 + pME071 | 61.1 | PD5_HC_C-terminus_PDL1 |
| TPP-993 | Human Fab | pME077 + pME080 | 48.4 | PD2 Fab |
| TPP-994 | Human Fab | pME078 + pME080 | 62.8 | PD2_HC_C-terminus_PDL1 |
| TPP-995 | Human Fab | pME079 + pME080 | 62.8 | N-terminus_PDL1_HC_PD2 |
| TPP-999 | Human Fab | pME081 + pME077 | 62.8 | PD2_LC_C-terminus_PDL1 |
| TPP-1001 | Human Fab | pME077 + pME082 | 62.8 | N-terminus_PDL1_LC_PD2 |
| TPP-1003 | Murine IgG1 | pME083 + pME084 | 147.4 | mIgG1 PD2 Ab |
| TPP-1004 | Murine IgG1 | pME085 + pME086 | 145.4 | mIgG1 PD5 Ab |
| TPP-1005 | Murine IgG1 | pME087 + pME088 | 144.9 | mIgG1 DWZ Ab |
| TPP-1008 | N/A | pME098 | 15.2 | Human_PDL1_V-domain_N-terminus |
| TPP-1009 | N/A | pME099 | 26 | Human_PDL1_V_C_Domain NP_054862.1 |
| TPP-1010 | N/A | pME100 | 13.9 | Human_PDL1_V-domain NP_054862.1 |
| TPP-1011 | N/A | pME101 | 14.4 | Human_PDL1_V-domain_C-Terminus |
| TPP-1986 | Murine IgG1 Fc Silent | N/A | 173 | N-terminus_PDL1_LC_PD5 |
| TPP-1694 | Murine IgG1 | pME085 + pADL0128 | 173.8 | N-terminus_mPDL1_LC_PD5 |
| TPP-1695 | Murine IgG1 | pME087 + pADL0129 | 173.3 | N-terminus_mPDL1_LC_DWZ |
| TPP-1697 | Human IgG2/4 | pADL0131 + pADL0132 | 172.8 | N-terminus_PDL1_LC_12B4 |
| TPP-1504 | Human IgG2/4 | pADL0123 + pME090 | 199.7 | N-terminus_B7-H4_LC_PD5 |
| TPP-1505 | Human IgG2/4 | pADL0124 + pME090 | 184.3 | N-terminus_B7-H5_LC_PD5 |
| TPP-1506 | Human IgG2/4 | pADL0125 + pME090 | 182.8 | N-terminus_HVEM_LC_PD5 |
| TPP-1894 | Human IgG2/4 | pADL0141 + pME090 | 201.4 | N-terminus_B7-H6_LC_PD5 |
| TPP-1898 | Human IgG2/4 | pADL0145 + pME090 | 175.1 | N-terminus_CTLA-4_LC_PD5 |
| TPP-1507 | Human IgG2/4 | pADL0126 + pME090 | 170.8 | N-terminus_PDL2_V-like_domain_LC_PD5 |
| TPP-2215 | Human IgG2/4 | pADL0176 + pME090 | 193.2 | N-terminus_PDL2_LC_PD5 |
| TPP-2216 | Human IgG2/4 | pADL0177 + pME090 | 193 | N-terminus_CD200_LC_PD5 |
| TPP-2218 | Human IgG2/4 | pADL0179 + pME090 | 242.2 | N-terminus_B7-H3_LC_PD5 |
| TPP-2220 | Human IgG2/4 | pADL0181 + pME090 | 188.1 | N-terminus_TIM-3_LC_PD5 |

TABLE 3

Construct Sequences

| SEQ ID NO: | Sequence Description | Construct Name | Sequence |
|---|---|---|---|
| 1 | PD5 HC Fab | pME071 | QLQLQESGPGLVKPSETLSLTCIVSGGSISRNSYYWG WIRQPPGKGLEWIGSIVYSGSTYHQPSLKSRVTIFLD TSKNQFFLKLTSVTAADTAVYYCARGTRATTWPPPIG |

TABLE 3-continued

Construct Sequences

| SEQ ID NO: | Sequence Description | Construct Name | Sequence |
|---|---|---|---|
| | | | YWGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVE PKSC |
| 2 | PD5 HC PDL1 Fab | pME072 | QLQLQESGPGLVKPSETLSLTCIVSGGSISRNSYYWG WIRQPPGKGLEWIGSIVYSGSTYHQPSLKSRVTIFLD TSKNQFFLKLTSVTAADTAVYYCARGTRATTWPPPIG YWGQGTLVTVSSASTKGPSVFPLAPSSKSTSGGTAAL GCLVKDYFPEPVTVSWNSGALTSGVHTFPAVLQSSGL YSLSSWTVPSSLGTQTYICNVNHKPSNTKVDKRVE PKSC*GGSSRSSSSGGGGSGGGG*FTVTVPKDLYVVEYG SNMTIECKFPVEKQLDLAALIVYWEMEDKNIIQFVHG EEDLKVQHSSYRQRARLLKDQLSLGNAALQITDVKLQ DAGVYRCMISYGGADYKRITVKVNA |
| 3 | PDL1 HC PD5 Fab | pME073 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA*GGSSRSSSSGGGGSGGGG*QLQLQESGPGLVKPSE TLSLTCIVSGGSISRNSYYWGWIRQPPGKGLEWIGSI VYSGSTYHQPSLKSRVTIFLDTSKNQFFLKLTSVTAA DTAVYYCARGTRATTWPPPIGYWGQGTLVTVSSASTK GPSVFPLAPSSKSTSGGTAALGCLVKDYFPEPVTVSW NSGALTSGVHTFPAVLQSSGLYSLSSVVTVPSSSLGT QTYICNVNHKPSNTKVDKRVEPKSC |
| 4 | PD5 LC Fab Human Lamda LC | pME074 | QSVLTQPPSVSAAPGQKVTVSCFGSSSNIGNYFASWY QQLPGAAPRLLIYGNNERPSGIPDRFSGSKSGTSATL VITGLQTGDEAAYYCATWDSSLSAVVFGGGTKLTVLG QPKANPTVTLFPPSSEELQANKATLVCLISDFYPGAV TVAWKADGSPVKAGVETTKPSKQSNNKYAASSYLSLT PEQWKSHRSYSCQVTHEGSTVEKTVAPTECS |
| 5 | PD5 LC PDL1 | pME075 | QSVLTQPPSVSAAPGQKVTVSCFGSSSNIGNYFASWY QQLPGAAPRLLIYGNNERPSGIPDRFSGSKSGTSATL VITGLQTGDEAAYYCATWDSSLSAVVFGGGTKLTVLG QPKANPTVTLFPPSSEELQANKATLVCLISDFYPGAV TVAWKADGSPVKAGVETTKPSKQSNNKYAASSYLSLT PEQWKSHRSYSCQVTHEGSTVEKTVAPTECS*GGSSRS SSSGGGGSGGGG*FTVTVPKDLYVVEYGSNMTIECKFP VEKQLDLAALIVYWEMEDKNIIQFVHGEEDLKVQHSS YRQRARLLKDQLSLGNAALQITDVKLQDAGVYRCMIS YGGADYKRITVKVNA |
| 6 | PDL1 LC PD5 | pME076 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA*GGSSRSSSSGGGGSGGGG*QSVLTQPPSVSAAPGQ KVTVSCFGSSSNIGNYFASWYQQLPGAAPRLLIYGNN ERPSGIPDRFSGSKSGTSATLVITGLQTGDEAAYYCA TWDSSLSAVVFGGGTKLTVLGQPKANPTVTLFPPSSE ELQANKATLVCLISDFYPGAVTVAWKADGSPVKAGVE TTKPSKQSNNKYAASSYLSLTPEQWKSHRSYSCQVTH EGSTVEKTVAPTECS |
| 7 | PD2 HC Fab | pME077 | EVQLVESGGGLVKPGGSLRLSCAASGFTFGSYSMTWV RQAPGKGLEWVSFISTVSTYIYYPDSVKGRFTISRDN AKNSLYLQMNSLRAEDTAVYYCARVSGRGSAARDGEK GTYYYYMDVWGKGTTVTVSSASTKGPSVFPLAPSSKS TSGGTAALGCLVKDYFPEPVTVSWNSGALTSGVHTFP AVLQSSGLYSLSSVVTVPSSSLGTQTYICNVNHKPSN TKVDKRVEPKSC |
| 8 | PD2 HC PDL1 Fab | pME078 | EVQLVESGGGLVKPGGSLRLSCAASGFTFGSYSMTWV RQAPGKGLEWVSFISTVSTYIYYPDSVKGRFTISRDN AKNSLYLQMNSLRAEDTAVYYCARVSGRGSAARDGEK GTYYYYMDVWGKGTTVTVSSASTKGPSVFPLAPSSKS TSGGTAALGCLVKDYFPEPVTVSWNSGALTSGVHTFP AVLQSSGLYSLSSVVTVPSSSLGTQTYICNVNHKPSN TKVDKRVEPKSC*GGSSRSSSSGGGGSGGGG*FTVTVPK DLYVVEYGSNMTIECKFPVEKQLDLAALIVYWEMEDK NIIQFVHGEEDLKVQHSSYRQRARLLKDQLSLGNAAL QITDVKLQDAGVYRCMISYGGADYKRITVKVNA |

TABLE 3-continued

Construct Sequences

| SEQ ID NO: | Sequence Description | Construct Name | Sequence |
|---|---|---|---|
| 9 | PD2 HC PDL1 Fab | pME079 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNAGGSSRSSSSGGGGSGGGGEVQLVESGGGLVKPGG SLRLSCAASGFTFGSYSMTWVRQAPGKGLEWVSFIST VSTYIYYPDSVKGRFTISRDNAKNSLYLQMNSLRAED TAVYYCARVSGRGSAARDGEKGTYYYMDVWGKGTTV TVSSASTKGPSVFPLAPSSKSTSGGTAALGCLVKDYF PEPVTVSWNSGALTSGVHTFPAVLQSSGLYSLSSVVT VPSSSLGTQTYICNVNHKPSNTKVDKRVEPKSC |
| 10 | PD2 Human Lambda LC | pME080 | SSELTQDPAVSVALGQTVTITCQGDSLRSYYASWYQQ KPGQAPVLVIFGKNNRPSGIPDRFSGSRSGNTASLTI TGAQAEDEADYFCDSRDSSANHWVFGGGTKLTVLQPK AAPSVTLFPPSSEELQANKATLVCLISDFYPGAVTVA WKADSSPVKAGVETTTPSKQSNNKYAASSYLSLTPEQ WKSHKSYSCQVTHEGSTVEKTVAPTECS |
| 11 | PD2 LC PDL1 Fab | pME081 | SSELTQDPAVSVALGQTVTITCQGDSLRSYYASWYQQ KPGQAPVLVIFGKNNRPSGIPDRFSGSRSGNTASLTI TGAQAEDEADYFCDSRDSSANHWVFGGGTKLTVLQPK AAPSVTLFPPSSEELQANKATLVCLISDFYPGAVTVA WKADSSPVKAGVETTTPSKQSNNKYAASSYLSLTPEQ WKSHKSYSCQVTHEGSTVEKTVAPTECS*GGSSRSSSS GGGGSGGGG*FTVTVPKDLYVVEYGSNMTIECKFPVEK QLDLAALIVYWEMEDKNIIQFVHGEEDLKVQHSSYRQ RARLLKDQLSLGNAALQITDVKLQDAGVYRCMISYGG ADYKRITVKVNA |
| 12 | PDL1 LC PD2 Fab | pME082 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNAGGSSRSSSSGGGGSGGGGSSELTQDPAVSVALGQ TVTITCQGDSLRSYYASWYQQKPGQAPVLVIFGKNNR PSGIPDRFSGSRSGNTASLTITGAQAEDEADYFCDSR DSSANHWVFGGGTKLTVLQPKAAPSVTLFPPSSEELQ ANKATLVCLISDFYPGAVTVAWKADSSPVKAGVETTT PSKQSNNKYAASSYLSLTPEQWKSHKSYSCQVTHEGS TVEKTVAPTECS |
| 13 | PD2 HC Hu IgG2/4 | pME089 | EVQLVESGGGLVKPGGSLRLSCAASGFTFGSYSMTWV RQAPGKGLEWVSFISTVSTYIYYPDSVKGRFTISRDN AKNSLYLQMNSLRAEDTAVYYCARVSGRGSAARDGEK GTYYYMDVWGKGTTVTVSSASTKGPSVFPLAPCSRS TSESTAALGCLVKDYFPEPVTVSWNSGALTSGVHTFP AVLQSSGLYSLSSVVTVPSSNFGTQTYTCNVDHKPSN TKVDKTVERKCCVECPPCPAPPVAGPSVFLFPPKPKD TLMISRTPEVTCVVVDVSQEDPEVQFNWYVDGVEVHN AKTKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPPV LDSDGSFFLYSRLTVDKSRWQEGNVFSCSVMHEALHN HYTQKSLSLSLGK |
| 14 | PD5 HC Hu IgG2/4 | pME090 | QLQLQESGPGLVKPSETLSLTCIVSGGSISRNSYYWG WIRQPPGKGLEWIGSIVYSGSTYHQPSLKSRVTIFLD TSKNQFFLKLTSVTAADTAVYYCARGTRATTWPPPIG YWGQGTLVTVSSASTKGPSVFPLAPCSRSTSESTAAL GCLVKDYFPEPVTVSWNSGALTSGVHTFPAVLQSSGL YSLSSVVTVPSSNFGTQTYTCNVDHKPSNTKVDKTVE RKCCVECPPCPAPPVAGPSVFLFPPKPKDTLMISRTP EVTCVVVDVSQEDPEVQFNWYVDGVEVHNAKTKPREE QFNSTYRVVSVLTVLHQDWLNGKEYKCKVSNKGLPSS IEKTISKAKGQPREPQVYTLPPSQEEMTKNQVSLTCL VKGFYPSDIAVEWESNGQPENNYKTTPPVLDSDGSFF LYSRLTVDKSRWQEGNVFSCSVMHEALHNHYTQKSLS LSLGK |
| 15 | DWZ HC Hu IgG2/4 | pME091 | EVQLLESGGDVVQPGGSLRLSCVASGFTLTNYVTAWV RRRPGKGLEWISGMTHGAVATYYSDSVRGRFSSSRDT SRSTLYLQMNDLTVEDTAIYYCAKSLHRSGTSLSYWG QGTLVTVSSASTKGPSVFPLAPCSRSTSESTAALGCL VKDYFPEPVTVSWNSGALTSGVHTFPAVLQSSGLYSL |

TABLE 3-continued

Construct Sequences

| SEQ ID NO: | Sequence Description | Construct Name | Sequence |
|---|---|---|---|
| | | | SSVVTVPSSNFGTQTYTCNVDHKPSNTKVDKTVERKC CVECPPCPAPPVAGPSVFLFPPKPKDTLMISRTPEVT CVVVDVSQEDPEVQFNWYVDGVEHNAKTKPREEQFN STYRVVSVLTVLHQDWLNGKEYKCKVSNKGLPSSIEK TISKAKGQPREPQVYTLPPSQEEMTKNQVSLTCLVKG FYPSDIAVEWESNGQPENNYKTTPPVLDSDGSFFLYS RLTVDKSRWQEGNVFSCSVMHEALHNHYTQKSLSLSL GK |
| 16 | PDL1 HC PD2 | pME092 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA*GGSSRSSSSGGGGSGGGG*EVQLVESGGGLVKPGG SLRLSCAASGFTFGSYSMTWVRQAPGKGLEWVSFIST VSTYIYYPDSVKGRFTISRDNAKNSLYLQMNSLRAED TAVYYCARVSGRGSAARDGEKGTYYYYMDVWGKGTTV TVSSASTKGPSVFPLAPCSRSTSESTAALGCLVKDYF PEPVTVSWNSGALTSGVHTFPAVLQSSGLYSLSSVVT VPSSNFGTQTYTCNVDHKPSNTKVDKTVERKCCVECP PCPAPPVAGPSVFLFPPKPKDTLMISRTPEVTCVVVD VSQEDPEVQFNWYVDGVEHNAKTKPREEQFNSTYRV VSVLTVLHQDWLNGKEYKCKVSNKGLPSSIEKTISKA KGQPREPQVYTLPPSQEEMTKNQVSLTCLVKGFYPSD IAVEWESNGQPENNYKTTPPVLDSDGSFFLYSRLTVD KSRWQEGNVFSCSVMHEALHNHYTQKSLSLSLGK |
| 17 | PDL1 HC PD5 | pME095 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA*GGSSRSSSSGGGGSGGGG*QLQLQESGPGLVKPSE TLSLTCIVSGGSISRNSYYWGWIRQPPGKGLEWIGSI VYSGSTYHQPSLKSRVTIFLDTSKNQFFLKLTSVTAA DTAVYYCARGTRATTWPPPIGYWGQGTLVTVSSASTK GPSVFPLAPCSRSTSESTAALGCLVKDYFPEPVTVSW NSGALTSGVHTFPAVLQSSGLYSLSSVVTVPSSNFGT QTYTCNVDHKPSNTKVDKTVERKCCVECPPCPAPPVA GPSVFLFPPKPKDTLMISRTPEVTCVVVDVSQEDPEV QFNWYVDGVEHNAKTKPREEQFNSTYRVVSVLTVLH QDWLNGKEYKCKVSNKGLPSSIEKTISKAKGQPREPQ VYTLPPSQEEMTKNQVSLTCLVKGFYPSDIAVEWESN GQPENNYKTTPPVLDSDGSFFLYSRLTVDKSRWQEGN VFSCSVMHEALHNHYTQKSLSLSLGK |
| 18 | DWZ LC | pME102 | <u>QSVLTQPPSASGTPGQNINISCSGTTSNIGGSNVDWY QHVPGTAPKLFIHSNNQRPSGVPARFSASKSGTSASL AISGLQSEDEADYYCATWDVRLLAYVFGSATEVTVLR HQPKANPTVTLFPPSSEELQANKATLVCLISDFYPGA VTVAWKADGSPVKAGVETTKPSKQSNNKYAASSYLSL TPEQWKSHRSYSCQVTHEGSTVEKTVAPTECS</u> |
| 19 | PD2 mIgG1 HC | pME083 | EVQLVESGGGLVKPGGSLRLSCAASGFTFGSYSMTWV RQAPGKGLEWVSFISTVSTYIYYPDSVKGRFTISRDN AKNSLYLQMNSLRAEDTAVYYCARVSGRGSAARDGEK GTYYYYMDVWGKGTTVTVSSAKTTPPSVYPLAPGSAA QTNSMVTLGCLVKGYFPEPVTVTWNSGSLSSGVHTFP AVLQSDLYTLSSSVTVPSSTWPSQTVTCNVAHPASST KVDKKIVPRDCGCKPCICTVPEVSSVFIFPPKPKDVL TITLTPKVTCVVVDISKDDPEVQFSWFVDDVEVHTAQ TKPREEQINSTFRSVSELPIMHQDWLNGKEFKCRVNS AAFPAPIEKTISKTKGRPKAPQVYTIPPPKEQMAKDK VSLTCMITNFFPEDITVEWQWNGQPAENYKNTQPIMD TDGSYFVYSKLNVQKSNWEAGNTFTCSVLHEGLHNHH TEKSLSHSPGK |
| 20 | PD2 mu kappa LC | pME084 | <u>SSELTQDPAVSVALGQTVTITCQGDSLRSYYASWYQQ KPGQAPVLVIFGKNNRPSGIPDRFSGSRSGNTASLTI TGAQAEDEADYFCDSRDSSANHWVFGGGTKLTVLQPK RADAAPTVSIFPPSSEQLTSGGASVVCFLNNFYPKDI NVKWKIDGSERQNGVLNSWTDQDSKDSTYSMSSTLTL TKDEYERHNSYTCEATHKTSTSPIVKSFNRNEC</u> |
| 21 | PD5 mIgG1 HC | pME085 | QLQLQESGPGLVKPSETLSLTCIVSGGSISRNSYYWG WIRQPPGKGLEWIGSIVYSGSTYHQPSLKSRVTIFLD TSKNQFFLKLTSVTAADTAVYYCARGTRATTWPPPIG |

TABLE 3-continued

Construct Sequences

| SEQ ID NO: | Sequence Description | Construct Name | Sequence |
|---|---|---|---|
| | | | YWGQGTLVTVSSAKTTPPSVYPLAPGSAAQTNSMVTL GCLVKGYFPEPVTVTWNSGSLSSGVHTFPAVLQSDLY TLSSSVTVPSSTWPSQTVTCNVAHPASSTKVDKKIVP RDCGCKPCICTVPEVSSVFIFPPKPKDVLTITLTPKV TCVVVDISKDDPEVQFSWFVDDVEVHTAQTKPREEQI NSTFRSVSELPIMHQDWLNGKEFKCRVNSAAFPAPIE KTISKTKGRPKAPQVYTIPPPKEQMAKDKVSLTCMIT NFFPEDITVEWQWNGQPAENYKNTQPIMDTDGSYFVY SKLNVQKSNWEAGNTFTCSVLHEGLHNHHTEKSLSHS PGK |
| 22 | PD5 mu kappa LC | pME086 | QSVLTQPPSVSAAPGQKVTVSCFGSSSNIGNYFASWY QQLPGAAPRLLIYGNNERPSGIPDRFSGSKSGTSATL VITGLQTGDEAAYYCATWDSSLSAVVFGGGTKLTVLG QPRADAAPTVSIFPPSSEQLTSGGASVVCFLNNFYPK DINVKWKIDGSERQNGVLNSWTDQDSKDSTYSMSSTL TLTKDEYERHNSYTCEATHKTSTSPIVKSFNRNEC |
| 23 | DWZ mIgG1 HC | pME087 | EVQLLESGGDVVQPGGSLRLSCVASGFTLTNYVTAWV RRRPGKGLEWISGMTHGAVATYYSDSVRGRFSSSRDT SRSTLYLQMNDLTVEDTAIYYCAKSLHRSGTSLSYWG QGTLVTVSSAKTTPPSVYPLAPGSAAQTNSMVTLGCL VKGYFPEPVTVTWNSGSLSSGVHTFPAVLQSDLYTLS SSVTVPSSTWPSQTVTCNVAHPASSTKVDKKIVPRDC GCKPCICTVPEVSSVFIFPPKPKDVLTITLTPKVTCV VVDISKDDPEVQFSWFVDDVEVHTAQTKPREEQINST FRSVSELPIMHQDWLNGKEFKCRVNSAAFPAPIEKTI SKTKGRPKAPQVYTIPPPKEQMAKDKVSLTCMITNFF PEDITVEWQWNGQPAENYKNTQPIMDTDGSYFVYSKL NVQKSNWEAGNTFTCSVLHEGLHNHHTEKSLSHSPGK |
| 24 | DWZ mu kappa LC | pME088 | QSVLTQPPSASGTPGQNINISCSGTTSNIGGSNVDWY QHVPGTAPKLFIHSNNQRPSGVPARFSASKSGTSASL AISGLQSEDEADYYCATWDVRLLAYVFGSATEVTVLR HRADAAPTVSIFPPSSEQLTSGGASVVCFLNNFYPKD INVKWKIDGSERQNGVLNSWTDQDSKDSTYSMSSTLT LTKDEYERHNSYTCEATHKTSTSPIVKSFNRNEC |
| 25 | PD5 mu Lambda LC | N/A | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNAGGSSRSSSSGGGGSGGGGQSVLTQPPSVSAAPGQ KVTVSCFGSSSNIGNYFASWYQQLPGAAPRLLIYGNN ERPSGIPDRFSGSKSGTSATLVITGLQTGDEAAYYCA TWDSSLSAVVFGGGTKLTVLGQPKSSPSVTLFPPSSE ELETNKATLVCTITDFYPGVVTVDWKVDGTPVTQGME TTQPSKQSNNKYMASSYLTLTARAWERHSSYSCQVTH EGHTVEKSLSRADCS |
| 26 | PD5 mu IgG1 Fc Silent™ | N/A | QLQLQESGPGLVKPSETLSLTCIVSGGSISRNSYYWG WIRQPPGKGLEWIGSIVYSGSTYHQPSLKSRVTIFLD TSKNQFFLKLTSVTAADTAVYYCARGTRATTWPPPIG YWGQGTLVTVSSAKTTPPSVYPLAPGSAAQTNSMVTL GCLVKGYFPEPVTVTWNSGSLSSGVHTFPAVLQSDLY TLSSSVTVPSSTWPSQTVTCNVAHPASSTKVDKKIVP RDCGCKPCICTVPEQSSVFIFPPKPKDVLMISLTPKV TCVVVDISKDDPEVQFSWFVDDVEVHTAQTKPREEQI NSTFRSVSELPILHQDWLNGKEFKCRVNSAAFPAPIE KTISKTKGRPKAPQVYTIPPPKEQMAKDKVSLTCMIT NFFPEDITVEWQWNGQPAENYKNTQPIMDTDGSYFVY SKLNVQKSNWEAGNTFTCSVLHEGLHNHHTEKSLSHS PGK |
| 27 | 12B4_HC | pADL0131 | LEVQLQQSGAELVRPGSSVKISCKASGYVFSNYWMNW VKQRPGQGLEWIGQIYPGDGDTNYNGKFKGKATLTAD KSSSTAYMQLSSLTSEDSAVYFCARREIYFDYWGQGT TVTVASTKGPSVFPLAPCSRSTSESTAALGCLVKDYF PEPVTVSWNSGALTSGVHTFPAVLQSSGLYSLSSVVT VPSSNFGTQTYTCNVDHKPSNTKVDKTVERKCCVECP PCPAPPVAGPSVFLFPPKPKDTLMISRTPEVTCVVVD |

TABLE 3-continued

Construct Sequences

| SEQ ID NO: | Sequence Description | Construct Name | Sequence |
|---|---|---|---|
| | | | VSQEDPEVQFNWYVDGVEVHNAKTKPREEQFNSTYRV VSVLTVLHQDWLNGKEYKCKVSNKGLPSSIEKTISKA KGQPREPQVYTLPPSQEEMTKNQVSLTCLVKGFYPSD IAVEWESNGQPENNYKTTPPVLDSDGSFFLYSRLTVD KSRWQEGNVFSCSVMHEALHNHYTQKSLSLSLGK |
| 28 | PDL1_LC_12B4 | pADL0132 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA_GGSSRSSSSGGGGSGGGG_DILLTQSPAILSVSPG ERVSFSCRASQSIGTSIHWYQQRTNGSPRLLIEYASE SISGIPSRFSGSGSGTDFTLSINSVESEDFAYYYCQQ SNGWPITFGGGTKLEIKRTVAAPSVFIFPPSDEQLKS GTASVVCLLNNFYPREAKVQWKVDNALQSGNSQESVT EQDSKDSTYSLSSTLTLSKADYEKHKVYACEVTHQGL SSPVTKSFNRGEC |
| 29 | Linker_PDL1_V-like_domain | pME098 | _GGSSRSSSSGGGGSGGGG_FTVTVPKDLYVVEYGSNMT IECKFPVEKQLDLAALIVYWEMEDKNIIQFVHGEEDL KVQHSSYRQRARLLKDQLSLGNAALQITDVKLQDAGV YRCMISYGGADYKRITVKVNA |
| 30 | PDL1_ECD | pME099 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNAPYNKINQRILVVDPVTSEHELTCQAEGYPKAEVI WTSSDHQVLSGKTTTTNSKREEKLFNVTSTLRINTTT NEIFYCTFRRLDPEENHTAELVIPELPLAHPPNER |
| 31 | PDL1_V-like_domain | pME100 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA |
| 32 | PDL1_V-like_domain_Linker_Hu IgG2/4 | pME101 | FTVTVPKDLYVVEYGSNMTIECKFPVEKQLDLAALIV YWEMEDKNIIQFVHGEEDLKVQHSSYRQRARLLKDQL SLGNAALQITDVKLQDAGVYRCMISYGGADYKRITVK VNA_GGSSRSSSSGGGGSGGGG_ASTKGPSVFPLAPCSR STSESTAALGCLVKDYFPEPVTVSWNSGALTSGVHTF PAVLQSSGLYSLSSVVTVPSSNFGTQTYTCNVDHKPS NTKVDKTVERKCCVECPPCPAPPVAGPSVFLFPPKPK DTLMISRTPEVTCVVVDVSQEDPEVQFNWYVDGVEVH NAKTKPREEQFNSTYRVVSVLTVLHQDWLNGKEYKCK VSNKGLPSSIEKTISKAKGQPREPQVYTLPPSQEEMT KNQVSLTCLVKGFYPSDIAVEWESNGQPENNYKTTPP VLDSDGSFFLYSRLTVDKSRWQEGNVFSCSVMHEALH NHYTQKSLSLSLGK |
| 33 | mPDL1_LC_PD5 | pADL0128 | FTITAPKDLYVVEYGSNVTMECRFPVERELDLLALVV YWEKEDEQVIQFVAGEEDLKPQHSNFRGRASLPKDQL LKGNAALQITDVKLQDAGVYCCIISYGGADYKRITLK VNA_GGSSRSSSSGGGGSGGGG_QSVLTQPPSVSAAPGQ KVTVSCFGSSSNIGNYFASWYQQLPGAAPRLLIYGNN ERPSGIPDRFSGSKSGTSATLVITGLQTGDEAAYYCA TWDSSLSAVVFGGGTKLTVLGQPRADAAPTVSIFPPS SEQLTSGGASVVCFLNNFYPKDINVKWKIDGSERQNG VLNSWTDQDSKDSTYSMSSTLTLTKDEYERHNSYTCE ATHKTSTSPIVKSFNRNEC |
| 34 | mPDL1_LC_DWZ | pADL0129 | FTITAPKDLYVVEYGSNVTMECRFPVERELDLLALVV YWEKEDEQVIQFVAGEEDLKPQHSNFRGRASLPKDQL LKGNAALQITDVKLQDAGVYCCIISYGGADYKRITLK VNA_GGSSRSSSSGGGGSGGGG_QSVLTQPPSASGTPGQ NINISCSGTTSNIGGSNVDWYQHVPGTAPKLFIHSNN QRPSGVPARFSASKSGTSASLAISGLQSEDEADYYCA TWDVRLLAYVFGSATEVTVLRHRADAAPTVSIFPPSS EQLTSGGASVVCFLNNFYPKDINVKWKIDGSERQNGV LNSWTDQDSKDSTYSMSSTLTLTKDEYERHNSYTCEA THKTSTSPIVKSFNRNEC |
| 35 | N-terminus_CTLA-4_LC_PD5 (TPP-1898) | pADL0145 | KAMHVAQPAVVLASSRGIASFVCEYASPGKATEVRVT VLRQADSQVTEVCAATYMMGNELTFLDDSICTGTSSG NQVNLTIQGLRAMDTGLYICKVELMYPPPYYLGIGNG TQIYVIDPEPCPDSD_GGSSRSSSSGGGGSGGGG_QSVL |

TABLE 3-continued

Construct Sequences

| SEQ ID NO: | Sequence Description | Construct Name | Sequence |
|---|---|---|---|
| | | | TQPPSVSAAPGQKVTVSCFGSSSNIGNYFASWYQQLP GAAPRLLIYGNNERPSGIPDRFSGSKSGTSATLVITG LQTGDEAAYYCATWDSSLSAVVFGGGTKLTVLGQPRT VAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC |
| 36 | N-terminus PDL2_V-like domain_LC_PD5 | pADL0126 | FTVTVPKELYIIEHGSNVTLECNFDTGSHVNLGAITA SLQKVENDTSPHRERATLLEEQLPLGKASFHIPQVQV RDEGQYQCIIIYGVAWDYKYLTLKVKA_GGSSRSSSSG GGGSGGGGQ_SVLTQPPSVSAAPGQKVTVSCFGSSSNI GNYFASWYQQLPGAAPRLLIYGNNERPSGIPDRFSGS KSGTSATLVITGLQTGDEAAYYCATWDSSLSAVVFGG GTKLTVLGQPRTVAAPSVFIFPPSDEQLKSGTASVVC LLNNFYPREAKVQWKVDNALQSGNSQESVTEQDSKDS TYSLSSTLTLSKADYEKHKVYACEVTHQGLSSPVTKS FNRGEC |
| 37 | N-terminus_PDL2_LC_PD5 | pADL0176 | FTVTVPKELYIIEHGSNVTLECNFDTGSHVNLGAITA SLQKVENDTSPHRERATLLEEQLPLGKASFHIPQVQV RDEGQYQCIIIYGVAWDYKYLTLKVKASYRKINTHIL KVPETDEVELTCQATGYPLAEVSWPNVSVPANTSHSR TPEGLYQVTSVLRLKPPPGRNFSCVFWNTHVRELTLA SIDLQSQMEPRTHPT_GGSSRSSSSGGGGSGGGGQ_SVL TQPPSVSAAPGQKVTVSCFGSSSNIGNYFASWYQQLP GAAPRLLIYGNNERPSGIPDRFSGSKSGTSATLVITG LQTGDEAAYYCATWDSSLSAVVFGGGTKLTVLGQPRT VAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC |
| 38 | N-terminus_CD200_LC_PD5 | pADL0177 | QVQVVTQDEREQLYTPASLKCSLQNAQEALIVTWQKK KAVSPENMVTFSENHGVVIQPAYKDKINITQLGLQNS TITFWNITLEDEGCYMCLFNTFGFGKISGTACLTVYV QPIVSLHYKFSEDHLNITCSATARPAPMVFWKVPRSG IENSTVTLSHPNGTTSVTSILHIKDPKNQVGKEVICQ VLHLGTVTDFKQTVNK_GGGSSRSSSSGGGGSGGGGQ_S VLTQPPSVSAAPGQKVTVSCFGSSSNIGNYFASWYQQ LPGAAPRLLIYGNNERPSGIPDRFSGSKSGTSATLVI TGLQTGDEAAYYCATWDSSLSAVVFGGGTKLTVLGQP RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| 39 | N-terminus B7-H3_LC_PD5 | pADL0179 | LEVQVPEDPVVALVGTDATLCCSFSPEPGFSLAQLNL IWQLTDTKQLVHSFAEGQDQGSAYANRTALFPDLLAQ GNASLRLQRVRVADEGSFTCFVSIRDFGSAAVSLQVA APYSKPSMTLEPNKDLRPGDTVTITCSSYQGYPEAEV FWQDGQGVPLTGNVTTSQMANEQGLFDVHSILRVVLG ANGTYSCLVRNPVLQQDAHSSVTITPQRSPTGAVEVQ VPEDPVVALVGTDATLRCSFSPEPGFSLAQLNLIWQL TDTKQLVHSFTEGRDQGSAYANRTALFPDLLAQGNAS LRLQRVRVADEGSFTCFVSIRDFGSAAVSLQVAAPYS KPSMTLEPNKDLRPGDTVTITCSSYRGYPEAEVFWQD GQGVPLTGNVTTSQMANEQGLFDVHSVLRVVLGANGT YSCLVRNPVLQQDAHGSVTITGQPMTFPPEA_GGSRS SSSGGGGSGGGGQ_SVLTQPPSVSAAPGQKVTVSCFGS SSNIGNYFASWYQQLPGAAPRLLIYGNNERPSGIPDR FSGSKSGTSATLVITGLQTGDEAAYYCATWDSSLSAV VFGGGTKLTVLGQPRTVAAPSVFIFPPSDEQLKSGTA SVVCLLNNFYPREAKVQWKVDNALQSGNSQESVTEQD SKDSTYSLSSTLTLSKADYEKHKVYACEVTHQGLSSP VTKSFNRGEC |
| 40 | N-terminus_TIM-3_LC_PD5 | pADL0181 | SEVEYRAEVGQNAYLPCFYTPAAPGNLVPVCWGKGAC PVFECGNVVLRTDERDVNYWTSRYWLNGDFRKGDVSL TIENVTLADSGIYCCRIQIPGIMNDEKFNLKVIKPA KVTPAPTRQRDFTAAFPRMLTTRGHGPAETQTLGSLP DINLTQISTLANELRDSRLANDLRDSGATIRI_GGGSS RSSSSGGGGSGGGGQ_SVLTQPPSVSAAPGQKVTVSCF GSSSNIGNYFASWYQQLPGAAPRLLIYGNNERPSGIP DRFSGSKSGTSATLVITGLQTGDEAAYYCATWDSSLS AVVFGGGTKLTVLGQPRTVAAPSVFIFPPSDEQLKSG TASVVCLLNNFYPREAKVQWKVDNALQSGNSQESVTE |

TABLE 3-continued

Construct Sequences

| SEQ ID NO: | Sequence Description | Construct Name | Sequence |
|---|---|---|---|
| | | | QDSKDSTYSLSSTLTLSKADYEKHKVYACEVTHQGLS SPVTKSFNRGEC |
| 41 | N-terminus_B7-H6_LC_PD5 | pADL0141 | DLKVEMMAGGTQITPLNDNVTIFCNIFYSQPLNITSM GITWFWKSLTFDKEVKVFEFFGDHQEAFRPGAIVSPW RLKSGDASLRLPGIQLEEAGEYRCEVVVTPLKAQGTV QLEVVASPASRLLLDQVGMKENEDKYMCESSGFYPEA INITWEKQTQKFPHPIEISEDVITGPTIKNMDGTFNV TSCLKLNSSQEDPGTVYQCVVRHASLHTPLRSNFTLT AARHSLSETEKTDNF*SGGSSRSSSSGGGGSGGGGQSV LTQPPSVSAAPGQKVTVSCFGSSSNIGNYFASWYQQL PGAAPRLLIYGNNERPSGIPDRFSGSKSGTSATLVIT GLQTGDEAAYYCATWDSSLSAVVFGGGTKLTVLGQPR TVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC* |
| 42 | N-terminus_B7-H4_LC_PD5 | pADL0123 | LIIGFGISGRHSITVTTVASAGNIGEDGILSCTFEPD IKLSDIVIQWLKEGVLGLVHEFKEGKDELSEQDEMFR GRTAVFADQVIVGNASLRLKNVQLTDAGTYKCYIITS KGKGNANLEYKTGAFSMPEVNVDYNASSETLRCEAPR WFPQPTVVWASQVDQGANFSEVSNTSFELNSENVTMK VVSVLYNVTINNTYSCMIENDIAKATGDIKVTESEIK RRSHLQLLNSKA*SGGSSRSSSSGGGGSGGGGQSVLTQ PPSVSAAPGQKVTVSCFGSSSNIGNYFASWYQQLPGA APRLLIYGNNERPSGIPDRFSGSKSGTSATLVITGLQ TGDEAAYYCATWDSSLSAVVFGGGTKLTVLGQPRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC* |
| 43 | N-terminus_B7-H5_LC_PD5 | pADL0124 | FKVATPYSLYVCPEGQNVTLTCRLLGPVDKGHDVTFY KTWYRSSRGEVQTCSERRPIRNLTFQDLHLHHGGHQA ANTSHDLAQRHGLESASDHHGNFSITMRNLTLLDSGL YCCLVVEIRHHHSEHRVHGAMELQVQTGKDAPSNCVV YPSSSQDSENITAA*GGSSRSSSSGGGGSGGGGQSVLT QPPSVSAAPGQKVTVSCFGSSSNIGNYFASWYQQLPG AAPRLLIYGNNERPSGIPDRFSGSKSGTSATLVITGL QTGDEAAYYCATWDSSLSAVVFGGGTKLTVLGQPRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC* |
| 44 | N-terminus_HVEM_LC_PD5 | pADL0125 | LPSCKEDEYPVGSECCPKCSPGYRVKEACGELTGTVC EPCPPGTYIAHLNGLSKCLQCQMCDPAMGLRASRNCS RTENAVCGCSPGHFCIVQDGDHCAACRAYATSSPGQR VQKGGTESQDTLCQNCPPGTFSPNGTLEECQHQTKCS WLVTKAGAGTSSSHWV*GGSSRSSSSGGGGSGGGGQSV LTQPPSVSAAPGQKVTVSCFGSSSNIGNYFASWYQQL PGAAPRLLIYGNNERPSGIPDRFSGSKSGTSATLVIT GLQTGDEAAYYCATWDSSLSAVVFGGGTKLTVLGQPR TVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC* |
| 45 | Anti-CD20 HC | Human IgG1 Fc | QVQLQQPGAELVKPGASVKMSCKASGYTFTSYNMHWV KQTPGRGLEWIGAIYPGNGDTSYNQKFKGKATLTADK SSSTAYMQLSSLTSEDSAVYYCARSTYYGGDWYFNVW GAGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPK SCDKTHTCPPCPAPEQSGGPSVFLFPPKPKDTLMISR TPEVTCVVVDVSHEDPEVKFNWYVDGVEVHNAKTKPR EEQYNSTYRVVSVLTVLHQDWLNGKEYKCKVSNKALP APIEKTISKAKGQPREPQVYTLPPSRDELTKNQVSLT CLVKGFYPSDIAVEWESNGQPENNYKTTPPVLDSDGS FFLYSKLTVDKSRWQQGNVFSCSVMHEALHNHYTQKS LSLSPGK |

TABLE 3-continued

Construct Sequences

| SEQ ID NO: | Sequence Description | Construct Name | Sequence |
|---|---|---|---|
| 46 | mPDL1_LC_Anti-CD20 | Human kappa light chain | FTITAPKDLYVVEYGSNVTMECRFPVERELDLLALVV YWEKEDEQVIQFVAGEEDLKPQHSNFRGRASLPKDQL LKGNAALQITDVKLQDAGVYCCIISYGGADYKRITLK VNAGGSSRSSSSGGGGAGGGGQIVLSQSPAILSASPG EKVTMTCRASSSVSYIHWFQQKPGSSPKPWIYATSNL ASGVPVRFSGSGSGTSYSLTISRVEAEDAATYYCQQW TSNPPTFGGGTKLEIKRTVAAPSVFIFPPSDEQLKSG TASVVCLLNNFYPREAKVQWKVDNALQSGNSQESVTE QDSKDSTYSLSSTLTLSKADYEKHKVYACEVTHQGLS SPVTKSFNRGEC |
| 47 | Anti-CD80 HC | Human IgG1 Fc | QVQLQESGPGLVKPSETLSLTCAVSGGSISGGYGWGW IRQPPGKGLEWIGSFYSSSGNTYYNPSLKSQVTISTD TSKNQFSLKLNSMTAADTAVYYCVRDRLFSVVGMVYN NWFDVWGPGVLVTVSSASTKGPSVFPLAPSSKSTSGG TAALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPEQSGGPSVFLFPPKPKD TLMISRTPEVTCVVVDVSHEDPEVKFNWYVDGVEVHN AKTKPREEQYNSTYRVVSVLTVLHQDWLNGKEYKCKV SNKALPAPIEKTISKAKGQPREPQVYTLPPSRDELTK NQVSLTCLVKGFYPSDIAVEWESNGQPENNYKTTPPV LDSDGSFFLYSKLTVDKSRWQQGNVFSCSVMHEALHN HYTQKSLSLSPGK |
| 48 | mPDL1_LC_Anti-CD80 | Human lambda light chain | FTITAPKDLYVVEYGSNVTMECRFPVERELDLLALVV YWEKEDEQVIQFVAGEEDLKPQHSNFRGRASLPKDQL LKGNAALQITDVKLQDAGVYCCIISYGGADYKRITLK VNAGGSSRSSSSGGGGAGGGGESVLTQPPSVSGAPGQ KVTISCTGSTSNIGGYDLHWYQQLPGTAPKLLIYDIN KRPSGISDRFSGSKSGTAASLAITGLQTEDEADYYCQ SYDSSLNAQVFGGGTRLTVLGQPKAAPSVTLFPPSSE ELQANKATLVCLISDFYPGAVTVAWKADSSPVKAGVE TTTPSKQSNNKYAASSYLSLTPEQWKSHRSYSCQVTH EGSTVEKTVAPTECS |

Example 2. Construction of Anti-DLAT IgG1 Murine Antibodies

Three of the anti-DLAT antibodies referenced in Thomson et al., 1998, *J. Hepatol.* 28(4): 582-94, designated PD2, PD5, and DWZ, were selected for cloning as: (i) human full-length antibodies were constructed with the autoantibody $V_H$-$C_{H1}$ and $V_L$-$C_L$ regions fused to a Fc variant region (IgG2/4); (ii) murine IgG1 Fc; (iii) PD5 as a murine IgG1 Fc variant with mutations to remove effector functions. Each of these antibodies was constructed with or without the human or mouse variable-like domain of the extracellular domain (ECD) of Programmed Death-Ligand 1 (PD-L1) linked to the N-terminus of the light chains. TPP-1986 was ordered from Absolute Antibody as a custom production consisting of their murine IgG1 Fc Silent isotype with PD5 variable region and human PD-L1 variable-like domain.

All murine light chain sequences are kappa light chains. The reference sequence sources for these antibodies are shown in Table 4, the sequences comprising the heavy and light chains are shown in Table 3 above, and the construct descriptions are shown in Table 5.

TABLE 4

Reference Sequences

| Reference Sequences | Accession # | Source |
|---|---|---|
| DWZ Heavy Chain Reference Protein Sequence | AJ001167.1 | GenBank |
| DWZ Light Chain Reference Protein Sequence | AJ001168.1 | GenBank |
| PD2 Heavy Chain Reference Protein Sequence | AJ001171.1 | GenBank |
| PD2 Light Chain Reference Protein Sequence | AJ001172.1 | GenBank |
| PD5 Heavy Chain Reference Protein Sequence | AJ001175.1 | GenBank |
| PD5 Light Chain Reference Protein Sequence | AJ001176.1 | GenBank |
| Murine PD-L1 Reference Protein Sequence | NP_068693.1 | NCBI |
| Murine PD-L1 Reference Protein Sequence | Q9EP73 | Uniprot |

TABLE 5

Construct Descriptions

| Protein ID | Isotype | Transfection Constructs | Molecular Weight (kDa) | Description |
|---|---|---|---|---|
| TPP-1003 | Murine IgG1 | pME083 + pME084 | 147.4 | mIgG1 PD2 Ab |
| TPP-1004 | Murine IgG1 | pME085 + pME086 | 145.4 | mIgG1 PD5 Ab |
| TPP-1005 | Murine IgG1 | pME087 + pME088 | 144.9 | mIgG1 DWZ Ab |
| TPP-1986 | Murine IgG1 Fc Silent | N/A | 173 | N-terminus_PDL1_LC_PD5 |
| TPP-1694 | Murine IgG1 | pME085 + pADL0128 | 173.8 | N-terminus_mPDL1_LC_PD5 |
| TPP-1695 | Murine IgG1 | pME087 + pADL0129 | 173.8 | N-terminus_mPDL1_LC_DWZ |

Example 3. Characterization of PD-L1 Targeted Fusions

Programmed Death 1 (PD-1) Fc chimera (R&D Systems, Catalog #1086-PD-050) was captured on the anti-human Fc tips (ForteBio, Catalog #18-5064) at 10 μg/mL in PBS, followed by binding to PD2 Fab fusion variants or Programmed Death Ligand 1 (PD-L1) Fc chimera (R&D Systems, Catalog #156-1B7-100) at 10 μg/mL or μg/mL in PBS, respectively. Final dissociation in PBS was performed in the last step on the Bio-Layer Interferometry (BLI) data.

Figure 1B:
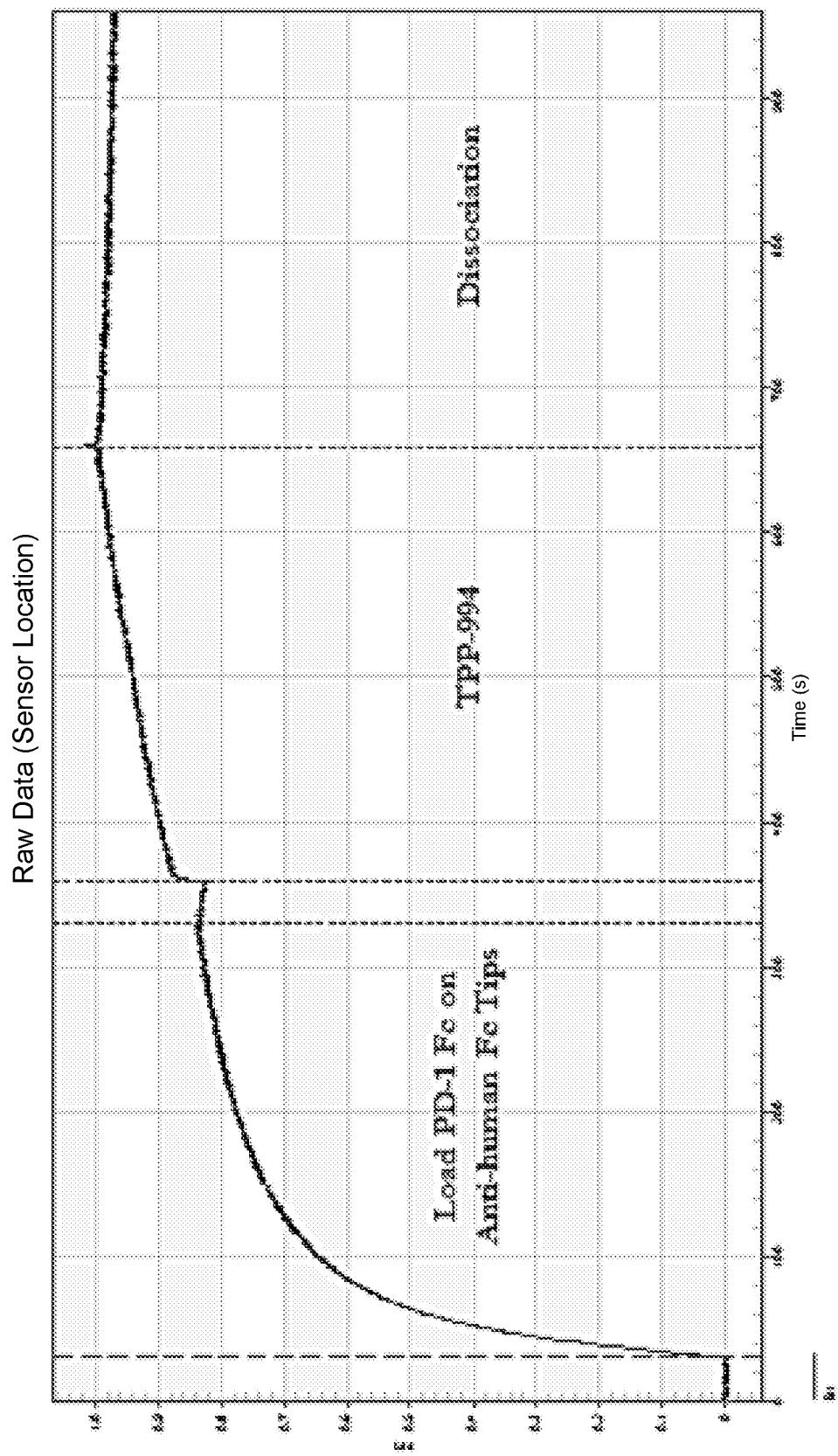
Figure 1C:
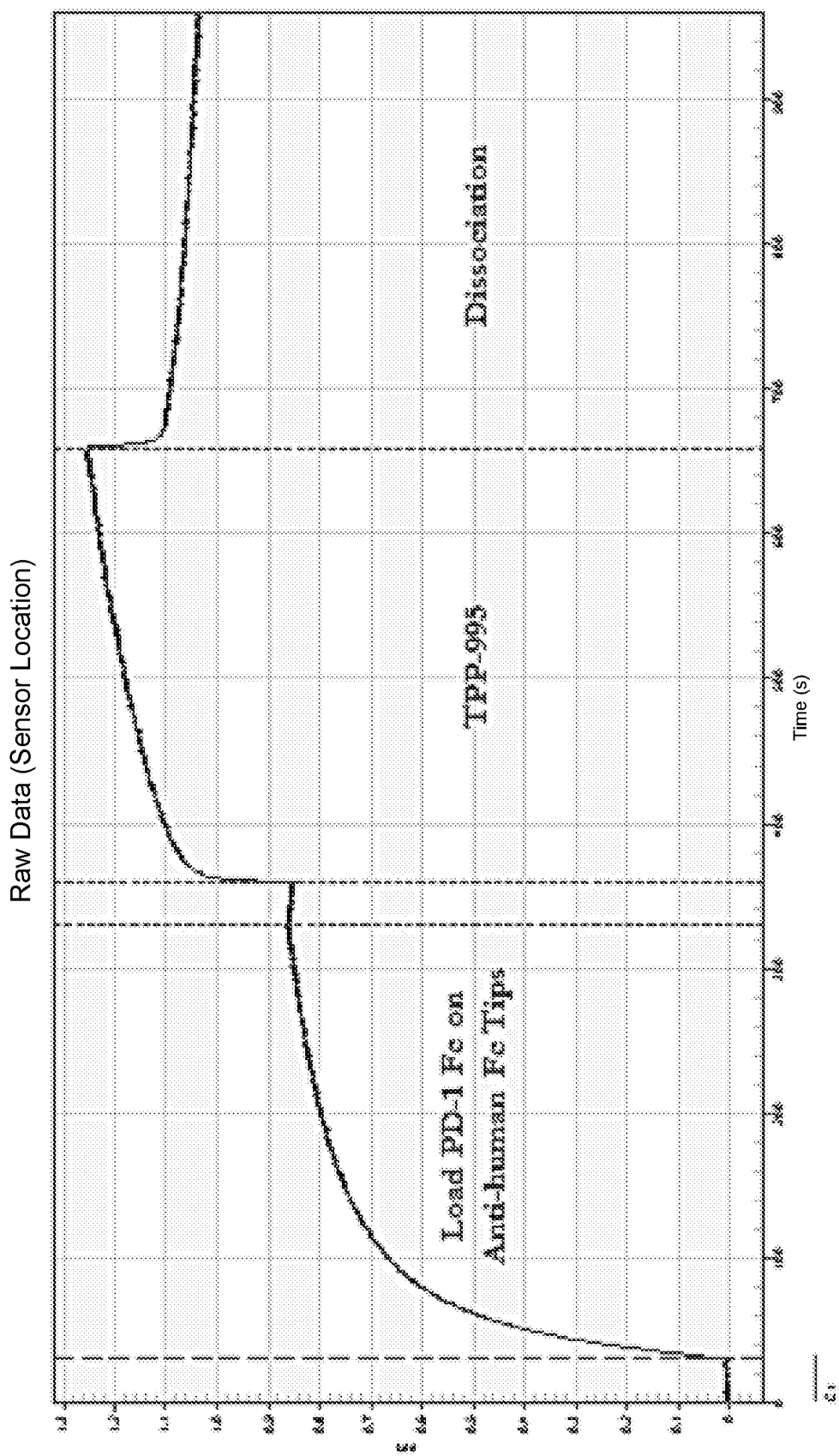
Figure 1D:
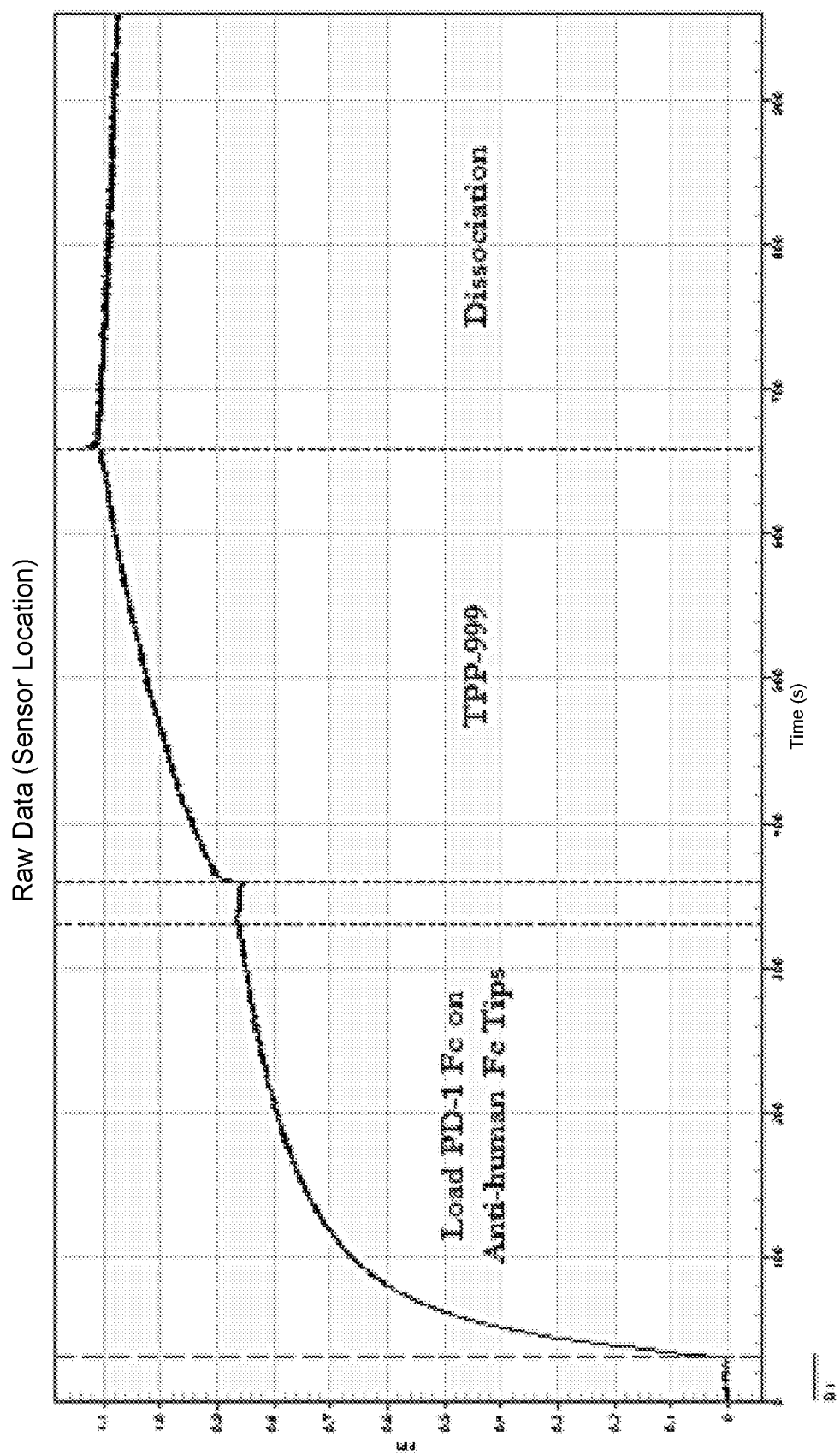
Figure 1E:
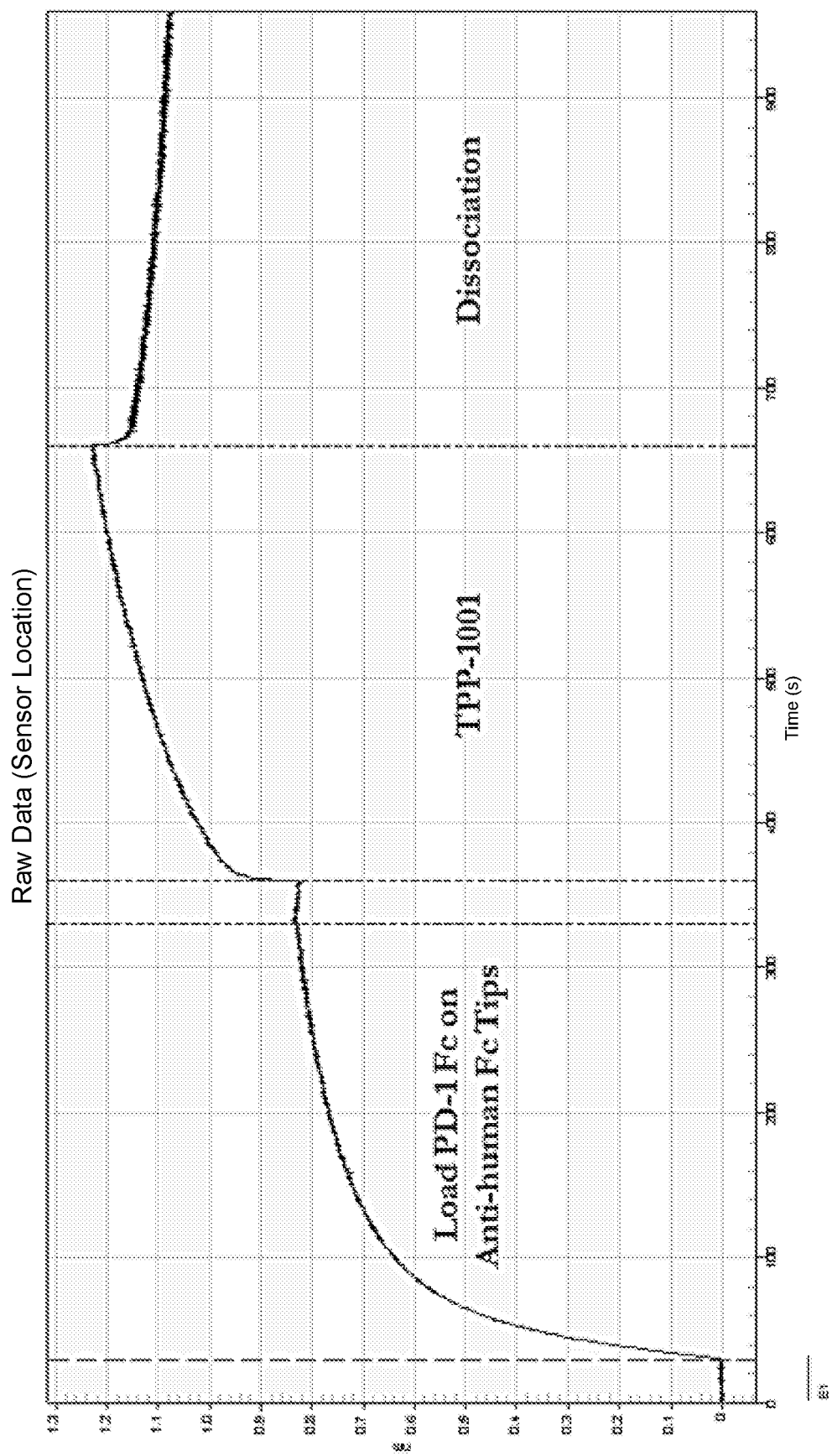
Figure 1F:
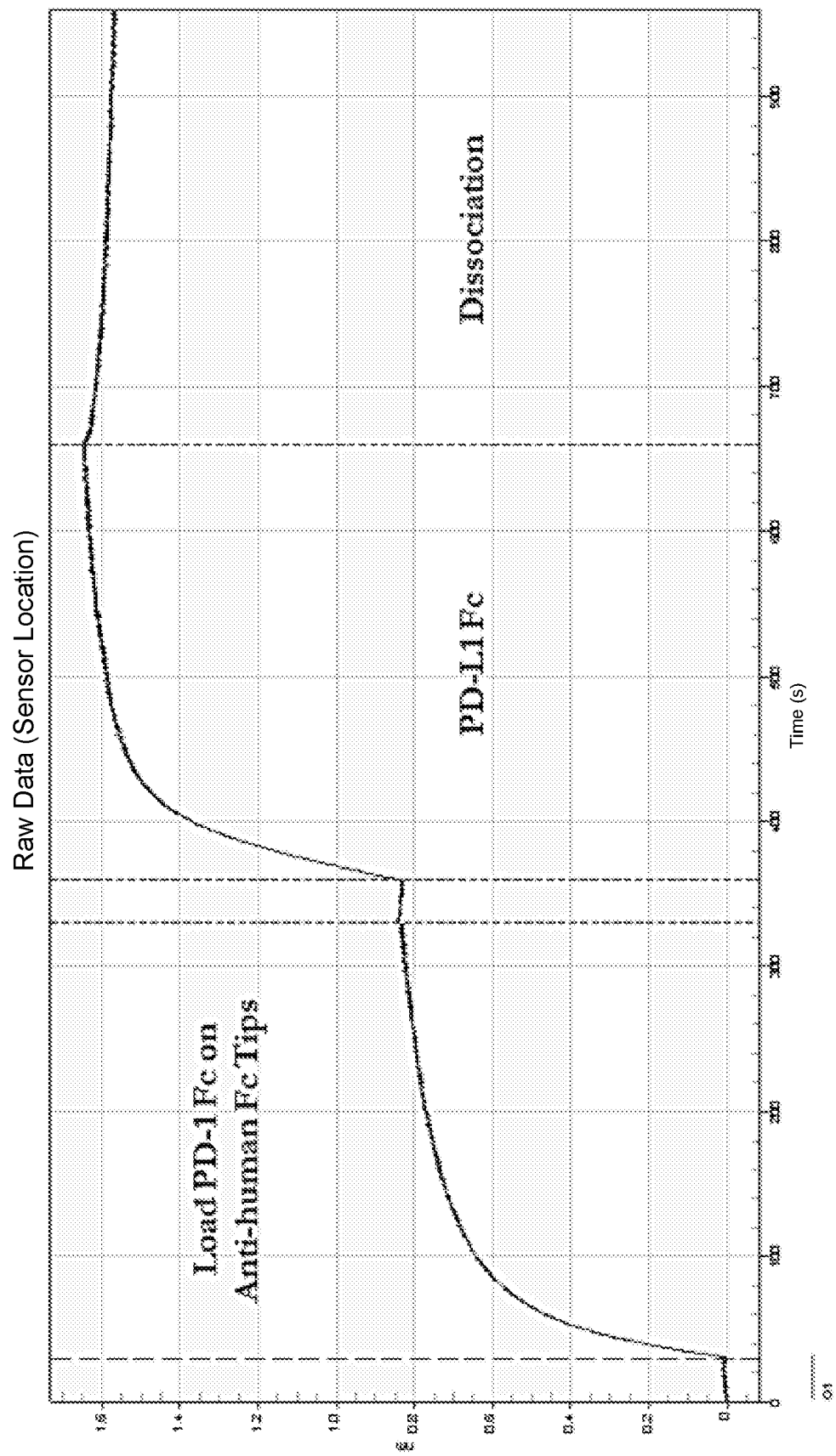
Figure 1G:
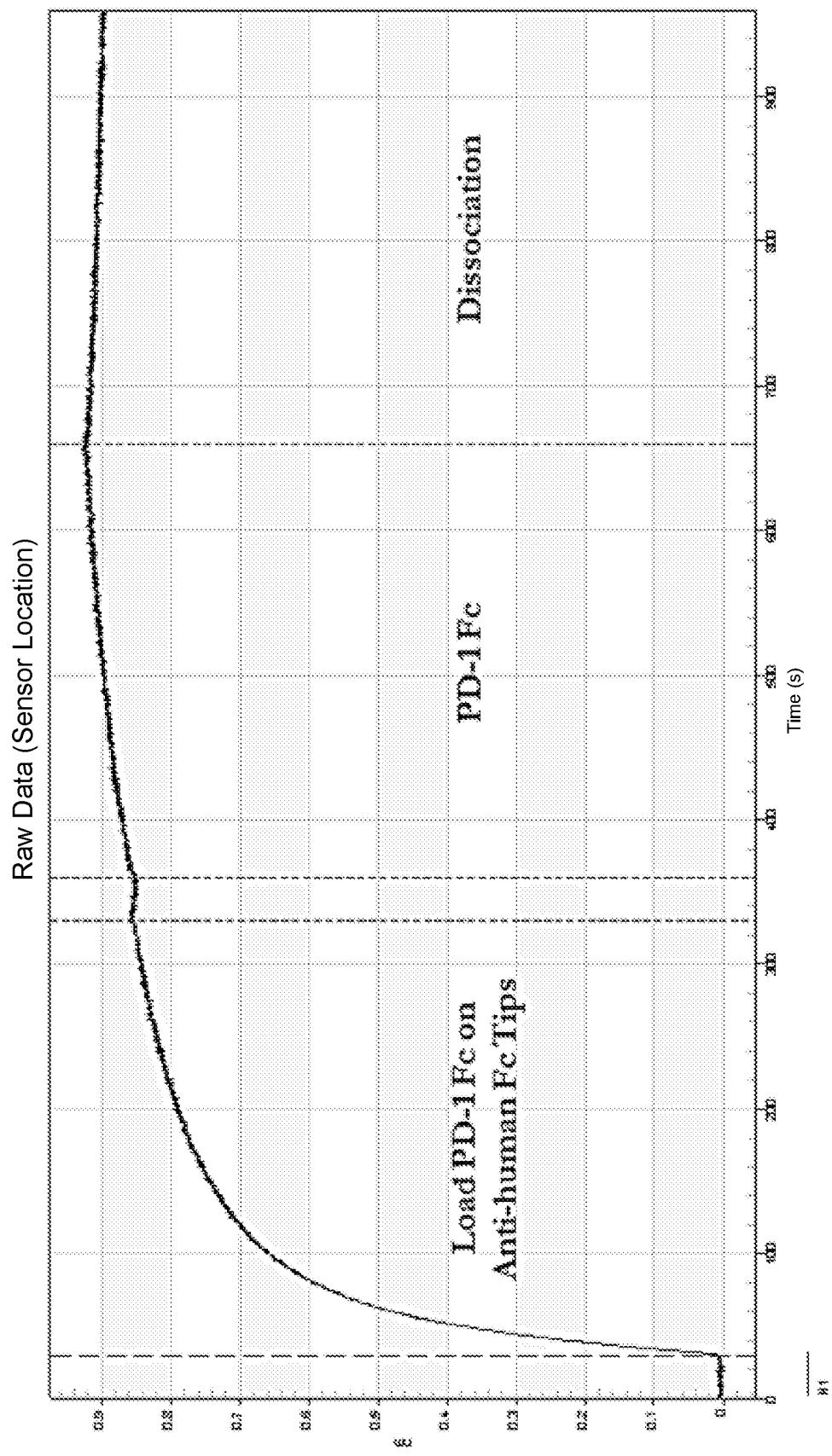

TPP-993 did not bind to PD-1 Fc because TPP-993 lacks a PD-L1 domain (FIG. 1A). TPP-994 and TPP-999 exhibited very little binding to PD-1 Fc (FIGS. 1B and 1D) while TPP-995 and TPP-1001 both exhibited binding to PD-1 Fc (FIGS. 1C and E). PD-L1 Fc, a dimeric protein having two PD-L1 proteins fused to a human Fc, bound PD-1 very strongly to PD-1 Fc (FIG. 1F), but did not bind to itself, demonstrating that the Fc portion of PD-L1 Fc did not non-specifically interact with the tips (FIG. 1G).

Example 4. Anti-DLAT Antibodies Bind Recombinant DLAT Protein

The three anti-DLAT murine IgG1 antibodies described in Example 2 were diluted to 40 μg/mL in PBS and loaded onto anti-mouse IgG1 Fc tips (ForteBio, Catalog #18-5090). Human DLAT recombinant protein (ProSpec, Catalog #ENZ-082) was diluted into PBS starting at 200 nM with three-fold dilutions down to 2.5 nM. Binding was determined by the association of the DLAT antigen with the respective antibodies using Bio-Layer Interferometry (BLI) deflections the Octet Red (ForteBio). Finally, a dissociation step in PBS was performed to determine dissociation from the bound antibodies.

Figure 2A:
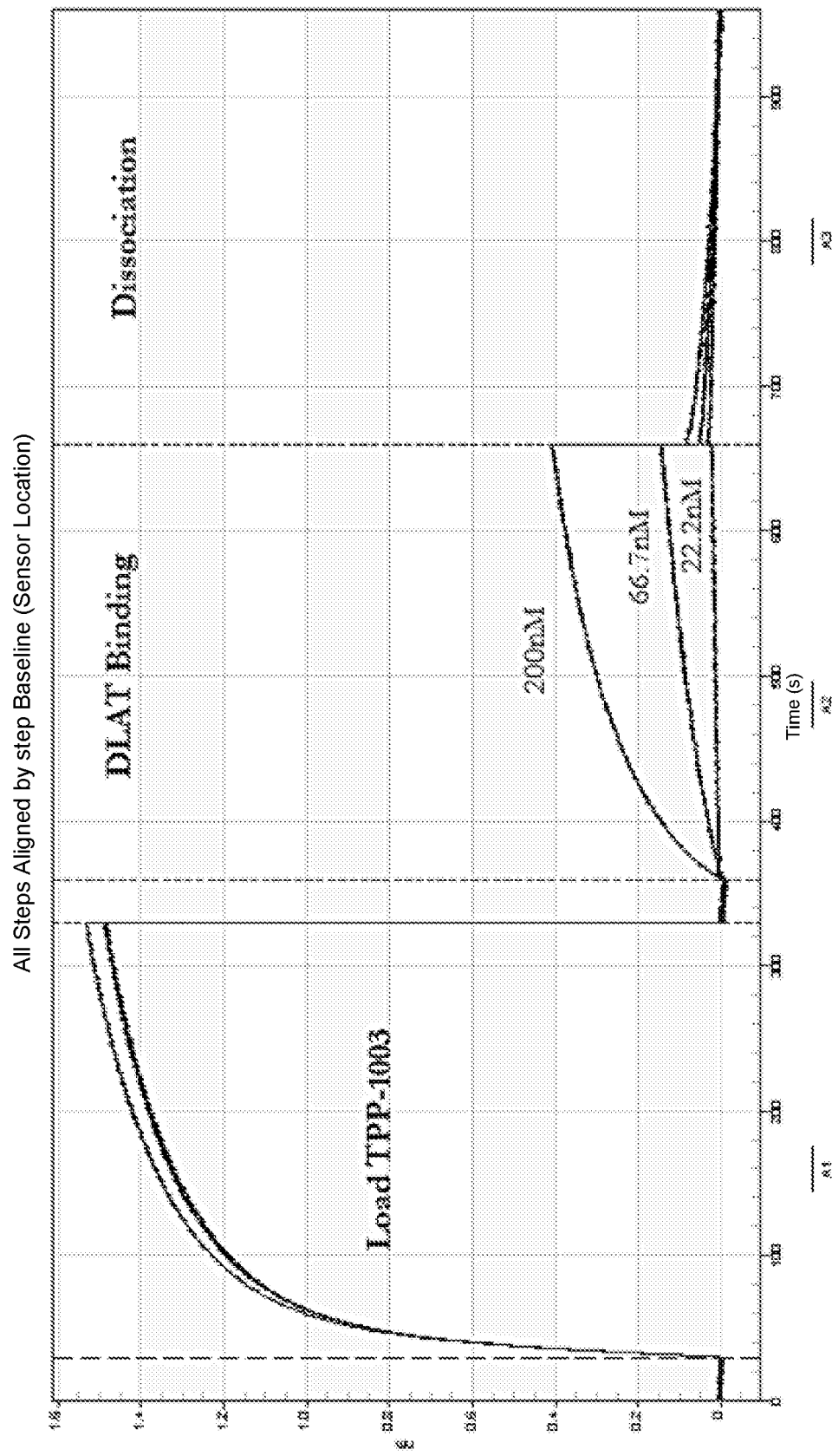
FIGS. 2A-2C show bio-layer interferometry results of mouse IgG1 chimera anti-DLAT antibodies to DLAT antigen.
Figure 2B:
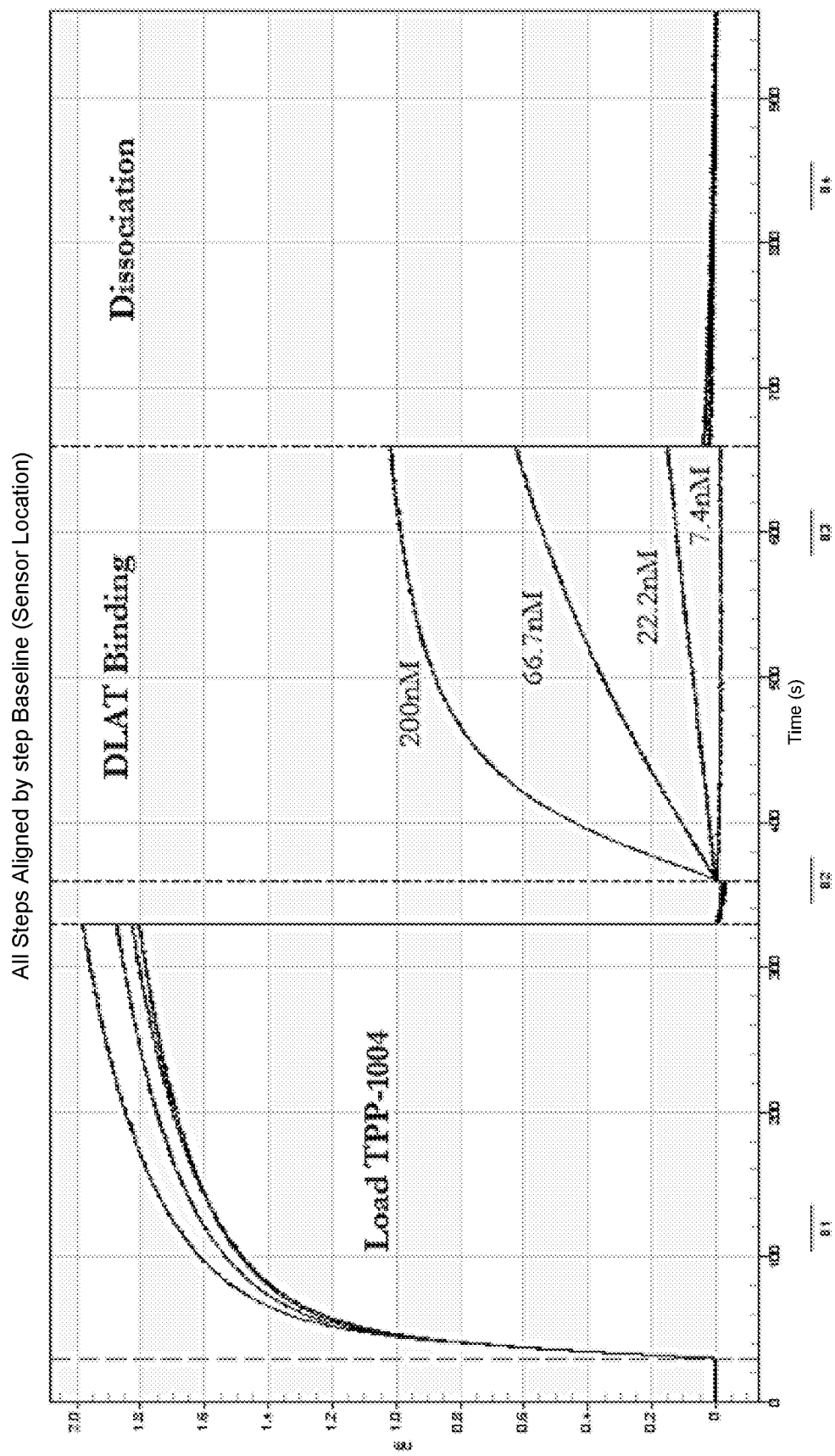
Figure 2C:
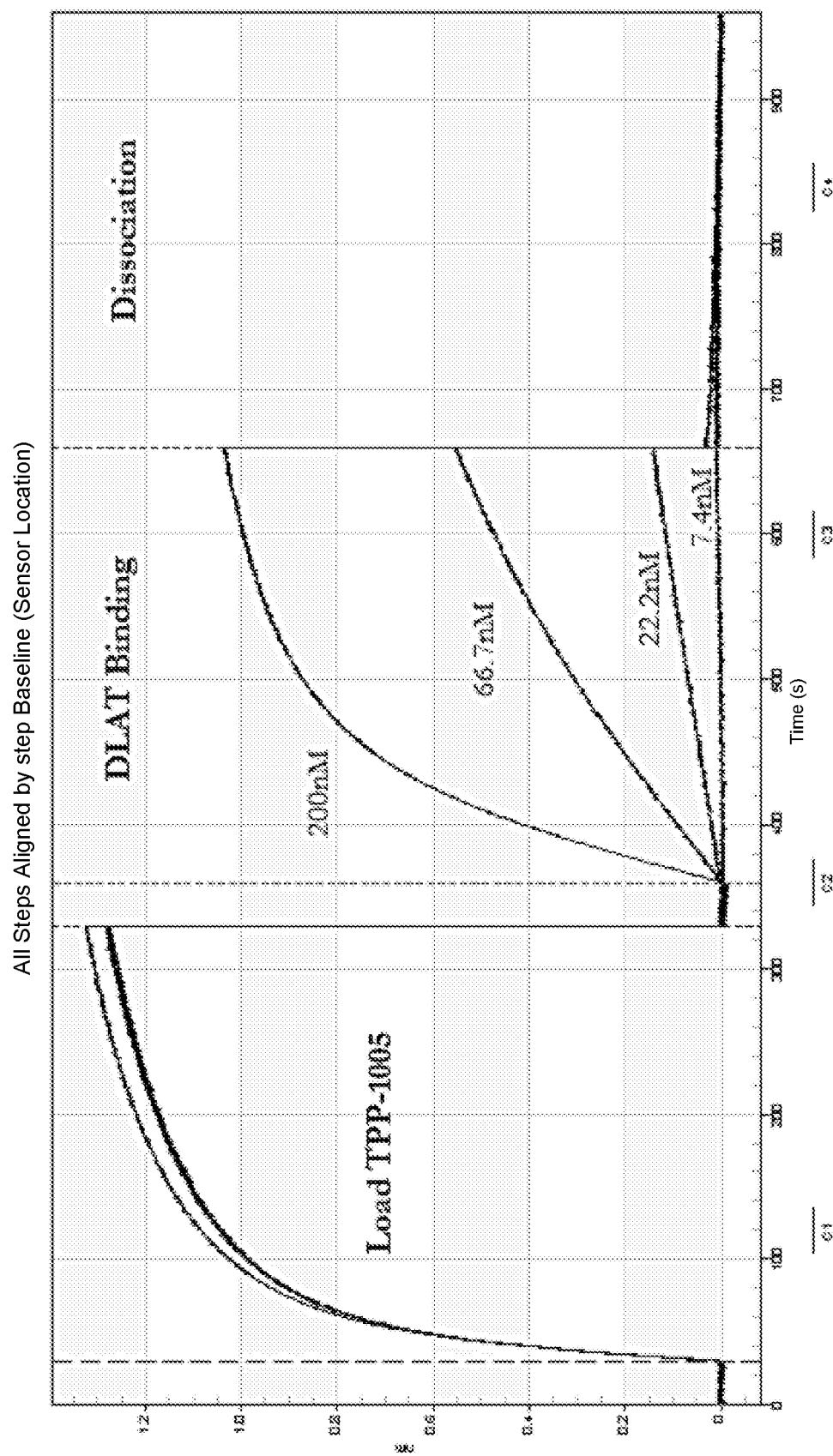

The on- and off-rates of the anti-DLAT murine IgG1 antibodies to DLAT antigen are shown in FIG. 2. Slow on-rates and fast off-rates observed for TPP-1003 suggested a weak affinity, whereas a slow off-rate observed for TPP-1004 (FIG. 2B) and TPP-1005 (FIG. 2C) suggested a high affinity to the DLAT antigen.

Example 5. Simultaneous Binding of the DLAT Antigen and PD-1 Fc by the Anti-DLAT PD-L1 Fusions As shown in Table 6 below and FIG. 3, Octet Red (ForteBio) was utilized for Bio-Layer Interferometry (BLI) to determine binding of the anti-DLAT human IgG2/4 antibodies to antibody PD-L1 fusions to associate with the DLAT antigen followed by binding to PD-1 Fc. This assay was utilized to determine the ability of the targeted PD-L1 fusions to simultaneously bind the DLAT antigen by the antibody and PD-1 Fc by the PD-L1 variable-like domain.

Antibodies and antibody fusions were diluted to 16 μg/mL in PBS and loaded onto anti-human IgG Fc tips (ForteBio, Catalog #18-5064). Human DLAT recombinant protein (ProSpec, Catalog #ENZ-082) was diluted into PBS to 10 μg/mL. PD-L1 Fc chimera (R&D Systems, Catalog #156-B7-100) and PD-1 Fc chimera (R&D Systems, Catalog #1086-PD-050) were diluted to 12.5 μg/mL in PBS. Finally, a dissociation step in PBS was performed to determine dissociation from the bound antibodies.

Results are summarized in Table 6 below and shown in FIGS. 3A-E. The two fusions of the PD-L1 variable-like domain to the N-terminus of the anti-DLAT antibodies, TPP-986 (FIG. 3B) and TPP-992 (FIG. 3D), were able to simultaneously bind the DLAT antigen and the PD-1 Fc. The fusion proteins lacking PD-L1, or having PD-L1 fused to the antibody C-terminus (FIG. 3C) of the light chain did not bind well to PD-1 Fc for this particular combination of antibody and immune inhibitor.

TABLE 6

Binding to DLAT Antigen and/or PD-1 Fc

| Construct | Bound to DLAT Antigen? | Bound to PD-1 Fc? |
|---|---|---|
| TPP-985, human IgG2/4 PD5 antibody | Yes | No |
| TPP-986, human IgG2/4 PD5 antibody, N-terminus PD-L1 HC | Yes | Yes |
| TPP-990, human IgG2/4 PD5 antibody, C-terminus PD-L1 LC | Yes | No |
| TPP-992, human IgG2/4 PD5 antibody, N-terminus PD-L1 LC | Yes | Yes |
| PD-L1 Fc control | No | Yes |

Example 6. Ability of the Constructs to Inhibit Human T-Cell Activation Bead Preparation Dihydrolipoamide Acetyltransferase (DLAT) human T-cell activation beads were prepared by conjugating 120 μg anti-human CD3, clone UCHT1 (Stemcell Technologies, Catalog #60011) to 3 mL of Dynabeads M-450 Epoxy (ThermoFisher, Catalog #14011) for 18 hours rotating at room temperature in 0.1M sodium phosphate buffer, pH 8.0. See FIG. 8 for visual representations of the various bead constructs. The next day, the beads were washed and an excess of 546 μg of human DLAT recombinant protein antigen (ProSpec, Catalog #ENZ-082) was added to the anti-CD3-coated beads and incubated for an additional 24 hours at room temperature. The DLAT and anti-CD3-coated beads ("human DLAT-aCD3 Beads" or "DLAT beads") (FIG. 8) were then washed and suspended to a concentration of 4×10$^8$ beads/mL in PBS with 0.1% w/v Bovine Serum Albumin. 100 µL aliquots were prepared and stored at −20° C. These human DLAT-aCD3 Beads were constructed to facilitate T-cell activation.

Figure 8:
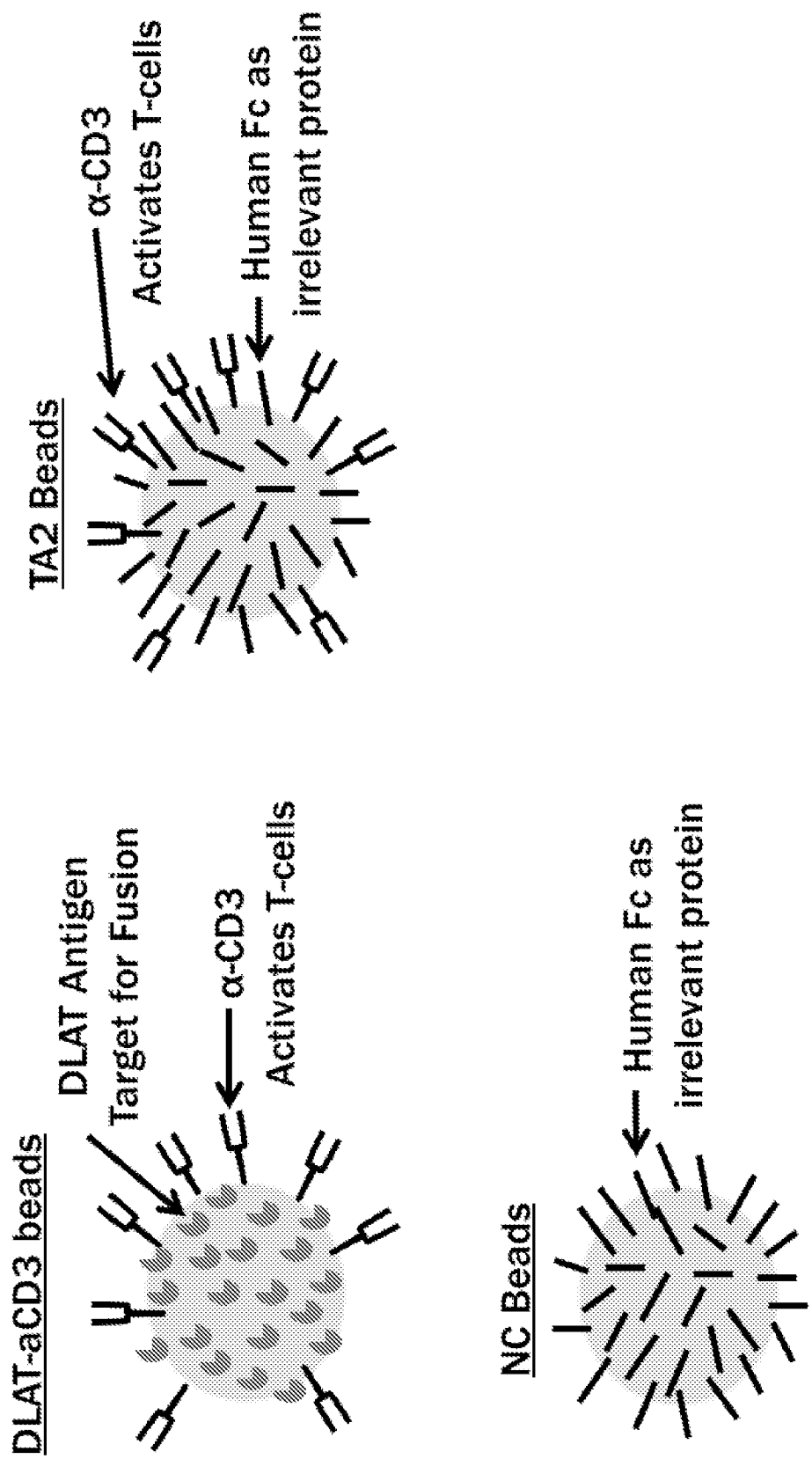
FIG. 8 is a schematic illustrating DLAT-aCD3 beads, T-cell activation beads (TA2 beads), and negative control (NC) beads used in human T-cell activation assays. DLAT-aCD3 beads were prepared by conjugating anti-human CD3 antibody and human DLAT recombinant protein, TA2 beads were prepared by conjugating anti-human CD3 antibody-coated beads with human IgG Fc, and NC beads were prepared by conjugating human IgG Fc with uncoated beads to prepare a no-activation control reagent.
Figure 9:
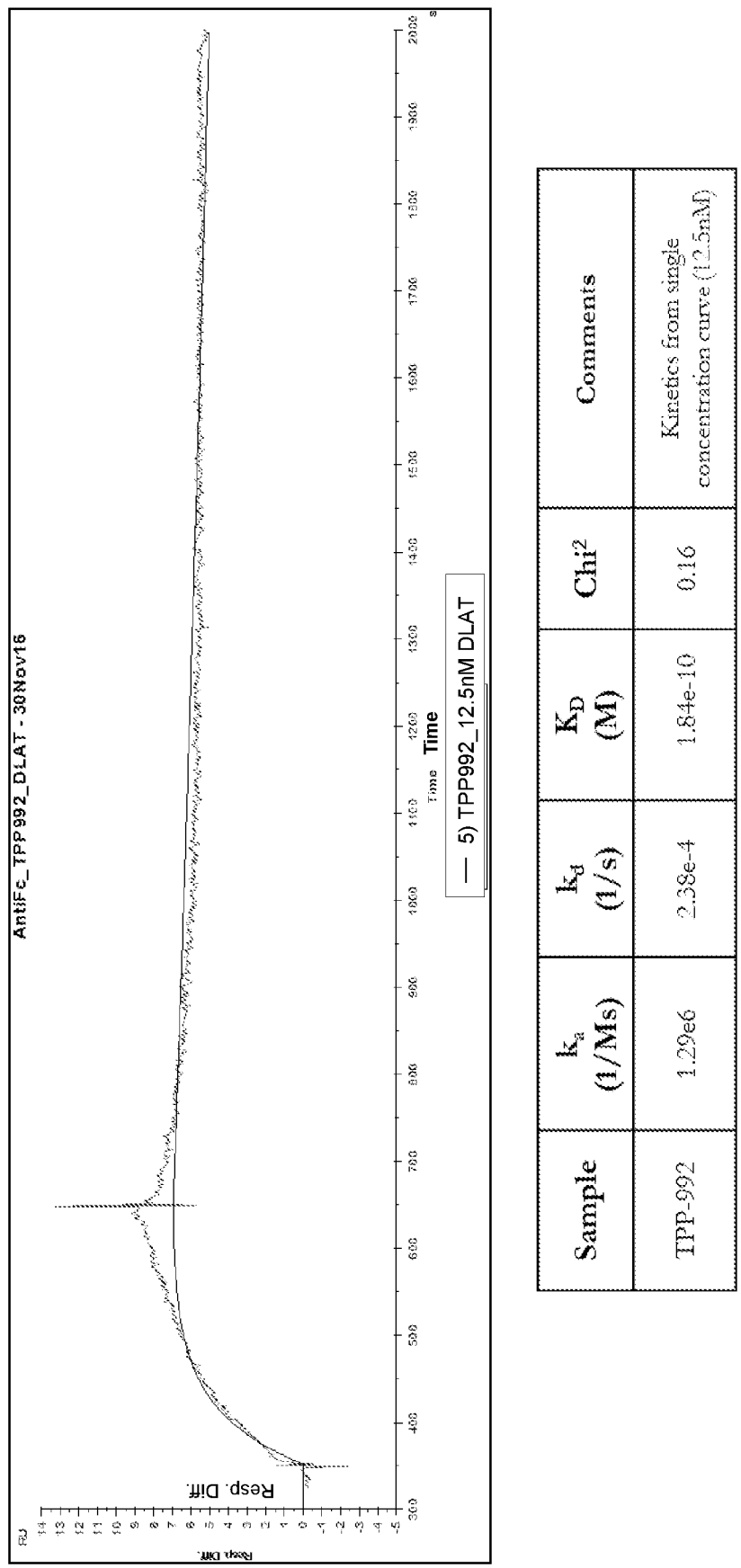
FIG. 9 depicts the binding affinity of TPP-992 (PD5 with PD-L1 V-like domain fused to the N-terminus of the light chain). TPP-992 had an affinity of 184 pM as determined using a single curve analysis by BIAcore.
Figure 10:
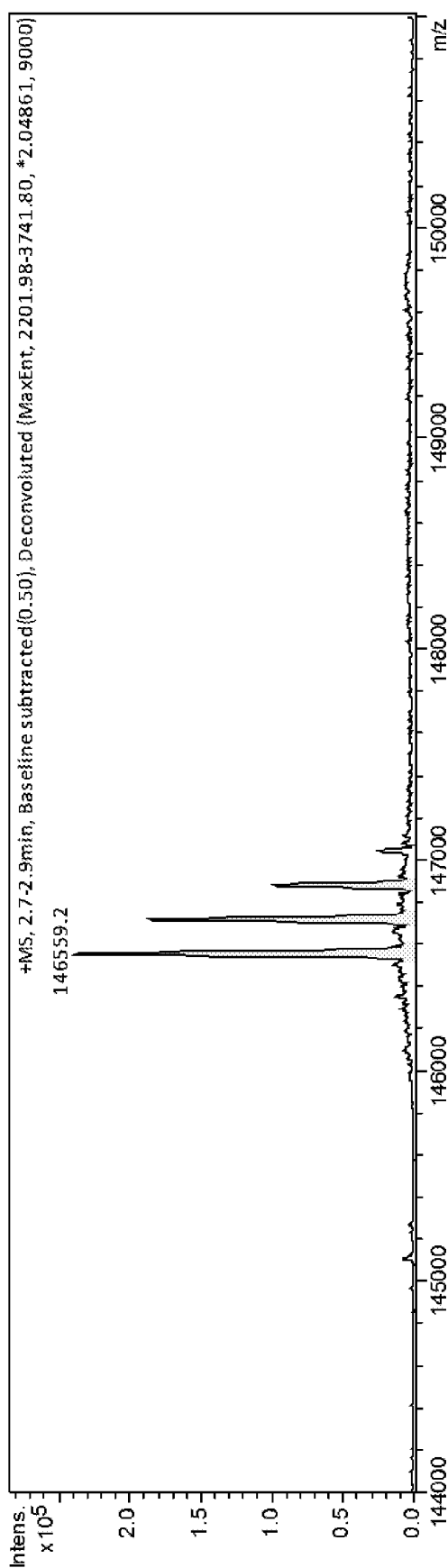
FIG. 10 depicts an electrospray ionization-time of flight mass spectra for TPP-985 and TPP-992.
Figure 11B:
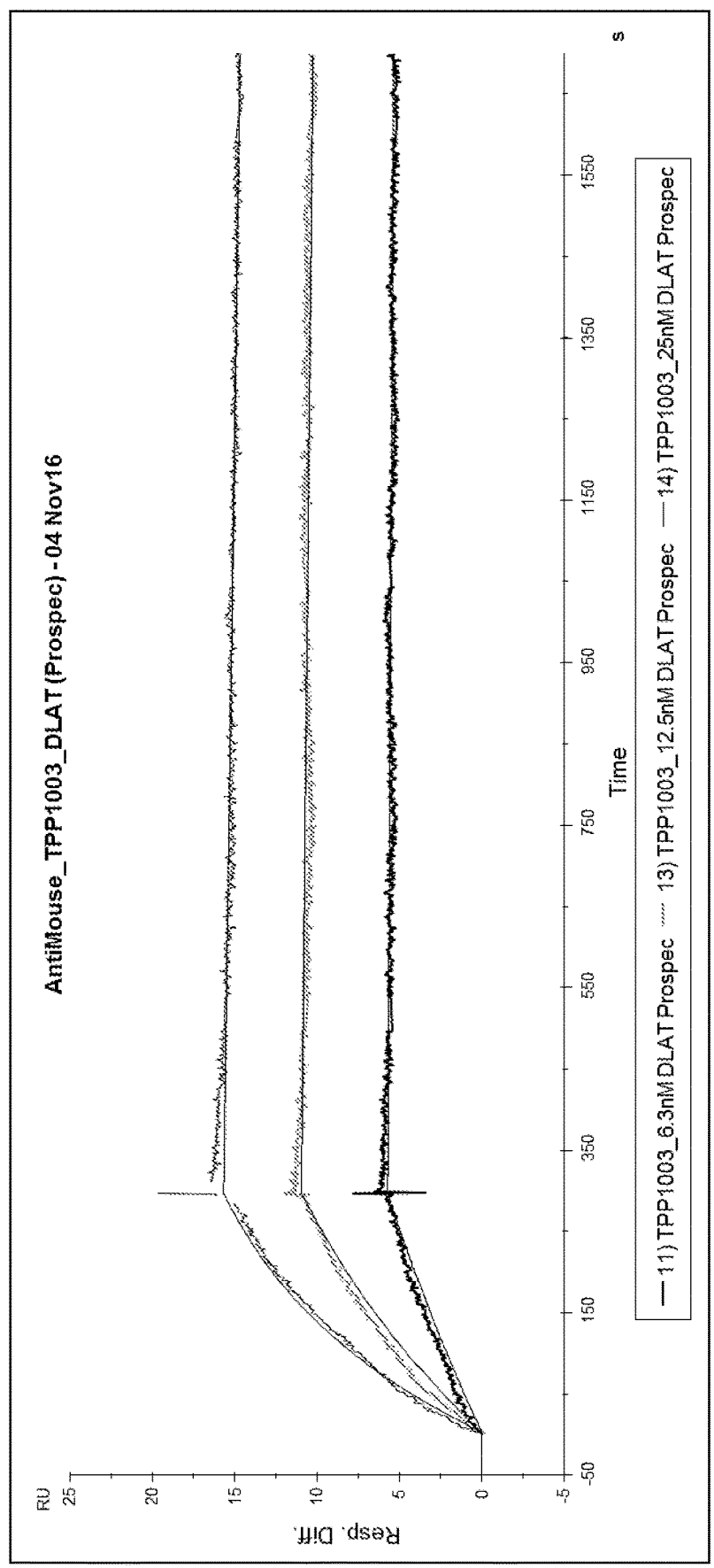
Figure 11C:
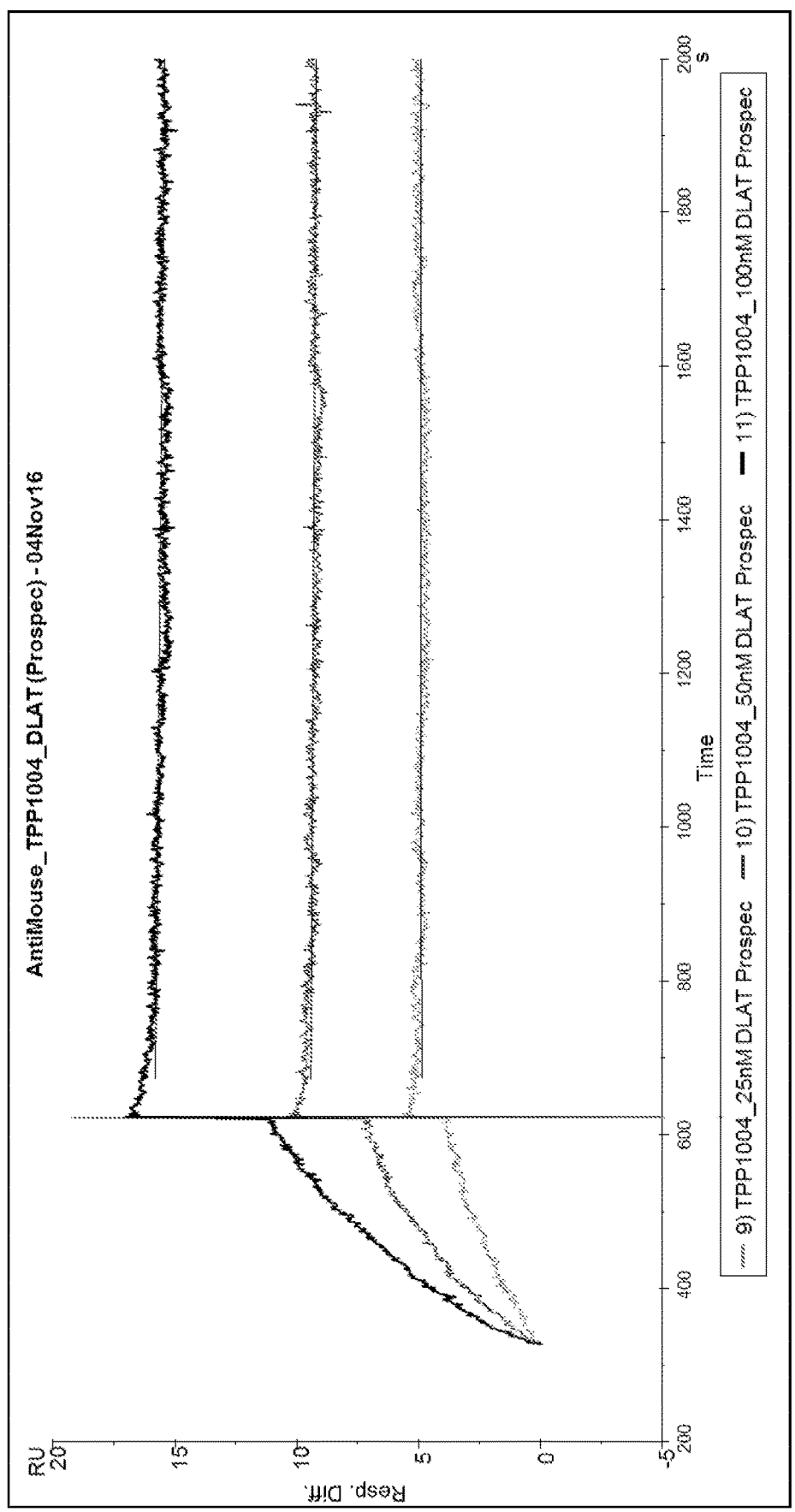
Figure 11D:
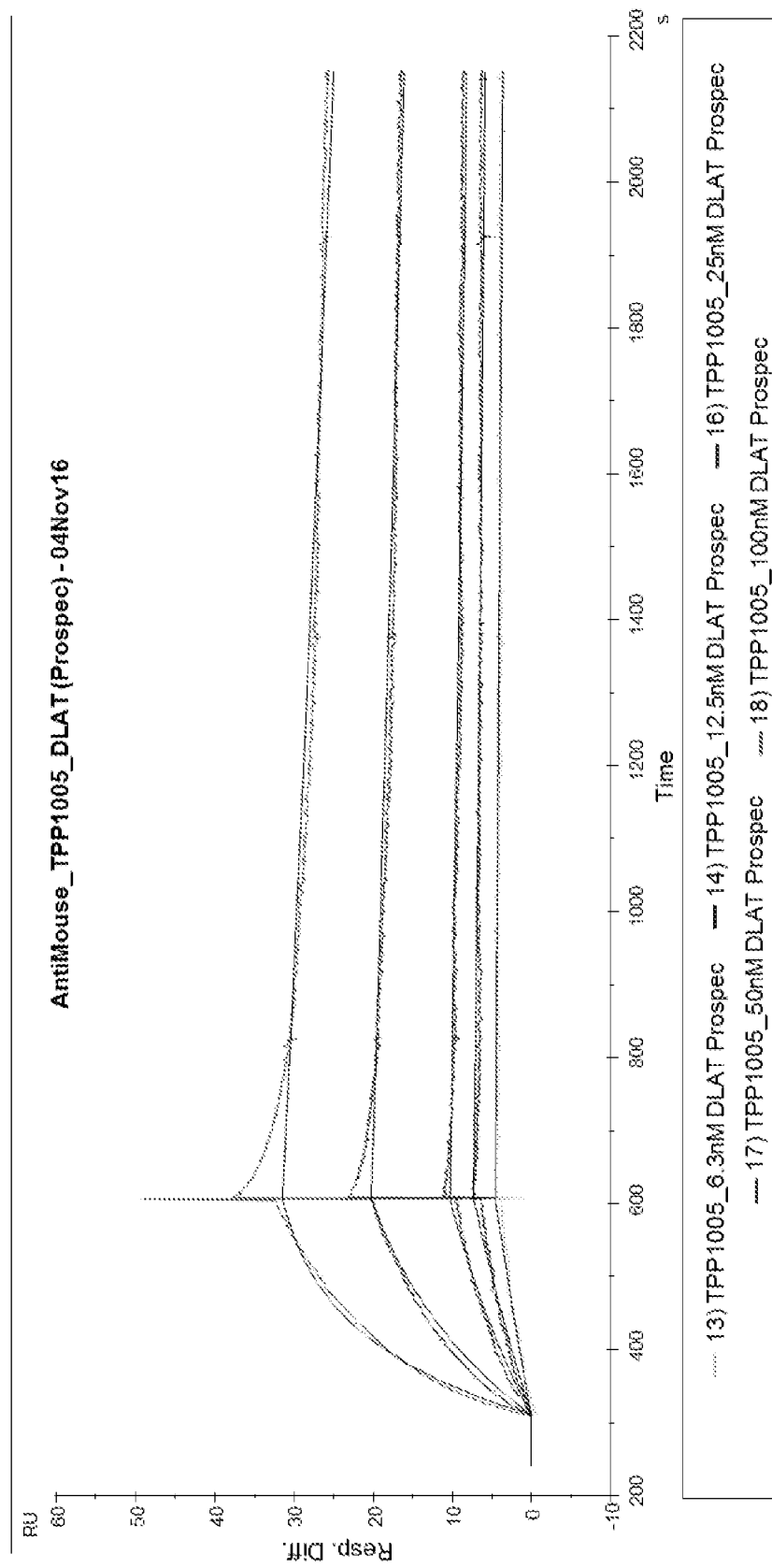

As shown in FIG. 8, T-cell activation beads ("TA2 beads") were prepared by conjugating anti-CD3-coated beads (as prepared in making the human DLAT-aCD3 beads) with negative control irrelevant human IgG Fc (Bethyl Labs, Catalog #P80-104).

Negative control ("NC") beads were prepared by conjugating human IgG Fc with uncoated beads for a no-activation control reagent. Bead conjugation was verified by flow cytometry prior to performing the T-cell activation assay.

Human T-cell Activation Assay

Human peripheral primary human pan-T-cells including CD4+ and CD8+ T-cells as well as some gamma/delta T-cell subsets (Stemcell Technologies, Catalog #70024) were stained with the CFSE Cell Proliferation Kit (ThermoFisher, Catalog #C34554) and then activated using DLAT-aCD3 beads, TA2 beads or NC beads, in the presence or absence of the anti-DLAT antibody or antibody PD-L1 fusions, TPP-985, TPP-986, TPP-992, or the PD-L1 Fc chimera as a non-targeted control (R&D Systems, Catalog #156-B7-100) at 260 nM or 65 nM in replicates of three. In addition, TPP-992 was titrated starting from 260 nM by two-fold dilutions down to 2 nM and combined with the DLAT-aCD3 beads as described. This assay was performed in a 96-well U-bottom tissue culture plate (Corning, Catalog #3799) with 1.5×10$^5$ cells/well with a 1:1.5 bead to cell ratio for 4 days at 37° C. with 5% $CO_2$. On the fourth day, flow cytometry was performed after staining with SYTOX™ Red Dead Cell stain (ThermoFisher, Catalog #S34859) following the manufacturer's protocol using the C6 Accuri Flow Cytometer with C6 Sampler (BD Biosciences) detectors FL-1 (CFSE) and FL-4 (SYTOX™ Red).

Figure 3A:
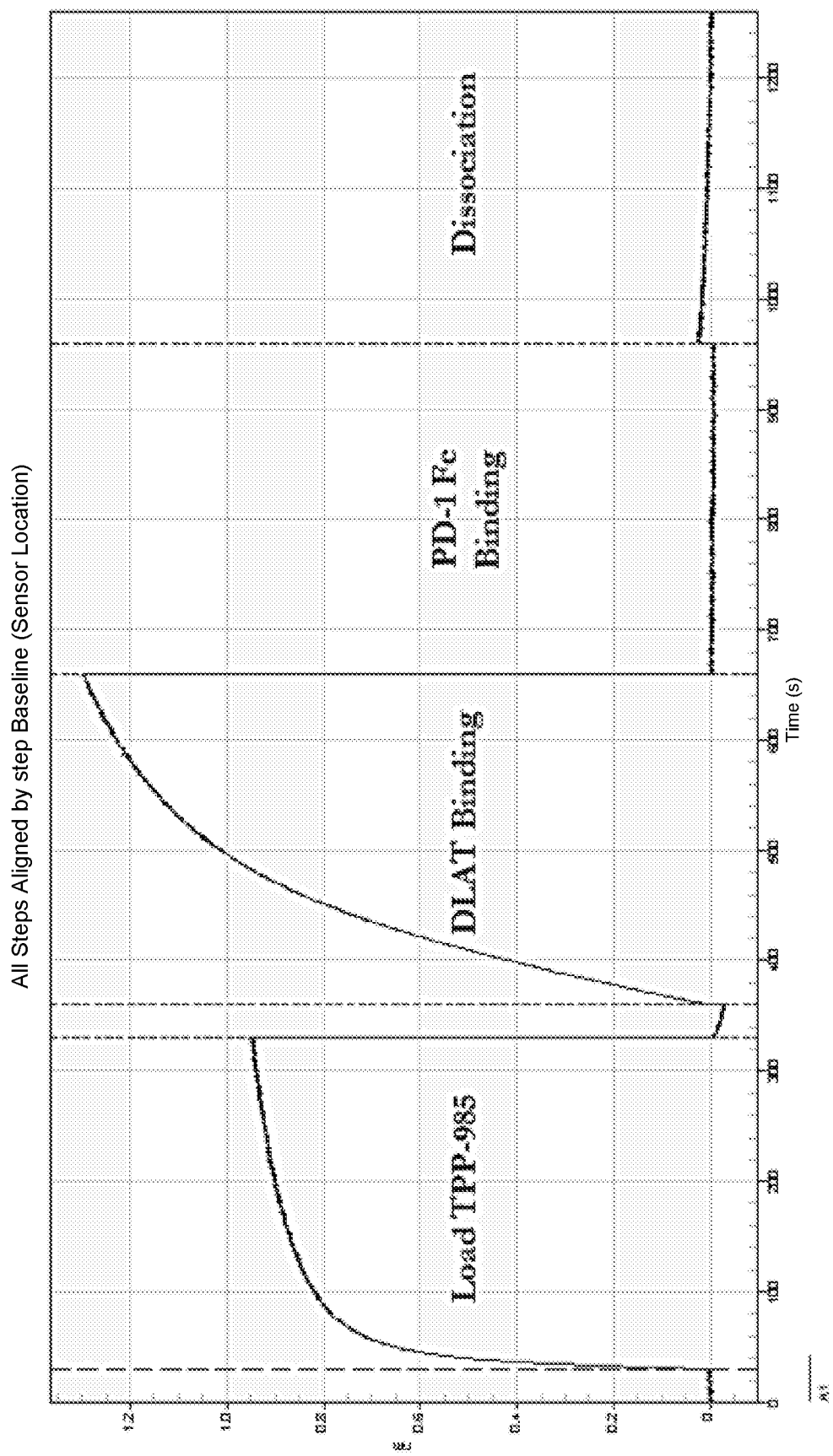
FIGS. 3A-3E show bio-layer interferometry results of simultaneous binding of human IgG2/4 anti-DLAT antibody PD-L1 V-like domain fusions to DLAT antigen and PD-1 Fc.
Figure 3B:
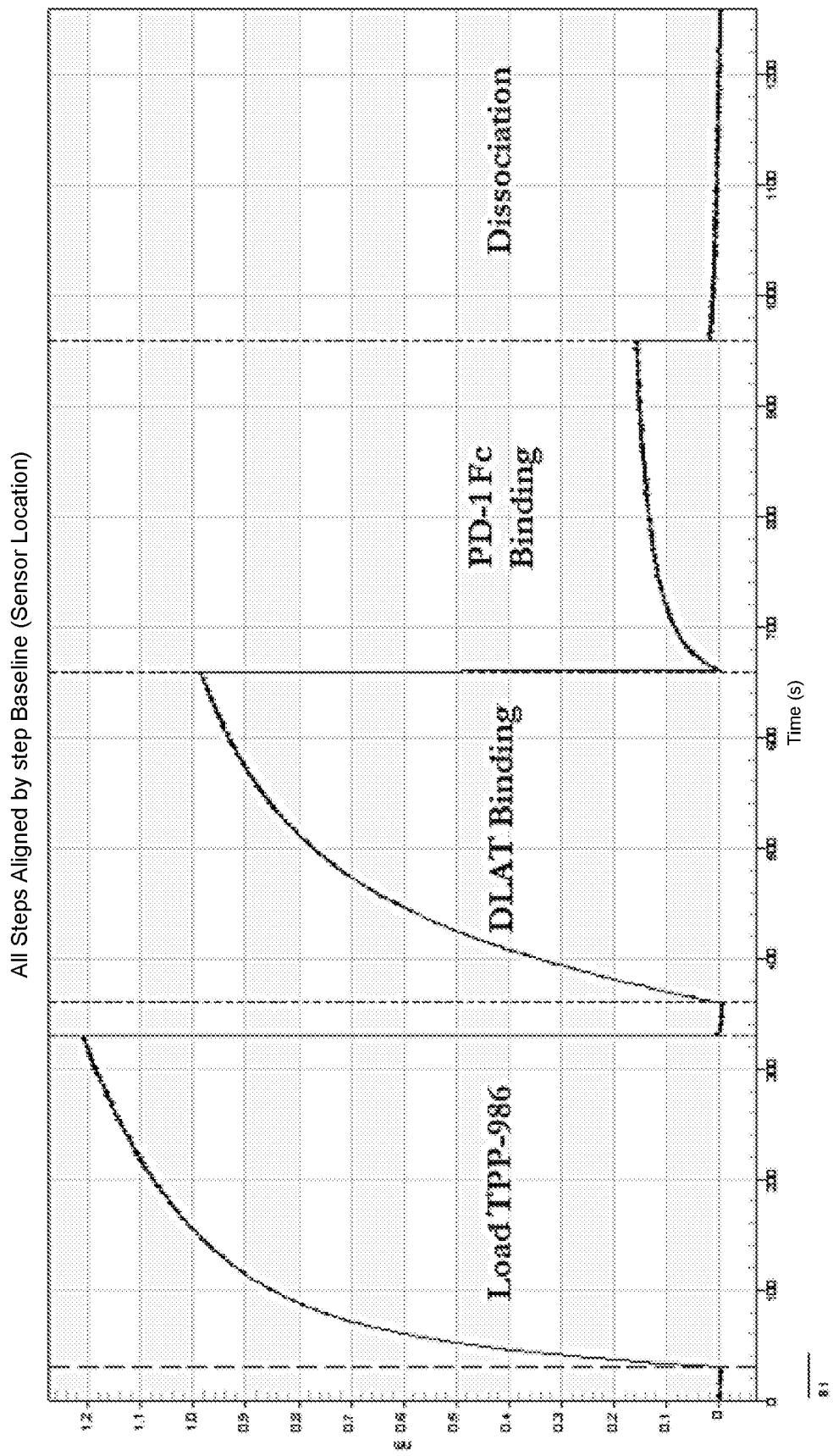
Figure 3C:
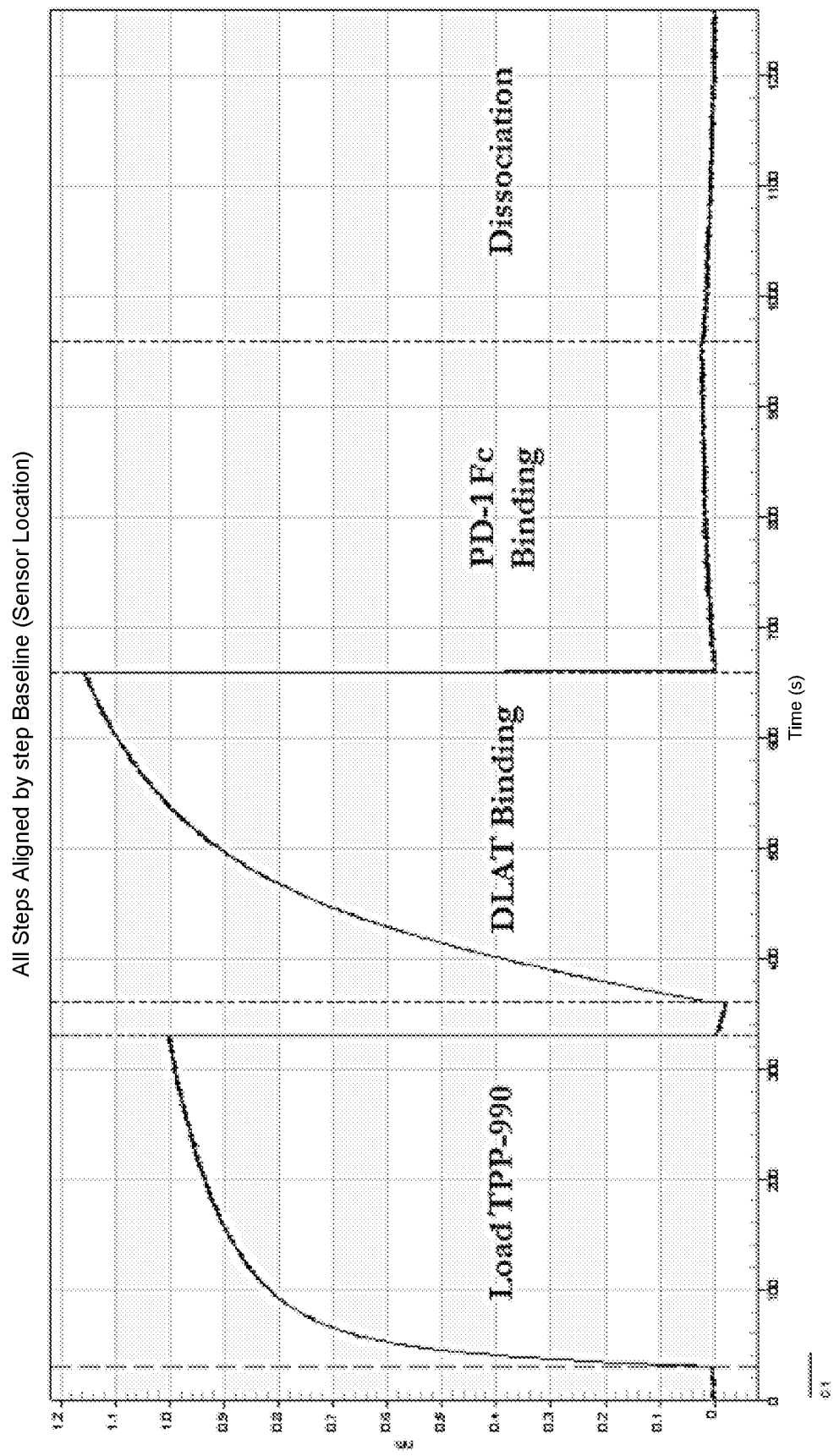
Figure 3D:
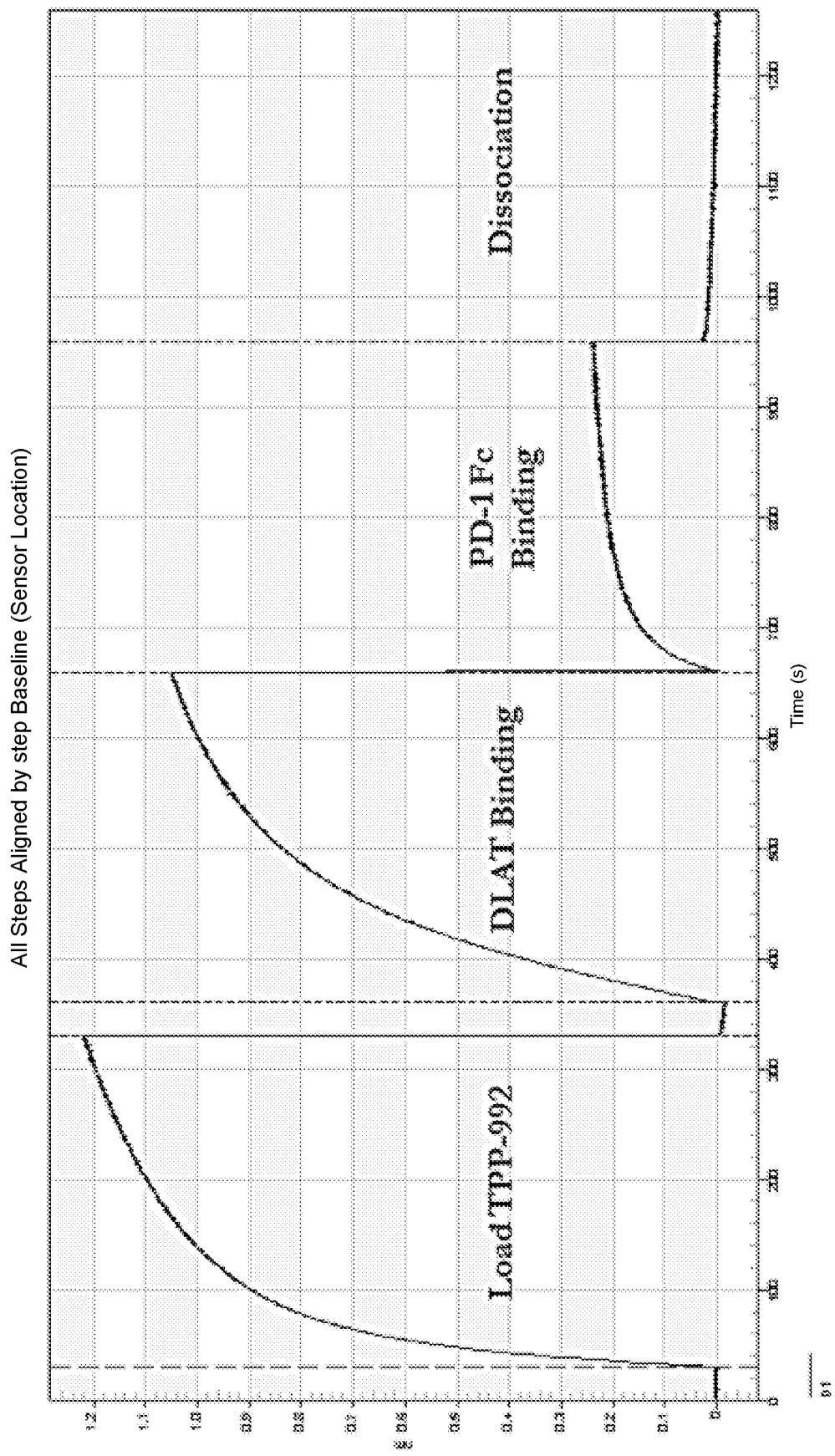
Figure 3E:
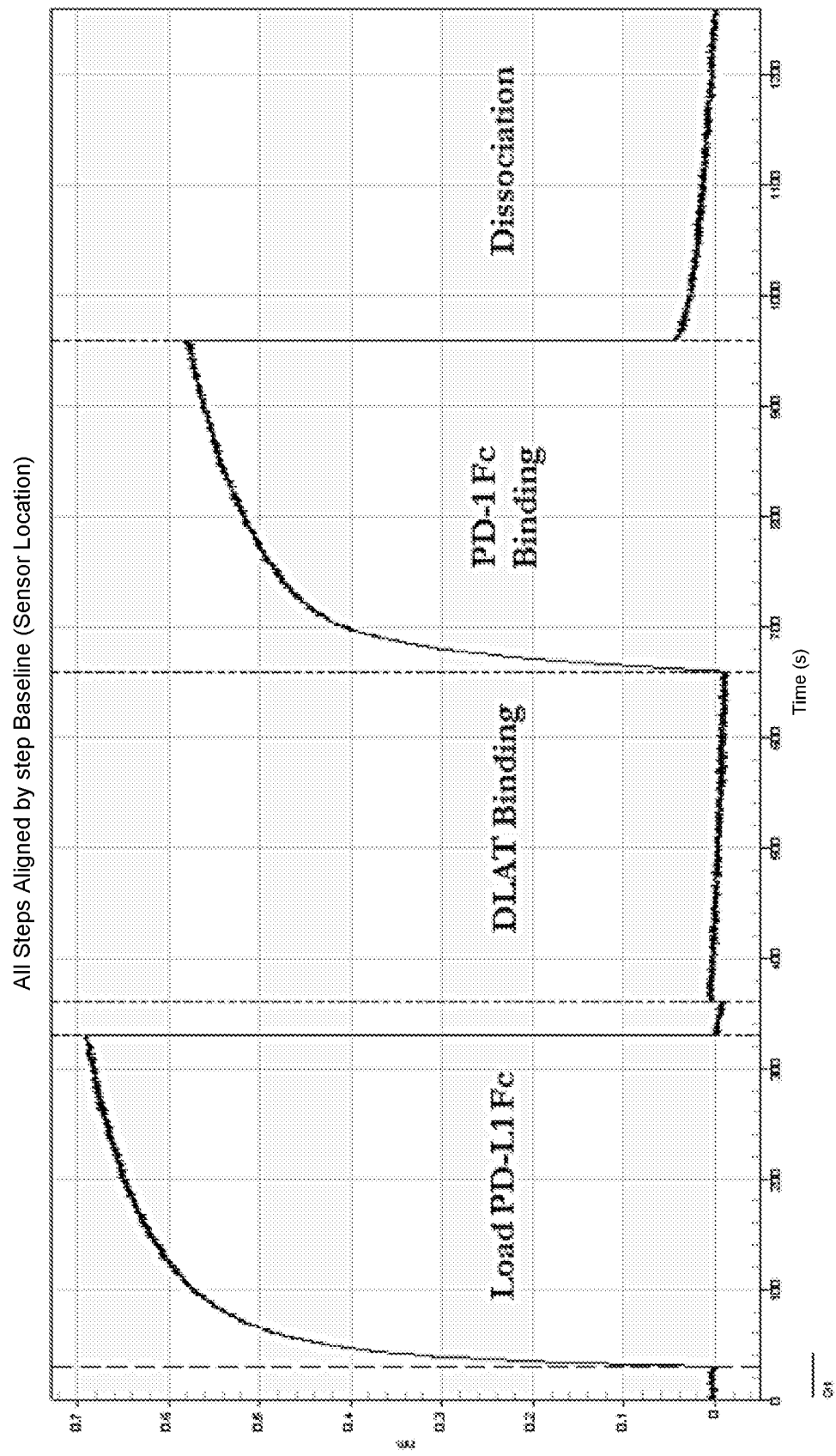

TPP-985 (human IgG2/4 PD5 antibody) bound to the DLAT antigen, but did not bind to PD-1 Fc (FIG. 3A). TPP-986 and TPP-992 (fusions of the PD-L1 V-like domain to the N-terminus of anti-DLAT antibodies) both exhibited the ability to simultaneously bind the DLAT antigen and PD-1 Fc (FIGS. 3B and 3D). TPP-990 (PD-L1 V-like domain fused to the C-terminus of an anti-DLAT antibody) bound the DLAT antigen, but did not bind PD-1 Fc (FIG. 3C). The PD-L1 Fc control bound to PD-1 Fc, but did not bind to the DLAT antigen (FIG. 3E).

As shown in FIG. 4, the decreased signal in the FL-1 mean fluorescence measurement represents the activated T-cells that have expanded into new generations of T-cells, as demonstrated by the decreasing dye concentration in each respective generation (FIG. 4A). Samples were gated to exclude the low Forward Scatter (FSC) and the FL-4+ (SYTOX™ Red) dead cells. The same gate was utilized to analyze all samples. The histograms shown in FIG. 4 were gated on the live T-cells. FIG. 4B illustrates that TPP-985, an anti-DLAT IgG2-4 with no PD-L1 variable-like domain present, showed no significant inhibition of T-cell activation.

Figure 4D:
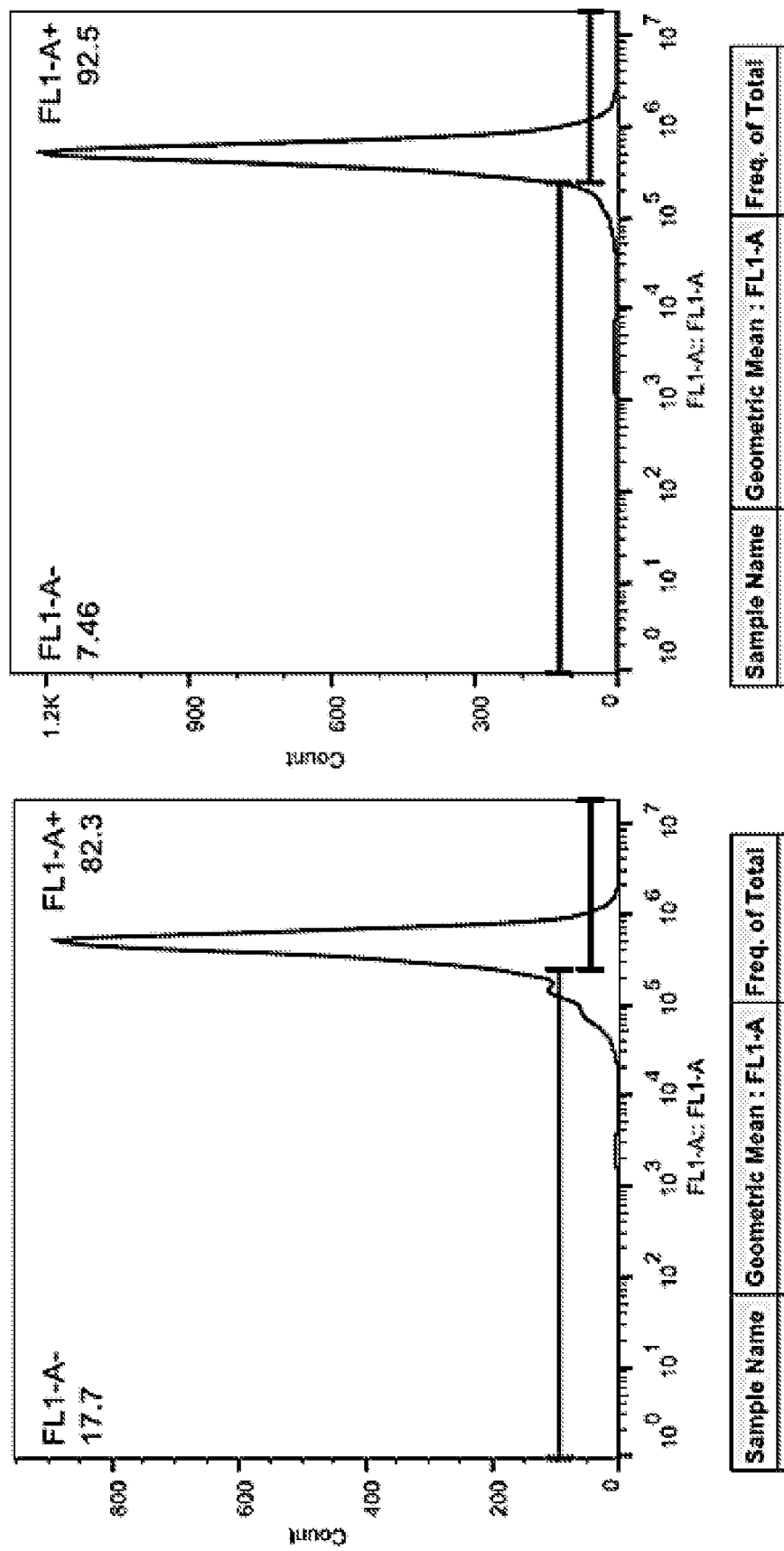
Figure 4E:
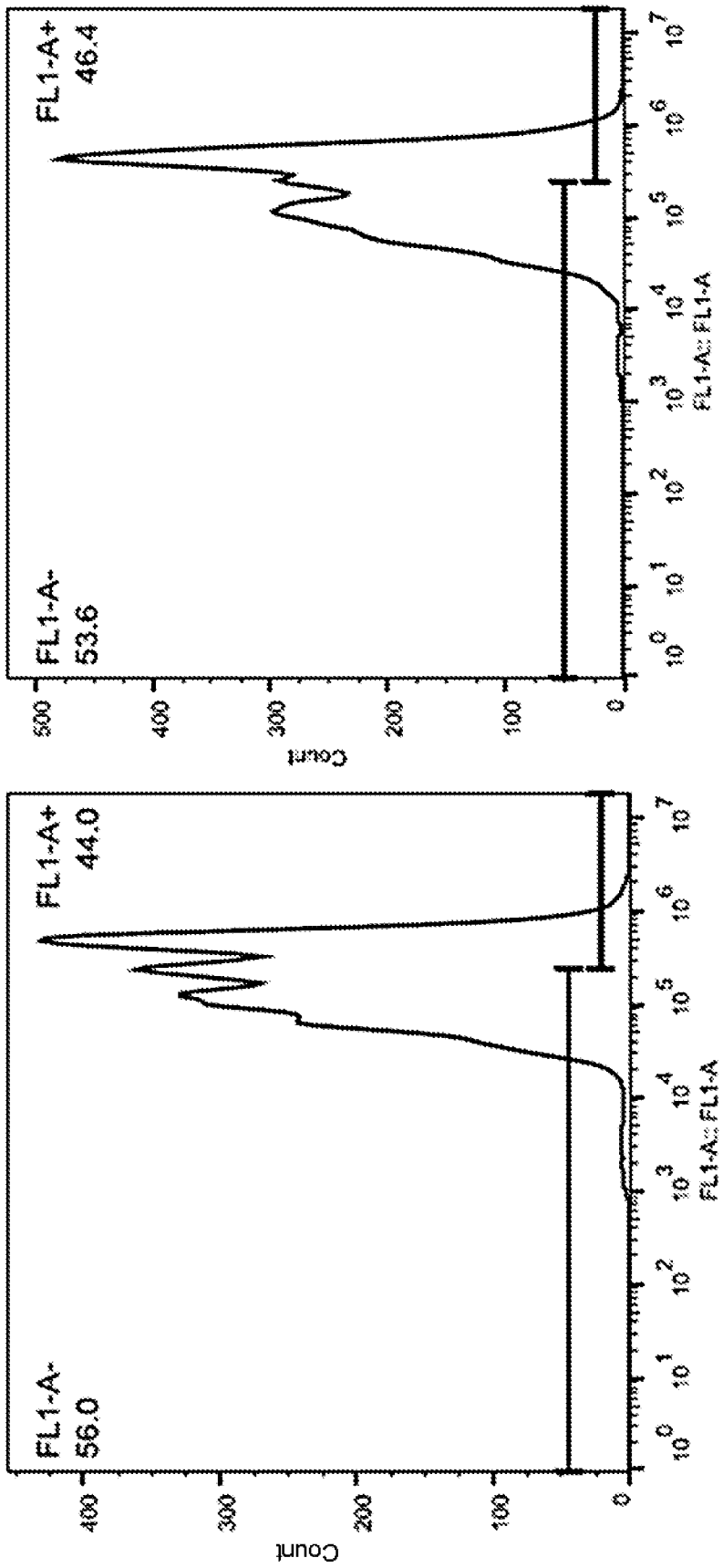
Figure 4F:
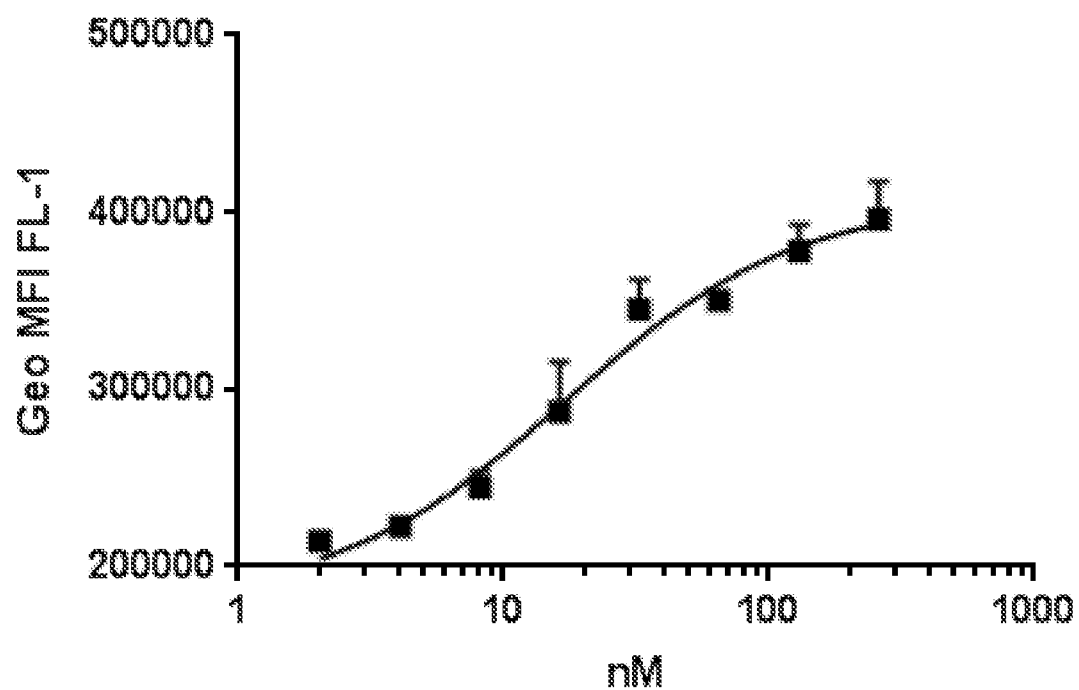

In summary, FIGS. 4A-4F show human T-cell activation for targeted PD-L1 fusion inhibition. Representative histograms of one of three replicates are shown for each sample at 260 nM and 65 nM concentrations of antibody fusions or non-targeted PD-L1 Fc. FIG. 4A illustrates that NC beads exhibited no activation of T-cells, whereas the DLAT-aCD3 beads demonstrated clear activation of the pan T-cells. FIG. 4B illustrates that TPP-985 (an anti-DLAT IgG2/4 antibody with no PD-L1 variable-like domain) exhibited no significant inhibition of T-cell activation. FIG. 4C illustrates that TPP-986 (an anti-DLAT antibody with PD-L1 fused at the N-terminus of the heavy chain) exhibited significant inhibition of T-cell activation at both the 65 nM and 260 nM concentrations. FIG. 4D illustrates that TPP-992 (an anti-DLAT antibody with PD-L1 fused at the N-terminus of the light chain) exhibited the most significant inhibition of T-cell activation, with complete inhibition at the 260 nM concentration. FIG. 4E illustrates that the non-targeting PD-L1 Fc chimera exhibited no significant inhibition of T-cell activation. FIG. 4F illustrates that the titration of TPP-992 demonstrated a dose-dependent inhibition of T-cell activation with an EC50 of 17 nM±4.5 nM.

For this particular antibody immune inhibitor fusion protein, N-terminal fusion of PD-L1 is the most effective design. To reiterate, the results shown in FIG. 4C show that TPP-986, which is an anti-DLAT IgG2/4 fused with PD-L1 on the N-terminus of the heavy chain, showed significant inhibition of human T-cell activation at both the 65 nM and 260 nM concentrations. TPP-992, (FIG. 4D) which is an anti-DLAT IgG2/4 fused with PD-L1 on the N-terminus of the light chain, showed the most significant inhibition of human T-cell activation of all of the samples tested, with nearly complete inhibition at the 260 nM concentration.

Figure 22A:
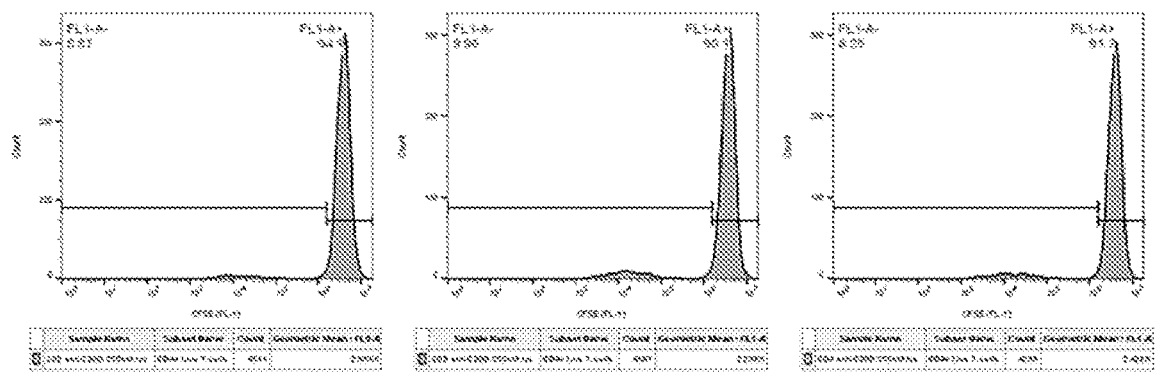
FIGS. 22A-22C illustrate histograms showing itration from 250 nM to 50 nM of anti-CD80_mPDL1 fusion incubated with CD80 activation beads for 4 days with human T-cells. The results demonstrate complete inhibition at 250 nM, partial inhibition at 100 nM and no significant inhibition at 50 nM.
Figure 22B:
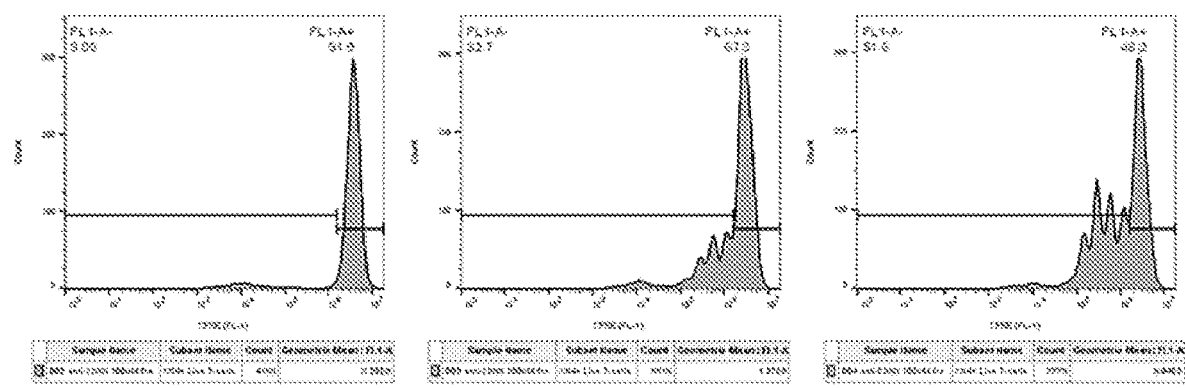
Figure 22C:
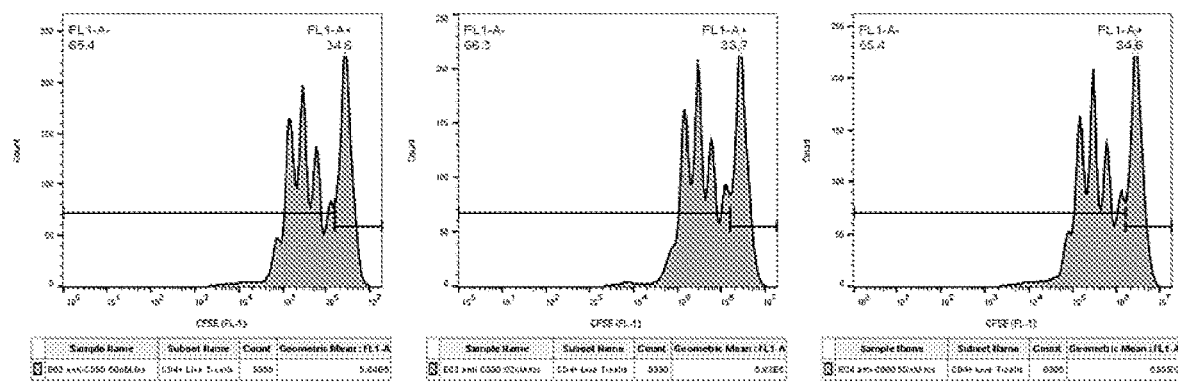
Figure 22D:
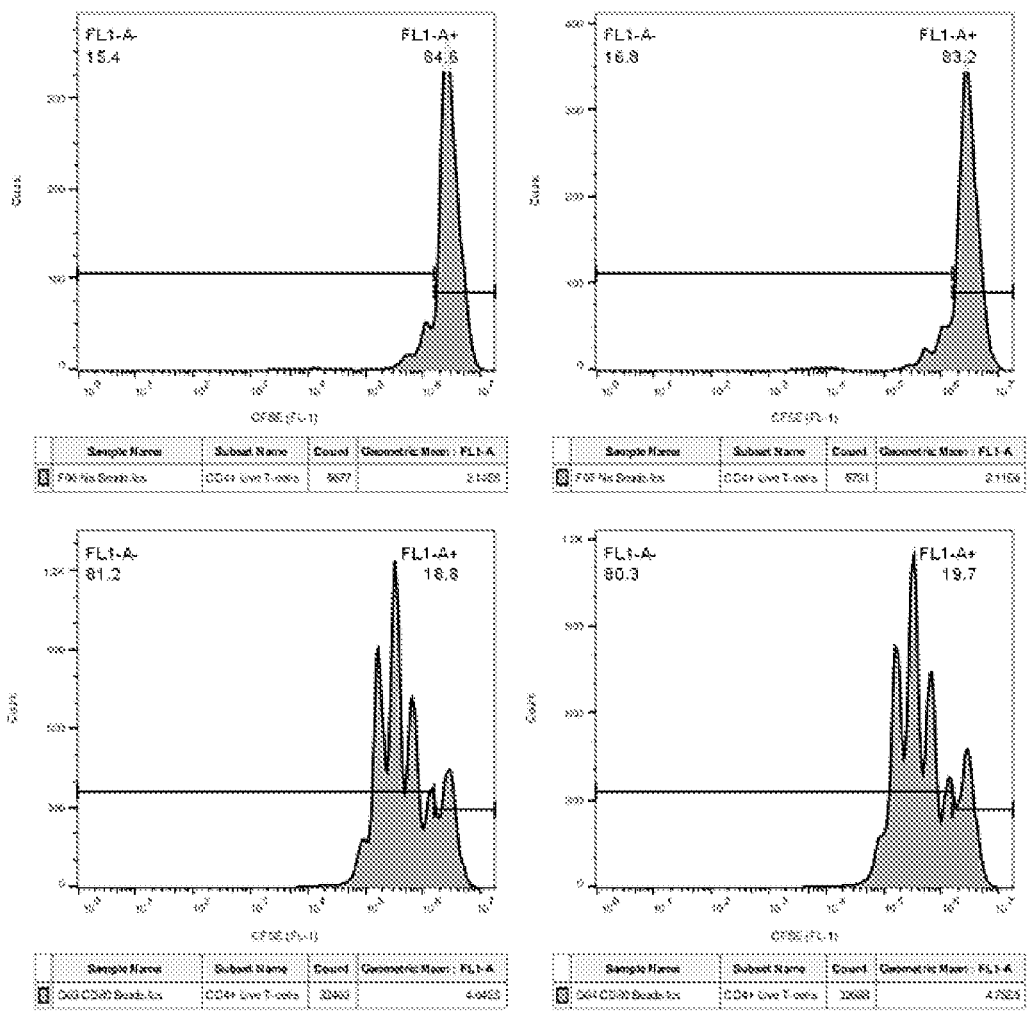
FIG. 22D shows the dilution of proliferation dye (CFSE) into the progeny T-cells observed by the multiple peaks on the histograms which indicate that the controls including no activation (labeled No Beads) had no activation and the activation control with the CD80 beads had significant activation.
Figures 22E, 22F:
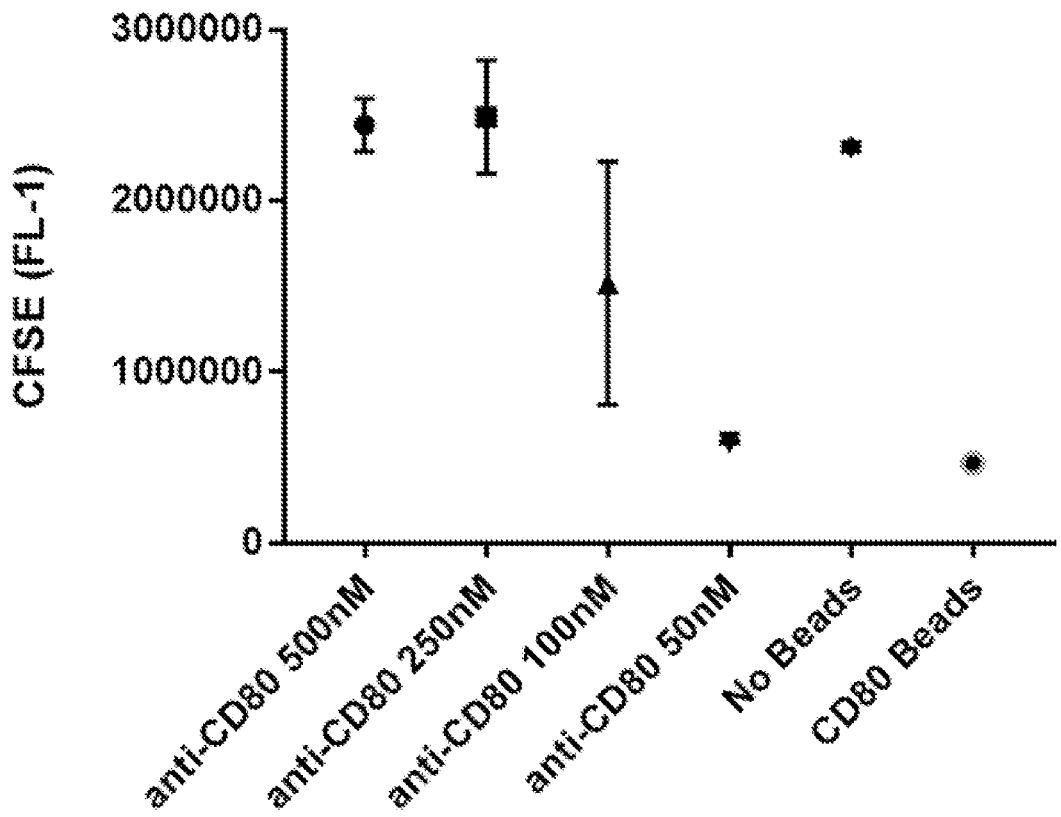
FIG. 22E is the graphical overview of the described results from above, the geometric mean of the CFSE is plotted vs the samples incubated.
FIG. 22F is the statiscal analysis of the results using Dunnett's multiple comparisons test.

FIGS. 22A-22C illustrate histograms showing titration from 250 nM to 50 nM of anti-CD80_mPDL1 fusion incubated with CD80 activation beads for 4 days with human T-cells. The results demonstrate complete inhibition at 250 nM, partial inhibition at 100 nM and no significant inhibition at 50 nM. FIG. 22D shows the dilution of proliferation dye (CFSE) into the progeny T-cells observed by the multiple peaks on the histograms which indicate that the controls including no activation (labeled No Beads) had no activation and the activation control with the CD80 beads had significant activation. FIG. 22E is the graphical overview of the described results from above, the geometric mean of the CFSE is plotted vs the samples incubated. FIG. 22F is the statiscal analysis of the results using Dunnett's multiple comparisons test.

Figure 23A:
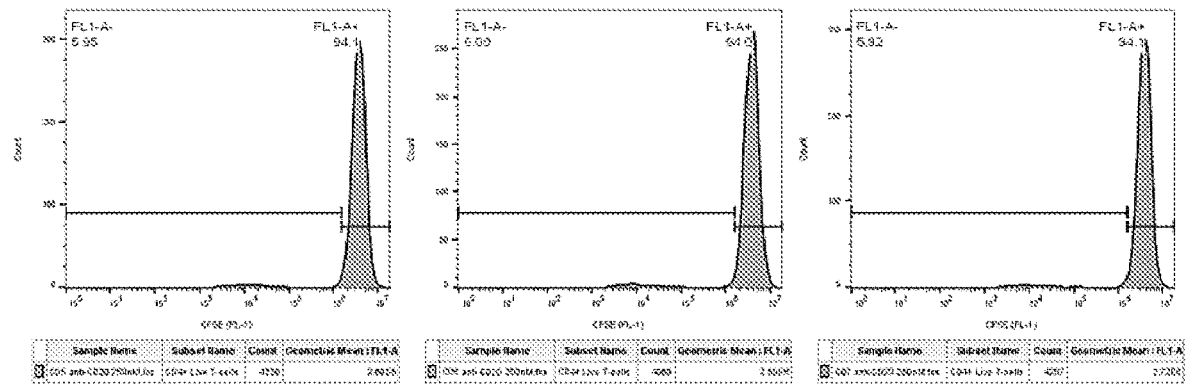
FIGS. 23A-23C demonstrate the titration of anti-CD20_mPDL1 fusion with CD20 activation beads from 250 nM to 50 nM incubated for 4 days with human T-cells. The results demonstrate complete inhibition at 250 nM, partial inhibition at 100 nM, and less inhibition at 50 nM.
Figure 23B:
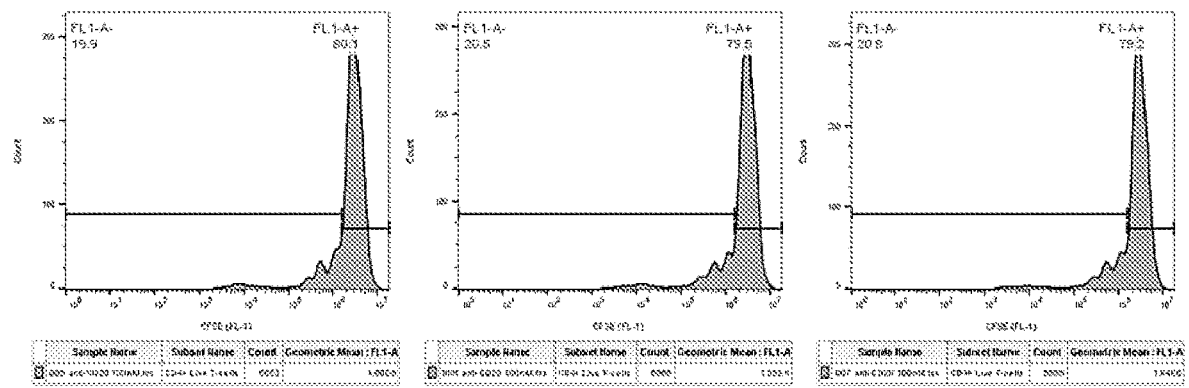
Figure 23C:
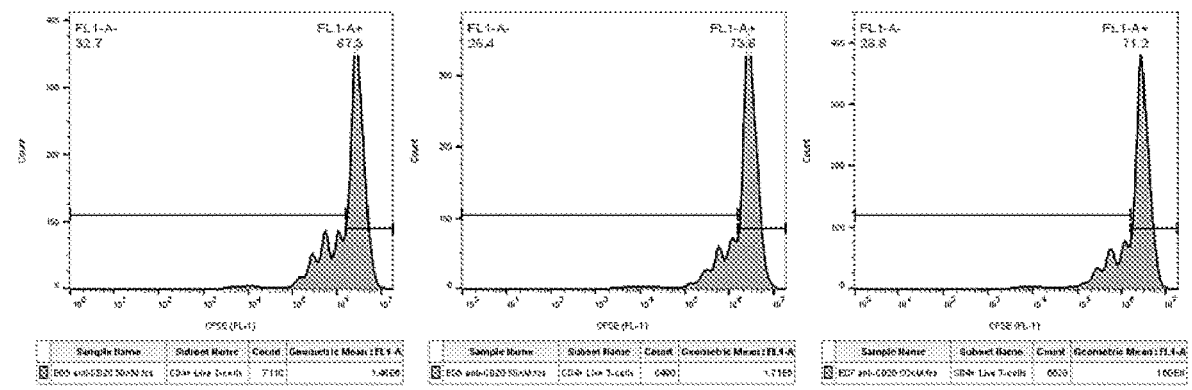
Figure 23D:
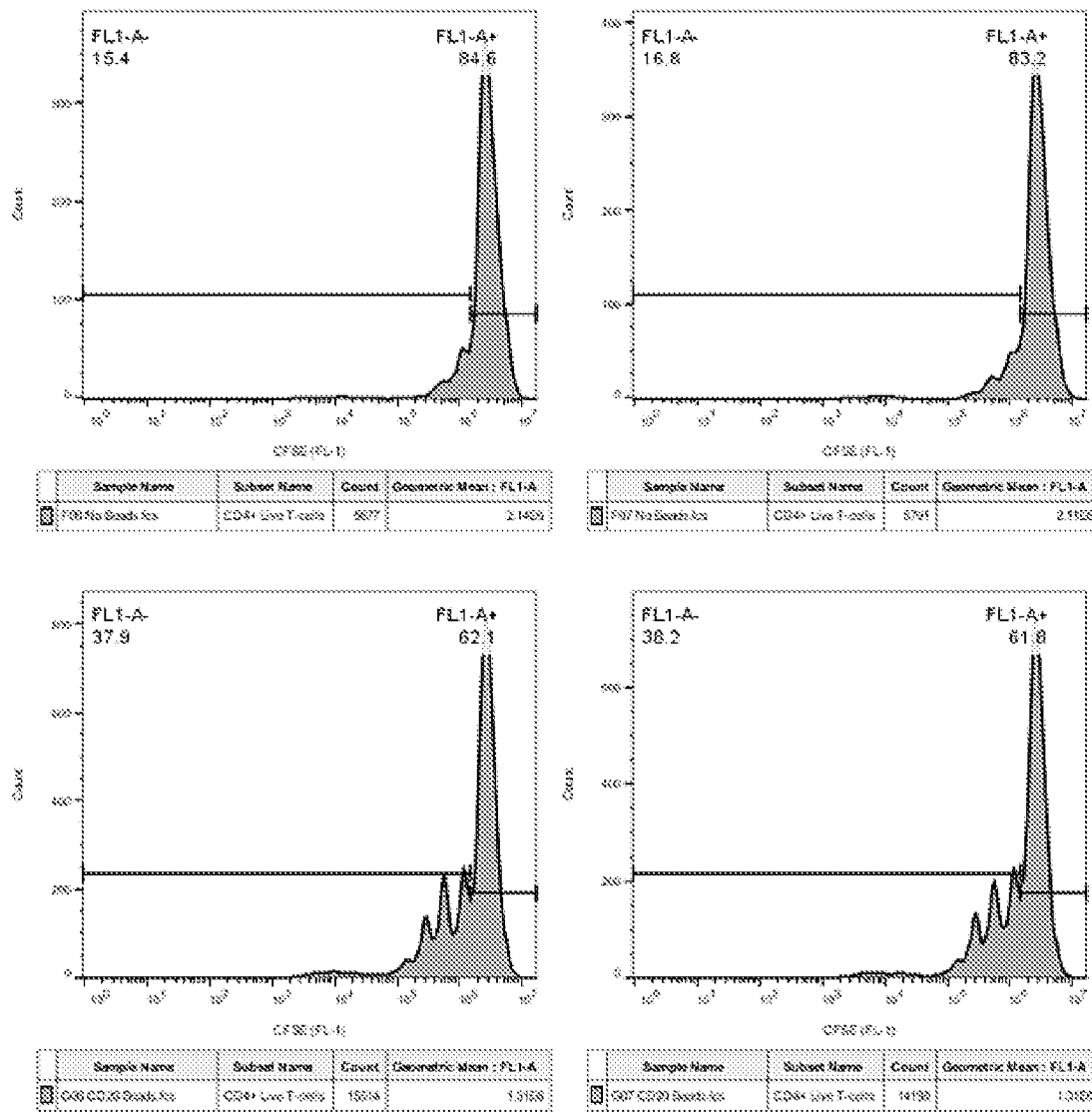
FIG. 23D illustrates the dilution of proliferation dye (CFSE) into the progeny T-cells observed by the multiple peaks indicating that activation of the T-cells by the CD20 beads occurred.
Figures 23E, 23F:
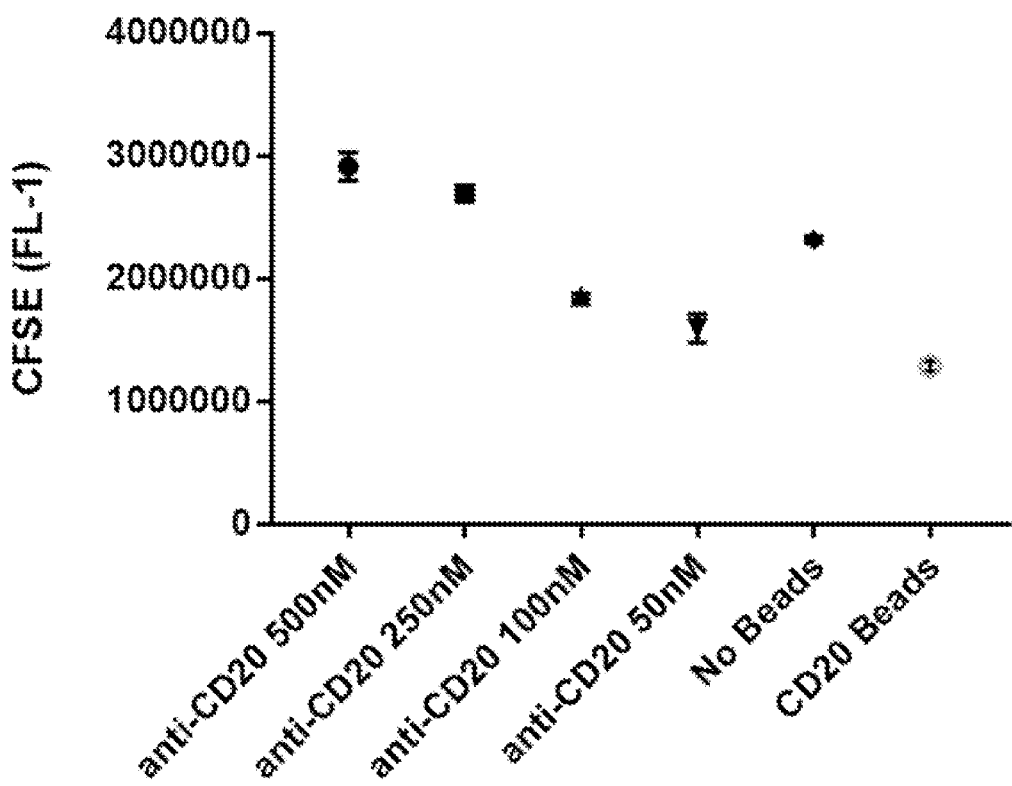
FIG. 23E represents the graphical overview of the geometric mean of the proliferation dye CFSE.
FIG. 23F is the statistical analysis of the described data demonstrating that all of the concentrations of the anti-CD20_mPDL1 were statistically significantly different from the CD20 beads showing inhibition of T-cell activation.

FIGS. 23A-23C demonstrate the titration of anti-CD20 mPDL1 fusion with CD20 activation beads from 250 nM to 50 nM incubated for 4 days with human T-cells. The results demonstrate complete inhibition at 250 nM, partial inhibition at 100 nM, and less inhibition at 50 nM. FIG. 23D illustrates the dilution of proliferation dye (CFSE) into the progeny T-cells observed by the multiple peaks indicating that activation of the T-cells by the CD20 beads occurred. FIG. 23E represents the graphical overview of the geometric mean of the proliferation dye CFSE. FIG. 23F is the statistical analysis of the described data demonstrating that all of the concentrations of the anti-CD20_mPDL1 were statistically significantly different from the CD20 beads showing inhibition of T-cell activation.

Example 7. T-Cell Activation Assay Fusion Targeting Evaluation

To determine whether the PD-L1 fusion needed to bind to surface bound DLAT in order to inhibit T-cell activation, the T-cell activation assay described above was performed on a sample combining TPP-985 (an anti-DLAT construct having no PD-L1 variable-like domain) with TPP-992 (an anti-DLAT IgG2/4 fused with PD-L1 on the N-terminus of the light chain) at 260 nM and 31 nM, respectively, in three replicates. The T-cell activation beads (TA2) were also tested with all of the fusion variants to determine if binding to the DLAT antigen was necessary for inhibiting T-cell activation.

Figure 5A:
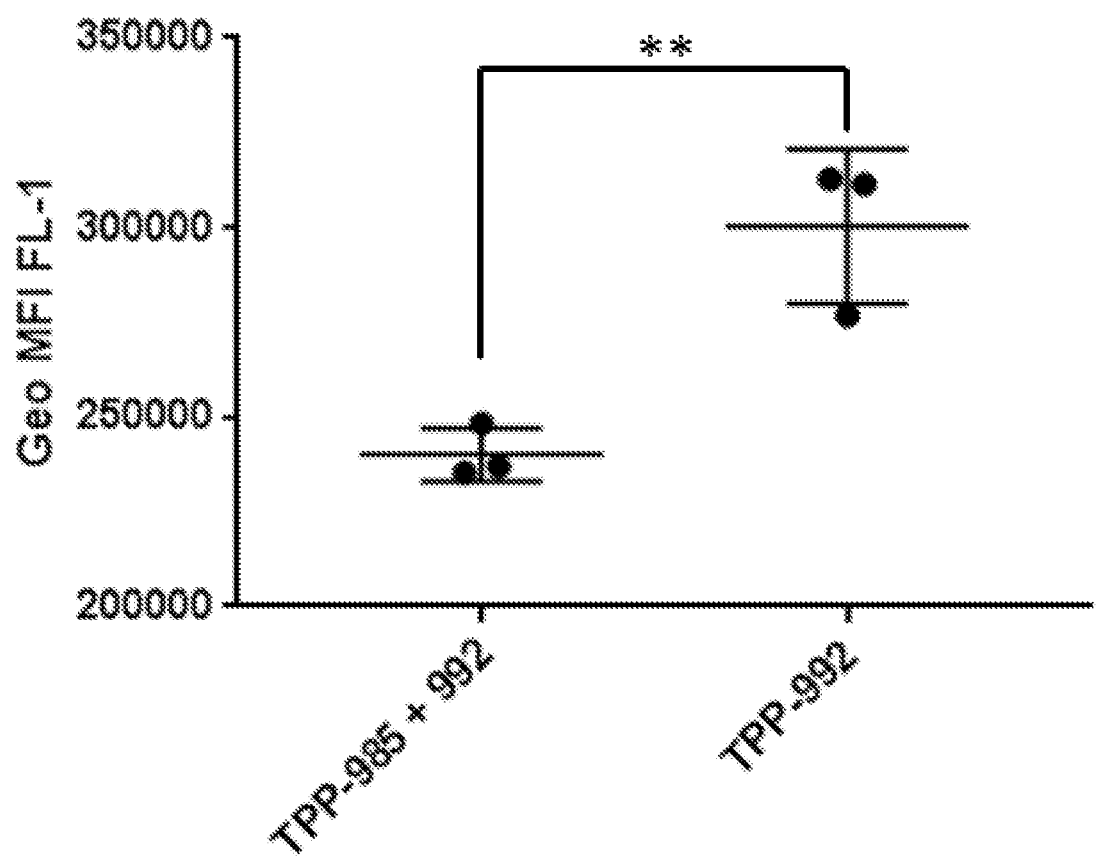
Figures 5B, 5C:
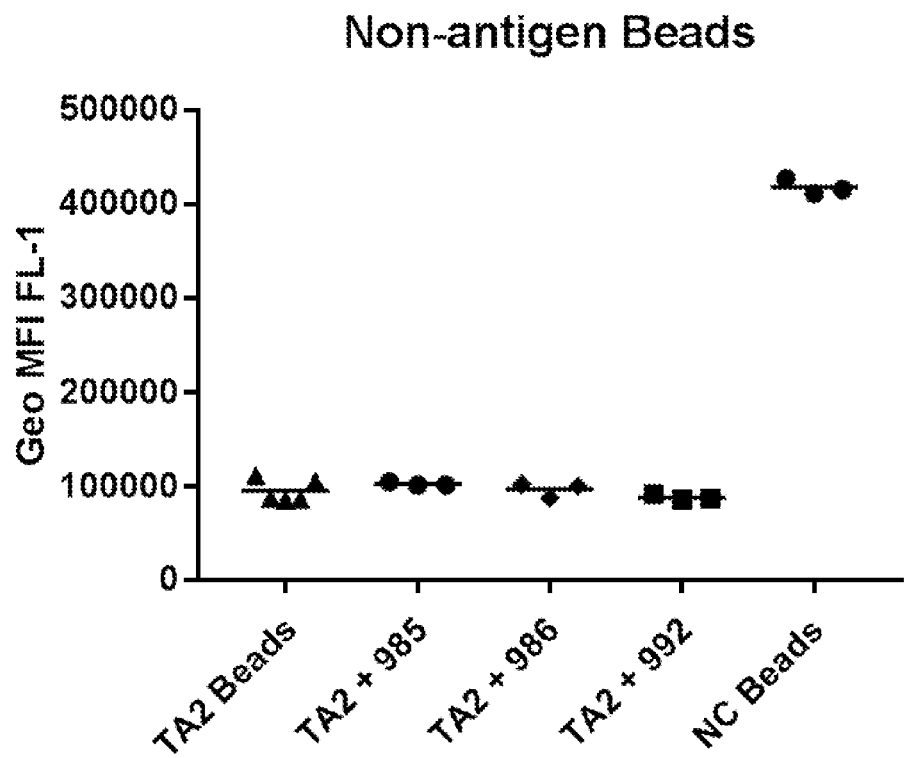

The results are shown in FIG. 5. These results show that the anti-DLAT PD-L1 fusion must bind to the DLAT on the surface of the beads in order to effectively inhibit T-cell activation.

Example 8. Statistical Analysis of T-Cell Activation Results

Statistical analysis was performed using the average geometric mean fluorescence of FL-1 (CFSE) intensity using FlowJo X software with gating as described, using the GraphPad Prism 7 software to calculate P values by One-way ANOVA multiple comparisons test. This method compares all samples to each other, providing the P values between all samples in the assay. GraphPad Prism 7 software was also utilized for all graphs displayed in figures, and all P value calculations shown. Results are shown in FIG. 6.

Figure 6A:
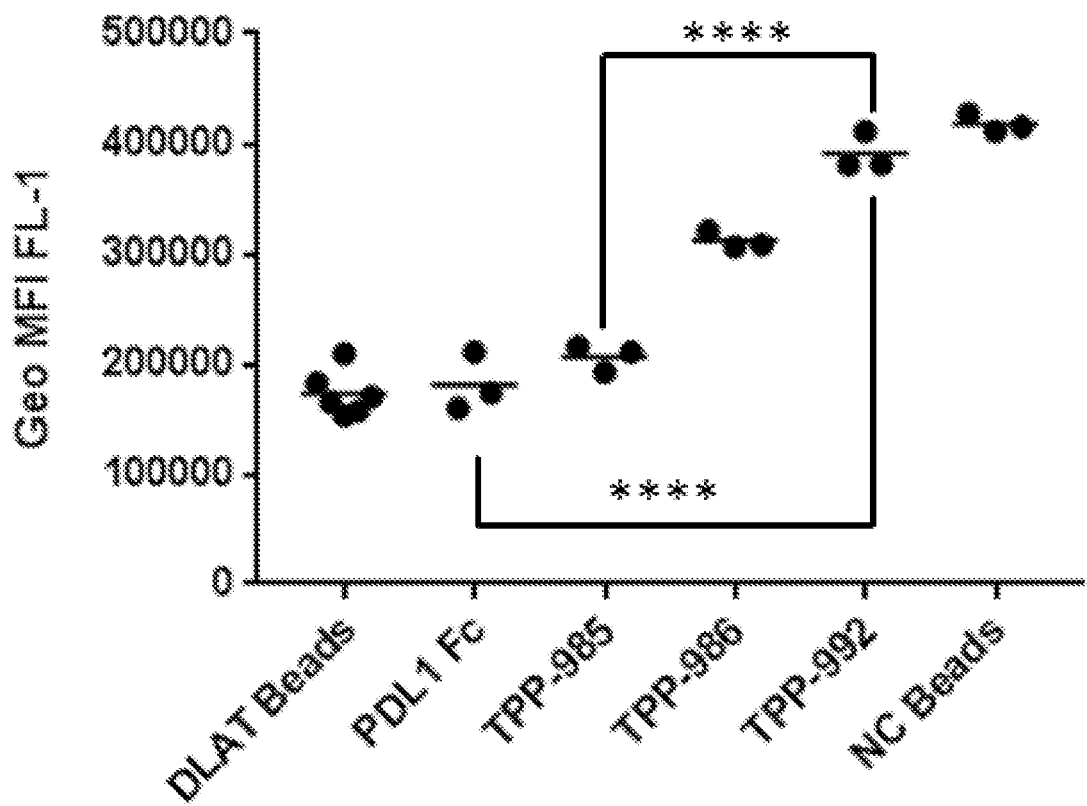
Figure 6C:
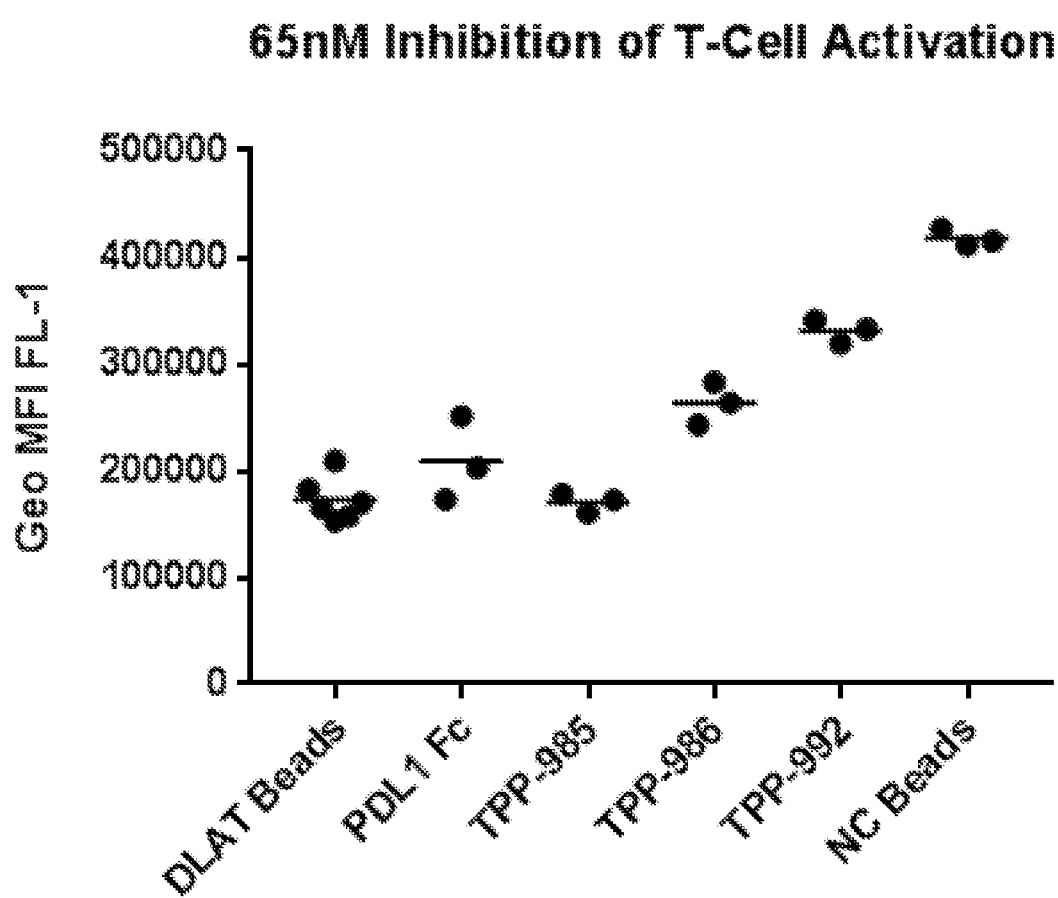

FIG. 6A shows that at the 260 nM concentration of the anti-DLAT PD-L1 fusions tested, TPP-992 (the anti-DLAT IgG2/4 construct with PD-L1 at the N-terminus of the light chain) demonstrated the greatest level of T-cell activation inhibition, with significantly greater activity inhibition than TPP-986 (the anti-DLAT IgG2/4 construct with PD-L1 at the N-terminus of the heavy chain). Both TPP-986 and TPP-992 showed significant inhibition of T-cell activation as compared to the human DLAT-aCD3 beads (referred to in the figure as DLAT Beads). TPP-992 was not significantly different than the no-activation NC beads, whereas TPP-986 was significantly different than the no-activation NC beads. FIG. 6B illustrates the statistical analysis summary of all samples in the T-cell activation assay.

No significant difference was observed when comparing the results with the DLAT-aCD3 beads in the presence or absence of the non-targeting PD-L1 Fc or TPP-985 (anti-DLAT IgG2/4 antibody with no PD-L1 fusion). At the 65 nM concentration, a lower level of T-cell activation inhibition was observed for all samples (see FIG. 6C). TPP-992 again demonstrated the most significant inhibition of T-cell activation, and showed significantly greater T-cell activation inhibition than the other fusion samples. In addition, the anti-DLAT PD-L1 fusion T-cell activation inhibition results demonstrated that TPP-986 was no longer significantly different from the PD-L1 Fc chimera at the 65 nM concentration. FIG. 6D illustrates the statistical analysis summary of T-cell activation inhibition for anti-DLAT antibody PD-L1 fusion proteins at the 65 nM concentration.

Figure 18A:
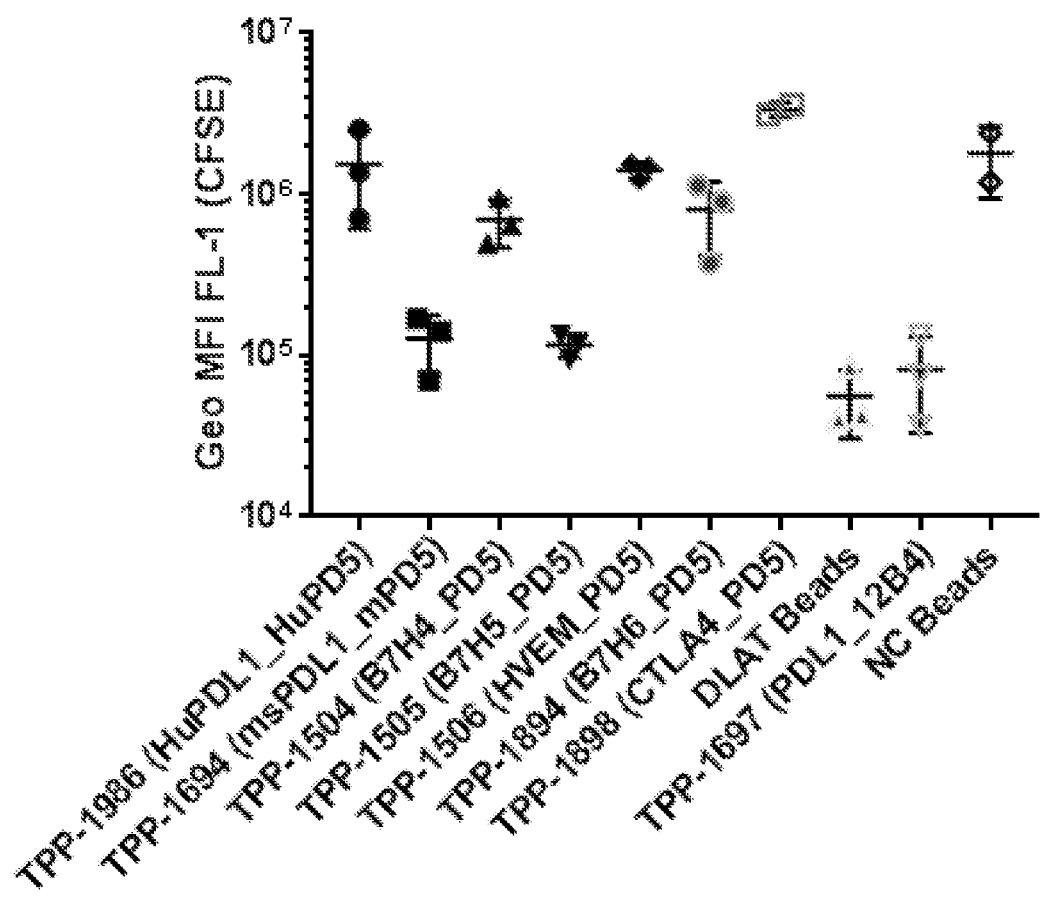
Figure 18C:
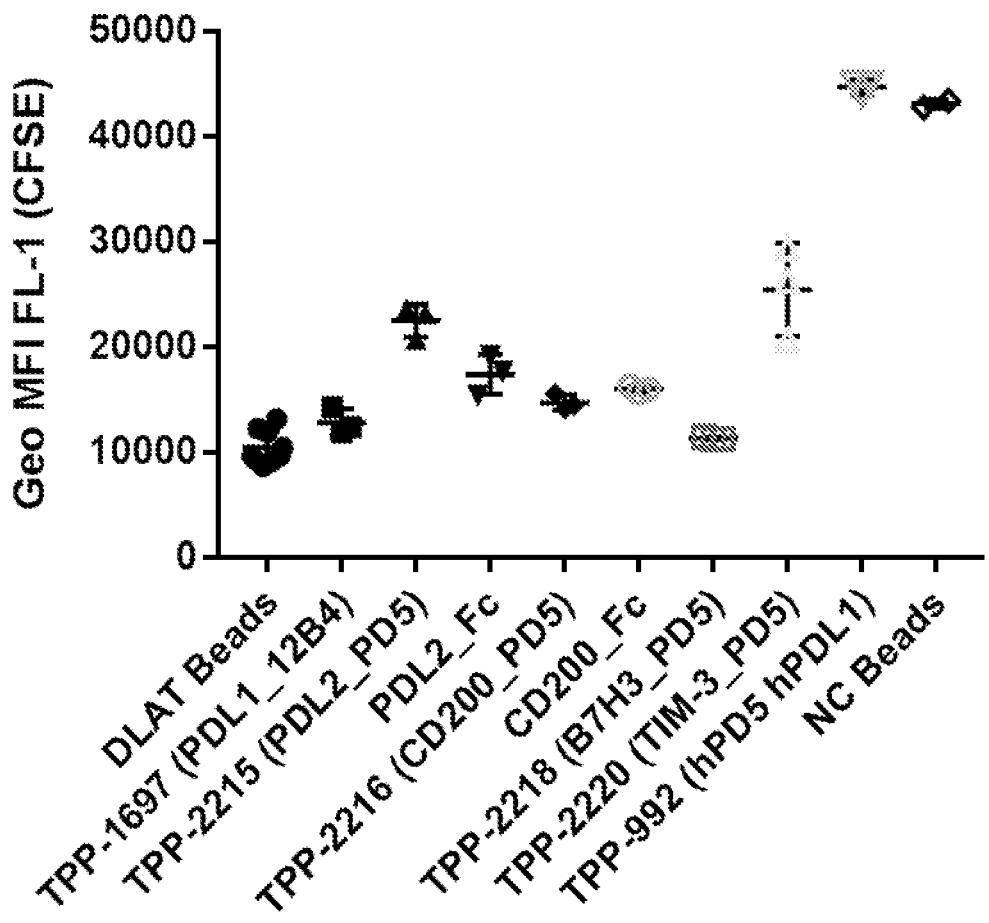
Figure 19A:
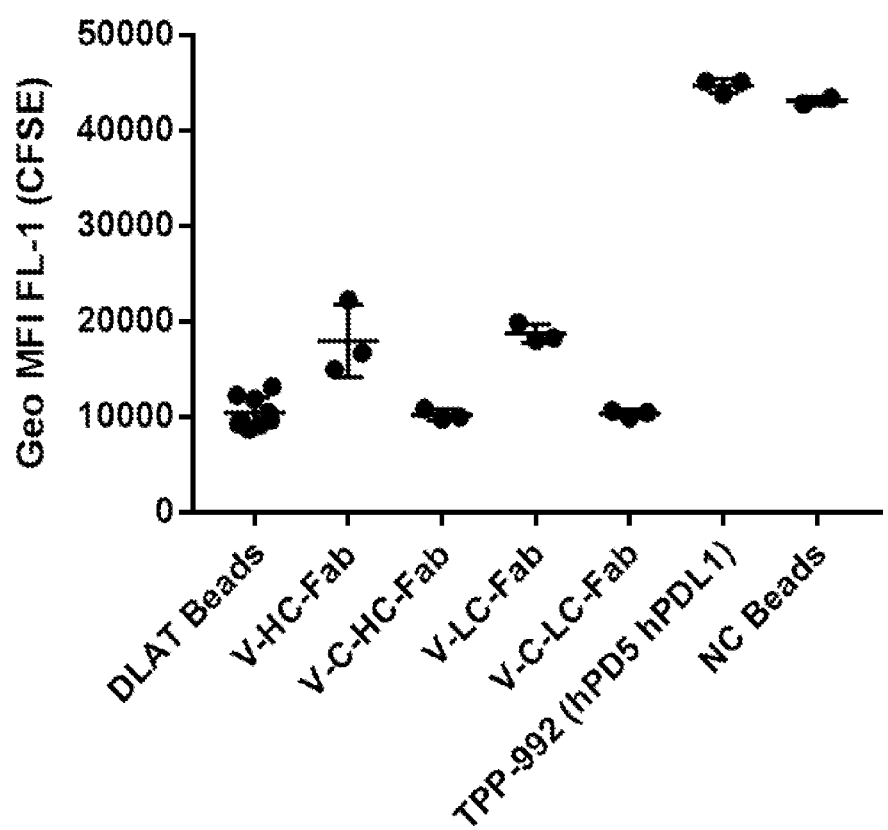

FIG. 18A illustrates that at 500 nM concentration of the anti-DLAT PD-L1 (TPP-1986), B7H4 (TPP-1504), HVEM (TPP-1506), B7H6 (TPP-1894) and CTLA4 (TPP-1898) fusions tested at day 7, inhibited T-cell activation. FIG. 18B illustrates the statistical analysis summary of all samples in the T-cell activation assay. FIG. 18C illustrates that at 500 nM concentration of the anti-DLAT PDL-2 (TPP-2215), CD200 (TPP-2216), TIM-3 (TPP-2220) and PD-5 (TTP-992) fusions showed inhibition of T cell activation at day 4. FIG. 18D illustrates the statistical analysis summary of T-cell activation inhibition for anti-DLAT antibody fusion proteins.

Example 9. Ability of the Constructs to Inhibit Mouse T-Cell Activation Bead Preparation Dihydrolipoamide Acetyltransferase mouse T-cell activation beads ("mouse DLAT-aCD3 beads") were prepared by conjugating 10 µg anti-mouse CD3, clone 145-2C11 (Stemcell Technologies, Catalog #60015) to 250 µL of Dynabeads M-450 Epoxy (ThermoFisher, Catalog #14011) for 24 hours rotating at room temperature in 0.1M sodium phosphate buffer, pH 8.0. The next day the mouse DLAT-aCD3 beads were washed and an excess of 50 µg of human DLAT recombinant protein (ProteinTech, Catalog #Ag22831) antigen was added to the mouse DLAT-aCD3 beads and incubated for an additional 48 hours at room temperature. The mouse DLAT-aCD3 beads were then washed and suspended to a concentration of $4\times10^7$ beads/mL in PBS with EasySep Buffer (Stemcell Technologies, Catalog #20144) and 250 μL aliquots were prepared and stored at −20° C.

Negative control ("NC") beads were previously prepared by conjugating human IgG Fc (Bethyl Labs, Catalog #P80-104) with uncoated beads for a no-activation control reagent. Bead conjugation was verified by flow cytometry prior to performing the mouse T-cell activation assay.

Mouse T-Cell Isolation from Spleens

Two six-week old female C57 mice were sacrificed and the spleens harvested into EasySep buffer (Stemcell Technologies, Catalog #20144). Splenocytes were harvested by dissociation of spleens by grinding between two frosted slides (ThermoFisher Catalog #6776214) into 5 mL EasySep buffer in a petri dish, filtered through a 40 μM Cell Strainer (Fisher Catalog #352340) into a 50 mL conical tube. The process was repeated for a second spleen and the combined cells were centrifuged at 300×g for 10 minutes. Splenocytes were adjusted to 1e8 cells/mL using EasySep buffer per Mouse T-cell Isolation Kit (Stemcell Technologies, Catalog #19851) protocol. Mouse T-cells were isolated following the protocol provided with the isolation kit using the Big Easy Magnet (Stemcell Technologies, Cat #18001).

Mouse T-Cell Activation Assay

Mouse T-cells isolated as described above were stained with 5 μM CFSE Cell Proliferation Kit (ThermoFisher, Catalog #C34554) dye in 10 mL EasySep buffer, incubated for 20 minutes in a 37° C. water bath, with sporadic mixing. 100 mL of TexMacs Media (Miltenyi Biosciences, Catalog #130-097-196) was added to stained cells and incubated for 5 minutes at 37° C. water bath to quench dye. Cells were centrifuged for 10 minutes at 400×g, supernatant discarded, and cell pellet was resuspended to 1.28e6 cells/mL with TexMacs Media supplemented with recombinant mouse IL-2 (Stemcell Technologies, Cat #78081). 3 μL of mouse DLAT-aCD3 beads were added to a 96-well U-bottom tissue culture plate (Corning, Catalog #3799) followed by monoclonal antibody PD-L1 fusions (mAb-PDL1) to a final concentration of 500 nM and 100 nM in replicates of three. The samples of antibody immune cell inhibitor fusion proteins evaluated in the murine T-cell activation assay include molecules are listed in Table 7 below. This assay was performed in a 96-well U-bottom tissue culture plate (Corning, Catalog #3799) with $1.3\times10^5$ cells/well with a 1:1 bead to cell ratio for 4 days at 37° C. with 5% $CO_2$. On the fourth day, flow cytometry was performed after staining with SYTOX™ Red Dead Cell stain (ThermoFisher, Catalog #534859) following the manufacturer's protocol using the C6 Accuri Flow Cytometer with C6 Sampler (BD Biosciences) detectors FL-1 (CFSE) and FL-4 (SYTOX™ Red).

TABLE 7

Antibody Immune Cell Inhibitor Fusion Proteins
Evaluated in Mouse T cell Activation Assay

| Protein ID | Isotype | Description |
| --- | --- | --- |
| TPP-1986 | mIgG1 | Human PDL1_Mouse PD5 |
| TPP-992 | Human IgG2/4 | Human PDL1_Human PD5 |
| TPP-1694 | Mouse IgG1 | Mouse PDL1_Mouse PD5 |
| TPP-1695 | Mouse IgG1 | Mouse PDL1_Mouse DWZ |
| TPP-1697 | Human IgG2/4 | Human PDL1_Human 12B4 Isotype control |
| TPP-1504 | Human IgG2/4 | Human B7-H4_Human PD5 |
| TPP-1505 | Human IgG2/4 | Human B7-H5_Human PD5 |
| TPP-1004 | Mouse IgG1 | Mouse PD5 |
| TTP-1984 | Mouse IgG1 | Mouse PDL1_Mouse PD5 |
| TTP-1985 | Mouse IgG1 | Mouse PDL1_Mouse 12b4 |
| TTP-1898 | Human IgG2/4 | CTLA4_PD5 |
| TTP-2246 | Mouse IgG1 | Mouse PD5 |

TABLE 8

Summary of Antibody Immune Cell Inhibitor Fusion Proteins
Evaluated in Mouse or Human T cell Activation Assays

| Fusion to anti-DLAT (PD5) | Result of T-cell Activation Inhibition |
| --- | --- |
| CTLA-4 | Inhibited human T-cells as potently as PD-L1 fusion in-vitro, TPP-1898 vs. DLAT beads (P Value = 0.0001). Complete inhibition observed for human & mouse T-cells. |
| (B7-H1) PD-L1 | Inhibited human & mouse T-cells, TPP-992 vs. DLAT beads (P Value = <0.0001). Fab fusion was not as potent as mab, full length PD-L1 ECD not as potent as V-like domain only when tested as Fabs. Complete inhibition observed for human & mouse T-cells. |
| HVEM (CD270) | Inhibited human T-cells as potently as PD-L1 fusion, TPP-1506 vs. DLAT beads (P Value = 0.0053). Complete inhibition observed for human & mouse T-cells. |
| B7-H4 (VTCN1, B7x) | Inhibited mouse & human T-cells. Not as potent as PD-L1 fusion, but close to complete inhibition observed in 7 day human T-cell assay. TPP-1504 vs. DLAT beads (P value = .3416). Complete inhibition observed in mouse T-cell assay. |
| B7-H6 (NCR3LG1) | Not as potent as PD-L1 fusion, but close to complete inhibition observed in 7 day human T-cell assay. Inhibited human T-cells (Day 7 was not significant w 95% CI), TPP-1894 vs. DLAT beads (P Value = 0.202). Similar potency to HVEM fusion. |
| TIM-3 | Full length TIM-3 fusion expressed well. Significantly inhibited human T-cells, not as potent as PD-L1 fusion, IC50 ~500 nM in 4 day assay. TPP-2220 vs. DLAT beads (P Value = <0.0001). |
| (B7-DC) PD-L2 | Full length PD-L2 ECD fusion expressed well, V-like domain only did not express. Significantly inhibited human T-cells; TPP-2215 vs. DLAT beads (P Value = <0.0001). Not as potent as PD-L1 fusion. Low levels of inhibition observed, only slightly more potent than PDL2_Fc. |
| CD200 | Full length ECD of CD200 as a fusion expressed well, v-like domain did not express as fusion. Statistically significant TPP-2216 vs. DLAT beads (P value = 0.0338) inhibition of human T-cells as targeted & non-targeted fusion (CD200_Fc). Not as potent as PD-L1 or other fusions. |
| B7-H3 (CD276) | Full length B7-H3 fusion expressed well. No significant inhibition observed. |
| B7-H5 (VISTA) | Expressed well as a fusion. No significant inhibition observed in repeated assays. |
| B7-H7 (HHLA2) | Did not express as individual V-like domains fused to PD5 or as full length ECD fusion. |

As shown in FIG. 12A, TPP-1986 provided complete inhibition of mouse T-cell activation at 500 nM with incomplete inhibition observed for 100 nM. FIG. 12B illustrates that TPP-1694 showed a significant difference as compared to the NC beads, but showed no significant difference as compared to TPP-1986 at 500 nM. A significant difference was observed at 100 nM for human TPP-1986 and TPP-992 versus mouse PD-L1-TPP-1694. FIG. 12C illustrates that TPP-1695 demonstrated a lower potency as compared to the PD5 human PD-L1 fusion variants at 500 nM and 100 nM concentrations with similar results observed for TPP-1694. FIG. 12D illustrates complete inhibition of mouse T-cell activation for TPP-992 at 500 nM with an incomplete inhibition for 100 nM. FIGS. 12E and 12F illustrate that TPP-1697 (non-targeted isotype control with human PD-L1) and TPP-1004 (murine IgG1 PD5 with no PD-L1 variable-like domain present), showed no significant inhibition of T-cell activation.

Figure 13A:
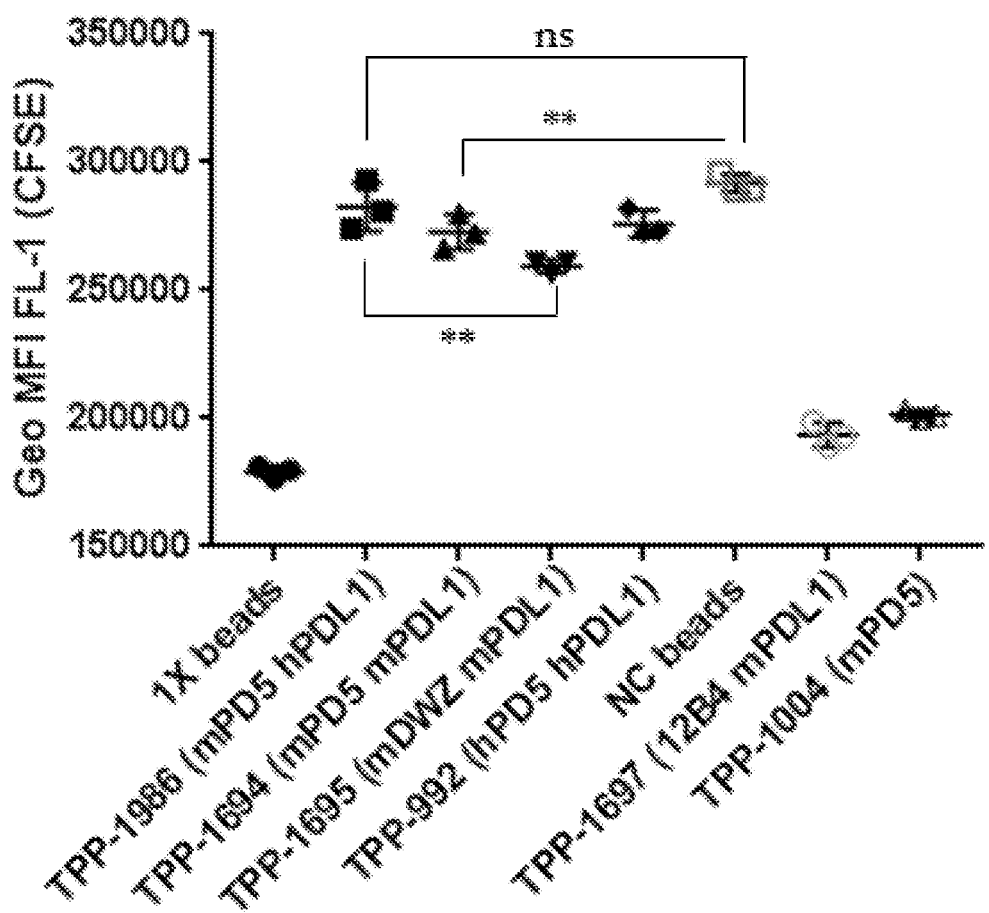

FIGS. 13A and 13B show the statistical analysis of the mouse T-cell activation results at 500 nM. FIG. 13A illustrates complete inhibition of mouse T-cells with TPP-1986 and TPP-992 fusions containing human PD-L1 as demonstrated by no significant difference as compared to the NC beads. An expected decrease in the geometric mean fluorescence intensity (Geo MFI) of FL-1 representing the CFSE dye diffusion into progeny cells for the 1× beads, TPP-1697, TPP-1004, was observed, illustrating activation of the murine T-cells with no significant differences observed between samples. FIG. 13B is a table of statistical analysis between samples at 500 nM concentrations using Tukey's multiple comparisons test.

Figure 14A:
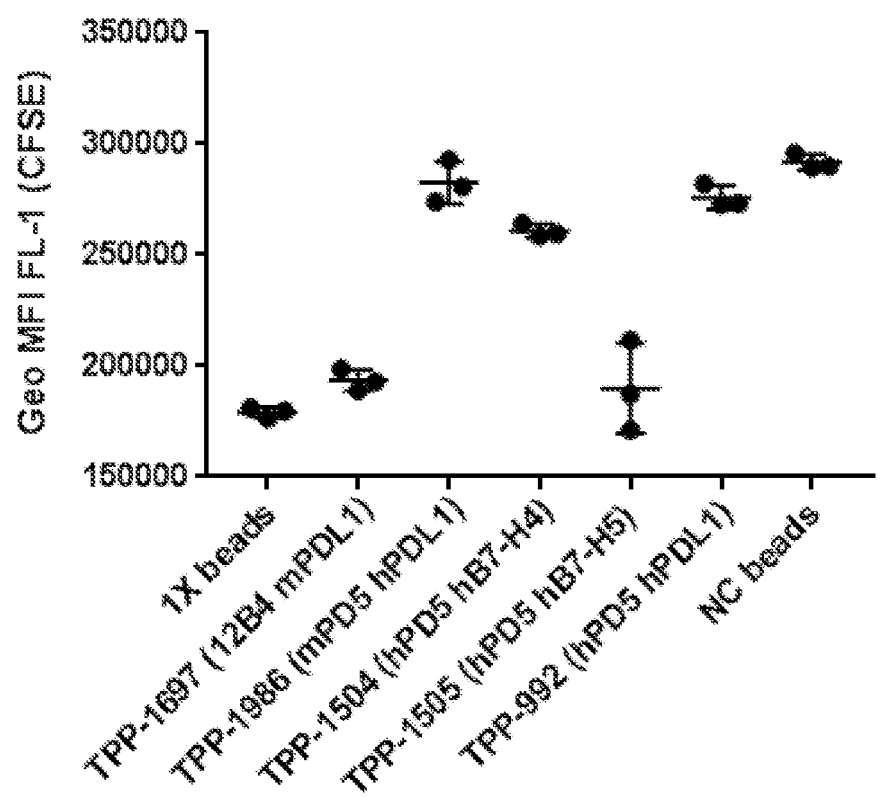

FIGS. 14A and 14B show the statistical analysis of the mouse T-cell activation results at 500 nM. FIG. 14A illustrates complete inhibition of mouse T-cells with TPP-TPP-992 with no statistically significant difference to TPP-1504 (hB7-H4) fusion and no significant difference as compared to the NC beads. An expected decrease in the geometric mean fluorescence intensity (Geo MFI) of FL-1 representing the CFSE dye diffusion into progeny cells for the 1× beads, TPP-1697, or NC beads, was observed, illustrating activation of the murine T-cells with no significant differences observed between samples. TPP-1505 (hB7-H5) fusion shows no significant difference to the 1× beads suggesting it did not inhibit T-cell activation. FIG. 14B is a table of statistical analysis between samples at 500 nM concentrations using Tukey's multiple comparisons test.

Figure 15A:
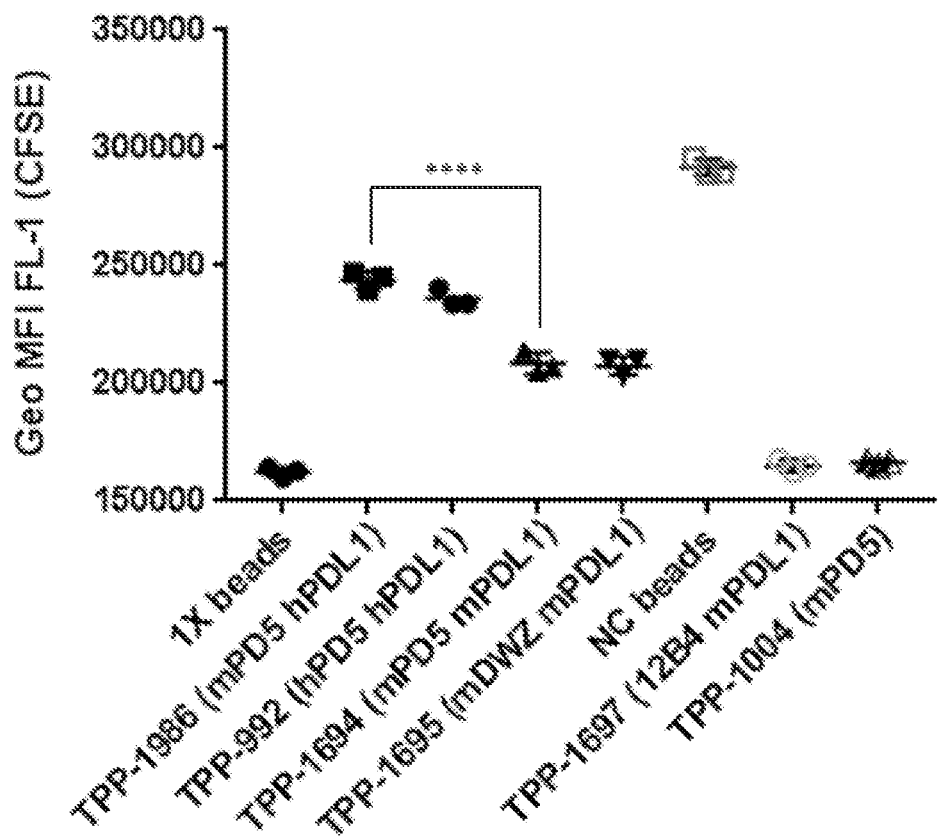
Figure 16A:
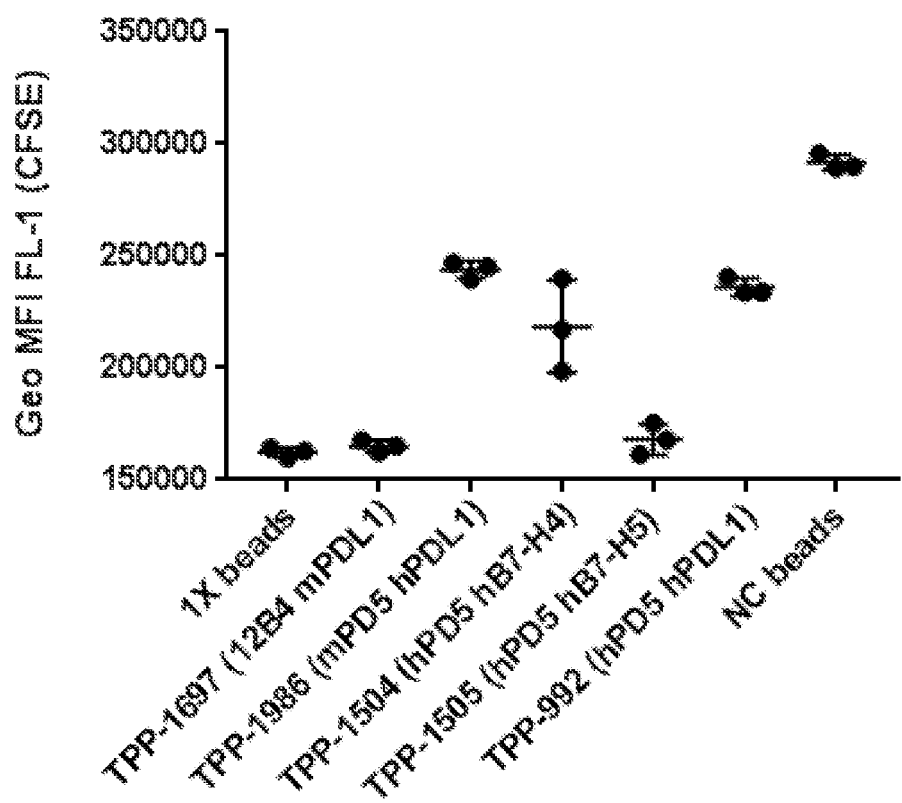
Figure 17:
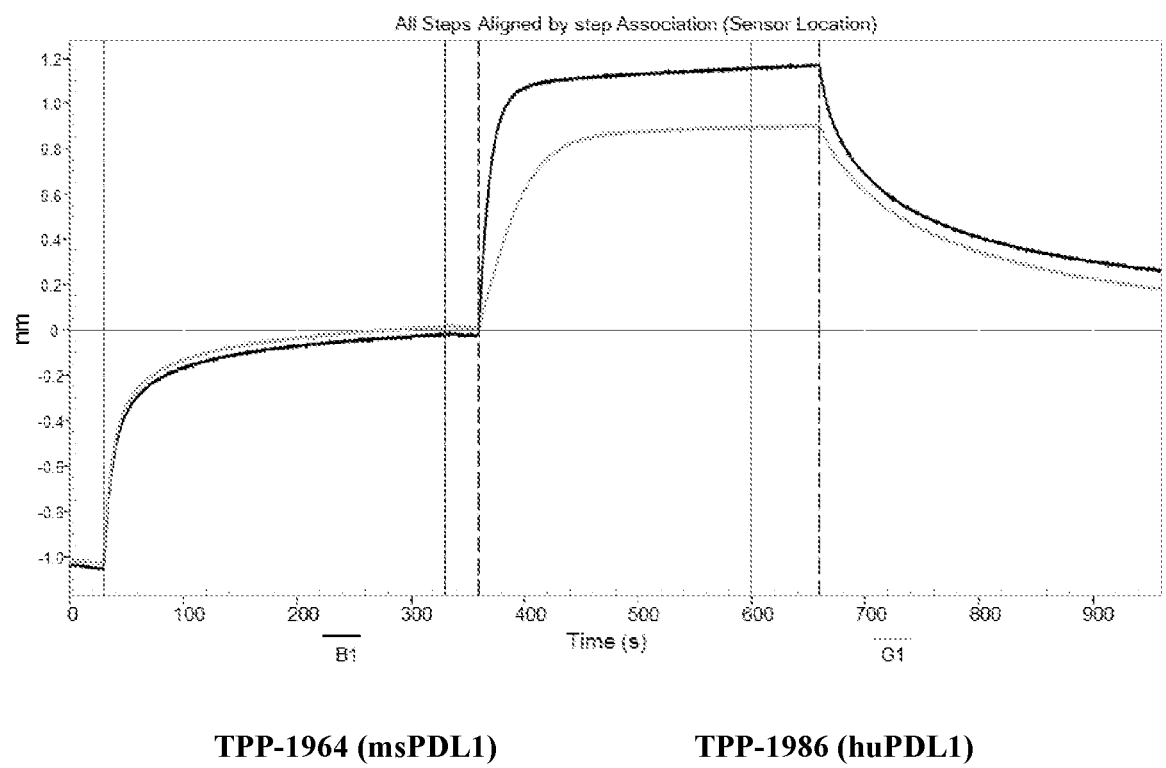
FIG. 17 illustrates that mouse PD-L1(TPP-1964) binds to human PD-1 with a faster on-rate than human PD-L1. PD-1 Fc (R&D Systems) was loaded onto anti-human IgG tips illustrated by the first observed deflection. The two fusions TPP-1964 (msPDL1) and TPP-1986 (huPDL1) bound PD-1 Fc. The increased slope observed for TPP-1964 (B1 sensor) suggests the mouse PD-L1 has a faster on-rate than the human PD-L1 on the TPP-1986 fusion (GI Fusion). This binding steps followed by the dissociation in PBS buffer.

FIGS. 15 and 16 show the statistical analysis of the mouse T-cell activation results at 100 nM. FIGS. 15A and 16A illustrate incomplete inhibition using fusions containing human PD-L1 and hB7-H4 as compared to the NC beads. A significant difference of human versus murine PD-L1 containing fusions was observed, suggesting human PD-L1 results in greater inhibition of mouse T-cells than mouse PD-L1 V-like domain. An expected decrease in the geometric mean fluorescence intensity (Geo MFI) of FL-1 representing the CFSE dye diffusion into progeny cells for the 1× beads, TPP-1697, TPP-1004, and TPP-1505 was observed illustrating activation of the murine T-cells with no significant differences between samples. FIGS. 15B and 16B are tables of statistical analysis between samples at 100 nM concentrations using Tukey's multiple comparisons test.

Figure 20A:
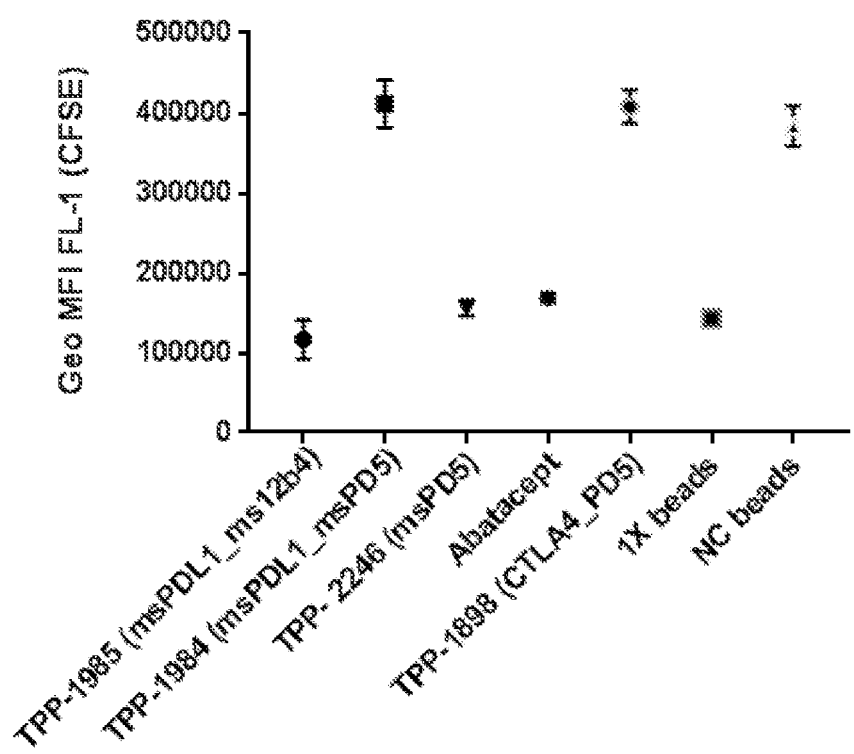
Figure 20B:
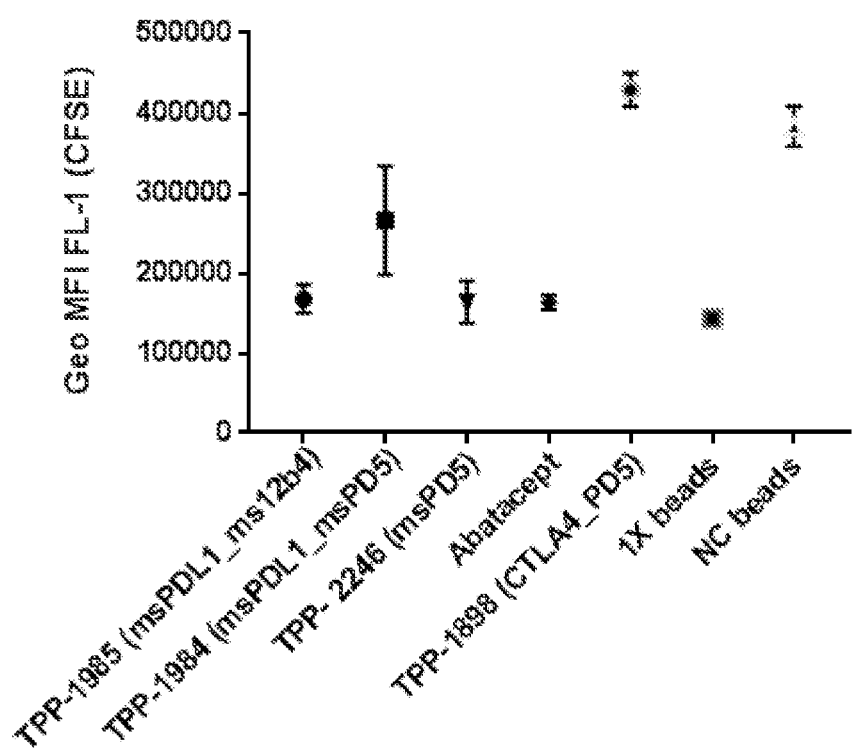
Figure 20C:
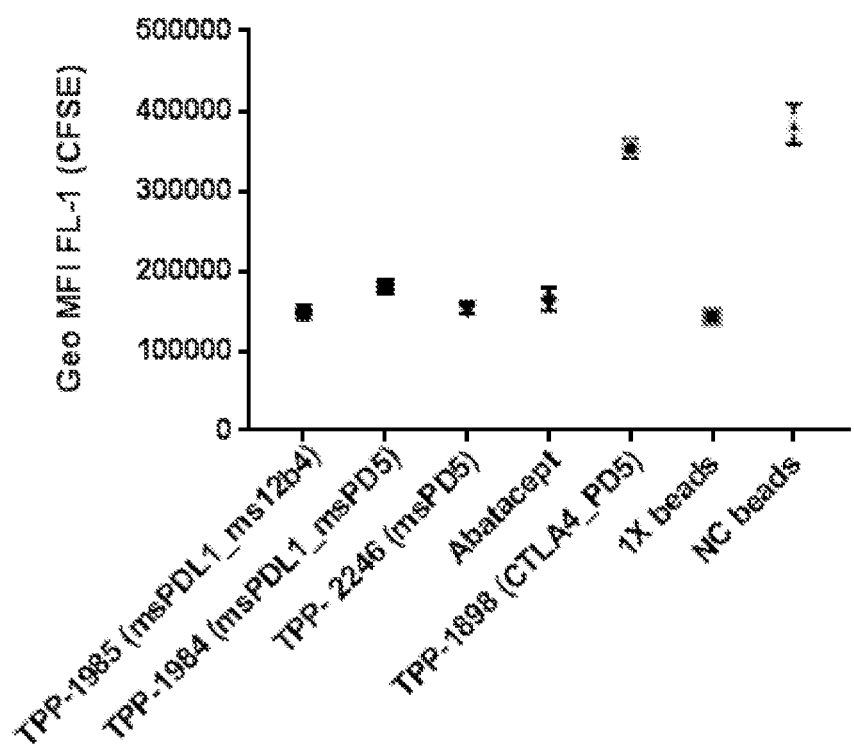

FIGS. 20A-20C illustrate the results of mouse T-cell activation at 7 days gated on the CD4+ cells. FIG. 20A illustrates that at the 500 nM concentration of the anti-DLAT PD-L1 (TPP-1984) and CTLA4 (TPP-1898) fusions tested at day 7, inhibited mouse T-cell activation completely. FIG. 20B illustrates that at the 125 nM concentration a lower level of T-cell activation inhibition was observed with TPP-1984 but not TPP-1898 that maintains no significant difference to the NC beads. FIG. 20C illustrates the anti-DLAT CTLA4 (TPP-1898) completely inhibits mouse T-cell activation at a 32 nM concentration in the 7 day assay. 1× beads, TPP-1985, and TPP-2246 all show the expected decrease of signal representing the expected decrease in the geometric mean fluorescence intensity (Geo MFI) of FL-1 representing the CFSE dye diffusion into progeny cells was observed illustrating activation of the murine T-cells with no significant differences between samples. FIG. 20D illustrates the statistical analysis summary of T-cell activation inhibition for anti-DLAT antibody fusion proteins at the three concentrations tested. The statistical analysis demonstrates the anti-DLAT CTLA4 is significantly more potent than the untargeted CTLA4 (Abatacept)

Figure 21A:
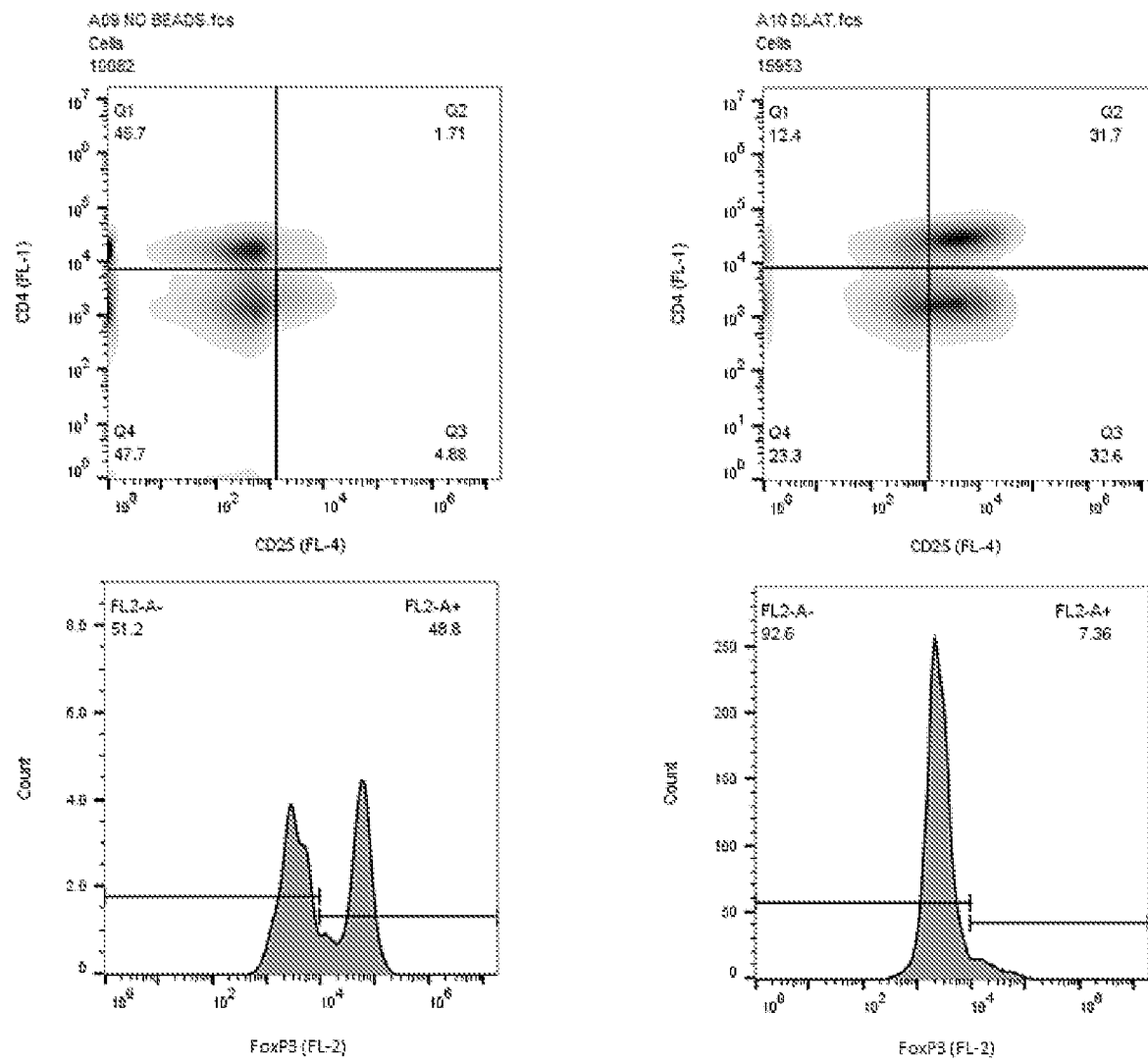
FIGS. 21A and 21B demonstrate the induction of regulatory T-cells (Tregs—CD4+, CD25+, FoxP3+) with the PD-L1 fusions anti-DLAT_PDL1 (labeled DLAT DRUG) and anti-VAP-1_PDL1 (labeled VAP-1 DRUG) combined with the respective activation beads.
Figure 21B:
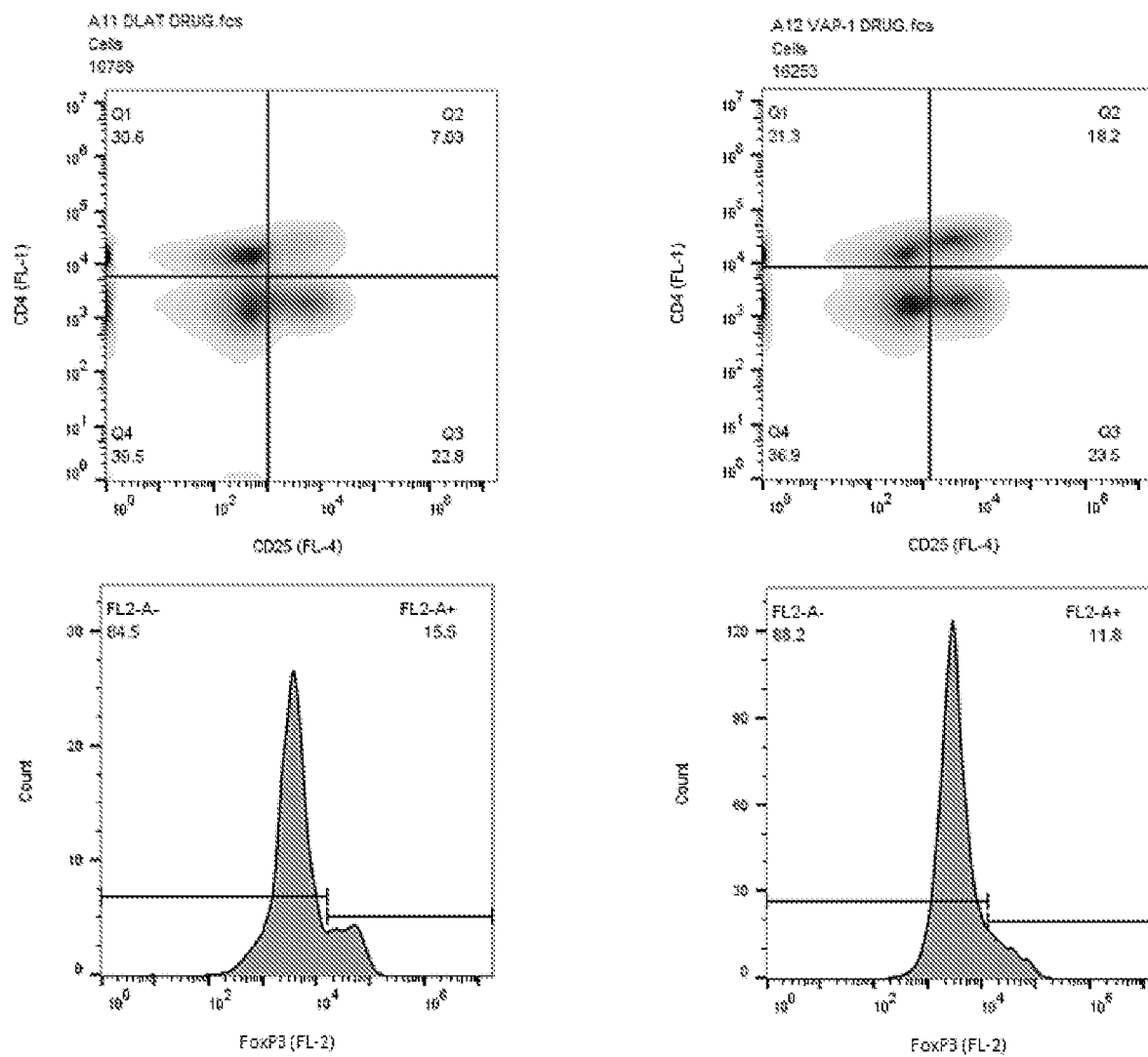

FIGS. 21A and 21B demonstrate the induction of regulatory T-cells (Tregs—CD4+, CD25+, FoxP3+) with the PD-L1 fusions anti-DLAT_PDL1 (labeled DLAT DRUG) and anti-VAP-1_PDL1 (labeled VAP-1 DRUG) combined with the respective activation beads. FIG. 21A illustrate flow cytometry results demonstrating low levels of CD25 for the no activation control (labeled NO BEADS) with 1.71% in quadrant 2 (Q2) representing the CD4+, CD25+ population. The histogram shown below the dot plot represents the intracellular staining with FoxP3 of the Q2 gated events. The activated T-cells (labeled DLAT) showed a significant increase in effector T-cells (Teff) in Q2, however a small percentage of these CD4+, CD25+ cells were Tregs (FoxP3+). FIG. 21B illustrates inhibition of the Teff population shown as 7% in Q2 with the addition of TPP-992 (labeled DLAT DRUG) to the DLAT activation beads, compared to 32% for DLAT beads only. In addition, from the Q2 population, the FoxP3 positive events went from 7% to 16% with the drug. Anti-VAP-1_PDL1 previously showed weaker inhibition in the T-cell activation assay using proliferation dye compared to the anti-DLAT_PDL1 (data not shown). This intermediate effect of anti-VAP-1 fusion was confirmed by the results of this assay; a higher percentage of Q2 events were observed (18%), with a lower induction of Tregs 12% compared to anti-DLAT_PDL1.

What is claimed is:

1. An antibody immune cell inhibitor fusion protein comprising four polypeptide chains that form two antigen binding sites and at least two immune cell receptor binding sites;

wherein two polypeptide chains have a structure represented by the formula $II_1$-$V_L$-$C_L$, and two polypeptide chains have a structure represented by the formula $II_3$-$V_H$-$C_{H1}$-Fc;

wherein:
- $V_L$ is an immunoglobulin light chain variable domain that specifically binds to dihydrolipoamide acetyltransferase;
- $V_H$ is an immunoglobulin heavy chain variable domain that specifically binds to dihydrolipoamide acetyltransferase;
- $C_L$ is an immunoglobulin light chain constant domain;
- $C_{H1}$ is the immunoglobulin $C_{H1}$ heavy chain constant domain;
- Fc is the immunoglobulin hinge region and $C_{H2}$ and $C_{H3}$ immunoglobulin heavy chain constant domains; and
- $II_1$ and $II_3$ are each independently an immune cell inhibitor domain of an immunoglobulin superfamily member or are absent;

wherein at least one of $II_1$ and $II_3$ is an immune cell inhibitor domain of an immunoglobulin superfamily member;

wherein the antibody immune cell inhibitor fusion protein specifically binds to dihydrolipoamide acetyltransferase and inhibits or diminishes activation of an immune effector cell only when bound to a target antigen at one or both of the antigen binding sites; and wherein the polypeptide chains comprise:
(a) the amino acid sequences of SEQ ID NO. 4 and SEQ ID NO. 17;
(b) the amino acid sequences of SEQ ID NO. 6 and SEQ ID NO. 14;
(c) the amino acid sequences of SEQ ID NO. 5 and SEQ ID NO. 14;
(d) the amino acid sequences of SEQ ID NO. 10 and SEQ ID NO. 16;
(e) the amino acid sequences of SEQ ID NO. 12 and SEQ ID NO. 13;
(f) the amino acid sequences of SEQ ID NO. 2 and SEQ ID NO. 4;
(g) the amino acid sequences of SEQ ID NO. 3 and SEQ ID NO. 4;
(h) the amino acid sequences of SEQ ID NO. 1 and SEQ ID NO. 6;
(i) the amino acid sequences of SEQ ID NO. 1 and SEQ ID NO. 5;
(j) the amino acid sequences of SEQ ID NO. 8 and SEQ ID NO. 10;
(k) the amino acid sequences of SEQ ID NO. 9 and SEQ ID NO. 10;
(l) the amino acid sequences of SEQ ID NO. 7 and SEQ ID NO. 11;
(m) the amino acid sequences of SEQ ID NO. 7 and SEQ ID NO. 12;
(n) the amino acid sequences of SEQ ID NO. 27 and SEQ ID NO. 28;
(o) the amino acid sequences of SEQ ID NO. 21 and SEQ ID NO. 33;
(p) the amino acid sequences of SEQ ID NO. 23 and SEQ ID NO. 34;
(q) the amino acid sequences of SEQ ID NO. 35 and SEQ ID NO. 14;
(r) the amino acid sequences of SEQ ID NO. 36 and SEQ ID NO. 14;
(s) the amino acid sequences of SEQ ID NO. 37 and SEQ ID NO. 14;
(t) the amino acid sequences of SEQ ID NO. 38 and SEQ ID NO. 14;
(u) the amino acid sequences of SEQ ID NO. 39 and SEQ ID NO. 14;

(v) the amino acid sequences of SEQ ID NO. 40 and SEQ ID NO. 14;
(w) the amino acid sequences of SEQ ID NO. 41 and SEQ ID NO. 14;
(x) the amino acid sequences of SEQ ID NO. 42 and SEQ ID NO. 14;
(y) the amino acid sequences of SEQ ID NO. 43 and SEQ ID NO. 14; or
(z) the amino acid sequences of SEQ ID NO. 44 and SEQ ID NO. 14.

2. An antibody immune cell inhibitor fusion protein comprising four polypeptide chains that form two antigen binding sites and at least two immune cell receptor binding sites;
wherein two polypeptide chains have a structure represented by the formula $II_1\text{-}L_1\text{-}V_L\text{-}C_L$ and two polypeptide chains have a structure represented by the formula $II_3\text{-}L_3\text{-}V_H\text{-}C_{H1}\text{-}Fc$;
wherein:
$V_L$ is an immunoglobulin light chain variable domain that specifically binds to dihydrolipoamide acetyltransferase;
$V_H$ is an immunoglobulin heavy chain variable domain that specifically binds to dihydrolipoamide acetyltransferase;
$C_L$ is an immunoglobulin light chain constant domain;
$C_{H1}$ is the immunoglobulin $C_{H1}$ heavy chain constant domain;
Fc is the immunoglobulin hinge region and $C_{H2}$ and $C_{H3}$ immunoglobulin heavy chain constant domains;
$L_1$ and $L_3$ are each independently a linker domain or are absent; and
$II_1$ and $II_3$ are each independently an immune cell inhibitor domain of an immunoglobulin superfamily member or are absent;
wherein at least one of $L_1$ and $L_3$ is a linker domain and at least one of $II_1$ and $II_3$ is an immune cell inhibitor domain of an immunoglobulin superfamily member;
wherein the antibody immune cell inhibitor fusion protein specifically binds to dihydrolipoamide acetyltransferase and inhibits or diminishes activation of an immune effector cell only when bound to a target antigen at one or both of the antigen binding sites; and
wherein the polypeptide chains comprise:
(a) the amino acid sequences of SEQ ID NO. 4 and SEQ ID NO. 17;
(b) the amino acid sequences of SEQ ID NO. 6 and SEQ ID NO. 14;
(c) the amino acid sequences of SEQ ID NO. 5 and SEQ ID NO. 14;
(d) the amino acid sequences of SEQ ID NO. 10 and SEQ ID NO. 16;
(e) the amino acid sequences of SEQ ID NO. 12 and SEQ ID NO. 13;
(f) the amino acid sequences of SEQ ID NO. 2 and SEQ ID NO. 4;
(g) the amino acid sequences of SEQ ID NO. 3 and SEQ ID NO. 4;
(h) the amino acid sequences of SEQ ID NO. 1 and SEQ ID NO. 6;
(i) the amino acid sequences of SEQ ID NO. 1 and SEQ ID NO. 5;
(j) the amino acid sequences of SEQ ID NO. 8 and SEQ ID NO. 10;
(k) the amino acid sequences of SEQ ID NO. 9 and SEQ ID NO. 10;
(l) the amino acid sequences of SEQ ID NO. 7 and SEQ ID NO. 11;
(m) the amino acid sequences of SEQ ID NO. 7 and SEQ ID NO. 12;
(n) the amino acid sequences of SEQ ID NO. 27 and SEQ ID NO. 28;
(o) the amino acid sequences of SEQ ID NO. 21 and SEQ ID NO. 33;
(p) the amino acid sequences of SEQ ID NO. 23 and SEQ ID NO. 34;
(q) the amino acid sequences of SEQ ID NO. 35 and SEQ ID NO. 14;
(r) the amino acid sequences of SEQ ID NO. 36 and SEQ ID NO. 14;
(s) the amino acid sequences of SEQ ID NO. 37 and SEQ ID NO. 14;
(t) the amino acid sequences of SEQ ID NO. 38 and SEQ ID NO. 14;
(u) the amino acid sequences of SEQ ID NO. 39 and SEQ ID NO. 14;
(v) the amino acid sequences of SEQ ID NO. 40 and SEQ ID NO. 14;
(w) the amino acid sequences of SEQ ID NO. 41 and SEQ ID NO. 14;
(x) the amino acid sequences of SEQ ID NO. 42 and SEQ ID NO. 14;
(y) the amino acid sequences of SEQ ID NO. 43 and SEQ ID NO. 14; or
(z) the amino acid sequences of SEQ ID NO. 44 and SEQ ID NO. 14.

3. The antibody immune cell inhibitor fusion protein of claim 1, wherein each of $II_1$ and $II_3$ is an immune cell inhibitor domain.

4. The antibody immune cell inhibitor fusion protein of claim 1, wherein at least one of $II_1$ and $II_3$ is an immune cell inhibitor domain and inhibits or diminishes activation of an immune effector cell involved in the immune response to self-tissue.

5. The antibody immune cell inhibitor fusion protein of claim 4, wherein at least one of $II_1$ and $II_3$ is an immune cell inhibitor domain that inhibits or diminishes activation of an immune effector cell involved in the immune response to self-tissue when an autoantibody is bound to the antigen at the site of an ongoing disease process.

6. The antibody immune cell inhibitor fusion protein of claim 1, wherein at least one of $II_1$ and $II_3$ is absent.

7. The antibody immune cell inhibitor fusion protein of claim 1, wherein the immune cell inhibitor domain comprises a Programmed Death Ligand 1 (PD-L1) domain, Programmed Death Ligand 2 (PD-L2) domain, B7 Homolog 3 (B7-H3) domain, B7 Homolog 4 (B7-H4) domain, Herpesvirus Entry Mediator (HVEM) domain, B7 Homolog 5 (B7-H5) domain, B7 Homolog 6 (B7-H6) domain, B7 Homolog 7 (B7-H7) domain, Cytotoxic T Lymphocyte-Associated 4 (CTLA-4) domain, CD200 domain, T-cell Immunoglobulin or Mucin Domains-Containing Protein 3 (TIM-3) domain.

8. A pharmaceutical composition comprising a therapeutically effective amount of the antibody immune cell inhibitor fusion protein of claim 1 and a pharmaceutically acceptable carrier.

9. A kit comprising the antibody immune cell inhibitor fusion protein of claim 1.

10. The antibody immune cell inhibitor fusion protein of claim 2, wherein at least one of $L_1$ and $L_3$ is absent.

* * * * *